US009394309B2

(12) United States Patent
Süßmeier et al.

(10) Patent No.: US 9,394,309 B2
(45) Date of Patent: Jul. 19, 2016

(54) SUBSTITUTED PHENYLIMIDAZOPYRAZOLES AND THEIR USE

(71) Applicant: BAYER INTELLECTUAL PROPERTY GmbH, Monheim (DE)

(72) Inventors: Frank Süßmeier, München (DE); Mario Lobell, Wuppertal (DE); Sylvia Grünewald, Berlin (DE); Michael Härter, Leverkusen (DE); Bernd Buchmann, Hohen Neuendorf (DE); Joachim Telser, Wuppertal (DE); Hannah Jöriβen, Essen (DE); Melanie Heroult, Berlin (DE); Antje Kahnert, Wuppertal (DE); Klemens Lustig, Wuppertal (DE); Niels Lindner, Wuppertal (DE)

(73) Assignees: Bayer Pharma Aktiengesellschaft, Berlin (DE); Bayer Intellectual Property GmbH, Monheim (DE)

( * ) Notice: Subject to any disclaimer, the term of this patent is extended or adjusted under 35 U.S.C. 154(b) by 375 days.

(21) Appl. No.: 13/748,043

(22) Filed: Jan. 23, 2013

(65) Prior Publication Data
US 2013/0190290 A1   Jul. 25, 2013

(30) Foreign Application Priority Data

Jan. 25, 2012   (EP) .................................. 12152515

(51) Int. Cl.
| *A61K 31/495* | (2006.01) |
| *A61K 31/00* | (2006.01) |
| *A61K 31/54* | (2006.01) |
| *A61K 31/501* | (2006.01) |
| *A61K 31/50* | (2006.01) |
| *A61K 31/415* | (2006.01) |
| *C07D 487/04* | (2006.01) |
| *A61K 31/496* | (2006.01) |
| *A61K 45/06* | (2006.01) |
| *A61K 31/5377* | (2006.01) |
| *A61K 31/4188* | (2006.01) |
| *A61K 31/4439* | (2006.01) |
| *A61K 31/4545* | (2006.01) |

(52) U.S. Cl.
CPC .......... *C07D 487/04* (2013.01); *A61K 31/4188* (2013.01); *A61K 31/4439* (2013.01); *A61K 31/4545* (2013.01); *A61K 31/496* (2013.01); *A61K 31/5377* (2013.01); *A61K 45/06* (2013.01)

(58) Field of Classification Search
CPC ............................ C07D 487/04; A61K 31/496
USPC ........ 514/210.21, 254.06, 233.2, 393, 253.09
See application file for complete search history.

(56) References Cited

PUBLICATIONS

Golub et al., Science, vol. 286, Oct. 15, 1999, pp. 531-537.*

* cited by examiner

*Primary Examiner* — San-Ming Hui

(57) ABSTRACT

The present application relates to novel 1-phenyl-1H-imidazo[1,2-b]pyrazole derivatives, to processes for their preparation, to their use for the treatment and/or prevention of diseases and to their use for preparing medicaments for the treatment and/or prevention of diseases, in particular angiogenic disorders and hyperproliferative disorders, where neovascularization plays a role, such as, for example, neoplastic disorders and tumor disorders. Such treatments can be carried out as monotherapy or else in combination with other medicaments or further therapeutic measures.

11 Claims, No Drawings

SUBSTITUTED PHENYLIMIDAZOPYRAZOLES AND THEIR USE

The present application relates to novel 1-phenyl-1H-imidazo[1,2-b]pyrazole derivatives, to processes for their preparation, to their use for the treatment and/or prevention of diseases and to their use for preparing medicaments for the treatment and/or prevention of diseases, in particular angiogenic disorders and hyperproliferative disorders, where neovascularization plays a role, such as, for example, neoplastic disorders and tumour disorders. Such treatments can be carried out as monotherapy or else in combination with other medicaments or further therapeutic measures.

The process of angiogenesis, i.e. the formation of new blood vessels from existing vessels [W. Risau, Nature 386, 671 (1997); R. K. Jain, Nat. Med. 9, 685 (2003)], is relatively rare in adult organisms (wound healing, ovarian cycle); it does, however, play an important role in pathological processes, in particular in tumour disorders including haemangiomas and haemangioblastomas, and also in inflammatory diseases and autoimmune disorders, cardiovascular disorders, kidney disorders, eye disorders and endometriosis with dysregulated angiogenesis.

Neoplastic disorders are the result of uncontrolled cell growth of various tissues. In many cases, the new cells penetrate into existing tissues (invasive growth), or they metastasize into remote organs. Neoplastic disorders occur in various organs and their progression is often tissue-specific. Accordingly, the term neoplastic disorder describes a large group of defined disorders of various organs, tissues and cell types.

Initially, nascent tumours are not vascularized. Pre-condition for further growth exceeding a volume of a few $mm^3$ is the formation of new blood vessels to provide the tumour with oxygen and nutrients. This induction of angiogenesis, also referred to as angiogenic switch, is one of the characterizing features of the development of cancer [Hanahan and Weinberg, Cell 100, 57 (2000)]. In addition, intratumoural neovascularization increases the probability that tumour cells enter the systemic circulation, and strong vascularization therefore increases the potential of metastasization.

The dependency of the tumours on neovascularization led to the inhibition of angiogenesis as a novel treatment principle in cancer therapy [Ferrara et al., Nature 438, 967 (2005); Carmeliet, Nature 438, 932 (2005)]. Here, the supply of the growing tumour is restricted by inhibiting the even concomitant growth of the vascular system. As a result, frequently the growth is delayed, the status quo is stabilized and the tumour even regresses. One of the most important pro angiogenesis factors is the vascular endothelial growth factor VEGF. Using a monoclonal antibody (bevacizumab) which neutralizes VEGF and inhibits the growth of blood vessels, it was possible to extend the life-expectancy of patients suffering from colorectal carcinoma. VEGFR kinase inhibitors such as sorafenib, sunitinib or pazopanib show positive results in the treatment of renal cell carcinomas, liver carcinomas and advanced stages of gastrointestinal stromal tumours (GIST). However, frequently the efficacy of the anti-angiogenic therapies available to date does not meet expectations, and in addition the side-effects are considerable. Accordingly, there is still a big need for novel compounds and methods with improved therapeutic efficacy.

In addition to VEGF-mediated signal transduction, numerous other signal transduction systems participate in the regulation of angiogenesis; however, the angiopoietin-Tie2 signal transduction system is one of the most endothelial cell-selective and most important signal generators for vascular stabilization and, together with VEGF, for the initiation of vascular growth.

The human angiopoietin-Tie signal transduction system consists of the two Type I receptor tyrosine kinases Tie1 and Tie2 (Tyr kinase with Ig and EGF homology domains) and the three secreted glycoprotein ligands angiopoietin 1 (Ang1), angiopoietin 2 (Ang2) and angiopoietin 4 (Ang4). These three ligands bind to Tie2, whereas hitherto no endogenous ligands have been identified for Tie1. Tie1 interacts with Tie2 and regulates its activity [Huang et al., Nat. Rev. Cancer 10, 575-585 (2010)]. Ang1 acts as Tie2 receptor agonist and induces, both in vitro and in vivo, multimerization and autophosphorylation of Tie2 at tyrosine residues in the intracellular C-terminal region of the receptor, which allows docking of various effectors such as, for example, DOKR (downstream of tyrosine kinase-related protein), GRB2 (growth factor receptor-bound protein 2), the p85 subunit of PI3K or SHP2 (SH2 domain-containing phosphatase) and results in the activation of several signal cascades downstream. Thus, the DOKR signal transduction cascade and various PI3K signal transduction cascades mediate Ang1-induced migration, tube formation and sprouting of endothelial cells, whereas the activated MAPK and PI3K-AKT signal paths have anti-apoptotic action and contribute to the survival of the endothelial cells [Eklund and Olsen, Exp. Cell Res. 312, 630-641 (2006)]. Ang2 was initially identified as Ang1 antagonist [Maisonpierre et al., Science 277, 55-60 (1997)] which inhibits the Ang1-stimulated Tie2 phosphorylation. However, Ang2 is capable in its own right to induce, under certain conditions in the absence of Ang1, Tie2 phosphorylation, and therefore acts like a partial agonist, depending on the experimental conditions.

The significance of the angiopoietin-Tie system for the development and maintenance of the vascular system is confirmed by knock-out and transgenic animal studies. The phenotypes of Tie2-deficient and Ang1-deficient mice are embryonally lethal and in a comparable manner characterized by incompletely formed, partially expanded vessels which lack the branched networks and the peri-endothelial support cells. Analysis of Tie2-deficient murine embryos further showed an important role for Tie2 in haematopoesis and the development of the endocardium. Tie1-deficient murine embryos die of oedema and bleedings which are a consequence of the poor structural state of the endothelial cells of the microvasculature. Ang2-deficient mice are viable and display no serious impairment of embryonal vascular development. There are, however, defects where postnatal vascular restructuring and angiogenesis take place, for example in the retina. In contrast, transgenic overexpression of Ang2 results in an impaired embryonal vessel formation with an embryonally lethal phenotype similar to Tie2- or Ang1-knock-out. The conditional overexpression of Ang2 in endothelial cells leads to complete inhibition of Tie2 phosphorylation in vivo, which supports the view of Ang2 as an Ang1 antagonist. Overexpression of Ang1 reduces the increased vascular permeability caused by inflammatory cytokines and systemic treatment with Ang1 couteracts the vascular permeability caused by VEGF [Augustin et al., Nat. Rev. Mol. Cell. Biol. 10, 165-177 (2009)].

The results of these loss-of-function and gain-of-function studies and of studies of the expression and function of angiopoietins and Tie receptors in the development of the Corpus luteum and the development of blood vessels in the retina indicate a fundamental role of the angiopoietin-Tie receptor system in the mediation of interactions between endothelial cells and surrounding pericytes or smooth muscle cells, which is of significance in particular for the process of angiogenesis consisting of the destabilization of an existing vessel, sprouting and invasion and the stabilization of the new vessels.

According to the hypotheses published in the literature, it is assumed that in resting vessels stabilized by murine cells (pericytes or smooth muscle cells) there is a constitutive Ang1-Tie2 signal transduction for maintaining vascular integrity and endothelial barrier. Ang1 is secreted constitutively by pericytes and activates the Tie2 receptor localized on the endothelial cells. This constitutive activation is controlled dynamically by Tie1 and in particular by autocrine-acting Ang2. Expression of Ang2 in endothelial cells is induced transcriptionally by cytokines, in particular VEGF, and hypoxia and is increased in tissues where angiogenesis and/or restructuring of vessels takes place. Ang2 stored in endothelial Weibel-Palade bodies can be released very rapidly, resulting in the displacement of the Ang1 bound to Tie2 and suppression of the Ang1-mediated signal transduction. This leads to the dissociation of the pericytes from the endothelial cells and reduced endothelial cell-cell contacts and thus to destabilization of the vessels with concomitant degradation of the basal membrane. In the absence of VEGF, this process leads to the apoptosis of the endothelial cells and vascular regression. If VEGF tissue concentrations are sufficiently high, for example as a result of hypoxic induction of the expression in the tumour, the endothelial cells are, depending on their localization in the destabilized vessel, stimulated to proliferate or migrate and in the end to form new vascular sprouts.

Moreover, Tie2 is expressed on a subpopulation of tumor-infiltrated CD11b$^+$ myeloid cells, the Tie2-expressing monocytes (TEMs). The circulating TEMs promote tumour angiogenesis with their pro-angiogenic properties which are enhanced by increased Ang2 [Coffelt et al., *Cancer Res.* 70, 5270-5280 (2010)].

In the pathological processes associated with anomal neovascularization, angiogenic growth factors and the receptors thereof are frequently increasingly expressed. Increased expression of Tie2 receptors was observed, for example, in the endothelium of metastasizing melanomas [Kaipainen et al., *Cancer Res.* 54, 6571-6577 (1994)], in breast cancer [Salven et al., *Br. J. Cancer* 74, 69-72 (1996)], in recurrent papillary thyroid cancer [Hsueh et al., *J. Surg. Oncol.* 103, 395-399 (2011)], in large liver tumours [Dhar et al., *Anticancer Res.* 22, 379-386 (2002)], in endometrial adenocarcinomas [Saito et al., *Pathol. Int.* 57, 140-147 (2007)] and in stomach cancer [Moon et al., *J. Korean Med. Sci.* 21, 272-278 (2006)].

Accordingly, it could be demonstrated that functional impairment of the Tie2 receptor in xenograft models of human Karposi sarkomas and SW1222 intestinal carcinomas by adenoviral administration of single-chain antibody fragments directed against Tie2 resulted in a significant reduction of the vascular density and the tumour growth [Popkov et al., *Cancer Res.* 65, 972-981 (2005)]. Furthermore, soluble angiopoietin-neutralizing Tie2 variants consisting of the Fc-fused extracellular ligand-binding Tie2 domain were used in xenograft tumour models for blocking angiopoietin-Tie2 signal transduction, and an inhibition of the growth and the vascularization of the experimental tumours was shown [Lin et al., *J. Clin. Invest.* 103, 159-165 (1999); Siemeister et al., *Cancer Res.* 59, 3185-3191 (1999)].

In the region of the Tie2 kinase domain, mutations were found that lead to ligand-independent Tie2 activation and are involved in the formation of venous vascular malformations [Wouters et al., *Eur. J. Hum. Genet.* 18, 414-420 (2010)].

Several studies have shown that overexpression of Ang2 and a resulting higher Ang2/Ang1 ratio in the tumour compared to normal tissue correlates with a poor prognosis. This includes various cancer indications, inter alia, for example breast cancer, liver cancer, ovarial carcinoma, metastasizing colon carcinoma, prostate cancer, lung cancer and multiple myeloma [Huang et al., *Nat. Rev. Cancer* 10, 575-585 (2010)].

In preclinical studies with antibodies directed against Ang2, or with peptide fusion proteins ("pepti-bodies"), which neutralize either Ang2 alone or both Ang2 and Ang1, it was possible to inhibit the growth of various experimental xenograft tumours and their vascularization [Oliner et al., *Cancer Cell* 6, 507-516 (2004); Brown et al., *Mol. Cancer. Ther.* 9, 145-156 (2010); Huang et al., *Clin. Cancer Res.* 17, 1001-1011 (2011)]. Furthermore, in several preclinical studies a significant improvement compared to monotherapies was achieved by combining angiopoietin-neutralizing proteins with VEGF signal transduction-blocking therapies or cytotoxic compounds [Brown et al., *Mol. Cancer Ther.* 9, 145-156 (2010); Coxon et al., *Mol. Cancer Ther.* 9, 2641-2651 (2010)].

In summary, in vitro and in vivo studies demonstrate the great significance of the angiopoietin-Tie2 system for tumour angiogenesis and persistent tumour growth and also involvement in lymphangiogenesis, metastasization and inflammatory processes [Huang et al., *Nat. Rev. Cancer* 10, 575-585 (2010)]. As a consequence, the angiopoietin-Tie2 system is increasingly the target of therapeutic strategies. These include, firstly, biological molecules directed against angiopoietins and, secondly, low-molecular-weight compounds inhibiting Tie2 kinase activity. AMG-386 (Amgen) and CVX-060 (Pfizer) are dual peptide fusion proteins which neutralize Ang1 and Ang2 and just Ang2, respectively, and which are in clinical development phase III and II, respectively. The dual Tie2/VEGFR-inhibitor CEP-11981 (Cephalon) is in phase I of clinical development.

Accordingly, it is an object of the present invention to provide novel compounds which inhibit Tie2 receptor kinase activity and can be used in this manner for the treatment and/or prevention of disorders, in particular neoplastic disorders and other angiogenic disorders.

WO 2008/042639-A1 describes N-phenylpyrimidinylpyrazolamines as multikinase inhibitors for the treatment of proliferative disorders. EP 2 327 704-A1 and WO 2010/125799-A1 disclose ureido-substituted fused azole derivatives, amongst others 1-phenyl-2,3-dihydro-1H-imidazo[1,2-b]pyrazoles, as PI3K inhibitors for the treatment of various disorders.

The present invention provides compounds of the general formula (I)

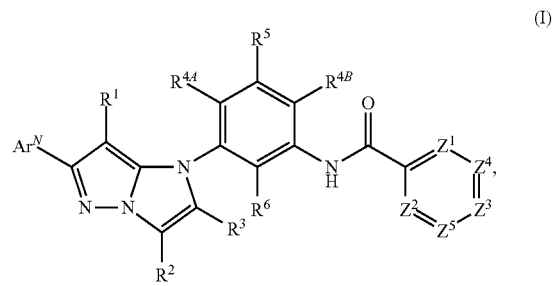

in which

Ar$^N$ represents 5- or 6-membered azaheteroaryl which, as characterizing structural feature, contains a ring nitrogen atom in the 3-position relative to the point of attachment of the heteroaryl ring as component of a C=N— or N=N double bond and which is selected from the group consisting of

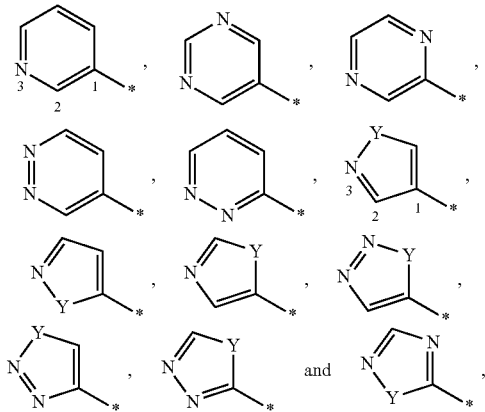

in which * marks the attachment to the imidazopyrazole grouping
and
Y represents O, S or NH, $R^1$ represents hydrogen or fluorine, $R^2$ represents hydrogen or $(C_1-C_4)$-alkyl, $R^3$ represents hydrogen, $R^{4A}$ and $R^{4B}$ independently of one another represent hydrogen, fluorine, chlorine, methyl, fluoromethyl, difluoromethyl, trifluoromethyl, hydroxymethyl, methoxymethyl, ethyl, hydroxy, methoxy or trifluoromethoxy, $R^5$ represents hydrogen, fluorine, chlorine or methyl, $R^6$ represents hydrogen, fluorine, methyl or hydroxy, $Z^1$ represents C—$R^{7A}$ or N, $Z^2$ represents C—$R^{7B}$ or N, $Z^3$ represents C—$R^8$ or N, $Z^4$ represents C—$R^9$ or N and $Z^5$ represents C—$R^{10}$ or N, where in total at most one of the ring members $Z^1$, $Z^2$, $Z^3$, $Z^4$ and $Z^5$ represents N and in which $R^{7A}$ and $R^{7B}$ independently of one another represent hydrogen, fluorine, chlorine, methyl, hydroxy or methoxy, $R^8$ represents hydrogen, fluorine, chlorine or methyl, $R^9$ represents hydrogen, pentafluorosulphanyl, (trifluoromethyl)sulphanyl, trimethylsilyl, $(C_1-C_6)$-alkyl, $(C_1-C_6)$-alkoxy, $(C_3-C_6)$-cycloalkyl, oxetanyl or tetrahydropyranyl, where $(C_1-C_6)$-alkyl and $(C_1-C_6)$-alkoxy may be substituted up to six times by fluorine
and
$(C_3-C_6)$-cycloalkyl, oxetanyl and tetrahydropyranyl may be substituted up to two times by identical or different radicals selected from the group consisting of fluorine, methyl, trifluoromethyl and hydroxy,
and $R^{10}$ represents hydrogen, fluorine, chlorine, bromine, cyano, $(C_1-C_6)$-alkyl, hydroxy, $(C_1-C_6)$-alkoxy, $(C_1-C_4)$-alkylsulphonyl, $(C_3-C_6)$-cycloalkyl, phenyl, 5- or 6-membered heteroaryl or a group of the formula -L$^1$-C(=O)—OR$^{11}$, -L$^1$-NR$^{12A}$R$^{12B}$, -L$^1$C(=O)—NR$^{13A}$R$^{13B}$, -L$^2$-S(=O)$_2$—NR$^{13A}$R$^{13B}$ or -L$^3$-R$^{14}$, where $(C_1-C_6)$-alkyl and $(C_1-C_6)$-alkoxy may be substituted by a radical selected from the group consisting of hydroxy, methoxy, ethoxy, 2-hydroxyethoxy, 2-methoxyethoxy, 2-ethoxyethoxy, amino, methylamino and dimethylamino or up to six times by fluorine
and $(C_3-C_6)$-cycloalkyl may be substituted up to two times by identical or different radicals selected from the group consisting of methyl, hydroxy, methoxy, ethoxy, amino, methylamino and dimethylamino
and phenyl and 5- or 6-membered heteroaryl may be substituted up to two times by identical or different radicals selected from the group consisting of fluorine, chlorine, cyano, methyl and trifluoromethyl, and in which $L^1$ represents a bond or —CH$_2$—, $L^2$ represents a bond or —CH$_2$—, $L^3$ represents a bond or —O—, $R^{11}$ represents hydrogen or $(C_1-C_4)$-alkyl, $R^{12A}$, $R^{12B}$, $R^{13A}$ and $R^{13B}$ independently of one another represent hydrogen or $(C_1-C_4)$-alkyl, where $(C_1-C_4)$-alkyl may in each case be substituted by a radical selected from the group consisting of hydroxy, methoxy, ethoxy, amino, methylamino and dimethylamino, or $R^{12A}$ and $R^{12B}$ and $R^{13A}$ and $R^{13B}$, respectively, are attached to one another and together with the nitrogen atom to which they are respectively attached form a 4- to 6-membered heterocycle which may contain a further ring heteroatom from the group consisting of N, O and S and which may be substituted up to two times by identical or different radicals selected from the group consisting of fluorine, cyano, $(C_1-C_4)$-alkyl, hydroxy, $(C_1-C_4)$-alkoxy and oxo, and $R^{14}$ represents a 4- to 6-membered heterocycle which is attached via a ring carbon atom and contains a ring heteroatom from the group consisting of N, O and S and which may be substituted up to two times by identical or different radicals selected from the group consisting of fluorine, cyano, $(C_1-C_4)$-alkyl, hydroxy, $(C_1-C_4)$-alkoxy and oxo, where $R^{10}$ does not represent hydrogen, fluorine, chlorine or bromine if $Z^4$ represents CH or N, and $Z^5$ does not represent N if $Z^4$ represents CH, and their salts, solvates and solvates of the salts.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as working examples and their salts, solvates and solvates of the salts, where the compounds included in the formula (I) and mentioned in the following are not already salts, solvates and solvates of the salts.

The compounds according to the invention can exist in different stereoisomeric forms depending on their structure, i.e. in the form of configuration isomers or optionally also as conformation isomers (enantiomers and/or diastereomers, including those in the case of atropisomers). The present invention therefore includes the enantiomers and diastereomers and their particular mixtures. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention includes all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by generally used processes known to those skilled in the art, for example by the methods described below and the methods described in the working examples, by using corresponding isotopic modifications of the particular reagents and/or starting compounds therein.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, N,N-diisopropylethylamine, monoethanolamine, diethanolamine, triethanolamine, dimethylaminoethanol, diethylaminoethanol, procaine, dicyclohexylamine, dibenzylamine, N-methylmorpholine, N-methylpiperidine, arginine, lysine and 1,2-ethylenediamine.

Solvates in the context of the invention are described as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The N-oxides of pyridyl rings and tertiary cyclic amine groupings contained in compounds according to the invention are similarly included in the present invention.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

In the context of the present invention, the substituents have the following meaning, unless specified otherwise:

($C_1$-$C_6$)-Alkyl, ($C_1$-$C_4$)-alkyl and ($C_2$-$C_4$)-alkyl in the context of the invention represent a straight-chain or branched alkyl radical having 1 to 6, 1 to 4 and 2 to 4 carbon atoms, respectively. There may be mentioned by way of example and preferably: methyl, ethyl, n-propyl, isopropyl, n-butyl, isobutyl, sec-butyl, tert-butyl, n-pentyl, 2-pentyl, 3-pentyl, neopentyl, n-hexyl, 2-hexyl and 3-hexyl.

($C_1$-$C_4$)-Alkylsulphonyl in the context of the invention represents a straight-chain or branched alkyl radical having 1 to 4 carbon atoms which is attached via a sulphonyl group [—S(=O)$_2$-] to the remainder of the molecule. There may be mentioned by way of example and preferably: methylsulphonyl, ethylsulphonyl, n-propylsulphonyl, isopropylsulphonyl, n-butylsulphonyl and tert-butylsulphonyl.

($C_1$-$C_6$)-Alkoxy, ($C_1$-$C_4$)-alkoxy and ($C_2$-$C_4$)-alkoxy in the context of the invention represent a straight-chain or branched alkoxy radical having 1 to 6, 1 to 4 and 2 to 4 carbon atoms, respectively. There may be mentioned by way of example and preferably: methoxy, ethoxy, n-propoxy, isopropoxy, n-butoxy, isobutoxy, sec-butoxy, tert-butoxy, n-pentoxy, 2-pentoxy, 3-pentoxy, neopentoxy, n-hexoxy, 2-hexoxy and 3-hexoxy.

($C_3$-$C_6$)-Cycloalkyl in the context of the invention represents a monocyclic saturated cycloalkyl group having 3 to 6 ring carbon atoms. There may be mentioned by way of example and preferably: cyclopropyl, cyclobutyl, cyclopentyl and cyclohexyl.

A 4- to 6-membered heterocycle in the context of the invention represents a monocyclic saturated heterocycle having a total of 4 to 6 ring atoms which contains one or two identical or different ring heteroatoms from the group consisting of N, O and S and is attached via a ring carbon atom or a ring nitrogen atom. Preference is given to a 4- to 6-membered heterocycle having one or two ring heteroatoms from the group consisting of N and O. The following may be mentioned by way of example: azetidinyl, oxetanyl, thietanyl, pyrrolidinyl, pyrazolidinyl, tetrahydrofuranyl, thiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl and thiomorpholinyl. Preference is given to azetidinyl, oxetanyl, pyrrolidinyl, tetrahydrofuranyl, piperidinyl, piperazinyl, tetrahydropyranyl and morpholinyl. Particular preference is given to azetidinyl, pyrrolidinyl, piperidinyl, piperazinyl and morpholinyl.

5- or 6-membered Heteroaryl in the definition of the radical $R^{10}$ represents a monocyclic aromatic heterocycle (heteroaromatic) having a total of 5 and 6 ring atoms, respectively, which contains up to three identical or different ring heteroatoms from the group consisting of N, O and S and is attached via a ring carbon atom or a ring nitrogen atom. The following may be mentioned by way of example: furyl, pyrrolyl, thienyl, pyrazolyl, imidazolyl, 1,2-oxazolyl(isoxazolyl), 1,3-oxazolyl, 1,2-thiazolyl(isothiazolyl), 1,3-thiazolyl, 1,2,3-triazolyl, 1,2,4-triazolyl, 1,2,4-oxadiazolyl, 1,3,4-oxadiazolyl, 1,2,4-thiadiazolyl, 1,3,4-thiadiazolyl, pyridyl, pyrimidinyl, pyridazinyl, pyrazinyl, 1,2,4-triazinyl and 1,3,5-triazinyl. Preference is given to 5-membered heteroaryl which contains a ring nitrogen atom ("azaheteroaryl") and may additionally contain a further ring heteroatom from the group consisting of N, O and S, such as pyrrolyl, pyrazolyl, imidazolyl, 1,2-oxazolyl, 1,3-oxazolyl, 1,2-thiazolyl and 1,3-thiazolyl.

An oxo substituent in the context of the invention represents an oxygen atom, which is bonded to a carbon atom or a sulphur atom via a double bond.

In the context of the present invention, all radicals which occur more than once are defined independently of one another. If radicals in the compounds according to the invention are substituted, the radicals may be mono- or polysubstituted, unless specified otherwise. Substitution by one, two or three identical or different substituents is preferred. Particular preference is given to substitution by one or two identical or different substituents. Very particular preference is given to substitution by one substituent.

A certain embodiment of the present invention comprises compounds of the formula (I) in which $Ar^N$ represents 5- or 6-membered azaheteroaryl which, as characterizing structural feature, contains a ring nitrogen atom in the 3-position relative to the point of attachment of the heteroaryl ring as component of a C=N— or N=N double bond and which is selected from the group consisting of

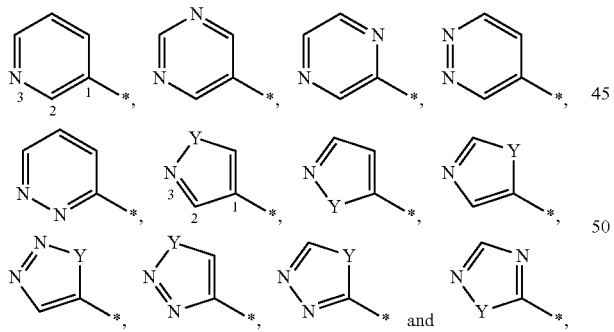

in which * marks the attachment to the imidazopyrazole grouping
and
Y represents O, S or NH,
$R^1$ represents hydrogen or fluorine,
$R^2$ represents hydrogen or $(C_1-C_4)$-alkyl,
$R^3$ represents hydrogen,
$R^{4A}$ and $R^{4B}$ independently of one another represent hydrogen, fluorine, chlorine, methyl, fluoromethyl, difluoromethyl, trifluoromethyl, hydroxymethyl, methoxymethyl, ethyl, hydroxy, methoxy or trifluoromethoxy,
$R^5$ represents hydrogen, fluorine, chlorine or methyl,
$R^6$ represents hydrogen, fluorine, methyl or hydroxy,
$Z^1$ represents C—$R^{7A}$ or N,
$Z^2$ represents C—$R^{7B}$ or N,
$Z^3$ represents C—$R^8$ or N,
$Z^4$ represents C—$R^9$ or N
and
$Z^5$ represents C—$R^{10}$ or N,
where in total at most one of the ring members $Z^1$, $Z^2$, $Z^3$, $Z^4$ and $Z^5$ represents N
and in which
$R^{7A}$ and $R^{7B}$ independently of one another represent hydrogen, fluorine, chlorine, methyl, hydroxy or methoxy,
$R^8$ represents hydrogen, fluorine, chlorine or methyl,
$R^9$ represents hydrogen, pentafluorosulphanyl, (trifluoromethyl)sulphanyl, trimethylsilyl, $(C_1-C_6)$-alkyl, $(C_1-C_6)$-alkoxy, $(C_3-C_6)$-cycloalkyl, oxetanyl or tetrahydropyranyl,
where $(C_1-C_6)$-alkyl and $(C_1-C_6)$-alkoxy may be substituted up to three times by fluorine
and
$(C_3-C_6)$-cycloalkyl, oxetanyl and tetrahydropyranyl may be substituted up to two times by identical or different radicals selected from the group consisting of fluorine, methyl, trifluoromethyl and hydroxy,
and
$R^{10}$ represents hydrogen, fluorine, chlorine, bromine, cyano, $(C_1-C_6)$-alkyl, hydroxy, $(C_1-C_6)$-alkoxy, $(C_1-C_4)$-alkylsulphonyl, $(C_3-C_6)$-cycloalkyl, phenyl, 5- or 6-membered heteroaryl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$,
where $(C_1-C_6)$-alkyl and $(C_1-C_6)$-alkoxy may be substituted by a radical selected from the group consisting of hydroxy, methoxy, ethoxy, 2-hydroxyethoxy, 2-methoxyethoxy, 2-ethoxyethoxy, amino, methylamino and dimethylamino or up to three times by fluorine
and
$(C_3-C_6)$-cycloalkyl may be substituted up to two times by identical or different radicals selected from the group consisting of methyl, hydroxy, methoxy, ethoxy, amino, methylamino and dimethylamino
and
phenyl and 5- or 6-membered heteroaryl may be substituted up to two times by identical or different radicals selected from the group consisting of fluorine, chlorine, cyano and methyl,
and in which
$L^1$ represents a bond or —$CH_2$—,
$L^2$ represents a bond or —$CH_2$—,
$L^3$ represents a bond or —O—,
$R^{11}$ represents hydrogen or $(C_1-C_4)$-alkyl,
$R^{12A}$, $R^{12B}$, $R^{13A}$ and $R^{13B}$ independently of one another represent hydrogen or $(C_1-C_4)$-alkyl,
where $(C_1-C_4)$-alkyl may in each case be substituted by a radical selected from the group consisting of hydroxy, methoxy, ethoxy, amino, methylamino and dimethylamino,
or
$R^{12A}$ and $R^{12B}$ and $R^{13A}$ and $R^{13B}$, respectively, are attached to one another and together with the nitrogen atom to which they are respectively attached form a 4- to 6-membered heterocycle which may contain a further ring heteroatom from the group consisting of N, O and S and which may be substituted up to two times by identical or different radicals selected from the group consisting of methyl, hydroxy and oxo,
and
$R^{14}$ represents a 4- to 6-membered heterocycle which is attached via a ring carbon atom and contains a ring heteroatom from the group consisting of N, O and S and which may be substituted up to two times by identical or different radicals selected from the group consisting of methyl, hydroxy and oxo,
where $R^{10}$ does not represent hydrogen, fluorine, chlorine or bromine if $Z^4$ represents CH or N, and $Z^5$ does not represent N if $Z^4$ represents CH,
and their salts, solvates and solvates of the salts.

Preference in the context of the present invention is given to compounds of the formula (I) in which
$Ar^N$ represents 5- or 6-membered azaheteroaryl selected from the group consisting of

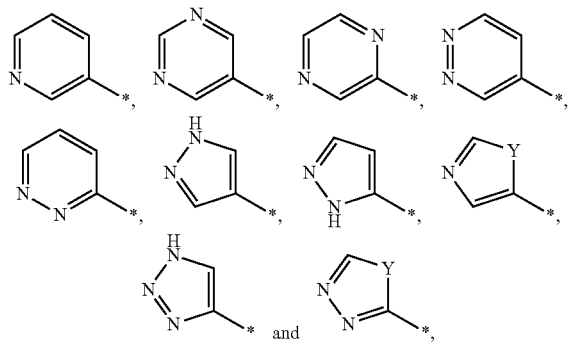

in which * marks the attachment to the imidazopyrazole grouping
and
Y represents S or NH,
$R^1$ represents hydrogen or fluorine,
$R^2$ represents hydrogen or $(C_1-C_4)$-alkyl,
$R^3$ represents hydrogen,
$R^{4A}$ and $R^{4B}$ independently of one another represent hydrogen, fluorine, chlorine, methyl, fluoromethyl, difluoromethyl, trifluoromethyl, ethyl or methoxy,
$R^5$ represents hydrogen, fluorine, chlorine or methyl,
$R^6$ represents hydrogen, fluorine, methyl or hydroxy,
$Z^1$ represents C—$R^{7A}$ or N,
$Z^2$ represents C—$R^{7B}$ or N,
$Z^3$ represents C—$R^8$ or N,
$Z^4$ represents C—$R^9$
and
$Z^5$ represents C—$R^{10}$ or N,
where in total at most one of the ring members $Z^1$, $Z^2$, $Z^3$ and $Z^5$ represents N
and in which
$R^{7A}$ and $R^{7B}$ independently of one another represent hydrogen or fluorine,
$R^8$ represents hydrogen or fluorine,
$R^9$ represents hydrogen, pentafluorosulphanyl, (trifluoromethyl)sulphanyl, $(C_1-C_4)$-alkyl, $(C_1-C_4)$-alkoxy, cyclopropyl, cyclobutyl or oxetanyl,
where $(C_1-C_4)$-alkyl and $(C_1-C_4)$-alkoxy may be substituted up to six times by fluorine
and
cyclopropyl, cyclobutyl and oxetanyl may be substituted up to two times by identical or different radicals selected from the group consisting of fluorine, methyl, trifluoromethyl and hydroxy,
and
$R^{10}$ represents hydrogen, fluorine, chlorine, bromine, cyano, $(C_1-C_4)$-alkyl, hydroxy, $(C_1-C_4)$-alkoxy, $(C_1-C_4)$-alkylsulphonyl, 5-membered azaheteroaryl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$,
where $(C_1-C_4)$-alkyl and $(C_1-C_4)$-alkoxy may be substituted by a radical selected from the group consisting of hydroxy, methoxy, ethoxy and amino or up to three times by fluorine and
5-membered azaheteroaryl may be substituted up to two times by methyl,
and in which
$L^1$ represents a bond or —$CH_2$—,
$L^2$ represents a bond,
$L^3$ represents a bond or —O—,
$R^{11}$ represents hydrogen or $(C_1-C_4)$-alkyl,
$R^{12A}$, $R^{12B}$, $R^{13A}$ and $R^{13B}$ independently of one another represent hydrogen or $(C_1-C_4)$-alkyl
or
$R^{12A}$ and $R^{12B}$ and $R^{13A}$ and $R^{13B}$, respectively, are attached to one another and together with the nitrogen atom to which they are respectively attached form a 4- to 6-membered heterocycle which may contain a further ring heteroatom from the group consisting of N and O and which may be substituted up to two times by identical or different radicals selected from the group consisting of fluorine, cyano, methyl, ethyl, hydroxy, methoxy and ethoxy,
and
$R^{14}$ represents a 4- to 6-membered heterocycle which is attached via a ring carbon atom and contains a ring heteroatom from the group consisting of N and O and which may be substituted up to two times by identical or different radicals selected from the group consisting of fluorine, cyano, methyl, ethyl, hydroxy, methoxy and ethoxy,
where $R^{10}$ does not represent hydrogen, fluorine, chlorine or bromine if $Z^4$ represents CH, and $Z^5$ does not represent N if $Z^4$ represents CH,
and their salts, solvates and solvates of the salts.

A further preferred embodiment of the present invention comprises compounds of the formula (I) in which
$Ar^N$ represents 5- or 6-membered azaheteroaryl selected from the group consisting of

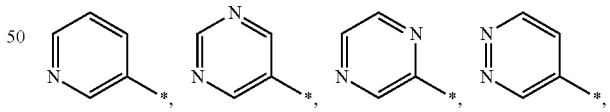

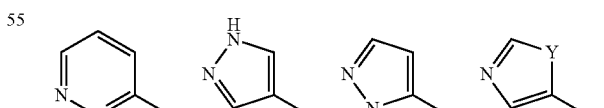

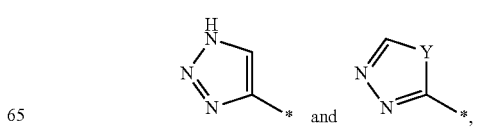

in which * marks the attachment to the imidazopyrazole grouping
and
Y represents S or NH,
$R^1$ represents hydrogen or fluorine,
$R^2$ represents hydrogen or $(C_1-C_4)$-alkyl,
$R^3$ represents hydrogen,
$R^{4A}$ and $R^{4B}$ independently of one another represent hydrogen, fluorine, chlorine, methyl, fluoromethyl, difluoromethyl, trifluoromethyl, ethyl or methoxy,
$R^5$ represents hydrogen, fluorine, chlorine or methyl,
$R^6$ represents hydrogen, fluorine, methyl or hydroxy,
$Z^1$ represents C—$R^{7A}$ or N,
$Z^2$ represents C—$R^{7B}$ or N,
$Z^3$ represents C—$R^8$ or N,
$Z^4$ represents C—$R^9$
and
$Z^5$ represents C—$R^{10}$ or N,
where in total at most one of the ring members $Z^1$, $Z^2$, $Z^3$ and $Z^5$ represents N and in which
$R^{7A}$ and $R^{7B}$ independently of one another represent hydrogen or fluorine,
$R^8$ represents hydrogen or fluorine,
$R^9$ represents hydrogen, pentafluorosulphanyl, (trifluoromethyl)sulphanyl, $(C_1-C_4)$-alkyl, $(C_1-C_4)$-alkoxy, cyclopropyl, cyclobutyl or oxetanyl,
where $(C_1-C_4)$-alkyl and $(C_1-C_4)$-alkoxy may be substituted up to three times by fluorine
and
cyclopropyl, cyclobutyl and oxetanyl may be substituted up to two times by identical or different radicals selected from the group consisting of fluorine, methyl, trifluoromethyl and hydroxy,
and
$R^{10}$ represents hydrogen, fluorine, chlorine, bromine, cyano, $(C_1-C_4)$-alkyl, hydroxy, $(C_1-C_4)$-alkoxy, $(C_1-C_4)$-alkylsulphonyl, 5-membered azaheteroaryl or a group of the formula $-L^1-C(=O)-OR^{11}$, $-L^1-NR^{12A}R^{12B}$, $-L^1-C(=O)-NR^{13A}R^{13B}$, $-L^2-S(=O)_2-NR^{13A}R^{13B}$ or $-L^3-R^{14}$,
where $(C_1-C_4)$-alkyl and $(C_1-C_4)$-alkoxy may be substituted by a radical selected from the group consisting of hydroxy, methoxy, ethoxy and amino or up to three times by fluorine
and
5-membered azaheteroaryl may be substituted up to two times by methyl,
and in which
$L^1$ represents a bond or —$CH_2$—,
$L^2$ represents a bond,
$L^3$ represents a bond or —O—,
$R^{11}$ represents hydrogen or $(C_1-C_4)$-alkyl,
$R^{12A}$, $R^{12B}$, $R^{13A}$ and $R^{13B}$ independently of one another represent hydrogen or $(C_1-C_4)$-alkyl
or
$R^{12A}$ and $R^{12B}$ and $R^{13A}$ and $R^{13B}$, respectively, are attached to one another and together with the nitrogen atom to which they are respectively attached form a 4- to 6-membered heterocycle which may contain a further ring heteroatom from the group consisting of N and O and which may be substituted by methyl or hydroxy,
and
$R^{14}$ represents a 4- to 6-membered heterocycle which is attached via a ring carbon atom and contains a ring heteroatom from the group consisting of N and O and which may be substituted by methyl or hydroxy, where $R^{10}$ does not represent hydrogen, fluorine, chlorine or bromine if $Z^4$ represents CH, and $Z^5$ does not represent N if $Z^4$ represents CH,
and their salts, solvates and solvates of the salts.

A particular embodiment of the present invention relates to compounds of the formula (I) in which
$R^1$ represents hydrogen or fluorine,
$R^2$ represents hydrogen or methyl,
and
$R^3$ represents hydrogen,
and their salts, solvates and solvates of the salts.

A further particular embodiment of the present invention relates to compounds of the formula (I) in which
$R^{4A}$ represents fluorine, chlorine, methyl or trifluoromethyl,
and their salts, solvates and solvates of the salts.

A further particular embodiment of the present invention relates to compounds of the formula (I) in which
$R^{4B}$ represents hydrogen, fluorine, chlorine or methyl,
and their salts, solvates and solvates of the salts.

A further particular embodiment of the present invention relates to compounds of the formula (I) in which
$R^5$ and $R^6$ each represent hydrogen,
and their salts, solvates and solvates of the salts.

A further particular embodiment of the present invention relates to compounds of the formula (I) in which
$Z^1$ and $Z^2$ each represent CH,
and their salts, solvates and solvates of the salts.

A further particular embodiment of the present invention relates to compounds of the formula (I) in which
$Z^3$ represents CH or N,
and their salts, solvates and solvates of the salts.

A further particular embodiment of the present invention relates to compounds of the formula (I) in which
$Z^4$ represents C—$R^9$, in which
$R^9$ represents pentafluorosulphanyl, (trifluoromethyl)sulphanyl, trimethylsilyl, $(C_1-C_4)$-alkyl, $(C_1-C_4)$-alkoxy, cyclopropyl, cyclobutyl or oxetanyl,
where $(C_1-C_4)$-alkyl and $(C_1-C_4)$-alkoxy may be substituted up to six times by fluorine
and
cyclopropyl, cyclobutyl and oxetanyl may be substituted up to two times by identical or different radicals selected from the group consisting of fluorine, methyl, trifluoromethyl and hydroxy,
and their salts, solvates and solvates of the salts.

Particular preference in the context of the present invention is given to compounds of the formula (I) in which
$Ar^N$ represents 5- or 6-membered azaheteroaryl of the formula in which * marks the attachment to the imidazopyrazole grouping
and
Y represents S or NH,
$R^1$ represents hydrogen or fluorine,
$R^2$ represents hydrogen or methyl, $R^3$ represents hydrogen,
$R^{4A}$ represents chlorine, methyl or trifluoromethyl,
$R^{4B}$ represents hydrogen, fluorine, chlorine or methyl,
$R^5$ represents hydrogen, fluorine, chlorine or methyl,
$R^6$ represents hydrogen, fluorine, methyl or hydroxy,
$Z^1$ represents CH,
$Z^2$ represents CH,
$Z^3$ represents CH or N,
$Z^4$ represents C—$R^9$, in which
  $R^9$ represents pentafluorosulphanyl, (trifluoromethyl)sulphanyl, trifluoromethyl, trifluoromethoxy, ($C_2$-$C_4$)-alkyl, ($C_2$-$C_4$)-alkoxy, cyclopropyl, cyclobutyl or oxetan-3-yl,
    where ($C_2$-$C_4$)-alkyl and ($C_2$-$C_4$)-alkoxy may be substituted up to five times by fluorine
    and
    cyclopropyl, cyclobutyl and oxetan-3-yl may be substituted by a radical selected from the group consisting of fluorine, methyl, trifluoromethyl and hydroxy,
and
$Z^5$ represents C—$R^{10}$, in which
  $R^{10}$ represents hydrogen, fluorine, chlorine, bromine, cyano, ($C_1$-$C_4$)-alkyl, hydroxy, ($C_1$-$C_4$)-alkoxy, methylsulphonyl, 1H-imidazol-1-yl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$,
    where ($C_1$-$C_4$)-alkyl and ($C_1$-$C_4$)-alkoxy may be substituted by a radical selected from the group consisting of hydroxy, methoxy, ethoxy and amino or up to three times by fluorine
    and
    1H-imidazol-1-yl may be substituted up to two times by methyl,
    and in which
    $L^1$ represents a bond or —$CH_2$—,
    $L^2$ represents a bond,
    $L^3$ represents a bond or —O—,
    $R^{11}$ represents hydrogen or ($C_1$-$C_4$)-alkyl,
    $R^{12A}$ and $R^{12B}$ independently of one another represent hydrogen or ($C_1$-$C_4$)-alkyl
    or
    $R^{12A}$ and $R^{12B}$ are attached to one another and together with the nitrogen atom to which they are attached form a 4- to 6-membered heterocycle which may contain a further ring heteroatom from the group consisting of N and O and which may be substituted by a radical selected from the group consisting of cyano, methyl, hydroxy and methoxy or up to two times with fluorine,
    $R^{13A}$ and $R^{13B}$ independently of one another represent hydrogen or ($C_1$-$C_4$)-alkyl,
    and
    $R^{14}$ represents a 4- to 6-membered heterocycle which is attached via a ring carbon atom and, as ring heteroatom, contains a nitrogen atom and which may be substituted by a radical selected from the group consisting of cyano, methyl, hydroxy and methoxy or up to two times with fluorine,
and their salts, solvates and solvates of the salts.

A further particularly preferred embodiment of the present invention relates to compounds of the formula (I) in which
$Ar^N$ represents 5- or 6-membered azaheteroaryl of the formula

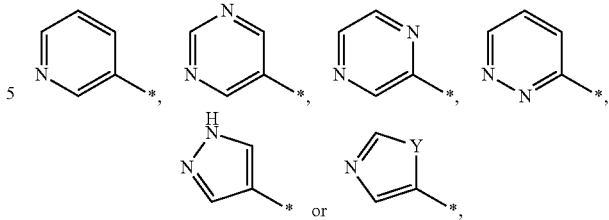

in which * marks the attachment to the imidazopyrazole grouping
and
Y represents S or NH,
$R^1$ represents hydrogen,
$R^2$ represents hydrogen or methyl,
$R^3$ represents hydrogen,
$R^{4A}$ represents chlorine, methyl or trifluoromethyl,
$R^{4B}$ represents hydrogen, fluorine, chlorine or methyl,
$R^5$ represents hydrogen, fluorine, chlorine or methyl,
$R^6$ represents hydrogen, fluorine, methyl or hydroxy,
$Z^1$ represents CH,
$Z^2$ represents CH,
$Z^3$ represents CH or N,
$Z^4$ represents C—$R^9$, in which
  $R^9$ represents pentafluorosulphanyl, trifluoromethyl, trifluoromethoxy, ($C_2$-$C_4$)-alkyl, ($C_2$-$C_4$)-alkoxy, cyclopropyl, cyclobutyl or oxetan-3-yl,
    where ($C_2$-$C_4$)-alkyl and ($C_2$-$C_4$)-alkoxy may be substituted up to three times by fluorine
    and
    cyclopropyl, cyclobutyl and oxetan-3-yl may be substituted by a radical selected from the group consisting of fluorine, methyl, trifluoromethyl and hydroxy,
and
$Z^5$ represents C—$R^{10}$, in which
  $R^{10}$ represents hydrogen, fluorine, chlorine, bromine, cyano, ($C_1$-$C_4$)-alkyl, hydroxy, ($C_1$-$C_4$)-alkoxy, methylsulphonyl, 1H-imidazol-1-yl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$,
    where ($C_1$-$C_4$)-alkyl and ($C_1$-$C_4$)-alkoxy may be substituted by a radical selected from the group consisting of hydroxy, methoxy, ethoxy and amino or up to three times by fluorine
    and
    1H-imidazol-1-yl may be substituted up to two times by methyl,
    and in which
    $L^1$ represents a bond or —$CH_2$—,
    $L^2$ represents a bond,
    $L^3$ represents a bond or —O—,
    $R^{11}$ represents hydrogen or ($C_1$-$C_4$)-alkyl,
    $R^{12A}$ and $R^{12B}$ independently of one another represent hydrogen or ($C_1$-$C_4$)-alkyl
    or
    $R^{12A}$ and $R^{12B}$ are attached to one another and together with the nitrogen atom to which they are attached form a 4- to 6-membered heterocycle which may contain a further ring heteroatom from the group consisting of N and O and which may be substituted by methyl or hydroxy, $R^{13A}$ and $R^{13B}$ independently of one another represent hydrogen or $(C_1-C_4)$-alkyl, and $R^{14}$ represents a 4- to 6-membered heterocycle which is attached via a ring carbon atom and, as ring heteroatom, contains a nitrogen atom and which may be substituted by methyl or hydroxy, and their salts, solvates and solvates of the salts.

Very particular preference in the context of the present invention is given to compounds of the formula (I) in which $Ar^N$ represents 5- or 6-membered azaheteroaryl of the formula

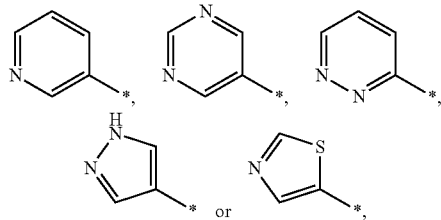

in which * marks the attachment to the imidazopyrazole grouping, $R^1$ represents hydrogen,
$R^2$ represents hydrogen or methyl,
$R^3$ represents hydrogen,
$R^{4A}$ represents chlorine or methyl,
$R^{4B}$ represents hydrogen, fluorine, chlorine or methyl,
$R^5$ represents hydrogen,
$R^6$ represents hydrogen,
$Z^1$ represents CH,
$Z^2$ represents CH,
$Z^3$ represents CH or N,
$Z^4$ represents C—$R^9$, in which
  $R^9$ represents pentafluorosulphanyl, (trifluoromethyl)sulphanyl, trifluoromethyl, 2-fluoropropan-2-yl, tert-butyl, 1,1,1-trifluoro-2-methylpropan-2-yl, trifluoromethoxy, 1,1,2,2-tetrafluoroethoxy or 3-methyloxetan-3-yl, and $Z^5$ represents C—$R^{10}$, in which
  $R^{10}$ represents hydrogen, fluorine, chlorine, cyano, hydroxy, $(C_1-C_4)$-alkoxy, methylsulphonyl, 2-methyl-1H-imidazol-1-yl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$,
  where $(C_1-C_4)$-alkyl and $(C_1-C_4)$-alkoxy may be substituted by a radical selected from the group consisting of hydroxy, methoxy, ethoxy and amino or up to three times by fluorine,
  and in which
  $L^1$ represents a bond or —$CH_2$—,
  $L^2$ represents a bond,
  $L^3$ represents a bond or —O—,
  $R^{11}$ represents hydrogen,
  $R^{12A}$ and $R^{12B}$ independently of one another represent hydrogen or methyl
  or
  $R^{12A}$ and $R^{12B}$ are attached to one another and together with the nitrogen atom to which they are attached form an azetidin-1-yl, pyrrolidin-1-yl- or piperidin-1-yl ring, each of which may be substituted by a radical selected from the group consisting of cyano, hydroxy and methoxy, or a piperazin-1-yl, 4-methylpiperazin-1-yl or morpholin-4-yl ring, $R^{13A}$ and $R^{13B}$ independently of one another represent hydrogen or methyl, and $R^{14}$ represents an azetidin-3-yl, pyrrolidin-3-yl, piperidin-3-yl or piperidin-4-yl ring, each of which may be substituted by hydroxy, and their salts, solvates and solvates of the salts.

A further very particularly preferred embodiment of the present invention relates to compounds of the formula (I) in which $Ar^N$ represents 5- or 6-membered azaheteroaryl of the formula

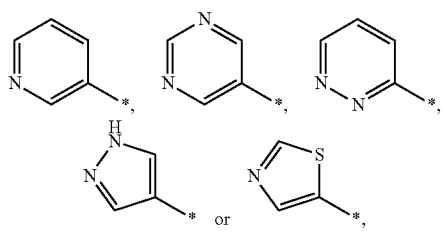

in which * marks the attachment to the imidazopyrazole grouping $R^1$ represents hydrogen,
$R^2$ represents hydrogen or methyl,
$R^3$ represents hydrogen,
$R^{4A}$ represents chlorine or methyl,
$R^{4B}$ represents hydrogen, fluorine, chlorine or methyl,
$R^5$ represents hydrogen,
$R^6$ represents hydrogen,
$Z^1$ represents CH,
$Z^2$ represents CH,
$Z^3$ represents CH or N,
$Z^4$ represents C—$R^9$, in which
  $R^9$ represents pentafluorosulphanyl, trifluoromethyl, tert-butyl or trifluoromethoxy, and $Z^5$ represents C—$R^{10}$, in which
  $R^{10}$ represents fluorine, chlorine, cyano, hydroxy, $(C_1-C_4)$-alkoxy, methylsulphonyl, 2-methyl-1H-imidazol-1-yl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$,
  where $(C_1-C_4)$-alkyl and $(C_1-C_4)$-alkoxy may be substituted by a radical selected from the group consisting of hydroxy, methoxy, ethoxy and amino or up to three times by fluorine,
  and in which
  $L^1$ represents a bond or —$CH_2$—,
  $L^2$ represents a bond,
  $L^3$ represents a bond or —O—,
  $R^{11}$ represents hydrogen,
  $R^{12A}$ and $R^{12B}$ independently of one another represent hydrogen or methyl
  or
  $R^{12A}$ and $R^{12B}$ are attached to one another and together with the nitrogen atom to which they are attached form an azetidin-1-yl, pyrrolidin-1-yl- or piperidin-1-yl ring, each of which may be substituted by hydroxy, or a piperazin-1-yl, 4-methylpiperazin-1-yl or morpholin-4-yl ring, $R^{13A}$ and $R^{13B}$ independently of one another represent hydrogen or methyl, and $R^{14}$ represents an azetidin-3-yl, pyrrolidin-3-yl, piperidin-3-yl or piperidin-4-yl ring, each of which may be substituted by hydroxy, and their salts, solvates and solvates of the salts.

The definitions of radicals indicated specifically in the respective combinations or preferred combinations of radicals are replaced as desired irrespective of the particular combinations indicated for the radicals also by definitions of radicals of other combinations. Combinations of two or more of the abovementioned preferred ranges are very particularly preferred.

The present invention furthermore provides a process for preparing the compounds of the formula (I) according to the invention, characterized in that either

[A] an aniline derivative of the formula (II)

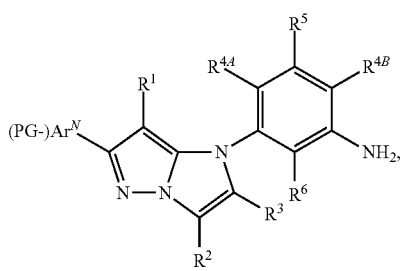

(II)

in which $Ar^N$, $R^1$, $R^2$, $R^3$, $R^{4A}$, $R^{4B}$, $R^5$ and $R^6$ have the meanings given above and (PG-) represents an optional nitrogen protective group in the case that Y in $Ar^N$ represents NH, is coupled in an inert solvent in the presence of a condensing agent with a carboxylic acid of the formula (III)

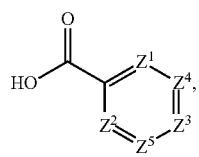

(III)

in which $Z^1$, $Z^2$, $Z^3$, $Z^4$ and $Z^5$ have the meanings given above, to give the carboxamide of the formula (IV)

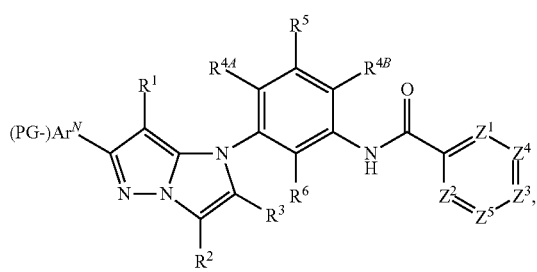

(IV)

in which $Ar^N$, (PG-), $R^1$, $R^2$, $R^3$, $R^{4A}$, $R^{4B}$, $R^5$, $R^6$, $Z^1$, $Z^2$, $Z^3$, $Z^4$ and $Z^5$ have the meanings given above, and the protective group PG, if present, is then removed, or

[B] a 1H-imidazo[1,2-b]pyrazole derivative of the formula (V)

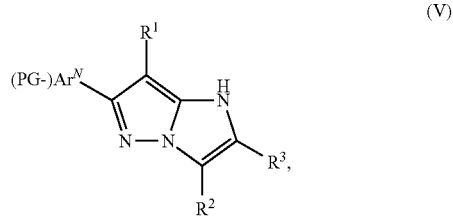

(V)

in which $Ar^N$, $R^1$, $R^2$ and $R^3$ have the meanings given above and (PG-) represents an optional nitrogen protective group in the case that Y in $Ar^N$ represents NH, is coupled in an inert solvent with copper(I) catalysis with a phenyl bromide of the formula (VI)

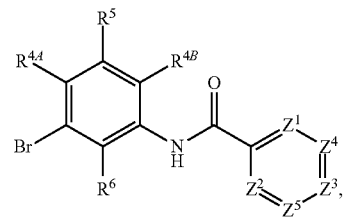

(VI)

in which $R^{4A}$, $R^{4B}$, $R^5$, $R^6$, $Z^1$, $Z^2$, $Z^3$, $Z^4$ and $Z^5$ have the meanings given above, to give the 1-phenyl-1H-imidazo[1,2-b]pyrazole derivative of the formula (IV)

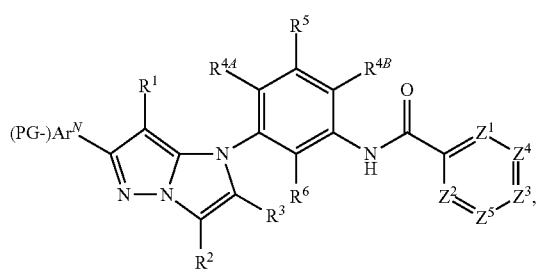

(IV)

in which $Ar^N$, (PG-), $R^1$, $R^2$, $R^3$, $R^{4A}$, $R^{4B}$, $R^5$, $R^6$, $Z^1$, $Z^2$, $Z^3$, $Z^4$ and $Z^5$ have the meanings given above, and the protective group PG, if present, is then removed,
or

[C] an aminopyrazole derivative of the formula (VII)

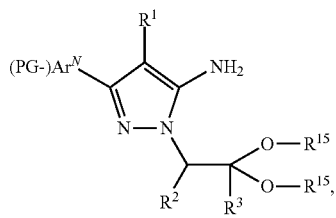

(VII)

in which $Ar^N$, $R^1$, $R^2$ and $R^3$ have the meanings given above, $R^{15}$ represents methyl or ethyl, and (PG-) represents an optional nitrogen protective group in the case that Y in $Ar^N$ represents NH, is coupled in an inert solvent under palladium catalysis with a phenyl bromide of the formula (VI)

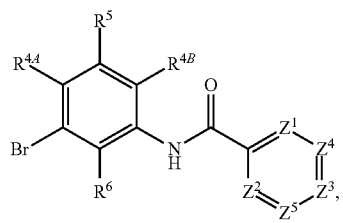

(VI)

in which $R^{4A}$, $R^{4B}$, $R^5$, $R^6$, $Z^1$, $Z^2$, $Z^3$, $Z^4$ and $Z^5$ have the meanings given above, to give a compound of the formula (VIII)

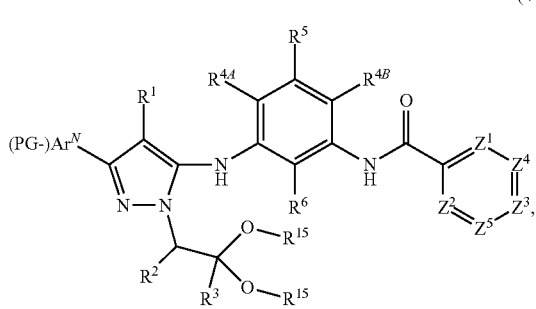

(VIII)

in which $Ar^N$, (PG-), $R^1$, $R^2$, $R^3$, $R^{4A}$, $R^{4B}$, $R^5$, $R^6$, $R^{15}$, $Z^1$, $Z^2$, $Z^3$, $Z^4$ and $Z^5$ have the meanings given above, the compound of the formula (VIII) is then cyclized by treatment with acid to give the 1-phenyl-1H-imidazo[1,2-b]pyrazole derivative of the formula (IV)

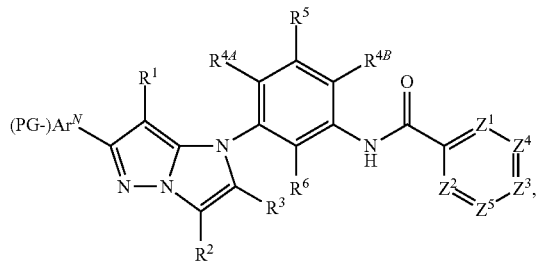

(IV)

in which $Ar^N$, (PG-), $R^1$, $R^2$, $R^3$, $R^{4A}$, $R^{4B}$, $R^5$, $R^6$, $Z^1$, $Z^2$, $Z^3$, $Z^4$ and $Z^5$ have the meanings given above, and the protective group PG, if present, is then removed, and the compounds of the formula (I) obtained in this manner are optionally converted with the appropriate (i) solvents and/or (ii) acids or bases into their solvates, salts and/or solvates of the salts.

In the case that group $Ar^N$ in formula (I) represents 5-membered azaheteroaryl of the structures shown above and ring member Y in this structure represents NH, it may be expedient or required in the above-described process steps to block this ring nitrogen atom temporarily with a protective group PG. Suitable for this purpose are known amino protective groups such as, in particular, benzyl, 4-methoxybenzyl, 2,4-dimethoxybenzyl or tetrahydro-2H-pyran-2-yl (THP). Introduction and removal of such protective groups are carried out by generally customary methods [see, for example, T. W. Greene and P. G. M. Wuts, *Protective Groups in Organic Synthesis*, Wiley, New York, 1999]. Preference is given to using the 4-methoxybenzyl group. The removal of this protective group in process step (IV)→(I) is preferably carried out with the aid of a strong anhydrous acid such as trifluoroacetic acid, hydrogen chloride or hydrogen bromide, if appropriate with addition of an inert solvent such as dichloromethane, 1,4-dioxane or glacial acetic acid.

Inert solvent for process step [A] (II)+(III)→(IV) [amide coupling] are, for example, ethers such as diethyl ether, diisopropyl ether, tert-butyl methyl ether, tetrahydrofuran, 1,4-dioxane, 1,2-dimethoxyethane or bis(2-methoxyethyl)ether, hydrocarbons such as benzene, toluene, xylene, hexane, cyclohexane or mineral oil fractions, halogenated hydrocarbons such as dichloromethane, trichloromethane, carbon tetrachloride, 1,2-dichlorothane, trichloroethylene or chlorobenzene, or dipolar aprotic solvents such as acetone, acetonitrile, ethyl acetate, pyridine, dimethyl sulphoxide (DMSO), N,N-dimethylformamide (DMF), N,N-dimethylacetamide (DMA), N,N'-dimethylpro-pyleneurea (DMPU) or N-methylpyrrolidinone (NMP). It is also possible to employ mixtures of such solvents. Preference is given to using dichloromethane, tetrahydrofuran, dimethylformamide or mixtures thereof.

Suitable condensing agents for these coupling reactions are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulphate or 2-tert-butyl 5-methylisoxazolium perchlorate, acyl-amino compounds such as 2-ethoxy-1-ethoxy-carbonyl-1,2-dihydroquinoline, α-chloroenamines such as 1-chloro-2-methyl-1-dimethylamino-1-propene, phosphorus compounds such as propane-phosphonic anhydride, diethyl cyanophosphonate, bis(2-oxo-3-oxazolidinyl)phosphoryl chloride, benzotriazol-1-yloxy-tris(dimethylamino)phosphonium hexafluorophosphate (BOP) or benzotriazol-1-yloxy-tris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N'N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with an activated ester component such as 1-hydroxybenzotriazole (HOBt), N-hydroxysuccinimide (HOSu), 4-nitrophenol or pentafluorophenol, and as base an alkali metal carbonate, for example sodium carbonate or potassium carbonate, or a tertiary amine base such as triethylamine, N-methylmorpholine, N-methylpiperidine, N,N-diisopropylethylamine, pyridine or 4-N,N-dimethylaminopyridine. Preference is given to using O-(7-azabenzotriazol-1-yl)-N,N,N',N'-tetramethyluronium hexafluorophosphate (HATU) or O-(benzotriazol-1-yl)-N,N,N',N'-tetramethyluronium tetrafluoroborate (TBTU) in combination with N-methylmorpholine or N,N-diisopropylethylamine as base.

The reaction [A] (II)+(III)→(IV) is generally carried out in a temperature range of from −20° C. to +60° C., preferably at from 0° C. to +40° C. The reaction can be carried out at atmospheric, at elevated or at reduced pressure (for example from 0.5 to 5 bar); in general, the reaction is carried out at atmospheric pressure.

The coupling reaction [B] (V)+(VI)→(IV) is carried out with the aid of a copper(I) catalyst such as copper(I) oxide, copper(I) bromide or copper(I) iodide, in the presence of a copper ligand such as 8-hydroxyquinoline or 1,10-phenanthroline, and an inorganic or organic carbonate base such as potassium carbonate, caesium carbonate or bis(tetraethylammonium) carbonate. Suitable inert solvents for this reaction are in particular toluene, xylene, 1,4-dioxane, acetonitrile, dimethyl sulphoxide (DMSO), N,N-dimethylformamide (DMF) or mixtures thereof, if appropriate with addition of water. Preference is given to using a system consisting of copper(I) iodide, 8-hydroxyquinoline and bis(tetraethylammonium) carbonate in dimethylformamide with about 10% water added [cf. L. Liu et al., J. Org. Chem. 70 (24), 10135-10138 (2005) and further literature cited therein]. The reaction is generally carried out in a temperature range of from +100° C. to +200° C., advantageously using a microwave oven.

Suitable palladium catalysts for the coupling reaction [C] (VII)+(VI)→(VIII) are, for example, palladium(II) acetate, palladium(II) chloride, bis(triphenylphosphine)palladium(II) chloride, bis(acetonitrile)palladium(II) chloride, tetrakis(triphenylphosphine)palladium(0), bis(dibenzylideneacetone)palladium(0), tris(dibenzylideneacetone)dipalladium(0) or [1,1'-bis(diphenylphosphino)ferrocene]palladium(II) chloride, in each case in combination with a suitable phosphine ligand such as, for example, 2-dicyclohexylphosphino-2',4',6'-triisopropylbiphenyl (X-Phos), 2-dicyclohexylphosphino-2',6'-dimethoxybiphenyl (S-Phos), 1,2,3,4,5-pentaphenyl-1'-(di-tert-butylphosphino)ferrocene (Q-Phos), 4,5-bis(diphenylphosphino)-9,9-dimethylxanthene (xantphos), 2,2'-bis(diphenylphosphino)-1,1'-binaphthyl (BI-NAP), 2-dicyclohexylphosphino-2'-(N,N-dimethyl-amino)biphenyl or 2-di-tert-butylphosphino-2'-(N,N-dimethylamino)biphenyl.

The coupling reaction [C] (VII)+(VI)→(VIII) is generally carried out in the presence of a base. Suitable bases are in particular alkali metal carbonates such as sodium carbonate, potassium carbonate or caesium carbonate, alkali metal phosphates such as sodium phosphate or potassium phosphate, alkali metal fluorides such as potassium fluoride or caesium fluoride, or alkali metal tert-butoxides such as sodium tert-butoxide or potassium tert-butoxide. The reaction is carried out in an inert solvent such as, for example, toluene, 1,2-dimethoxyethane, tetrahydrofuran, 1,4-dioxane, dimethyl sulphoxide (DMSO), N,N-dimethylformamid (DMF), N,N-dimethylacetamide (DMA) or mixtures thereof in a temperature range of from +80° C. to +200° C., where here, too, heating by means of a microwave apparatus may be advantageous.

For this coupling reaction, preference is given to using a catalyst/ligand/base system consisting of palladium(II) acetate, 4,5-bis(diphenylphosphino)-9,9-dimethylxanthene (xantphos) and caesium carbonate, and 1,4-dioxane as solvent.

The cyclization [C] (VIII)→(IV) is preferably carried out by heating the acetal (VIII) with an aqueous acid such as, for example, sulphuric acid in an alcoholic solvent such as methanol or ethanol, where once more carrying out the reaction with microwave irradiation may be advantageous.

In the case that the azaheteroaryl group $Ar^N$ in (VIII) is present in THP-protected form (PG=tetrahydro-2H-pyran-2-yl), under the cyclization reaction conditions mentioned this protective group is removed, too, such that here the corresponding compound of the formula (I) according to the invention is obtained directly as reaction product. If a benzyl, 4-methoxybenzyl or 2,4-dimethoxybenzyl protective group is present in $Ar^N$, this is removed in a subsequent separate reaction step (IV)→(I), as described above.

Further compounds of the formula (I) according to the invention can, if expedient, also be prepared by converting functional groups of individual radicals and substituents, in particular those listed under $R^9$ and $R^{10}$, starting with other compounds of the formula (I) obtained by the above processes or precursors thereof. These conversions are carried out by customary methods familiar to the person skilled in the art and include, for example, reactions such as nucleophilic or electrophilic substitution reactions, transition metal-catalyzed coupling reactions (for example Ullmann reaction, Buchwald-Hartwig reaction, Suzuki coupling, Negishi coupling), addition reactions of organometallic compounds (for example Grignard compounds or organilithium compounds) on carbonyl compounds, oxidation and reduction reactions, hydrogenation, alkylation, acylation, sulphonylation, amination, hydroxylation, the formation of nitriles, carboxylic esters, carboxamides and sulfonamides, ester cleavage and hydrolysis and also introduction and removal of tempory protective groups.

Compounds of the formula (I) can also be prepared, if expedient, by introducing into the starting materials of the process variants described above instead of the substituents $R^9$ and/or $R^{10}$ initially other functional groups not within the scope of the meanings of $R^9$ and $R^{10}$, respectively, which are then converted by subsequent transformations familiar to the person skilled in the art (such as those mentioned in an exemplary manner above) into the respective substituents $R^9$ and $R^{10}$. Examples of such functional groups serving as "precursor" for $R^9$ and/or $R^{10}$ are radicals such as chlorine, bromine, iodine, nitro, hydroxy, methanesulphonate (mesylate), trifluoromethanesulphonate (triflate), formyl and alkylcarbonyl [cf. also the preparation of the working examples and their precursors described in detail in the experimental part below].

The aminopyrazole intermediate of the formula (VII) from process route [C] can be prepared by acid-catalyzed condensation of a cyanoenamine or -enol of the formula (IX)

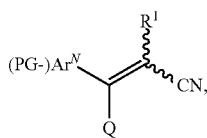
(IX)

in which $Ar^N$, (PG-) and $R^1$ have the meanings given above and

Q represents $NH_2$ or OH, with a hydrazinoacetal of the formula (X)

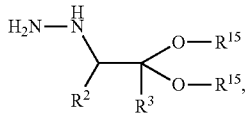
(X)

in which $R^2$, $R^3$ and $R^{15}$ have the meanings given above.

The reaction is preferably carried out in an alcoholic solvent such as methanol or ethanol in a temperature range of from +60° C. to +120° C., the use of a microwave oven being advantageous. A particularly suitable acid catalyst is aqueous hydrochloric acid. Instead of the enols of the formula (IX) [Q=OH], it is also possible to employ corresponding enolate salts such as, for example, lithium enolates, sodium enolates or potassium enolates, for the reaction.

The 1H-imidazo[1,2-b]pyrazole intermediate of the formula (V) from process route [B] is accessible analogously to the reaction [C] (VIII)→(IV) by acid-catalyzed cyclization of the aminopyrazole acetal (VII).

Likewise starting with aminopyrazole (VII), the aniline intermediate of the formula (II) from process route [A] can be obtained by (i) palladium-catalyzed coupling of (VII) with a meta-nitrophenyl bromide of the formula (XI)

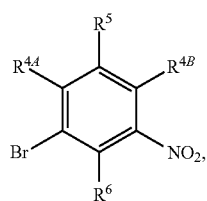
(XI)

in which $R^{4A}$, $R^{4B}$, $R^5$ and $R^6$ have the meanings given above, to give the N-arylated compound of the formula (XII)

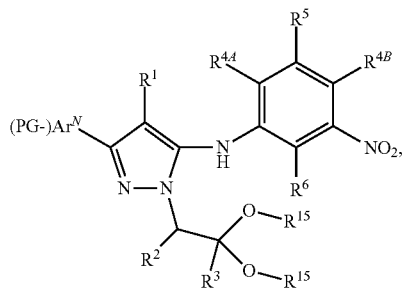
(XII)

in which $Ar^N$, (PG-), $R^1$, $R^2$, $R^3$, $R^{4A}$, $R^{4B}$, $R^5$, $R^6$ and $R^{15}$ have the meanings given above, (ii) subsequent acid-catalyzed cyclization to the 1-phenyl-1H-imidazo[1,2-b]pyrazole of the formula (XIII)

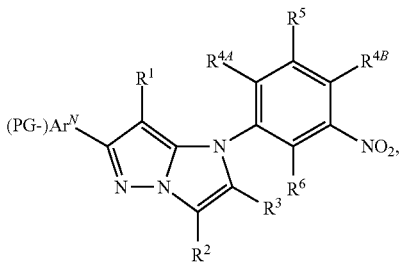
(XIII)

in which $Ar^N$, (PG-), $R^1$, $R^2$, $R^3$, $R^{4A}$, $R^{4B}$, $R^5$ and $R^6$ have the meanings given above, and (iii) subsequent reduction of the nitro group in (XIII).

The coupling reaction (VII)+(XI)→(XII) and the cyclization (XII)→(XIII) are carried out in a manner analogous to that described above in the context of process route [C] for the reactions (VII)+(VI)→(VIII) and (VIII)→(IV).

The reduction of the nitro group to the amine in process step (XIII)→(II) can be carried out, for example, with the aid of tin(II) chloride or by catalytical hydrogenation with gaseous hydrogen or, in the sense of a transfer hydrogenation, in the presence of hydrogen donors such as ammonium formate, cyclohexene or cyclohexadiene. The preferred method is the palladium(0)-catalyzed hydrogenation with ammonium formate. The reaction is preferably carried out in an alcoholic solvent such as methanol or ethanol, if appropriate with addition of water, in a temperature range of from +20° C. to +100° C.

The meta-amidophenyl bromide intermediate of the formula (VI) from process routes [B] and [C] can be obtained in a simple manner by coupling an aniline of the formula (XIV)

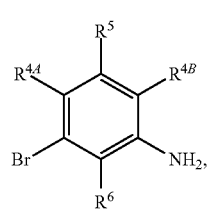
(XIV)

in which $R^{4A}$, $R^{4B}$, $R^5$ and $R^6$ have the meanings given above, with a carboxylic acid of the formula (III) or a corresponding carbonyl chloride of the formula (XV)

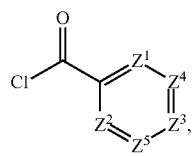

(XV)

in which $Z^1$, $Z^2$, $Z^3$, $Z^4$ and $Z^5$ have the meanings given above.

The carboxylic acid amidation (XIV)+(III)→(VI) is carried out by customary methods with the aid of a condensing agent under reaction conditions similar to those described above for the analogous reaction [A] (II)+(III)→(IV). Preferably, the condensing agent used is O-(7-azabenzotriazol-1-yl)-N,N,N',N'-tetramethyluronium hexafluorophosphate (HATU) and the base is N,N-diisopropylethylamine.

If the corresponding carbonyl chloride (XV) is used, coupling with the amine component (XIV) is carried out in the presence of a customary organic auxiliary base such as triethylamine, N,N-diisopropylethylamine, N-methylmorpholine, N-methylpiperidine, pyridine, 2,6-lutidine, 4-N,N-dimethylaminopyridine, 1,8-diazabicyclo[5.4.0]undec-7-ene (DBU) or 1,5-diazabicyclo[4.3.0]non-5-ene (DBN). Preference is given to using triethylamine or N,N-diisopropylethylamine. The reaction is generally carried out in an inert solvent such as dichloromethane in a temperature range of from −20° C. to +60° C., preferably from 0° C. to +40° C.

The compounds of the formulae (III), (IX), (X), (XI), (XIV) and (XV) are commercially available or have been described as such in the literature, or they can be prepared in a manner obvious to the person skilled in the art analogously to the methods published in the literature. Numerous detailed procedures and literature references for preparing the starting materials can also be found in the Experimental Part in the section on the preparation of the starting materials and intermediates.

The preparation of the compounds according to the invention can be illustrated in an exemplary manner by the reaction schemes below:

Scheme 1

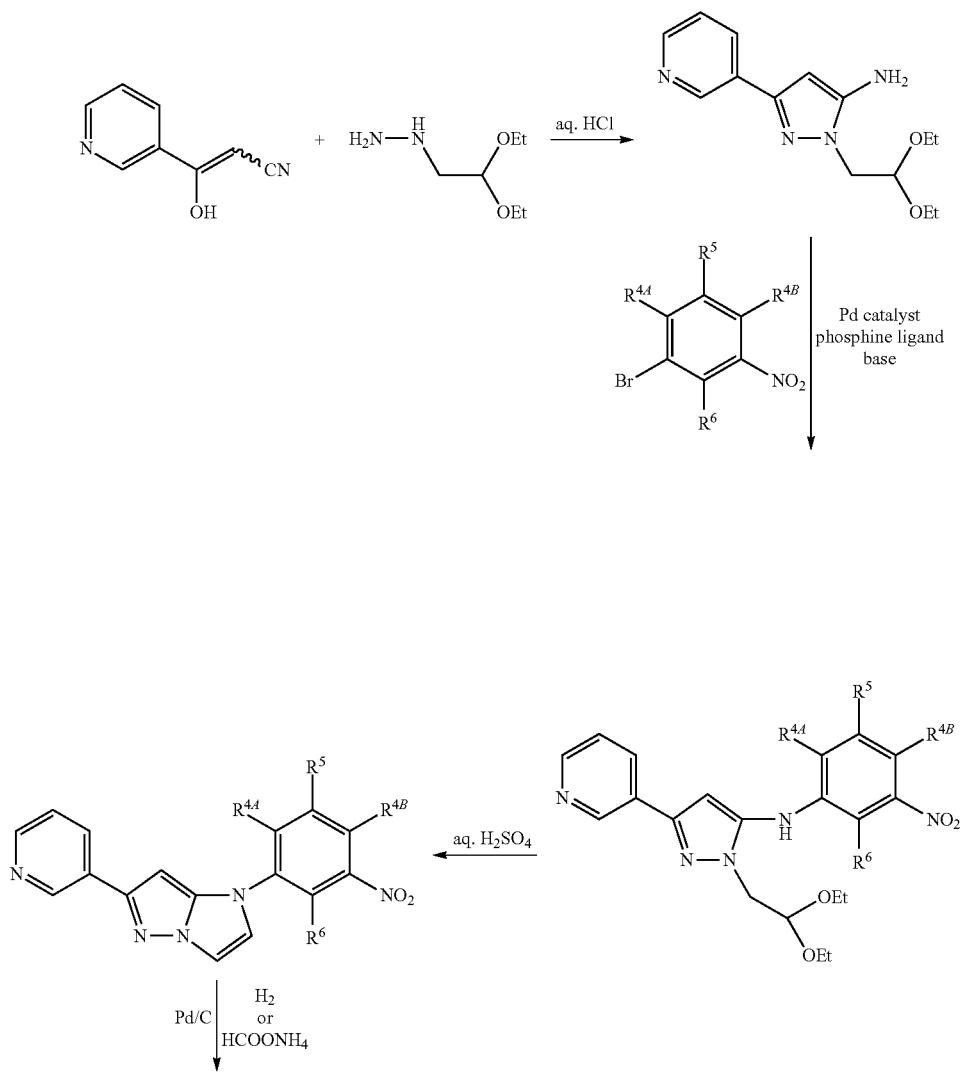

-continued
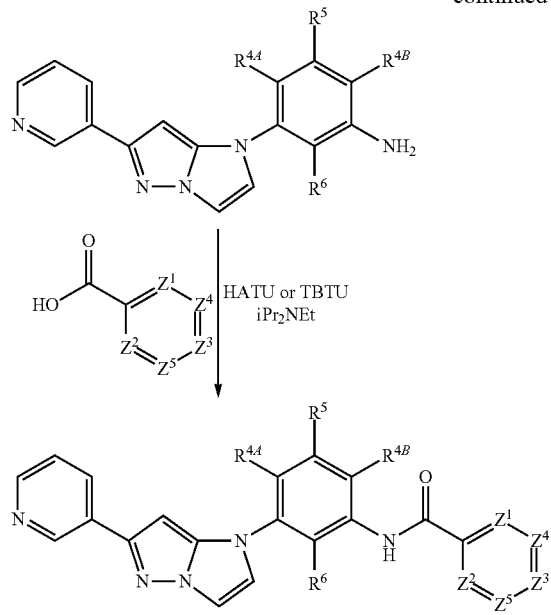
Scheme 2
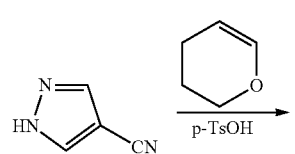
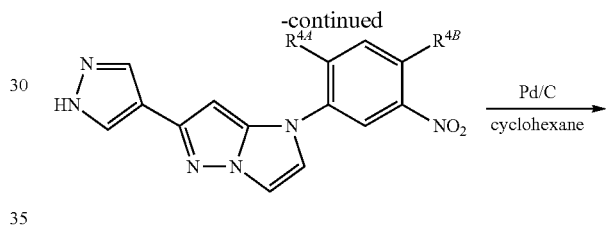
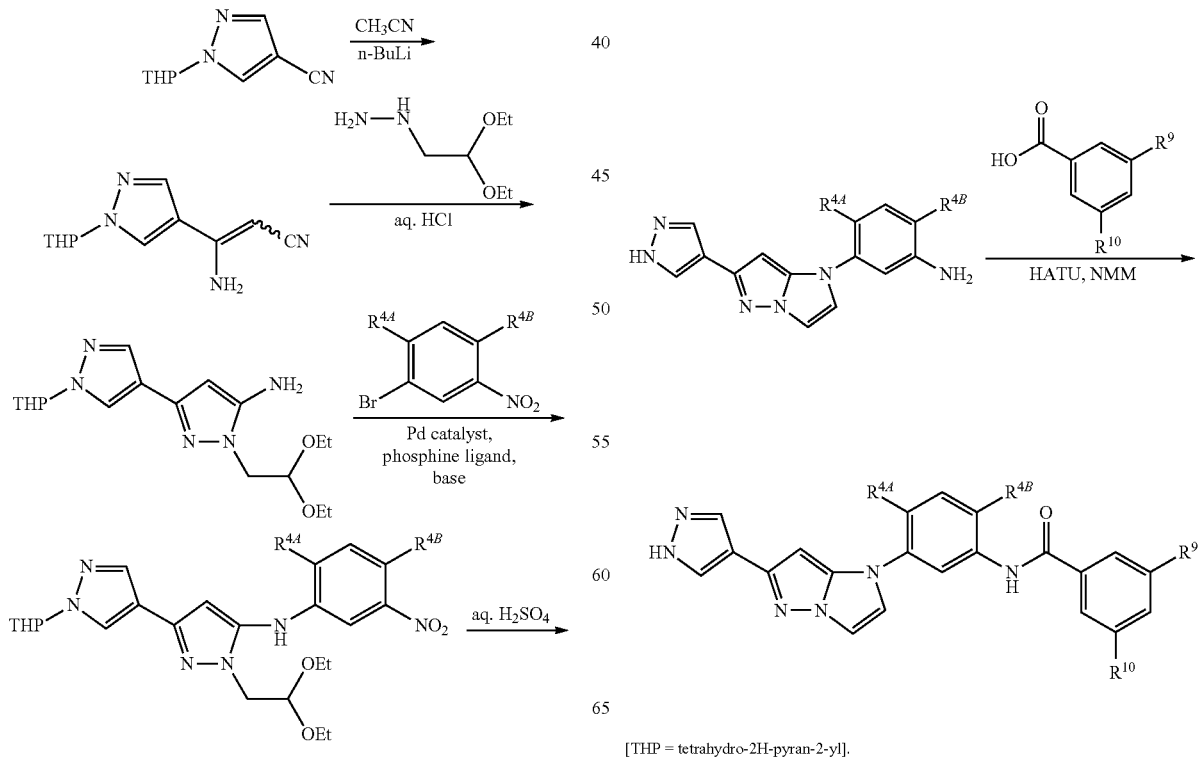
[THP = tetrahydro-2H-pyran-2-yl].

Scheme 3
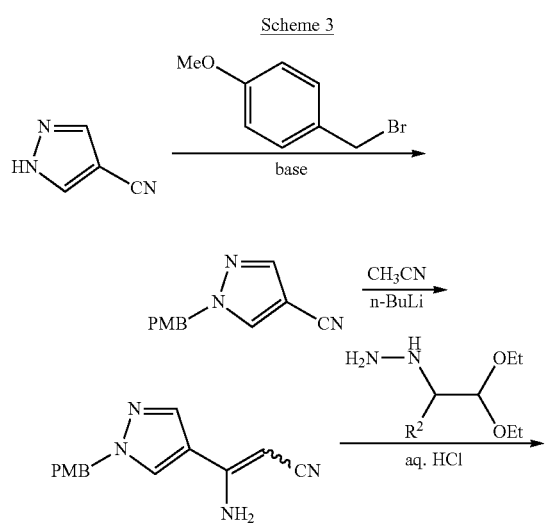
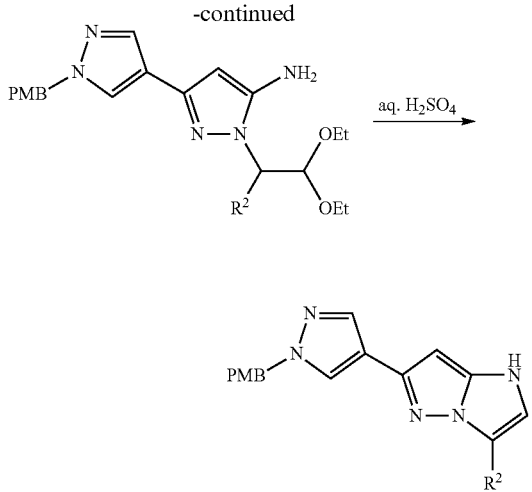
[PMB = para-methoxybenzyl].
Scheme 4
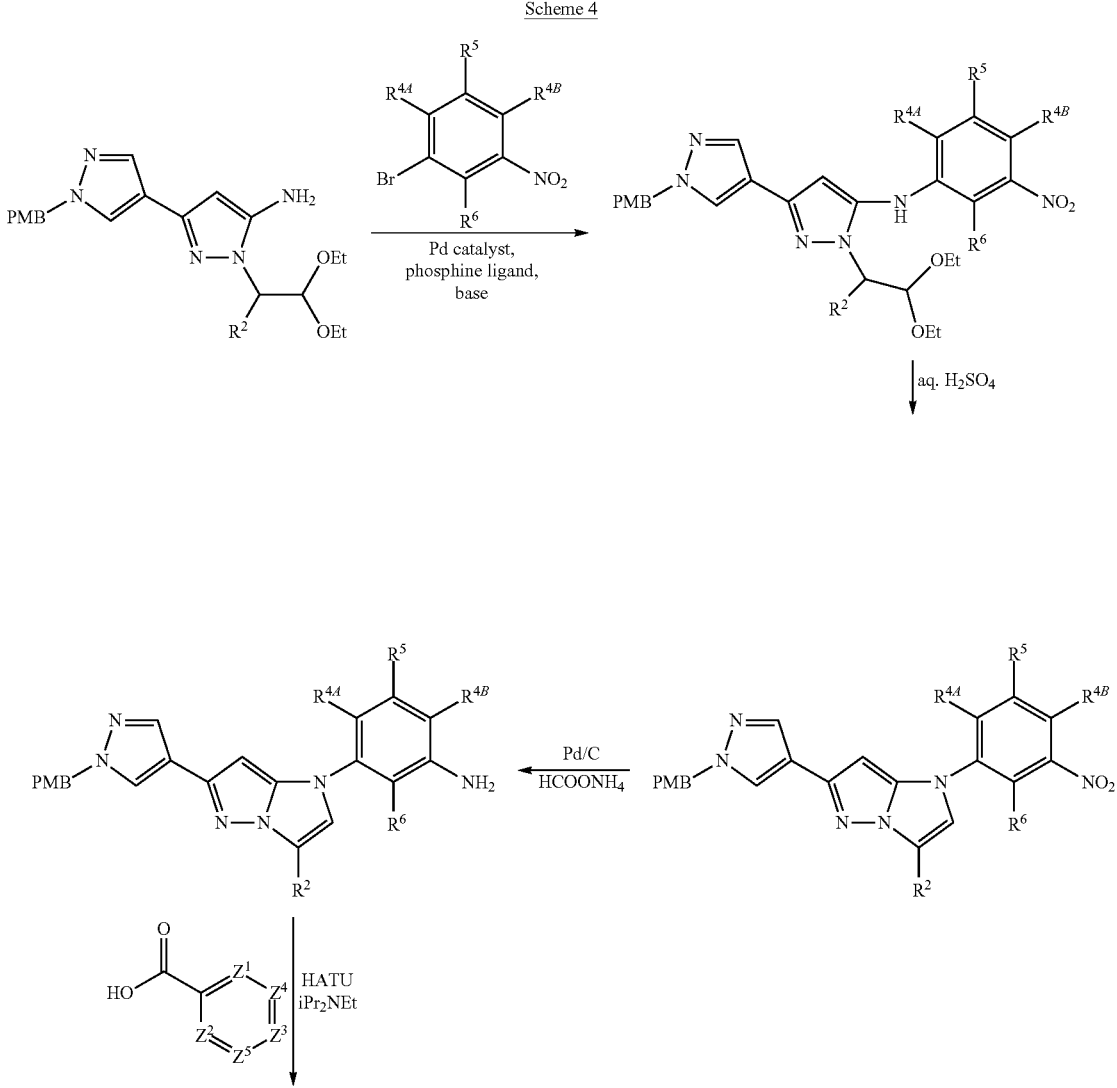

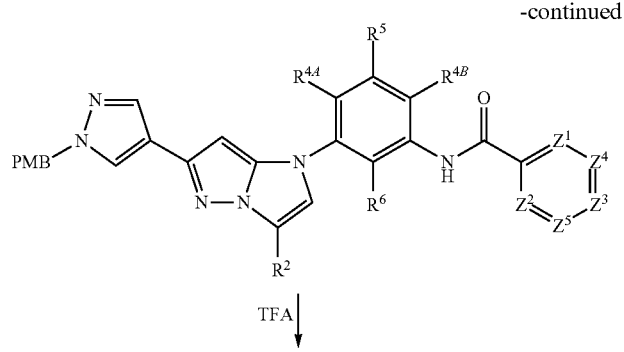
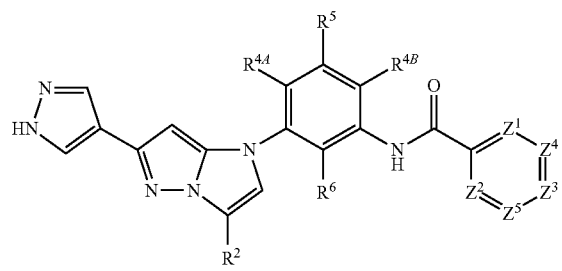
Scheme 5
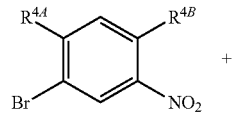
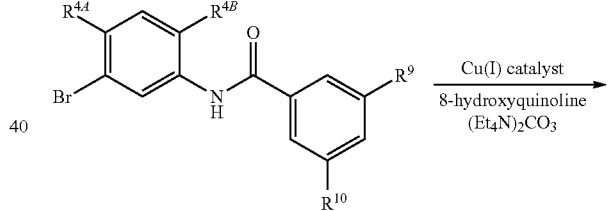
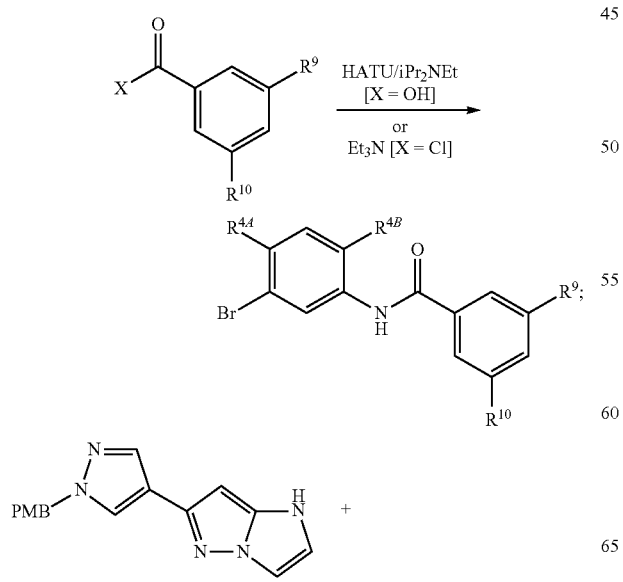

Scheme 6

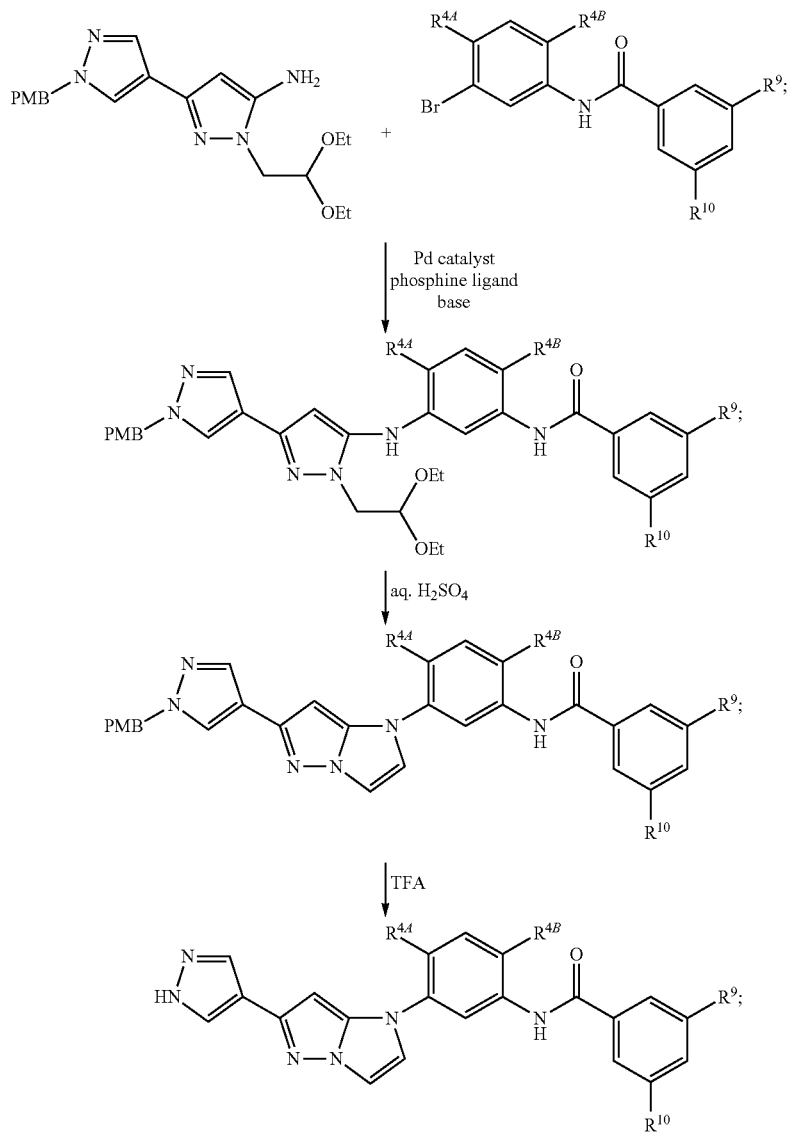

The compounds according to the invention have valuable pharmacological properties and can be used for the prevention and treatment of disorders in humans and animals.

The compounds according to the invention are highly potent inhibitors of Tie2 receptor kinase and can be administered orally. By virtue of this activity profile, the compounds according to the invention are suitable in particular for the treatment of angiogenic disorders in humans and mammals in general.

These angiogenic disorders include in particular neoplastic disorders and tumour disorders which, in the context of the present invention, is to be understood as meaning in particular the following disorders, but without being limited thereto: breast carcinomas and breast tumours (mammary carcinomas including ductal and lobular forms, also in situ), tumours of the respiratory tract (small-cell and non-small-cell lung carcinoma, bronchial carcinomas), brain tumours (for example of the brain stem and of the hypothalamus, astrocytoma, ependymoma, glioblastoma, glioma, medulloblastoma, meningioma and neuro-ectodermal and pineal tumours), tumours of the digestive organs (oesophagus, stomach, gall bladder, small intestine, large intestine, rectum and anal carcinomas), liver tumours (inter alia hepatocellular carcinoma, cholangiocellular carcinoma and mixed hepatocellular and cholangiocellular carcinomas), tumours of the head and neck region (larynx, hypopharynx, nasopharynx, oropharynx, lips and oral cavity carcinomas, oral melanomas), skin tumours (basaliomas, spinaliomas, squamous epithelial carcinomas, Kaposi sarcoma, malignant melanomas, non-melanoma skin cancer, Merkel cell skin cancer, mast cell tumours), tumours of the supporting and connective tissue (inter alia soft tissue sarcomas, osteosarcomas, malignant fibrous histiocytomas, chondrosarcomas, fibrosarkomas, haemangiosarcomas, leiomyosarcomas, liposarcomas, lymphosarcomas and rhabdomyosarcomas), tumours of the eyes (inter alia intraocular melanoma and retinoblastoma), tumours of the endocrine and exocrine glands (for example thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testicles in men). These also include proliferative disorders of the blood, the lymph system and the spinal cord, in solid form and as circulating cells, such as leukaemias, lymphomas and myeloproliferative diseases, for example acute myeloid, acute lymphoblastic, chronic myeloic, chronic lymphocytic and hair cell leukaemia, multiple myeloma (plasmocytoma) and AIDS-correlated lymphomas, Hodgkin's lymphomas, non-Hodgkin's lymphomas, cutaneous T cell lymphomas, Burkitt's lymphomas and lymphomas in the central nervous system.

For the purpose of the present invention, the treatment of the neoplastic disorders mentioned above may comprise both a treatment of the solid tumours and a treatment of metastasizing or circulating forms thereof.

By virtue of their activity profile, the compounds according to the invention are particularly suitable for the treatment of breast, colorectal, liver, kidney and ovarial carcinomas, glioblastomas, acute myeloic leukaemia (AML), chronic myeloic leukaemia (CML) and multiple myeloma.

Furthermore, the compounds of the present invention can be used for treating blood vessel malformations such as haemangiomas, haemangioblastomas, cavernomas and lymphangiomas, and further disorders associated with excessive or anormal angiogenesis. These include, inter alia, diabetic retinopathy, ischaemic retinal vene occlusion and retinopathy of prematurity, age-related macular degeneration, neovascular glaucoma, psoriasis, retrolental fibroplasia, angiofibroma, inflammation, rheumatic arthritis, restenosis, in-stent restenosis and restenosis after vessel implantation, endometriosis, kidney disorders (for example glomerulonephritis, diabetic nephropathy, malignant nephrosclerosis) and fibrotic disorders (for example liver cirrhosis, mesangiosis, arteriosclerosis). In addition, the compounds according to the invention are also suitable for treating pulmonary hypertension.

The well-described diseases of man mentioned above can also occur with a comparable aetiology in other mammals and can likewise be treated there with the compounds of the present invention.

In the context of the present invention, the term "treatment" or "treat" includes the inhibition, delay, arrest, amelioration, attenuation, limitation, reduction, suppression, reversal or cure of a disease, a condition, a disorder, an injury and a health impairment, of the development, course or the progression of such states and/or the symptoms of such states. Here, the term "therapy" is understood to be synonymous with the term "treatment".

In the context of the present invention, the terms "prevention", "prophylaxis" or "precaution" are used synonymously and refer to the avoidance or reduction of the risk to get, to contract, to suffer from or to have a disease, a condition, a disorder, an injury or a health impairment, a development or a progression of such states and/or the symptoms of such states.

The treatment or the prevention of a disease, a condition, a disorder, an injury or a health impairment may take place partially or completely.

Thus, the invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides the use of the compounds according to the invention in a method for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

The compounds according to the invention can be employed by themselves or, if required, in combination with one or more other pharmacologically active substances, as long as this combination does not lead to undesirable and unacceptable side effects. Accordingly, the present invention furthermore provides medicaments comprising at least one of the compounds according to the invention and one or more further active compounds, in particular for the treatment and/or prevention of the abovementioned diseases.

For example, the compounds of the present invention can be combined with known anti-angiogenic, anti-hyperproliferative, cytostatic or cytotoxic substances for the treatment of neoplastic disorders. Suitable active compounds in the combination which may be mentioned by way of example are: abarelix, abiraterone, aclarubicin, afatinib, aflibercept, aldesleukin, alemtuzumab, alitretinoin, altretamine, AMG-386, aminoglutethimide, amonafide, amrubicin, amsacrine, anastrozole, andromustine, arglabin, asparaginase, axitinib, 5-azacitidine, basiliximab, belotecan, bendamustin, bevacizumab, bexaroten, bicalutamide, bisantrene, bleomycin, bortezomib, bosutinib, brivanib-alaninate, buserelin, busulfan, cabazitaxel, calcium folinate, calcium levofolinate, camptothecin, capecitabine, carboplatin, carmofur, carmustine, catumaxomab, cediranib, celmoleukin, cetuximab, chlorambucil, chlormadinone, chlormethine, cidofovir, cisplatin, cladribine, clodronic acid, clofarabine, combretastatin, crisantaspase, crizotinib, CVX-060, cyclophosphamide, cyproterone, cytarabine, dacarbazine, dactinomycin, darbepoetin-alfa, darinaparsin, dasatinib, daunorubicin, decitabine, degarelix, denileukin-diftitox, denosumab, deslorelin, dibrospidium chloride, docetaxel, dovitinib, doxifluridine, doxorubicin, dutasteride, eculizumab, edrecolomab, eflornithine, elliptinium acetate, eltrombopag, endostatin, enocitabine, epimbicin, epirubicin, epitiostanol, epoetin-alfa, epoetin-beta, epothilone, eptaplatin, eribulin, erlotinib, estradiol, estramustine, etoposide, everolimus, exatecan, exemestane, exisulind, fadrozole, fenretinide, filgrastim, finasteride, flavopiridol, fludarabine, 5-fluorouracil, fluoxymesterone, flutamide, foretinib, formestane, fotemustine, fulvestrant, ganirelix, gefitinib, gemcitabine, gemtuzumab, gimatecan, gimeracil, glufosfamide, glutoxim, goserelin, histrelin, hydroxyurea, ibandronic acid, ibritumomab-tiuxetan, idarubicin, ifosfamide, imatinib, imiquimod, improsulfan, intedanib, interferon alpha, interferon alpha 2a, interferon alpha 2b, interferon beta, interferon-gamma, interleukin-2, ipilimumab, irinotecan, ixabepilone, lanreotide, lapatinib, lasofoxifene, lenalidomide, lenograstim, lentinan, lestaurtinib, letrozole, leuprorelin, levamisole, linifanib, linsitinib, lisuride, lobaplatin, lomustine, lonidamine, lurtotecan, mafosfamide, mapatumumab, masitinib, masoprocol, medroxyprogesterone, megestrol, melarsoprol, melphalan, mepitiostane, mercaptopurine, methotrexate, methyl-aminolevulinate, methyltestosterone, mifamurtide, mifepristone, miltefosine, miriplatin, mitobronitol, mitoguazone, mitolactol, mitomycin, mitotane, mitoxantrone, molgramostim, motesanib, nandrolon, nedaplatin, nelarabine, neratinib, nilotinib, nilutamide, nimotuzumab, nimustine, nitracrine, nolatrexed, ofatumumab, oprelvekin, oxaliplatin, paclitaxel, palifermin, pamidronic acid, panitumumab, pazopanib, pegaspargase, PEG-epoetin beta, pegfilgrastim, PEG-interferon alpha-2b, pelitrexol, pemetrexed, pemtumomab, pentostatin, peplomycin, perfosfamide, pertuzumab, picibanil, pirambicin, pirarubicin, plerixafor, plicamycin, poliglusam, polyestradiol phosphate, porfimer-sodium, prala-trexate, prednimustine, procarbazine, procodazole, quinagolide, raloxifene, raltitrexed, ranibizumab, ranimustine, razoxane, regorafenib, risedronic acid, rituximab, romidepsin, romiplostim, rubitecan, saracatinib, sargramostim, satraplatin, selumetinib, sipuleucel-T, sirolimus, sizofiran, sobuzoxane, sorafenib, streptozocin, sunitinib, talaporfin, tamibarotene, tamoxifen, tandutinib, tasonermin, teceleukin, tegafur, telatinib, temoporfin, temozolomide, temsirolimus, teniposide, testolactone, testosterone, tetrofosmin, thalidomide, thiotepa, thymalfasin, tioguanine, tipifarnib, tivozanib, toceranib, tocilizumab, topotecan, toremifene, tositumomab, trabectedin, trastuzumab, treosulfan, tretinoin, triapin, trilostane, trimetrexate, triptorelin, trofosfamide, ubenimex, valrubicin, vandetanib, vapreotide, varlitinib, vatalanib, vemurafenib, vidarabine, vinblastine, vincristine, vindesine, vinflunine, vinorelbin, volociximab, vorinostat, zinostatin, zoledronic acid, zorubicin.

Generally, the following aims can be pursued with the combination of compounds of the present invention with other agents having anti-angiogenic, anti-hyperproliferative, cytostatic or cytotoxic action:
- an improved activity in slowing down the growth of a tumour, in reducing its size or even in its complete elimination compared with treatment with an individual active compound;
- the possibility of employing the chemotherapeutics used in a lower dosage than in monotherapy;
- the possibility of a more tolerable therapy with fewer side effects compared with individual administration;
- the possibility of treatment of a broader spectrum of tumour diseases;
- achievement of a higher rate of response to the therapy;
- a longer survival time of the patient compared with present-day standard therapy.

The compounds according to the invention can moreover also be employed in combination with radiotherapy and/or surgical intervention.

The present invention furthermore provides medicaments which comprise at least one compound according to the invention, conventionally together with one or more inert, non-toxic, pharmaceutically suitable auxiliary substances, and the use thereof for the abovementioned purposes.

The compounds according to the invention can act systemically and/or locally. They can be administered in a suitable manner for this purpose, such as e.g. orally, parenterally, pulmonally, nasally, sublingually, lingually, buccally, rectally, dermally, transdermally, conjunctivally, otically or as an implant or stent.

The compounds according to the invention can be administered in suitable administration forms for these administration routes.

Administration forms which function according to the prior art, release the compounds according to the invention rapidly and/or in a modified manner and contain the compounds according to the invention in crystalline and/or amorphized and/or dissolved form are suitable for oral administration, such as e.g. tablets (non-coated or coated tablets, for example with coatings which are resistant to gastric juice or dissolve in a delayed manner or are insoluble and control the release of the compound according to the invention), tablets or films/oblates, films/lyophilisates or capsules which disintegrate rapidly in the oral cavity (for example hard or soft gelatine capsules), sugar-coated tablets, granules, pellets, powders, emulsions, suspensions, aerosols or solutions, are suitable for oral administration.

Parenteral administration can be effected with bypassing of an absorption step (e.g. intravenously, intraarterially, intracardially, intraspinally or intralumbally) or with inclusion of an absorption (e.g. intramuscularly, subcutaneously, intracutaneously, percutaneously or intraperitoneally). Administration forms which are suitable for parenteral administration are, inter alia, injection and infusion formulations in the form of solutions, suspensions, emulsions, lyophilisates or sterile powders.

For the other administration routes e.g. inhalation medicament forms (inter alia powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents are suitable.

Oral or parenteral administration is preferred, in particular oral and intravenous administration.

The compounds according to the invention can be converted into the administration forms mentioned. This can be effected in a manner known per se by mixing with inert, non-toxic, pharmaceutically suitable auxiliary substances. These auxiliary substances include inter alia carrier substances (for example microcrystalline cellulose, lactose, mannitol), solvents (e.g. liquid polyethylene glycols), emulsifiers and dispersing or wetting agents (for example sodium dodecyl sulphate, polyoxysorbitan oleate), binders (for example polyvinylpyrrolidone), synthetic and natural polymers (for example albumin), stabilizers (e.g. antioxidants, such as, for example, ascorbic acid), dyestuffs (e.g. inorganic pigments, such as, for example, iron oxides) and flavour and/or smell correctants.

In general, it has proven advantageous in the case of parenteral administration to administer amounts of from about 0.001 to 1 mg/kg, preferably about 0.01 to 0.5 mg/kg of body weight to achieve effective results. In the case of oral administration the dosage is about 0.01 to 100 mg/kg, preferably about 0.01 to 20 mg/kg and very particularly preferably 0.1 to 10 mg/kg of body weight.

Nevertheless it may be necessary to deviate from the amounts mentioned, and in particular depending on the body weight, administration route, individual behaviour towards the active compound, nature of the formulation and point in time or interval at which administration takes place. Thus in some cases it may be sufficient to manage with less than the abovementioned minimum amount, while in other cases the upper limit mentioned must be exceeded. In the case where relatively large amounts are administered, it may be advisable to spread these into several individual doses over the day.

The following working examples illustrate the invention. The invention is not limited to the examples.

The percentage data in the following tests and examples are percentages by weight, unless stated otherwise; parts are parts by weight. The solvent ratios, dilution ratios and concentration data of liquid/liquid solutions in each case relate to the volume.

A. EXAMPLES

Abbreviations and Acronyms abs. absolute
aq. aqueous, aqueous solution
br. broad (in NMR)
Ex. Example
Bu butyl
CI chemical ionization (in MS)
d doublet (in NMR)
d day(s)
DAST diethylaminosulphur trifluoride
DBU 1,8-diazabicyclo[5.4.0]undec-7-ene
TLC thin layer chromatography
DCI direct chemical ionization (in MS)
dd doublet of doublet (in NMR)
DMAP 4-N,N-dimethylaminopyridine
DME 1,2-dimethoxyethane
DMF N,N-dimethylformamide
DMSO dimethyl sulphoxide
dq doublet of quartet (in NMR)
dt doublet of triplet (in NMR)
EI electron impact ionization (in MS)
eq. equivalent(s)
ESI electrospray ionization (in MS)
Et ethyl
GC gas chromatography
GC/MS gas chromatography-coupled mass spectrometry
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high pressure, high performance liquid chromatography
$^i$Pr isopropyl
konz. concentrated
LC/MS liquid chromatography-coupled mass spectrometry
Lit. literature (reference)
m multiplet (in NMR)
Me methyl
min minute(s)
MPLC medium pressure liquid chromatography (on silica gel; also called "flash chromatography")
MS mass spectrometry
NBS N-bromosuccinimide
n-Bu n-butyl
NMM N-methylmorpholine
NMP N-methyl-2-pyrrolidinone
NMR nuclear magnetic resonance spectrometry
Pd/C palladium on activated carbon
PEG polyethylene glycol
PMB para-methoxybenzyl
Pr propyl
p-TsOH para-toluenesulphonic acid
Q-Phos 1,2,3,4,5-pentaphenyl-1'-(di-tert-butylphosphino)ferrocene
quart quartet (in NMR)
quint quintet (in NMR)
$R_f$ retention index (in DC)
RT room temperature
$R_t$ retention time (in HPLC)
s singlet (in NMR)
sept septet (in NMR)
t triplet (in NMR)
TBTU N-[(1H-benzotriazol-1-yloxy)(dimethylamino)methylene]-N-methylmethanaminium tetrafluoroborate
$^t$Bu tert-butyl
TFA trifluoroacetic acid
THF tetrahydrofuran
THP tetrahydro-2H-pyran-2-yl
UV ultraviolet spectrometry
v/v volume to volume ratio (of a solution)
xantphos 4,5-bis(diphenylphosphino)-9,9-dimethylxanthene HPLC, LC/MS and GC/MS Methods:

Method 1 (LC/MS):
Instrument: Micromass Quattro Premier with Waters UPLC Acquity; column: Thermo Hypersil GOLD 1.9 µm, 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; temperature: 50° C.; UV detection: 210 nm.

Method 2 (LC/MS):
Instrument: Micromass Quattro Premier with Waters UPLC Acquity; column: Thermo Hypersil GOLD 1.9 µm, 50 mm×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; flow rate: 0.3 ml/min; temperature: 50° C.; UV detection: 210 nm.

Method 3 (LC/MS):
Instrument: Waters Acquity SQD UPLC system; column: Waters Acquity UPLC HSS T3 1.8 µm, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; temperature: 50° C.; UV detection: 210-400 nm.

Method 4 (LC/MS):
Instrument: Waters Acquity SQD UPLC system; column: Waters Acquity UPLC HSS T3 1.8 µm, 30 mm×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.60 ml/min; temperature: 50° C.; UV detection: 208-400 nm.

Method 5 (LC/MS):
Instrument: Waters Acquity UPLC/MS 100-800 Dalton, 20 V (Waters ZQ 4000); column: BEH C18 (Waters), 2.1 mm×50 mm, 1.7 µm; mobile phase A: water/0.05% formic acid, mobile phase B: acetonitrile/0.05% formic acid; gradient: 10% B→98% B in 1.7 min, 90% B for 0.2 min, 98% B→2% B in 0.6 min; flow rate: 1.3 ml/min; UV detection: 200-400 nm.

Method 6 (LC/MS):
Instrument: Waters Acquity UPLC/MS 100-800 Dalton, 20 V (Waters SQD); column: BEH C18 (Waters), 2.1 mm×50 mm, 1.7 µm; mobile phase A: water/0.05% formic acid, mobile phase B: acetonitrile/0.05% formic acid; gradient: 10% B→98% B in 1.7 min, 90% B for 0.2 min, 98% B→2% B in 0.6 min; flow rate: 0.8 ml/min; UV detection: 200-400 nm.

Method 7 (LC/MS):
Instrument: Waters Acquity UPLC/MS SQD; column: Acquity UPLC BEH C18, 1.7 µm, 50 mm×2.1 mm; mobile phase A: water/0.1% formic acid, mobile phase B: acetonitrile; gradient: 0-1.6 min 1% B→99% B, 1.6-2.0 min 99% B; flow rate: 0.8 ml/min; temperature: 60° C.; UV detection (DAD): 210-400 nm.

Method 8 (GC/MS):
Instrument: Micromass GCT, GC 6890; column: Restek RTX-35, 15 m×200 µm×0.33 µm; constant helium flow: 0.88 ml/min; oven: 70° C.; inlet: 250° C.; gradient: 70° C., 30° C./min 310° C. (maintained for 3 min).

Method 9 (Preparative HPLC):
Column: Reprosil-Pur C18, 10 µm, 250 mm×30 mm; mobile phase: acetonitrile/water with 0.1% formic acid; gradient: 10:90→90:10.

Method 10 (Preparative HPLC):
System: SFC Prep 200; column: 2-ethylpyridine 12µ, 300 mm×100 mm; mobile phase: carbon dioxide/methanol; gradient: 85:15→70:30; total run time 5 min.

Method 11 (Preparative HPLC):
Column: Reprosil-Pur C18, 10 µm, 250 mm×30 mm; mobile phase: acetonitrile/water with 0.05% trifluoroacetic acid; gradient: 30:70→100:0.

Method 12 (Preparative HPLC):
Column: Reprosil-Pur C18, 10 µm, 250 mm×40 mm; mobile phase: acetonitrile/water with 0.05% trifluoroacetic acid; gradient: 30:70→100:0.

Method 13 (Preparative HPLC):
Column: Reprosil-Pur C18, 10 µm, 250 mm×40 mm; mobile phase: acetonitrile/water with 0.05% trifluoroacetic acid; gradient: 15:85→100:0.

Method 14 (Preparative HPLC):
Column: Reprosil-Pur C18, 10 µm, 250 mm×40 mm; mobile phase: methanol/water with 0.05% trifluoroacetic acid; gradient: 30:70→100:0.

Method 15 (Preparative HPLC):
Column: Reprosil-Pur C18, 10 µm, 250 mm×30 mm; mobile phase: methanol/water with 0.05% trifluoroacetic acid; gradient: 30:70→100:0.

Method 16 (Preparative HPLC):
Column: XBridge C18, 5 µm, 100 mm×30 mm; mobile phase: water with 0.1% formic acid/acetonitrile; gradient: 99:1→1:99.

Method 17 (Preparative HPLC):
Column: Reprosil-Pur C18, 10 µm, 250 mm×40 mm; mobile phase: methanol/water with 0.05% trifluoroacetic acid; gradient: 15:85→100:0.

Method 18 (Preparative HPLC):
Column: Reprosil-Pur C18, 10 µm, 250 mm×30 mm; mobile phase: acetonitrile/water with 0.05% trifluoroacetic acid; gradient: 20:80→100:0.

Method 19 (Preparative HPLC):
Column: Reprosil-Pur C18, 10 µm, 250 mm×30 mm; mobile phase: methanol/water with 0.05% trifluoroacetic acid; gradient: 40:60→100:0.

Method 20 (Preparative HPLC):
Column: Reprosil-Pur C18, 10 µm, 250 mm×40 mm; mobile phase: acetonitrile/water with 0.05% trifluoroacetic acid; gradient: 20:80→100:0.

Method 21 (Preparative HPLC):
Column: Reprosil-Pur C18, 10 µm, 250 mm×30 mm; mobile phase: methanol/water with 0.05% trifluoroacetic acid; gradient: 50:50→100:0.

Method 22 (Preparative HPLC):
Column: Sunfire C18, 5 µm, 75 mm×30 mm; mobile phase: acetonitrile/water/trifluoroacetic acid 45:50:5 (isocratic).

Method 23 (Preparative HPLC):
Column: Sunfire C18, 5 µm, 75 mm×30 mm; mobile phase: acetonitrile/water; gradient: 20:80→95:5.

Method 24 (Preparative HPLC):
Column: XBridge C18, 5 µm, 150 mm×19 mm; mobile phase: acetonitrile/water/0.2% aq. diethylamine; gradient: 45:50:5→60:35:5.

Method 25 (Preparative HPLC):
Column: GROM-SiL 120 ODS-4HE, 10 µm, 40 mm×250 mm; mobile phase: methanol/water+0.05% trifluoroacetic acid; gradient: 0-8 min 35% methanol, 8-20 min ramp to 55% methanol, 20-32 min ramp to 70% methanol, then isocratic 70% methanol; flow rate: 50 ml/min.

Method 26 (Preparative HPLC):
Column: Interchim Puriflash-SiHC, 120 g cartridge; mobile phase: cyclohexane/ethyl acetate; gradient: 0-8 min isocratic 80:20, 8-25 min ramp to 40:60, 25-55 min isocratic 40:60; flow rate: 25 ml/min.

Method 27 (Preparative HPLC):
Column: GROM-SiL 120 ODS-4HE, 10 µm, 30 mm×250 mm; mobile phase: methanol/water+0.05% trifluoroacetic acid; gradient: 0-3 min 20% methanol, 3-20 min ramp to 50% methanol, 20-45 min isocratic 50% methanol; flow rate: 25 ml/min.

Method 28 (Preparative HPLC):
Column: Kromasil C18 5 µm 100 A, 30 mm×250 mm; mobile phase: acetonitrile/water+0.05% trifluoroacetic acid; gradient: 0-15 min 50% acetonitrile, 15-32 min ramp to 70% acetonitrile, 32-50 min isocratic 70% acetonitrile; flow rate: 25 ml/min.

Method 29 (Preparative HPLC):
Column: Kromasil C18 5 µm 100 A, 20 mm×250 mm; mobile phase: acetonitrile/water+0.05% trifluoroacetic acid; gradient: 0-5 min 30% acetonitrile, 5-20 min ramp to 70% acetonitrile, 20-30 min ramp to 80% acetonitrile, 30-45 min isocratic 80% acetonitrile; flow rate: 12 ml/min.

Method 30 (Preparative HPLC):
Column: Kromasil C18 5 µm 100 A, 20 mm×250 mm; mobile phase: acetonitrile/water+0.05% trifluoroacetic acid; gradient: 0-8 min 10% acetonitrile, 8-15 min ramp to 25% acetonitrile, 15-25 min ramp to 30% acetonitrile, 25-50 min isocratic 30% acetonitrile; flow rate: 15 ml/min.

Method 31 (LC/MS):
MS instrument: Waters SQD; HPLC instrument: Waters UPLC; column: Zorbax SB-Aq (Agilent), 50 mm×2.1 mm, 1.8 µm; mobile phase A: water+0.025% formic acid, mobile phase B: acetonitrile+0.025% formic acid; gradient: 0.0 min 98% A→0.9 min 25% A→1.0 min 5% A→1.4 min 5% A→1.41 min 98% A→1.5 min 98% A; oven: 40° C.; flow rate: 0.60 ml/min; UV detection (DAD): 210 nm.

Method 32 (Preparative HPLC):
Column: Reprosil-Pur C18, 10 µm, 250 mm×30 mm; mobile phase: acetonitrile/water with 0.1% formic acid; gradient: 40:60→100:0 over a period of 20 min.

Method 33 (Preparative HPLC):
Column: Reprosil-Pur C18, 10 µm, 250 mm×30 mm; mobile phase: acetonitrile/water with 0.1% formic acid; gradient: 30:70→95:5 over a period of 38 min.

Method 34 (Preparative HPLC):
Column: Daicel Chiralpak AZ-H, 5 µm, 250 mm×4.6 mm; mobile phase: isohexane/ethanol with 0.2% diethylamine 50:50 (isocratic).

Method 35 (Preparative HPLC):
Column: Sunfire C18, 5 µm, 75 mm×30 mm; mobile phase: acetonitrile/water 55:45 (isocratic).

Method 36 (Preparative HPLC):
Column: Chromatorex C18, 10 µm, 250 mm×30 mm; mobile phase: acetonitrile/water with 0.1% formic acid; gradient: 30:70→95:5 over a period of 20 min.

Method 37 (Preparative HPLC):
Column: Chromatorex C18, 10 µm, 250 mm×30 mm; mobile phase: acetonitrile/water with 0.1% formic acid; gradient: 20:80→95:5 over a period of 20 min.

Method 38 (Preparative HPLC):

Column: Chromatorex C18, 10 μm, 250 mm×30 mm; mobile phase: acetonitrile/water with 0.1% formic acid; gradient: 10:90→95:5 over a period of 20 min.

The following descriptions of the coupling patterns of $^1$H NMR signals are based on the optical appearance of the signals in question and do not necessarily correspond to a strict, physically accurate interpretation. In general, the stated chemical shift refers to the centre of the signal in question; in the case of broad multiplets, a range is stated.

Melting points and melting ranges are, if stated, uncorrected.

All reactants or reagents whose preparation is not explicitly described hereinbelow were obtained commercially from generally accessible sources. For all remaining reactants or reagents whose preparation is likewise not described hereinbelow and which were not commercially available or which were obtained from sources not generally accessible, a reference to the published literature describing their preparation is given.

Starting Materials and Intermediates

Example 1A 1-(2,2-Diethoxyethyl)-1'-(tetrahydro-2H-pyran-2-yl)-1H,1'H-3,4'-bipyrazole-5-amine

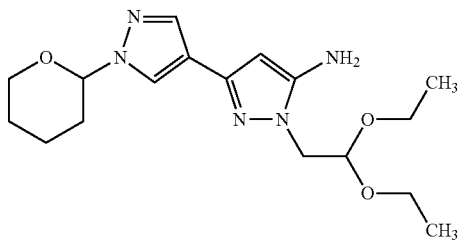 [SMILES: CCOC(Cn1nc(-c2cnn(C3CCCCO3)c2)cc1N)OCC]

Step 1: 1-(Tetrahydro-2H-pyran-2-yl)-1H-pyrazole-4-carbonitrile

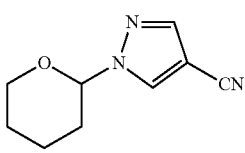 [SMILES: N#Cc1cnn(C2CCCCO2)c1]

The reaction was carried out in a 3 liter three-necked flask with internal thermometer under argon. 50 g (537 mmol) of 1H-pyrazole-4-carbonitrile were suspended in 1.66 liter of methylene chloride and, after 3 h, cooled to 3° C. using an ice bath. At this temperature, 10.2 g (53.7 mmol) of 4-toluenesulphonic acid monohydrate were added. At 3° to 6° C., 58.8 ml (54.2 g, 644 mmol) of 3,4 dihydro-2H-pyran were then added dropwise over a period of 30 min. The reaction was then stirred at RT overnight. The clear reaction solution was then washed with 2 M aqueous sodium carbonate solution and with water, dried over magnesium sulphate, filtered and concentrated. The residue was triturated with cyclohexane and the solid obtained was filtered off with suction and dried in a vacuum drying cabinet at 30° C. for 4 h. This gave 91.8 g (96% of theory) of the title compound as a light-yellow powder.

$^1$H NMR (400 MHz, DMSO-d$_6$, δ/ppm): 8.76 (s, 1H), 8.11 (s, 1H), 5.50 (dd, J$^1$=9.66 Hz, J$^2$=2.57 Hz, 1H), 4.02-3.82 (m, 1H), 3.72-3.56 (m, 1H), 2.15-1.82 (m, 3H), 1.76-1.40 (m, 4H).

LC/MS (Method 3, ESIpos): R$_t$=0.70 min, m/z=178 [M+H]$^+$.

Step 2: (2E)-3-Amino-3-[1-(tetrahydro-2H-pyran-2-yl)-1H-pyrazol-4-yl]acrylonitrile

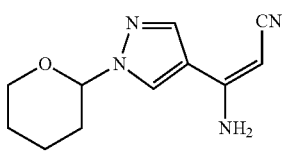 [SMILES: N#C/C=C(/N)c1cnn(C2CCCCO2)c1]

Under argon, 2.8 ml (53.6 mmol) of acetonitrile were initially charged in 150 ml of THF, and 21.4 ml (53.6 mmol) of a 2.5 M solution of n-buthyllithium in n-hexane were added at −70° C. After 15 min at −70° C., a solution of 9.5 g (53.6 mmol) of the compound of Example 1A/Step 1 in 20 ml of THF was added a little at a time. The reaction was stirred at −70° C. for 1 h and then at RT for 1 h, 1 ml of water was then added and the mixture was diluted with ethyl acetate. The organic phase was separated off, washed with saturated sodium chloride solution, dried over sodium sulphate, filtered and concentrated. The residue was triturated with tert-butyl methyl ether, and the crystals were filtered off and dried under reduced pressure. This gave 6.46 g (54% of theory) of the title compound.

$^1$H NMR (400 MHz, DMSO-d$_6$, δ/ppm): 8.36 (s, 1H), 7.89 (s, 1H), 6.64 (s, 2H), 5.39 (dd, 1H), 4.29 (s, 1H), 3.91 (d, 1H), 3.70-3.46 (m, 1H), 2.16-1.38 (m, 6H).

LC/MS (Method 1, ESIpos): R$_t$=0.78 min, m/z=219 [M+H]$^+$.

Step 3: 1-(2,2-Diethoxyethyl)-1'-(tetrahydro-2H-pyran-2-yl)-1H,1'H-3,4'-bipyrazole-5-amine

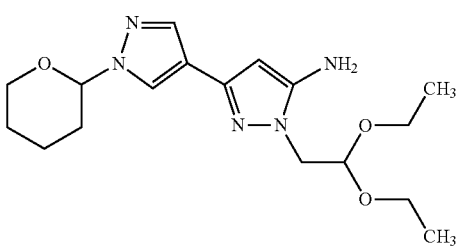 [SMILES: CCOC(Cn1nc(-c2cnn(C3CCCCO3)c2)cc1N)OCC]

15.2 g (69.6 mmol) of the compound of Example 1A/Step 2 and 11.4 g (76.6 mmol) of (2,2-di-ethoxyethyl)hydrazine were dissolved in 150 ml of ethanol. 0.7 ml of 1 M hydrochloric acid were added, and the solution was divided into several microwave reactor vessels (20 ml). Each batch was heated in a single-mode microwave reactor (Biotage Emrys Optimizer) at 120° C. for 1 h. After the reaction had ended the batches were combined, the solvent was distilled off under reduced pressure and the residue was extracted three times with ethyl acetate. The combined organic phases were washed with dilute sodium bicarbonate solution, dried over sodium sulphate, filtered and concentrated under reduced pressure. The crude product was purified chromatographically (silica gel, mobile phase gradient cyclohexane/ethyl acetate 1:1→100% ethyl acetate, the column was washed with ethyl acetate/methanol 20:1). This gave 17.4 g (67% of theory) of the title compound.

$^1$H NMR (400 MHz, DMSO-$d_6$, δ/ppm): 8.02 (s, 1H), 7.64 (s, 1H), 5.47 (s, 2H), 5.10 (s, 2H), 4.78 (s, 1H), 3.92 (d, 3H), 3.73-3.37 (m, 5H), 1.91 (br. s, 3H), 1.53 (d, 3H), 1.06 (t, 6H).

LC/MS (Method 3, ESIpos): $R_t$=0.79 min, m/z=350 [M+H]$^+$.

Example 2A 1-(2,2-Diethoxyethyl)-1'-(4-methoxybenzyl)-1H,1'H-3,4'-bipyrazole-5-amine

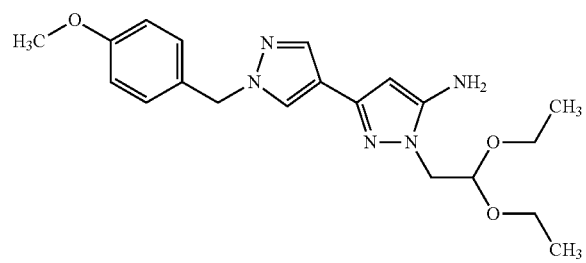 [SMILES: CCOC(Cn1nc(-c2cnn(Cc3ccc(OC)cc3)c2)cc1N)OCC]

Step 1:
1-(4-Methoxybenzyl)-1H-pyrazole-4-carbonitrile

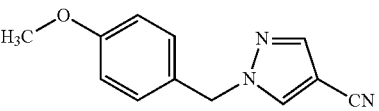 [SMILES: COc1ccc(Cn2cc(C#N)cn2)cc1]

At 0° C., 1 g (10.7 mmol) of 1H-pyrazole-4-carbonitrile and 2.4 g (11.8 mmol) of 4-methoxybenzyl bromide were initially charged in 22 ml of THF. 1.3 g (11.8 mmol) of potassium tert-butoxide were added a little at a time, and the reaction was stirred at RT overnight. The precipitated solid was then filtered off, and the mother liquor was freed from the solvent on a rotary evaporator. The residue was dissolved in ethyl acetate and the solution was washed with water and saturated sodium chloride solution, dried over sodium sulphate, filtered and concentrated. This gave 2 g (87% of theory) of the title compound, which was used without further purification for the subsequent step.

GC/MS (Method 8, EIpos): $R_t$=6.73 min, m/z=213 [M]$^+$.

Step 2: (2E)-3-Amino-3-[1-(4-methoxybenzyl)-1H-pyrazol-4-yl]acrylonitrile

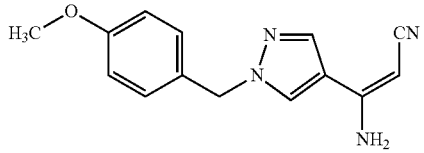 [SMILES: COc1ccc(Cn2cc(/C(N)=C\C#N)cn2)cc1]

105 ml of THF were initially charged and cooled to −70° C. 25.8 ml (41.3 mmol) of a 1.6 M solution of n-butyllithium in n-hexane were then added. With vigorous stirring, 2.2 ml (41.3 mmol) of acetonitrile were added dropwise over a period of 5 min, and the reaction was stirred for another 10 min. A solution of 8.0 g (37.5 mmol) of the compound of Example 2A/Step 1 in 4 ml of THF was then added dropwise at −70° C. The reaction mixture was stirred initially at −70° C. for 30 min and then at RT for 1 h. With ice bath cooling, 12 ml of water were then added, and the reaction was concentrated on a rotary evaporator. The residue was taken up in 100 ml of ethyl acetate, and the solution was washed with in each case 50 ml of water and saturated sodium chloride solution, dried over sodium sulphate, filtered and concentrated. The oily residue was dissolved in 20 ml of methylene chloride, and a little cyclohexane was added. Slow concentration at RT under atmospheric pressure resulted in the formation of a precipitate, which was filtered off. The solid was washed with n-pentane and dried under reduced pressure. This gave 4.26 g (44.6% of theory) of the title compound.

$^1$H NMR (400 MHz, DMSO-$d_6$, δ/ppm): 8.20 (s, 1H), 7.85 (s, 1H), 7.21 (d, 2H), 6.91 (d, 2H), 6.61 (s, 2H), 5.23 (s, 2H), 4.20 (s, 1H), 3.73 (s, 3H).

LC/MS (Method 3, ESIpos): $R_t$=0.81 min, m/z=255 [M+H]$^+$.

Step 3: 1-(2,2-Diethoxyethyl)-1'-(4-methoxybenzyl)-1H,1'H-3,4'-bipyrazol-5-amine

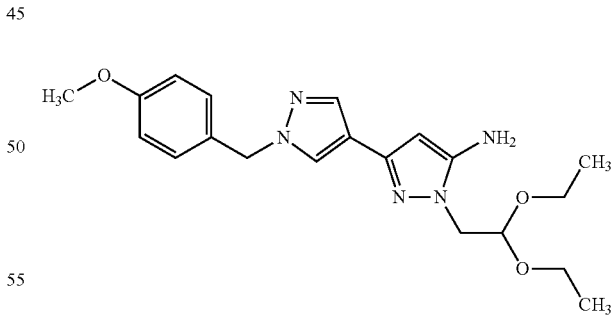

1.27 g (4.99 mmol) of the compound of Example 2A/Step 2 and 0.77 g (5.2 mmol) of (2,2-di-ethoxyethyl)hydrazine were initially charged in 10.6 ml of ethanol, and 50 µl of 1 M hydrochloric acid were added. The reaction was stirred at 120° C. in a microwave oven (Biotage Initiator, with Dynamic Field Tuning) for 45 min. The solvent was then removed under reduced pressure. The crude product obtained in this manner (1.87 g, 97% of theory) was used without further purification for subsequent reactions.

LC/MS (Method 4, ESIpos): R$_t$=0.76 min, m/z=372 [M+H]$^+$.

Example 3A 1-(1,1-Dimethoxypropan-2-yl)-1'-(4-methoxybenzyl)-1H,1'H-3,4'-bipyrazole-5-amine

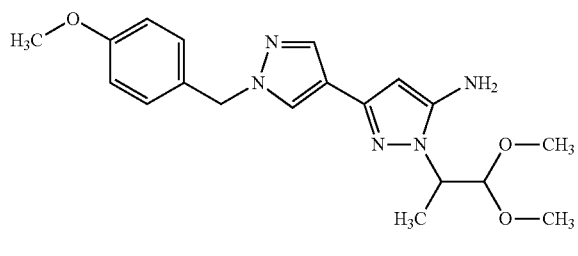

Step 1: (1,1-Dimethoxypropan-2-yl)hydrazine

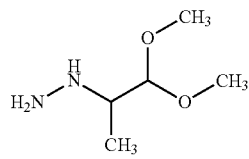

6.25 g (34.1 mmol) of 2-bromo-1,1-dimethoxypropane and 6.65 ml (137 mmol) of hydrazine hydrate were stirred under reflux in an oil bath at 140° C. for 6 h. After cooling, the two-phase reaction mixture was extracted with 50 ml of tert-butyl methyl ether. The organic phase was filtered, the filtrate was concentrated on a rotary evaporator and the residue was dried under high vacuum. This gave 1.89 g (21% of theory) of a pale yellow oil which was reacted directly, without further purification, in the subsequent reaction.

Step 2: 1-(1,1-Dimethoxypropan-2-yl)-1'-(4-methoxybenzyl)-1H,1'H-3,4'-bipyrazole-5-amine

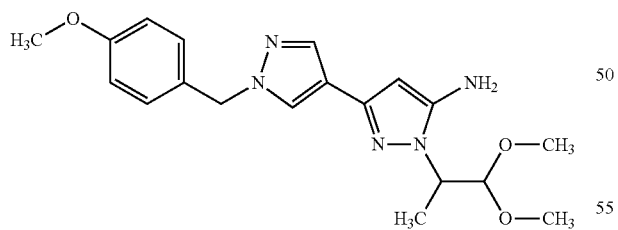

1.35 g (5.31 mmol) of the compound of Example 2A/Step 2 and 1.78 g of the compound from Example 3A/Step 1 were dissolved in 32 ml of methanol and 53 μl (53 μmol) of 1 M hydrochloric acid were added. The solution was divided into two batches and stirred in a microwave oven (Biotage Initiator, with Dynamic Field Tuning) at 120° C. for 15 min. The two batches were then re-combined and concentrated on a rotary evaporator. The residue was purified by preparative HPLC (Method 10). This gave 990 mg (50% of theory) of the title compound.

$^1$H NMR (400 MHz, DMSO-d$_6$, δ/ppm): 7.90 (s, 1H), 7.58 (s, 1H), 7.22 (d, 2H), 6.90 (d, 2H), 5.39 (s, 1H), 5.21 (s, 1H), 5.10 (s, 2H), 4.53 (d, 1H), 4.24 (quin, 1H), 3.73 (s, 3H), 3.10 (s, 3H), 1.29 (d, 3H).

LC/MS (Method 3, ESIpos): R$_t$=0.79 min, m/z=372 [M+H]$^+$.

Example 4A 1-(2,2-Diethoxyethyl)-3-(pyridin-3-yl)-1H-pyrazole-5-amine

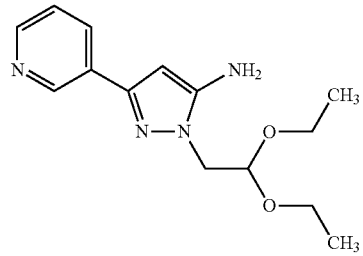 [SMILES: CCOC(Cn1nc(-c2cccnc2)cc1N)OCC]

With gentle heating, 125 g (812 mmol, purity 95%) of 3-oxo-3-(pyridin-3-yl)propionitrile [lit. for example: P. Seneci et al., Synth. Commun. 1999, 29 (2), 311-341; also available commercially] were dissolved in 1.25 liters of ethanol. 126 g (853 mmol) of (2,2-diethoxyethyl)hydrazine and 4.1 ml (4.06 mmol) of 1 M hydrochloric acid were then added. The reaction mixture was heated under reflux for 4 h, and all volatile components were then substantially removed on a rotary evaporator. The residue obtained was taken up in ethyl acetate, and the solution was washed with water and dried over anhydrous magnesium sulphate. After filtration, the mixture was evaporated to dryness. The residue that remained was triturated with diisopropyl ether at RT. The resulting solid was then filtered off with suction and dried under high vacuum. This gave 153 g (65% of theory, purity 96%) of the title compound.

$^1$H NMR (400 MHz, DMSO-d$_6$, δ/ppm): 8.88 (d, 1H), 8.44 (dd, 1H), 8.02 (dt, 1H), 7.37 (dd, 1H), 5.79 (s, 1H), 5.29 (s, 2H), 4.85 (t, 1H), 4.02 (d, 2H), 3.70-3.62 (m, 2H), 3.48-3.40 (m, 2H), 1.07 (t, 6H).

LC/MS (Method 3, ESIpos): R$_t$=0.52 min, m/z=277 [M+H]$^+$.

Example 5A

6-[1-(4-Methoxybenzyl)-1H-pyrazol-4-yl]-1H-imidazo[1,2-b]pyrazole

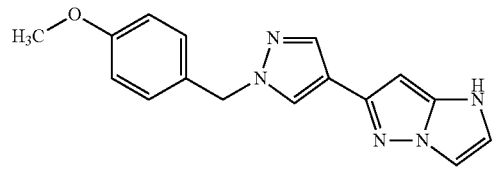 [SMILES: COc1ccc(Cn2cc(-c3cc4[nH]ccn4n3)cn2)cc1]

In a microwave oven (Biotage Initiator, with Dynamic Field Tuning), 155 mg (0.40 mmol) of the compound of Example 2A in 0.4 ml of ethanol and 0.2 ml of 2 M sulphuric acid were heated at 120° C. for 15 min. The reaction was then purified directly by preparative HPLC (Method 11). The product fractions were concentrated and the residue was dried under high vacuum. This gave 54 mg (46% of theory) of the title compound.

¹H NMR (400 MHz, DMSO-d₆, δ/ppm): 11.44 (br, 1H), 8.08 (s, 1H), 7.79 (s, 1H), 7.58 (s, 1H), 7.25 (d, 2H), 7.22 (s, 1H), 6.91 (d, 2H), 6.03 (s, 1H), 5.27 (s, 2H), 3.73 (s, 3H).

LC/MS (Method 3, ESIpos): R$_t$=0.72 min, m/z=294 [M+H]⁺.

Example 6A

4-Methyl-3-[6-(pyridin-3-yl)-1H-imidazo[1,2-b]pyrazol-1-yl]aniline

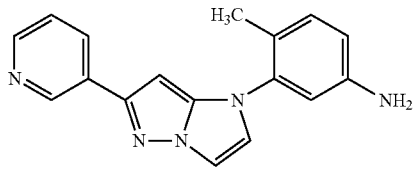

Step 1: 1-(2,2-Diethoxyethyl)-N-(2-methyl-5-nitrophenyl)-3-(pyridin-3-yl)-1H-pyrazole-5-amine

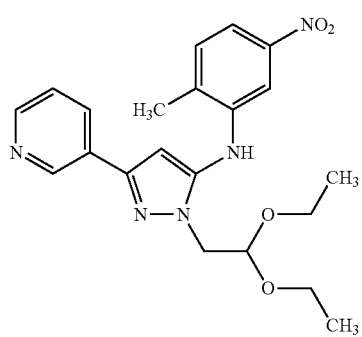 [SMILES: CCOC(Cn1nc(-c2cccnc2)cc1Nc1cc([N+](=O)[O-])ccc1C)OCC]

Under argon, 155 g (561 mmol) of the compound of Example 4A together with 133 g (617 mmol) of 2-bromo-4-nitrotoluene, 12.6 g (56.1 mmol) of palladium(II) acetate, 48.7 g (84.1 mmol) of xantphos [4,5-bis(diphenylphosphino)-9,9-dimethylxanthene] and 548 g (1683 mmol) of caesium carbonate in 3.1 liters of 1,4-dioxane were heated at reflux. After 4 h, the mixture was cooled to RT and filtered through kieselguhr, and the filtrate was concentrated on a rotary evaporator. The crude product obtained in this manner was purified by filtration with suction through silica gel (mobile phase gradient ethyl acetate/petroleum ether 4:1→100% ethyl acetate). The product fractions were combined and freed from the solvent on a rotary evaporator. Trituration with diisopropyl ether at RT, removal of the solid by filtration with suction and drying under high vacuum gave 195 g (84% of theory) of the title compound.

¹H NMR (400 MHz, DMSO-d₆, δ/ppm): 9.04 (d, 1H), 8.52 (dd, 1H), 8.18 (dt, 1H), 7.64-7.61 (m, 2H), 7.50 (d, 1H), 7.46-7.42 (m, 2H), 6.80 (s, 1H), 4.90 (t, 1H), 4.18 (d, 2H), 3.64-3.56 (m, 2H), 3.47-3.40 (m, 2H), 2.38 (s, 3H), 1.00 (t, 6H).

LC/MS (Method 3, ESIpos): R$_t$=1.03 min, m/z=412 [M+H]⁺, 823 [2M+H]⁺.

Step 2: 1-(2-Methyl-5-nitrophenyl)-6-(pyridin-3-yl)-1H-imidazo[1,2-b]pyrazole

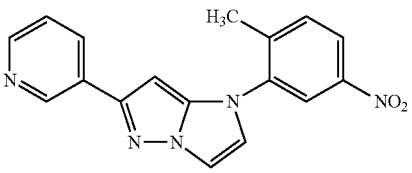 [SMILES: Cc1ccc([N+](=O)[O-])cc1-n1ccn2nc(-c3cccnc3)cc12]

496 ml (992 mmol) of 2 M sulphuric acid were added to a solution of 170 g (413 mmol) of the compound of Example 6A/Step 1 in 1.7 liters of ethanol, and the mixture was heated under reflux for 4 h. This resulted in the precipitation of a white solid. After cooling to RT, the solid was filtered off with suction and washed with a little ethanol. The solid was then divided between water and ethyl acetate and the heterogeneous mixture was made neutral to slightly alkaline by addition of dilute aqueous sodium hydroxide solution. The organic phase was separated off and freed from the solvent on a rotary evaporator. The residue obtained was triturated with a little acetonitrile at RT, and the solid was filtered off with suction and dried under high vacuum. This gave 127 g (93% of theory, 97% pure) of the title compound.

¹H NMR (400 MHz, DMSO-d₆, δ/ppm): 9.06 (d, 1H), 8.49 (dd, 1H), 8.31 (d, 1H), 8.26 (dd, 1H), 8.19 (dt, 1H), 7.98 (d, 1H), 7.79 (d, 1H), 7.66 (d, 1H), 7.43 (dd, 1H), 6.46 (s, 1H), 2.43 (s, 3H).

LC/MS (Method 3, ESIpos): R$_t$=0.97 min, m/z=320 [M+H]⁺.

Step 3: 4-Methyl-3-[6-(pyridin-3-yl)-1H-imidazo[1,2-b]pyrazol-1-yl]aniline

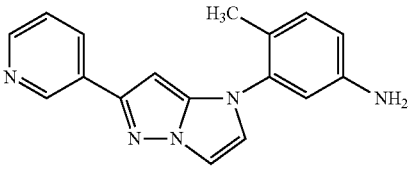

In two batches, in each case 63.5 g (398 mmol) of the compound of Example 6A/Step 2 were dissolved in 1.25 liters of ethanol and 6.35 g of palladium (10% on activated carbon) were added. The mixture was hydrogenated at RT under an atmosphere of hydrogen at atmospheric pressure for 48 h. The mixture was then filtered through a little kieselguhr to remove the catalyst. The filtrate was concentrated to dryness on a rotary evaporator. The crude products of both batches were combined and, at RT, triturated with diisopropyl ether to which a little ethyl acetate had been added. Removal of the solid by filtration with suction and drying under high vacuum gave 108 g (94% of theory) of the title compound.

¹H NMR (400 MHz, DMSO-d₆, δ/ppm): 9.05 (d, 1H), 8.47 (dd, 1H), 8.18 (dt, 1H), 7.83 (d, 1H), 7.43 (d, 1H), 7.41 (dd, 1H), 7.06 (d, 1H), 6.63 (d, 1H), 6.59 (dd, 1H), 6.29 (s, 1H), 2.08 (s, 3H).

LC/MS (Method 3, ESIpos): $R_t$=0.59 min, m/z=290 [M+H]$^+$.

Example 7A

4-Methyl-3-[6-(1H-pyrazol-4-yl)-1H-imidazo[1,2-b]pyrazol-1-yl]aniline

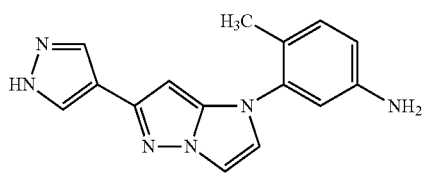

Step 1: 1-(2,2-Diethoxyethyl)-N-(2-methyl-5-nitrophenyl)-1'-(tetrahydro-2H-pyran-2-yl)-1H,1'H-3,4'-bipyrazole-5-amine

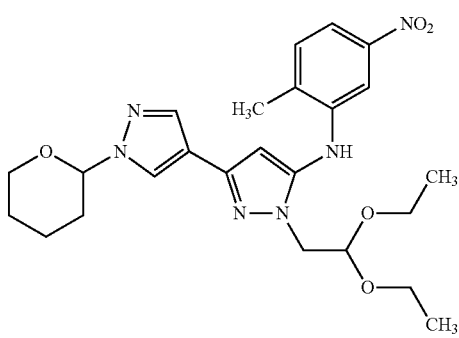 [SMILES: CCOC(Cn1nc(-c2cnn(C3CCCCO3)c2)cc1Nc1cc([N+](=O)[O-])ccc1C)OCC]

Under argon, 12.3 g (35.2 mmol) of the compound of Example 1A, 9.9 g (45.8 mmol) of 2-bromo-4-nitrotoluene, 0.79 g (3.52 mmol) of palladium(II) acetate, 22.9 g (70.4 mmol) of caesium carbonate and 2.04 g (3.52 mmol) of xantphos [4,5-bis(diphenylphosphino)-9,9-dimethylxanthene] in 170 ml of 1,4-dioxane were heated at reflux for 4 h. After cooling to RT, the mixture was filtered through kieselguhr and the filtrate was concentrated on a rotary evaporator. The residue was taken up in ethyl acetate and the mixture was washed with semiconcentrated sodium bicarbonate solution and then with concentrated sodium chloride solution. The organic phase was dried over anhydrous sodium sulphate and concentrated. The crude product was purified chromatographically on silica gel (mobile phase gradient dichloromethane/ethyl acetate 2:1→1:3). This gave 15.9 g (92% of theory) of the title compound.

$^1$H NMR (400 MHz, DMSO-d$_6$, δ/ppm): 8.20 (s, 1H), 7.80 (s, 1H), 7.60 (dd, 1H), 7.52 (s, 1H), 7.48 (d, 1H), 7.41 (d, 1H), 6.40 (d, 1H), 5.41 (dd, 1H), 4.83 (t, 1H), 4.09 (d, 2H), 3.93 (m, 1H), 3.67-3.54 (m, 3H), 3.41 (m, 2H), 2.36 (s, 3H), 2.11 (m, 1H), 1.94 (m, 2H), 1.68 (m, 1H), 1.55 (m, 2H), 0.99 (t, 6H).

LC/MS (Method 4, ESIpos): $R_t$=1.20 min, m/z=485 [M+H]$^+$.

Step 2: 1-(2-Methyl-5-nitrophenyl)-6-(1H-pyrazol-4-yl)-1H-imidazo[1,2-b]pyrazole

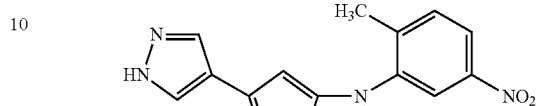

The compound from Example 7A/Step 1 (5.5 g, 11.3 mmol) was dissolved in 80 ml of ethanol, and 17 ml of 2 M sulphuric acid were added. The reaction was then divided into five 20 ml-microwave reactor vessels, and each batch was heated in a single-mode microwave reactor (Biotage Emrys Optimizer) at 120° C. for 15 min. The batches were then combined again, poured into dilute aqueous sodium bicarbonate solution and extracted twice with methylene chloride. The combined organic phases were dried over sodium sulphate, filtered and concentrated. In four portions, the residue was purified by preparative HPLC (Method 25). This gave 2.1 g (86% pure, 52% of theory) of the title compound.

$^1$H NMR (400 MHz, DMSO-d$_6$, δ/ppm): 8.26-8.22 (m, 2H), 7.90 (s, 2H), 7.83 (d, 1H), 7.78 (d, 1H), 7.51 (d, 1H), 6.00 (s, 1H), 2.43 (s, 3H).

LC/MS (Method 3, ESIpos): $R_t$=0.75 min, m/z=309 [M+H]$^+$.

Step 3: 4-Methyl-3-[6-(1H-pyrazol-4-yl)-1H-imidazo[1,2-b]pyrazol-1-yl]aniline

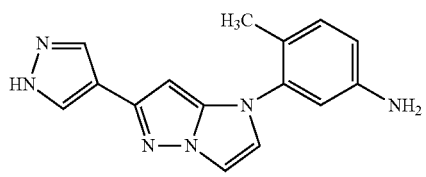 [SMILES: Cc1ccc(N)cc1-n1ccn2nc(-c3cn[nH]c3)cc12]

The compound from Example 7A/Step 2 (906 mg, 2.94 mmol) was dissolved in 45 ml of ethanol and 10% Pd/C (272 mg) and cyclohexene (3.30 ml, 32.3 mmol) were added under argon. The reaction was heated under reflux for 16 h, then filtered off with suction through kieselguhr and concentrated. The title compound was obtained in a yield of 810 mg (99% of theory).

$^1$H NMR (400 MHz, DMSO-d$_6$, δ/ppm): 7.80 (s, 2H), 7.71 (d, 1H), 7.32 (d, 1H), 7.12 (d, 1H), 6.74 (s, 1H), 6.69 (d, 1H), 5.86 (s, 1H), 2.11 (s, 3H).

LC/MS (Method 4, ESIpos): $R_t$=0.58 min, m/z=278 [M+H]$^+$.

Example 8A

3-{6-[1-(4-Methoxybenzyl)-1H-pyrazol-4-yl]-1H-imidazo[1,2-b]pyrazol-1-yl}-4-methylaniline trifluoroacetate

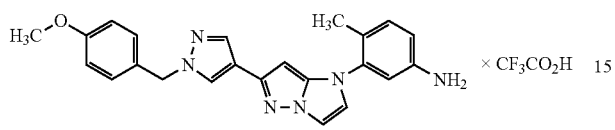

Step 1: 1-(2,2-Diethoxyethyl)-1'-(4-methoxybenzyl)-N-(2-methyl-5-nitrophenyl)-1H,1'H-3,4'-bipyrazole-5-amine

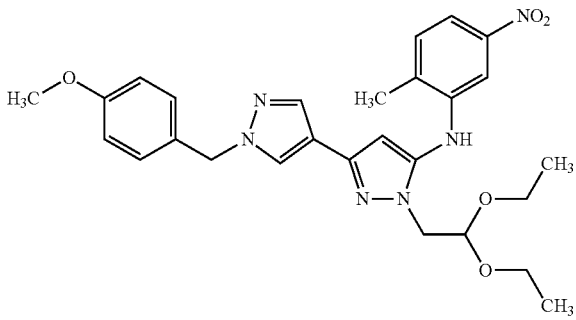 [SMILES: CCOC(Cn1nc(-c2cnn(Cc3ccc(OC)cc3)c2)cc1Nc1cc([N+](=O)[O-])ccc1C)OCC]

Under argon, a mixture of the compound from Example 2A (2.9 g, 7.5 mmol), 2-bromo-4-nitrotoluene (2.11 g, 9.78 mmol), palladium(II) acetate (0.17 g, 0.75 mmol), caesium carbonate (4.90 g, 15.1 mmol) and xantphos (4,5-bis(diphenylphosphino)-9,9-dimethylxanthene; 0.44 g, 0.75 mmol) in 37 ml of 1,4-dioxane was divided into several 20 ml-microwave reactor vessels. Each batch was heated in a single-mode microwave reactor (Biotage Emrys Optimizer) at 150° C. for 30 min. The batches were subsequently combined and filtered through kieselguhr, and the filtrate was concentrated on a rotary evaporator. The residue was taken up in ethyl acetate and washed with semiconcentrated sodium bicarbonate solution and then with concentrated sodium chloride solution. The organic phase was dried over anhydrous sodium sulphate and concentrated. The crude product was purified chromatographically (Method 26). This gave 2.74 g (70% of theory) of the title compound.

$^1$H NMR (400 MHz, DMSO-$d_6$, δ/ppm): 8.08 (s, 1H), 7.75 (s, 1H), 7.60 (dd, 1H), 7.49 (s, 1H), 7.46 (d, 1H), 7.40 (d, 1H), 7.26 (d, 2H), 6.34 (s, 1H), 5.25 (s, 2H), 4.80 (t, 1H), 4.07 (d, 2H), 3.73 (s, 3H), 3.60-3.52 (m, 2H), 3.44-3.36 (m, 2H), 2.35 (s, 3H), 0.98 (t, 3H).

LC/MS (Method 4, ESIpos): $R_t$=1.25 min, m/z=521 [M+H]$^+$.

Step 2: 6-[1-(4-Methoxybenzyl)-1H-pyrazol-4-yl]-1-(2-methyl-5-nitrophenyl)-1H-imidazo-[1,2-b]pyrazole

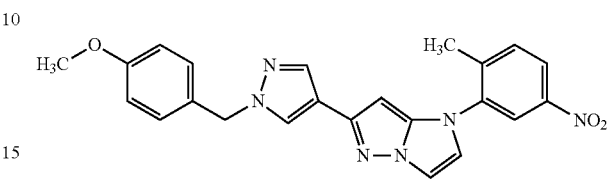

1.70 g (3.27 mmol) of the compound of Example 8A/Step 1 were dissolved in 12 ml of ethanol. 1.63 ml of 2 M sulphuric acid were added, and the mixture was heated in a single-mode microwave reactor (Biotage Emrys Optimizer) at 120° C. for 35 min. After the reaction had ended, the mixture was poured into dilute aqueous sodium bicarbonate solution and extracted twice with dichloromethane. The combined organic phases were dried over sodium sulphate, filtered and concentrated under reduced pressure. The title compound was obtained in a yield of 1.32 g (80% of theory, 85% pure).

$^1$H NMR (400 MHz, DMSO-$d_6$, δ/ppm): 8.24-8.21 (m, 2H), 8.04 (s, 1H), 7.82 (s, 1H), 7.75 (s, 2H), 7.53 (s, 1H), 7.22 (d, 2H), 6.90 (d, 2H), 5.98 (s, 1H), 5.23 (s, 2H), 3.71 (s, 1H), 2.42 (s, 3H).

LC/MS (Method 3, ESIpos): $R_t$=1.00 min, m/z=429 [M+H]$^+$.

Step 3: 3-{6-[1-(4-Methoxybenzyl)-1H-pyrazol-4-yl]-1H-imidazo[1,2-b]pyrazol-1-yl}-4-methylaniline trifluoroacetate

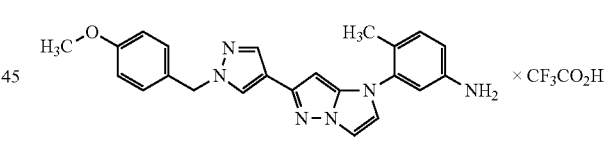

789 mg (1.25 mmol; purity 67%) of the compound from Example 8A/Step 2 together with 393 mg (6.23 mmol) of ammonium formate and 16.0 mg (0.02 mmol) of 10% palladium on activated carbon were initially charged in 11 ml of ethanol and 0.55 ml of water. The reaction was stirred in a single-mode microwave reactor (Biotage Emrys Optimizer) at 90° C. for 1 h. After cooling, insoluble components were filtered off, the filtrate was concentrated under reduced pressure and the residue was purified by preparative HPLC (Method 27). This gave 510 mg (80% of theory) of the title compound.

$^1$H NMR (400 MHz, DMSO-$d_6$, δ/ppm): 8.04 (s, 1H), 7.74 (s, 1H), 7.73 (d, 1H), 7.35 (d, 1H), 7.25-7.20 (m, 3H), 6.92-6.81 (m, 4H), 5.85 (s, 1H), 5.25 (s, 2H), 3.73 (s, 3H), 2.14 (s, 3H).

LC/MS (Method 3, ESIpos): $R_t$=0.86 min, m/z=399 [M+H]$^+$.

Example 9A

3-{6-[1-(4-Methoxybenzyl)-1H-pyrazol-4-yl]-3-methyl-1H-imidazo[1,2-b]pyrazol-1-yl}-4-methylaniline

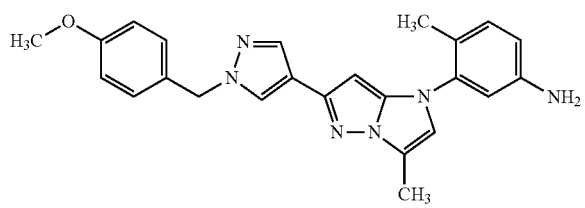 [SMILES: COc1ccc(Cn2cc(-c3cc4n(-c5cc(N)ccc5C)cc(C)n4n3)cn2)cc1]

Step 1: 1-(1,1-Dimethoxypropan-2-yl)-1'-(4-methoxybenzyl)-N-(2-methyl-5-nitrophenyl)-1H,1'H-3,4'-bipyrazole-5-amine

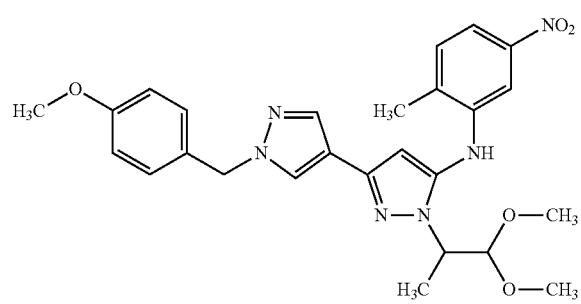

980 mg (2.64 mmol) of the compound of Example 3A and 627 mg (2.90 mmol) of 2-bromo-4-nitrotoluene were dissolved in 13 ml of dioxane, the mixture was degassed with argon and 59 mg (0.26 mmol) of palladium(II) acetate, 229 mg (0.40 mmol) of xantphos [4,5-bis(diphenylphosphino)-9,9-dimethylxanthene] and 2.57 g (7.91 mmol) of caesium carbonate were added. The mixture was heated in a microwave oven (Biotage Initiator, with Dynamic Field Tuning) at 150° C. for 30 min. The reaction was then filtered through kieselguhr, the filtrate was concentrated under reduced pressure and the residue was subjected to flash chromatography on silica gel (mobile phase dichloromethane/ethyl acetate 2:1). This gave 980 mg (73% of theory) of the title compound.

$^1$H NMR (400 MHz, DMSO-d$_6$, δ/ppm): 8.07 (s, 1H), 7.75 (s, 1H), 7.57-7.56 (m, 2H), 7.37 (d, 1H), 7.34 (d, 1H), 7.26 (d, 2H), 6.91 (d, 2H), 6.27 (s, 1H), 5.25 (s, 2H), 4.53 (d, 1H), 4.30 (m, 1H), 3.73 (s, 3H), 3.30 (s, 3H), 3.07 (s, 3H), 2.36 (s, 3H), 1.39 (d, 3H).

LC/MS (Method 4, ESIpos): $R_t$=1.19 min, m/z=507 [M+H]$^+$.

Step 2: 6-[1-(4-Methoxybenzyl)-1H-pyrazol-4-yl]-3-methyl-1-(2-methyl-5-nitrophenyl)-1H-imidazo[1,2-b]pyrazole

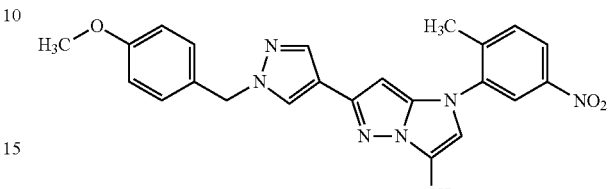

980 mg (385 mmol) of the compound of Example 9A/Step 1 in 9.8 ml of methanol together with 1.16 ml (2.32 mmol) of 2 M sulphuric acid were heated in a microwave oven (Biotage Initiator, with Dynamic Field Tuning) at 120° C. for 60 min. The reaction was then concentrated under reduced pressure and the residue was taken up in ethyl acetate. The organic phase was washed with saturated sodium bicarbonate solution and saturated sodium chloride solution, dried over sodium sulphate, filtered and concentrated on a rotary evaporator. The residue was dried under high vacuum. This gave 792 mg (93% of theory) of the title compound.

$^1$H NMR (400 MHz, DMSO-d$_6$, δ/ppm): 8.21-8.18 (m, 2H), 8.09 (s, 1H), 7.76 (s, 1H), 7.74 (d, 1H), 7.28 (d, 1H), 7.25 (d, 2H), 6.91 (d, 2H), 5.99 (s, 1H), 5.24 (s, 2H), 3.73 (s, 3H), 2.42 (s, 3H), 2.40 (s, 3H).

LC/MS (Method 3, ESIpos): $R_t$=1.05 min, m/z=443 [M+H]$^+$.

Step 3: 3-{6-[1-(4-Methoxybenzyl)-1H-pyrazol-4-yl]-3-methyl-1H-imidazo[1,2-b]pyrazol-1-yl}-4-methylaniline

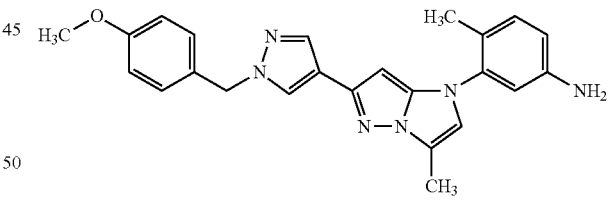

790 mg (1.78 mmol) of the compound of Example 9A/Step 2, 563 mg (8.93 mmol) of ammonium formate and 23 mg (0.02 mmol) of palladium (10% on carbon) in 9.6 ml of ethanol and 0.5 ml of water were heated under reflux for 1.5 h. The mixture was then concentrated under reduced pressure, the residue was suspended in dichloromethane, sodium sulphate was added and the mixture was filtered. The filtrate was concentrated under reduced pressure and the residue was dried under high vacuum. This gave 740 mg (96% of theory) of the title compound.

$^1$H NMR (400 MHz, DMSO-d$_6$, δ/ppm): 8.07 (s, 1H), 7.75 (s, 1H), 7.25 (d, 2H), 7.01 (m, 2H), 6.91 (d, 2H), 6.57 (d, 1H), 6.53 (dd, 1H), 5.82 (s, 1H), 5.23 (s, 2H), 5.17 (br, 2H), 3.73 (s, 3H), 2.37 (s, 3H), 2.07 (s, 3H).

LC/MS (Method 3, ESIpos): $R_t$=0.95 min, m/z=413 [M+H]$^+$.

Example 10A

4-Methoxy-3-[6-(pyridin-3-yl)-1H-imidazo[1,2-b]pyrazol-1-yl]aniline

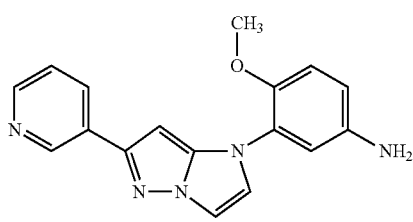

Step 1: 1-(2,2-Diethoxyethyl)-N-(2-methoxy-5-nitrophenyl)-3-(pyridin-3-yl)-1H-pyrazole-5-amine

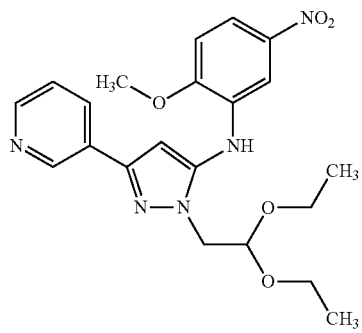 [SMILES: CCOC(Cn1nc(-c2cccnc2)cc1Nc1cc([N+](=O)[O-])ccc1OC)OCC]

200 mg (0.72 mmol) of the compound of Example 4A together with 201 mg (0.87 mmol) of 2-bromo-4-nitroanisole were dissolved in 3.6 ml of dioxane, the mixture was degassed with argon and 16 mg (0.07 mmol) of palladium(II) acetate, 63 mg (0.11 mmol) of xantphos [4,5-bis(diphenylphosphino)-9,9-dimethylxanthene] and 589 mg (1.81 mmol) of caesium carbonate were added. The mixture was heated in a microwave oven (Biotage Initiator, with Dynamic Field Tuning) at 150° C. for 30 min. The reaction was then filtered through kieselguhr, the filtrate was concentrated under reduced pressure and the residue was separated by preparative HPLC (Method 12) into its components. The product-containing fractions were combined and, under reduced pressure, concentrated almost completely. The residue was made alkaline with a little saturated aqueous sodium bicarbonate solution. The precipitate formed was filtered off, washed with water and dried. This gave 210 mg (92% pure, 62% of theory) of the title compound.

LC/MS (Method 2, ESIpos): $R_t$=2.15 min, m/z=428 [M+H]$^+$.

Step 2: 1-(2-Methoxy-5-nitrophenyl)-6-(pyridin-3-yl)-1H-imidazo[1,2-b]pyrazole

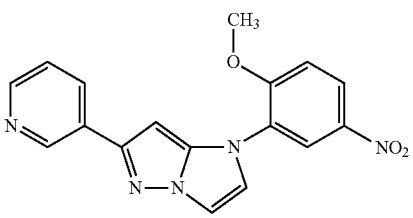 [SMILES: COc1ccc([N+](=O)[O-])cc1-n1ccn2nc(-c3cccnc3)cc12]

A solution of 210 mg (0.49 mmol) of the compound of Example 10A/Step 1 in 4.8 ml of ethanol and 0.49 ml (0.98 mmol) of 2 M sulphuric acid was heated in a microwave oven (Biotage Initiator, with Dynamic Field Tuning) at 120° C. for 15 min. The reaction was then purified directly by preparative HPLC (Method 12). The product-containing fractions were combined and concentrated almost completely under reduced pressure. The residue was made alkaline with a little saturated aqueous sodium bicarbonate solution, and the precipitate formed was filtered off, washed with water and dried. This gave 112 mg (89% pure, 61% of theory) of the title compound.

LC/MS (Method 4, ESIpos): $R_t$=0.73 min, m/z=336 [M+H]$^+$.

Step 3: 4-Methoxyl-3-[6-(pyridin-3-yl)-1H-imidazo[1,2-b]pyrazol-1-yl]aniline

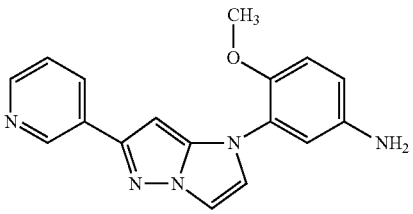

110 mg (89% pure, 0.29 mmol) of the compound of Example 10A/Step 2, 92 mg (1.46 mmol) of ammonium formate and 31 mg (0.1 mmol) of palladium (10% on carbon) in 9.7 ml ethanol and 0.97 ml of water were heated under reflux for 15 min. The mixture was then concentrated under reduced pressure, the residue was suspended in dichloromethane, sodium sulphate was added and the mixture was filtered. The filtrate was concentrated under reduced pressure and the residue was dried under high vacuum. This gave 46 mg (50% of theory) of the title compound.

LC/MS (Method 3, ESIpos): $R_t$=0.52 min, m/z=306 [M+H]$^+$.

Example 11A 2,4-Dimethyl-3-[6-(pyridin-3-yl)-1H-imidazo[1,2-b]pyrazol-1-yl]aniline

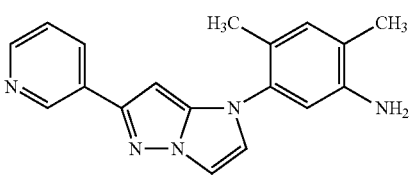 [SMILES: Cc1cc(C)c(-n2ccn3nc(-c4cccnc4)cc23)cc1N]

Step 1: 1-(2,2-Diethoxyethyl)-N-(2,4-dimethyl-5-nitrophenyl)-3-(pyridin-3-yl)-1H-pyrazole-5-amine

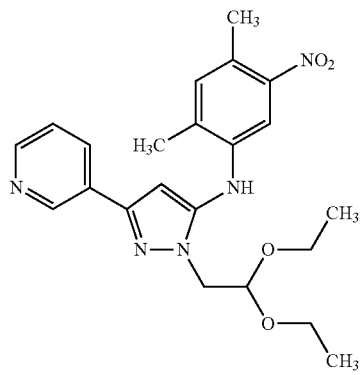 [SMILES: CCOC(Cn1nc(-c2cccnc2)cc1Nc1cc([N+](=O)[O-])c(C)cc1C)OCC]

Variant A:

200 mg (0.72 mmol) of the compound of Example 4A together with 200 mg (0.87 mmol) of 1-bromo-2,4-dimethyl-5-nitrobenzene were reacted and worked up analogously to the procedure of Example 10A/Step 1. This gave 200 mg (86% pure, 56% of theory) of the title compound.

LC/MS (Method 3, ESIpos): $R_t$=1.06 min, m/z=426 [M+H]$^+$.

Variant B:

1.02 g (3.68 mmol) of the compound of Example 4A together with 931 mg (4.05 mmol) of 1-bromo-2,4-dimethyl-5-nitrobenzene were dissolved in 15 ml of dioxane, the mixture was degassed with argon and 83 mg (0.37 mmol) of palladium(II) acetate, 319 mg (0.55 mmol) of xantphos [4,5-bis(diphenylphosphino)-9,9-dimethylxanthene] and 3.60 g (11.0 mmol) of caesium-carbonate were added. The mixture was heated in a microwave oven (Biotage Initiator, with Dynamic Field Tuning) at 140° C. for 60 min. The crude products of three identical reactions of this kind were combined and then filtered through kieselguhr. The filtrate was concentrated under reduced pressure and the residue was separated into its components by MPLC (silica gel, mobile phase cyclohexane/ethyl acetate 1:1→1:2). The product-containing fractions were combined and concentrated to dryness under reduced pressure. This gave a total of 4.18 g (89% of theory) of the title compound.

$^1$H NMR (400 MHz, CDCl$_3$, δ/ppm): 9.02 (m, 1H), 8.55 (dd, 1H), 8.07 (dt, 1H), 7.76 (s, 1H), 7.33 (dd, 1H), 7.11 (s, 1H), 6.66 (s, 1H), 6.41 (s, 1H), 4.81 (t, 1H), 4.27 (d, 2H), 3.88-3.80 (m, 2H), 3.66-3.58 (m, 2H), 2.52 (s, 3H), 2.32 (s, 3H), 1.26 (t, 6H).

LC/MS (Method 3, ESIpos): $R_t$=1.07 min, m/z=426 [M+H]$^+$.

Step 2: 1-(2,4-Dimethyl-5-nitrophenyl)-6-(pyridin-3-yl)-1H-imidazo[1,2-b]pyrazole

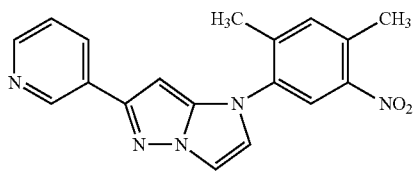 [SMILES: Cc1cc(C)c([N+](=O)[O-])cc1-n1ccn2nc(-c3cccnc3)cc12]

Variant A:

A solution of 195 mg (86% pure, 0.40 mmol) of the compound of Example 11A/Step 1 in 3.9 ml of ethanol and 0.39 ml (0.78 mmol) of 2 M sulphuric acid was heated in a microwave oven (Biotage Initiator, with Dynamic Field Tuning) at 120° C. for 15 min. The reaction was then stirred into 50 ml of ethyl acetate. The mixture was washed with saturated aqueous potassium carbonate solution and saturated aqueous sodium chloride solution, dried over sodium sulphate, filtered and concentrated under reduced pressure. Drying of the residue under reduced pressure gave 136 mg (85% pure, 88% of theory) of the title compound.

LC/MS (Method 2, ESIpos): $R_t$=1.89 min, m/z=334 [M+H]$^+$.

Variant B:

A solution of 4.17 g (9.81 mmol) of the compound of Example 11A/Step 1 in 42 ml of ethanol and 9.8 ml (19.6 mmol) of 2 M sulphuric acid was divided into four microwave reaction vessels which were then each heated in a microwave oven (Biotage Initiator, with Dynamic Field Tuning) at 130° C. for 15 min. The contents of the four reaction vessels were then stirred into about 100 ml of water. By addition of saturated aqueous sodium bicarbonate solution the aqueous phase was adjusted to a neutral pH. The mixture was then extracted repeatedly with ethyl acetate. The combined organic extracts were washed with saturated aqueous sodium chloride solution, dried over magnesium sulphate, filtered and concentrated under reduced pressure. The residue obtained was triturated with a little acetonitrile and filtered off again, and the solid was dried under high vacuum. This gave 2.8 g (85% of theory) of the title compound.

$^1$H NMR (400 MHz, DMSO-d$_6$, δ/ppm): 9.05 (m, 1H), 8.49 (dd, 1H), 8.18 (dt, 1H), 8.12 (s, 1H), 7.94 (d, 1H), 7.65 (s, 1H), 7.60 (d, 1H), 7.42 (dd, 1H), 6.42 (s, 1H), 2.59 (s, 3H), 2.35 (s, 3H).

LC/MS (Method 4, ESIpos): $R_t$=0.84 min, m/z=334 [M+H]$^+$.

Step 3: 2,4-Dimethyl-3-[6-(pyridin-3-yl)-1H-imidazo[1,2-b]pyrazol-1-yl]aniline

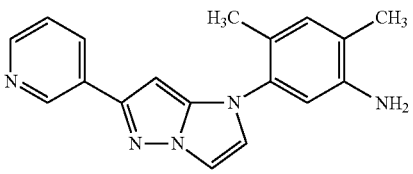 [SMILES: Cc1cc(C)c(-n2ccn3nc(-c4cccnc4)cc23)cc1N]

Variant A:

135 mg (85% pure, 0.34 mmol) of the compound of Example 11A/Step 2 were converted analogously to the procedure of Example 10A/Step 3 into 110 mg (87% pure, 92% of theory) of the title compound.

$^1$H NMR (400 MHz, DMSO-d$_6$, δ/ppm): 9.04 (d, 1H), 8.47 (dd, 1H), 8.17 (dt, 1H), 7.82 (d, 1H), 7.42-7.37 (m, 2H), 6.97 (s, 1H), 6.67 (s, 1H), 6.25 (s, 1H), 4.99 (s, 2H), 2.09 (s, 3H), 2.05 (s, 3H).

LC/MS (Method 2, ESIpos): $R_t$=1.63 min, m/z=304 [M+H]$^+$.

Variant B:

2.78 g (8.34 mmol) of the compound of Example 11A/Step 2, 2.63 g (41.7 mmol) of ammonium formate and 107 mg (0.10 mmol) of palladium (10% on carbon) in 55 ml of ethanol and 5.5 ml of water were heated under reflux for 2.5 h. The catalyst was then filtered off through kieselguhr and the filtrate was concentrated under reduced pressure. The residue was taken up in dichloromethane and washed successively with saturated aqueous sodium bicarbonate solution, water and saturated aqueous sodium chloride solution. After drying with anhydrous magnesium sulphate the mixture was filtered and the filtrate was concentrated under reduced pressure. The residue was dried under high vacuum. This gave 2.18 g (86% of theory) of the title compound.

$^1$H NMR (400 MHz, CDCl$_3$, δ/ppm): 9.04 (d, 1H), 8.52 (dd, 1H), 8.14 (dt, 1H), 7.46 (d, 1H), 7.32 (dd, 1H), 7.04 (s, 1H), 6.87 (d, 1H), 6.69 (s, 1H), 5.97 (s, 1H), 3.67 (br. s, 2H), 2.21 (s, 3H), 2.14 (s, 3H).

LC/MS (Method 4, ESIpos): R$_t$=0.68 min, m/z=304 [M+H]$^+$.

Example 12A

2-Fluoro-4-methyl-3-[6-(pyridin-3-yl)-1H-imidazo[1,2-b]pyrazol-1-yl]aniline

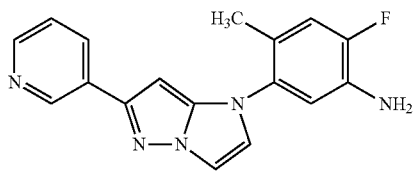

Step 1: 1-Bromo-4-fluoro-2-methyl-5-nitrobenzene

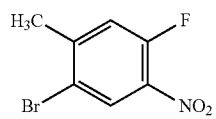

2.21 g (16.7 mmol) of nitronium tetrafluoroborate were suspended in 30 ml of dichloromethane. A solution of 3.0 g (15.9 mmol) of 2-bromo-5-fluorotoluene in 30 ml of dichloromethane was added dropwise under reflux. The mixture was then stirred under reflux for another 6 h. The mixture was then poured onto ice and extracted with dichloromethane, and the organic phase was washed with water, dried over sodium sulphate and concentrated on a rotary evaporator. This gave a yellow oil which formed crystals overnight. These were separated off, washed with 2 ml of pentane and dried. This gave 265 mg (6.9% of theory) of the title compound.

GC/MS (Method 8, EIpos): R$_t$=4.49 min, m/z=232/234 [M]$^+$.

Step 2: 1-(2,2-Diethoxyethyl)-N-(4-fluoro-2-methyl-5-nitrophenyl)-3-(pyridin-3-yl)-1H-pyrazole-5-amine

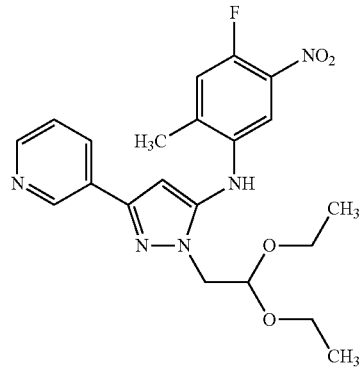 [SMILES: CCOC(Cn1nc(-c2cccnc2)cc1Nc1cc([N+](=O)[O-])c(F)cc1C)OCC]

250 mg (0.91 mmol) of the compound of Example 4A together with 254 mg (1.09 mmol) of the compound of Example 12A/Step 1 were reacted and worked up analogously to the procedure of Example 10A/Step 1. In deviation from this procedure, the product-containing fractions which had been obtained after preparative HPLC, concentrated to a residual volume and made alkaline with a little saturated sodium bicarbonate solution were extracted with ethyl acetate. The organic phase was washed saturated aqueous sodium chloride solution, dried over sodium sulphate, filtered and concentrated under reduced pressure. Drying of the residue gave 120 mg (85% pure, 26% of theory) of the title compound.

LC/MS (Method 3, ESIpos): R$_t$=1.03 min, m/z=430 [M+H]$^+$.

Step 3: 1-(4-Fluoro-2-methyl-5-nitrophenyl)-6-(pyridin-3-yl)-1H-imidazo[1,2-b]pyrazole

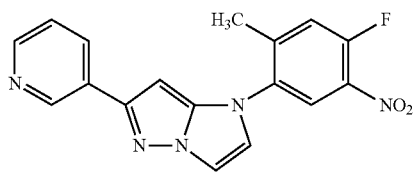 [SMILES: Cc1cc(F)c([N+](=O)[O-])cc1-n1ccn2nc(-c3cccnc3)cc12]

A solution of 120 mg (85% pure, 0.28 mmol) of the compound of Example 12A/Step 2 in 2.8 ml of ethanol and 0.28 ml (0.56 mmol) of 2 M sulphuric acid was heated in a microwave oven (Biotage Initiator, with Dynamic Field Tuning) at 120° C. for 30 min. The reaction was then concentrated under reduced pressure and the residue was suspended in ethyl acetate. The mixture was washed with saturated aqueous sodium bicarbonate solution, dried over sodium sulphate, filtered and concentrated under reduced pressure. Drying of the residue gave 85 mg (90% pure, 81% of theory) of the title compound.

$^1$H NMR (400 MHz, DMSO-d$_6$, δ/ppm): 9.04 (d, 1H), 8.49 (dd, 1H), 8.28 (d, 1H), 8.17 (dt, 1H), 7.95 (d, 1H), 7.82 (d, 1H), 7.60 (d, 1H), 7.42 (dd, 1H), 6.44 (s, 1H), 2.39 (s, 3H).

LC/MS (Method 2, ESIpos): $R_t$=1.81 min, m/z=338 [M+H]$^+$.

Step 4: 2-Fluoro-4-methyl-5-[6-(pyridin-3-yl)-1H-imidazo[1,2-b]pyrazol-1-yl]aniline

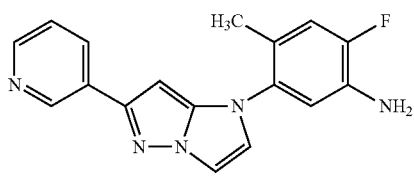

80 mg (0.23 mmol) of the compound of Example 12A/Step 3 were reacted analogously to the procedure of Example 10A/Step 3 to give 65 mg (94% pure, 84% of theory) of the title compound. Here, in deviation from the procedure, the mixture was stirred under reflux for 30 min (instead of 15 min).

$^1$H NMR (400 MHz, DMSO-$d_6$, δ/ppm): 9.04 (d, 1H), 8.47 (dd, 1H), 8.18 (dt, 1H), 7.84 (d, 1H), 7.43-7.38 (m, 2H), 7.09 (d, 1H), 6.82 (d, 1H), 6.28 (s, 1H), 5.29 (br, 2H), 2.07 (s, 3H).

LC/MS (Method 3, ESIpos): $R_t$=0.67 min, m/z=308 [M+H]$^+$.

Example 13A

4-Fluoro-3-[6-(pyridin-3-yl)-1H-imidazo[1,2-b]pyrazol-1-yl]aniline

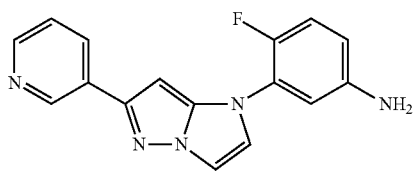

Step 1: 1-(2,2-Diethoxyethyl)-N-(2-fluoro-5-nitrophenyl)-3-(pyridin-3-yl)-1H-pyrazole-5-amine

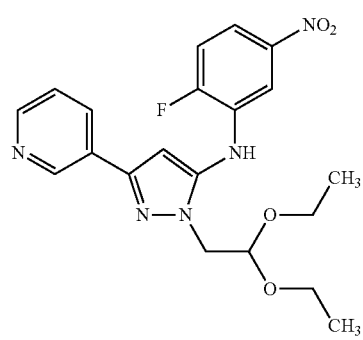 [SMILES: CCOC(Cn1nc(-c2cccnc2)cc1Nc1cc([N+](=O)[O-])ccc1F)OCC]

Under nitrogen, 576 mg (2.08 mmol) of the compound of Example 4A together with 504 mg (2.29 mmol) of 2-bromo-1-fluoro-4-nitrobenzene, 49.8 mg (0.21 mmol) of palladium (II) acetate, 181 mg (0.31 mmol) of xantphos [4,5-bis(diphenylphosphino)-9,9-dimethylxanthene] and 2.04 g (6.25 mmol) of caesium carbonate in 8.6 ml of 1,4-dioxane were heated under reflux for 1 h. After cooling, the mixture was filtered through Celite, the filter cake was washed with dioxane and the filtrate was concentrated under reduced pressure. The crude product obtained in this manner was combined with the crude product from a test reaction carried out analogously starting with 100 mg (0.36 mmol) of the compound of Example 4A and the combined products were purified on a Biotage system (100 g Snap column; mobile phase gradient hexane/ethyl acetate, from 0% ethyl acetate increasing slowly to 100% ethyl acetate, then ethyl acetate/methanol, increasing slowly to 80% methanol). This gave 342 mg (38% of theory) of the title compound.

$^1$H NMR (400 MHz, DMSO-$d_6$, δ/ppm): 9.00 (d, 1H), 8.49 (dd, 1H), 8.36 (s, 1H), 8.14 (dt, 1H), 7.62-7.73 (m, 2H), 7.38-7.53 (m, 2H), 6.85 (s, 1H), 4.84 (t, 1H), 4.17 (d, 2H), 3.56 (dq, 2H), 3.39 (dq, 2H), 0.95 (t, 6H).

LC/MS (Method 6, ESIpos): $R_t$=1.18 min, m/z=416 [M+H]$^+$.

Step 2: 1-(2-Fluoro-5-nitrophenyl)-6-(pyridin-3-yl)-1H-imidazo[1,2-b]pyrazole

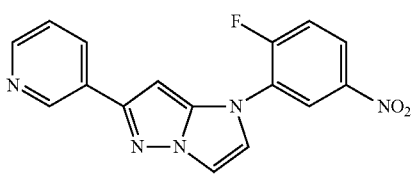 [SMILES: O=[N+]([O-])c1ccc(F)c(-n2ccn3nc(-c4cccnc4)cc23)c1]

0.99 ml (1.97 mmol) of 2 M sulphuric acid was added to a solution of 341 mg (0.82 mmol) of the compound of Example 13A/Step 1 in 10 ml of ethanol and the mixture was then heated in a microwave reactor at 130° C. for 30 min. After cooling, the reaction mixture was added to 15 ml of saturated aqueous potassium carbonate solution and stirred. The mixture was extracted twice with in each case 50 ml of ethyl acetate, and the combined organic phases were washed with saturated sodium chloride solution. After drying over sodium sulphate and filtration, the mixture was concentrated under reduced pressure. The crude product obtained in this manner was purified on a Biotage system (50 g Snap column; mobile phase gradient hexane/ethyl acetate, from 0% ethyl acetate increasing steadily to 100% ethyl acetate, then ethyl acetate/methanol, increasing slowly to 80% methanol). This gave 198 mg (67% of theory) of the title compound.

$^1$H NMR (400 MHz, DMSO-$d_6$, δ/ppm): 9.04 (d, 1H), 8.52 (dd, 1H), 8.48 (dd, 1H), 8.29 (ddd, 1H), 8.18 (dt, 1H), 8.00 (d, 1H), 7.82 (dd, 1H), 7.76 (dd, 1H), 7.41 (dd, 1H), 6.61 (d, 1H).

LC/MS (Method 6, ESIpos): $R_t$=0.87 min, m/z=324 [M+H]$^+$.

Step 3: 4-Fluoro-3-[6-(pyridin-3-yl)-1H-imidazo[1,2-b]pyrazol-1-yl]aniline

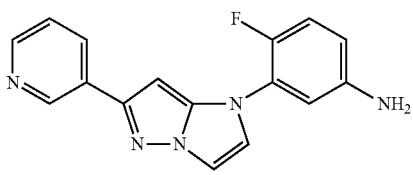

13 mg of palladium (10% on activated carbon) were added to a solution of 198 mg (0.61 mmol) of the compound of Example 13A/Step 2 in a mixture of 7.55 ml of ethanol and 0.38 ml of water. After addition of 193 mg (3.1 mmol) of ammonium formate, the reaction mixture was heated under reflux for 1 h. After cooling, the mixture was filtered off, the filtrate was diluted with ethyl acetate and the organic phase was washed with saturated aqueous sodium chloride solution. After drying over sodium sulphate and filtration, the mixture was concentrated under reduced pressure. The crude product obtained in this manner of the title compound (149 mg, 70% of theory) was reacted further without additional purification.

$^1$H NMR (400 MHz, DMSO-d$_6$, δ/ppm): 9.02 (d, 1H), 8.46 (dd, 1H), 8.16 (dt, 1H), 7.87 (d, 1H), 7.51 (t, 1H), 7.40 (dd, 1H), 7.11 (dd, 1H), 6.82 (dd, 1H), 6.46-6.54 (m, 2H), 5.28 (br. s, 2H).

LC/MS (Method 6, ESIpos): R$_t$=0.74 min, m/z=294 [M+H]$^+$.

Example 14A

2-Methyl-5-[6-(pyridin-3-yl)-1H-imidazo[1,2-b]pyrazol-1-yl]aniline

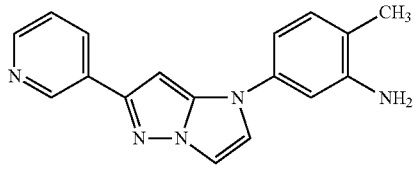

Step 1: 1-(2,2-Diethoxyethyl)-N-(4-methyl-3-nitrophenyl)-3-(pyridin-3-yl)-1H-pyrazole-5-amine

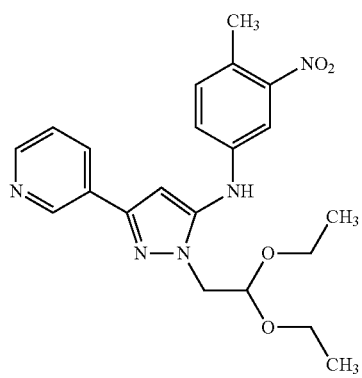 [SMILES: CCOC(Cn1nc(-c2cccnc2)cc1Nc1ccc(C)c([N+](=O)[O-])c1)OCC]

Analogously to Example 13A/Step 1, a test reaction of 200 mg (0.72 mmol) and the main reaction of 1.76 g (6.37 mmol) of the compound of Example 4A and 172 mg (0.80 mmol) and 1.51 g (7.01 mmol), respectively, of 4-bromo-2-nitrotoluene gave 1.11 g (40% of theory) of the title compound and 842 mg (29% of theory) of a slightly impure batch of the title compound.

$^1$H NMR (400 MHz, DMSO-d$_6$, δ/ppm): 8.99 (d, 1H), 8.47 (dd, 1H), 8.40 (s, 1H), 8.12 (dt, 1H), 7.48 (d, 1H), 7.39 (dd, 1H), 7.30 (d, 1H), 7.17 (dd, 1H), 6.70 (s, 1H), 4.85 (t, 1H), 4.14 (d, 2H), 3.57 (dq, 2H), 3.36 (dq, 2H), 2.38 (s, 3H), 0.96 (t, 6H).

LC/MS (Method 6, ESIpos): R$_t$=1.19 min, m/z=412 [M+H]$^+$.

Step 2: 1-(4-Methyl-3-nitrophenyl)-6-(pyridin-3-yl)-1H-imidazo[1,2-b]pyrazole

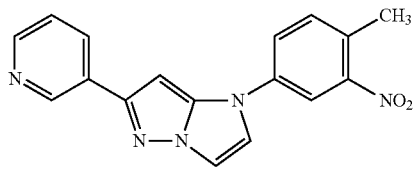 [SMILES: Cc1ccc(-n2ccn3nc(-c4cccnc4)cc23)cc1[N+](=O)[O-]]

Analogously to Example 13A/Step 2, a test reaction of 841 mg (2.04 mmol) and the main reaction of 1.1 g (2.67 mmol) of the compound of Example 14A/Step 1 gave a crude product which was initially purified on a Biotage system (100 g Snap column; mobile phase gradient hexane/ethyl acetate, from 0% ethyl acetate increasing steadily to 100% ethyl acetate, then ethyl acetate/methanol, from 0% methanol increasing slowly to 80% methanol). This gave 623 mg (69% of theory) of the title compound and material which was still impure. The impure material was purified once more by chromatography on a Biotage system (25 g Snap column; mobile phase gradient ethyl acetate/methanol, from 0% methanol increasing slowly to 80% methanol). This gave a further 225 mg (25% of theory) of the title compound.

$^1$H NMR (400 MHz, DMSO-d$_6$, δ/ppm): 9.08 (d, 1H), 8.49 (dd, 1H), 8.18-8.24 (m, 2H), 8.07 (d, 1H), 7.99 (d, 1H), 7.96 (dd, 1H), 7.65 (d, 1H), 7.43 (ddd, 1H), 7.02 (s, 1H), 2.49 (s, 2H).

LC/MS (Method 5, ESIpos): R$_t$=0.93 min, m/z=320 [M+H]$^+$.

Step 3: 2-Methyl-5-[6-(pyridin-3-yl)-1H-imidazo[1,2-b]pyrazol-1-yl]aniline

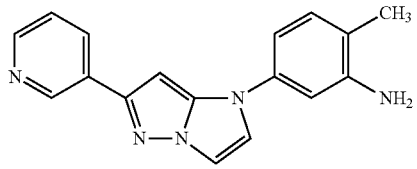 [SMILES: Cc1ccc(-n2ccn3nc(-c4cccnc4)cc23)cc1N]

Analogously to Example 13A/Step 3, a test reaction of 225 mg (0.71 mmol) and the main reaction of 622 mg (1.95 mmol) of the compound of Example 14A/Step 2 gave a crude product of the title compound (730 mg, 95% of theory) which was reacted further without additional purification.

$^1$H NMR (400 MHz, DMSO-d$_6$, δ/ppm): 9.04 (d, 1H), 8.47 (dd, 1H), 8.17 (dt, 1H), 7.85 (d, 1H), 7.72 (d, 1H), 7.42 (dd, 1H), 7.02 (d, 1H), 6.94 (d, 1H), 6.73-6.78 (m, 2H), 5.13 (br. s, 2H), 2.05 (s, 3H).

Example 15A

3-Bromo-5-(pentafluoro-λ⁶-sulphanyl)benzoic acid

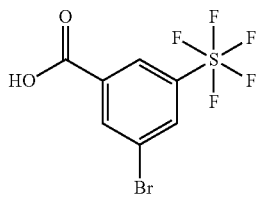 [SMILES: O=C(O)c1cc(Br)cc(S(F)(F)(F)(F)F)c1]

150 g (604 mmol) of 3-(pentafluoro-λ⁶-sulphanyl)benzoic acid [lit. e.g.: C. Zarantonello et al., *J. Fluorine Chem.* 2007, 128 (12), 1449-1453; WO 2005/047240-A1; also available commercially] were initially charged in 300 ml of trifluoroacetic acid, and 90 ml of concentrated sulphuric acid were added. 161.4 g (907 mmol) of N-bromosuccinimide (NBS) were added to the resulting clear solution. The reaction mixture was then stirred at a temperature of 50° C. overnight (about 18 h). After cooling to RT, the mixture was carefully stirred into about 2.25 liters of ice water. The precipitated product was filtered off with suction, washed with water and dried under high vacuum. This gave 193 g (96% of theory, 98% pure) of the title compound.

$^1$H NMR (400 MHz, DMSO-$d_6$, δ/ppm): 14.03 (br, 1H), 8.47 (t, 1H), 8.32 (t, 1H), 8.26 (dd, 1H).

LC/MS (Method 3, ESIneg): $R_t$=0.99 min, m/z=325/327 [M−H]⁻.

Example 16A

3-[4-(tert-Butoxycarbonyl)piperazin-1-yl]-5-(pentafluoro-λ⁶-sulphanyl)benzoic acid

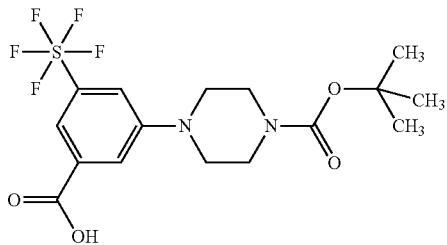 [SMILES: CC(C)(C)OC(=O)N1CCN(c2cc(C(=O)O)cc(S(F)(F)(F)(F)F)c2)CC1]

3.0 g (9.2 mmol) of the compound of Example 15A and 2.05 g (11.0 mmol) of tert-butyl piperazine-1-carboxylate were initially charged in 80 ml of toluene and the mixture was degassed with argon. 135 mg (0.18 mmol) of [2-(2-aminoethyl)phenyl](chloro)palladiumdicyclohexyl-(2',4',6'-triisopropylbiphenyl-2-yl)phosphane/tert-butyl methyl ether adduct, 87.5 mg (0.18 mmol) of dicyclohexyl(2',4',6'-triisopropylbiphenyl-2-yl)phosphane and 2.1 g (22.0 mmol) of sodium tert-butoxide were added successively to this solution. The mixture was stirred at 110° C. for 3 h. After this, another 67.8 mg (0.09 mmol) of [2-(2-aminoethyl)phenyl](chloro)palladiumdicyclohexyl-(2',4',6'-triisopropylbiphenyl-2-yl)phosphane/tert-butyl methyl ether adduct and 43.8 mg (0.09 mmol) of dicyclohexyl(2',4',6'-triisopropylbiphenyl-2-yl)phosphane were added and the mixture was stirred at 110° C. for a further 3 h. The hot mixture was then filtered through kieselguhr, and the mother liquor was concentrated on a rotary evaporator. The residue was suspended in 50 ml of pH 7 buffer solution and the precipitated solid was filtered off. The filter cake was washed with water and dried under reduced pressure. The residue was triturated with 20 ml of methylene chloride, the suspension was filtered again and the filter cake was once more dried under reduced pressure. This gave 2.98 g (72% of theory) of the title compound.

$^1$H NMR (400 MHz, DMSO-$d_6$, δ/ppm): 7.71 (s, 1H), 7.66 (s, 1H), 7.22 (s, 1H), 3.47 (m, 4H), 3.15 (m, 4H), 1.42 (s, 9H).

LC/MS (Method 4, ESIpos): $R_t$=1.19 min, m/z=433 [M+H]⁺.

Example 17A 3-(4-Methylpiperazin-1-yl)-5-(pentafluoro-λ⁶-sulphanyl)benzoic acid trifluoroacetate

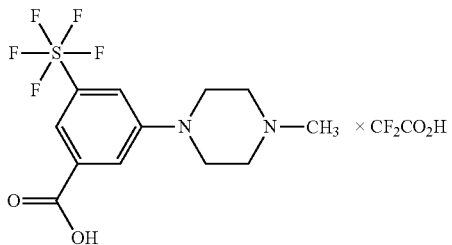

2.5 g (7.6 mmol) of the compound of Example 15A and 0.92 g (9.17 mmol) of 1-methylpiperazine were dissolved in 50 ml of toluene and the mixture was degassed with argon. 126 mg (0.15 mmol) of [2-(2-aminoethyl)phenyl](chloro)palladium-dicyclohexyl(2',4',6'-triisopropylbiphenyl-2-yl)phosphane/tert-butyl methyl ether adduct, 73 mg (0.15 mmol) of dicyclohexyl(2',4',6'-triisopropylbiphenyl-2-yl)phosphane and 1.76 g (18.3 mmol) of sodium tert-butoxide were added successively to this solution. The reaction was stirred under reflux for 4 h and then filtered through kieselguhr whilst still hot, and the filtrate was concentrated on a rotary evaporator. The residue was suspended in 10 ml of tert-butyl methyl ether and extracted twice with in each case 15 ml of 1 M aqueous sodium hydroxide solution. The aqueous phase was neutralized with concentrated hydrochloric acid and concentrated on a rotary evaporator, and the residue was purified by preparative HPLC (Method 13). This gave 1.06 g (30% of theory) of the title compound.

$^1$H NMR (400 MHz, DMSO-$d_6$, δ/ppm): 7.73 (s, 2H), 7.69 (s, 1H), 3.60-3.20 (br, 8H), 2.85 (s, 3H).

LC/MS (Method 3, ESIpos): $R_t$=0.57 min, m/z=347 [M+H]⁺.

Example 18A 3-(Morpholin-4-yl)-5-(pentafluoro-λ⁶-sulphanyl)benzoic acid

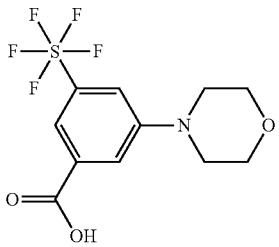 [SMILES: O=C(O)c1cc(N2CCOCC2)cc(S(F)(F)(F)(F)F)c1]

1.5 g (4.6 mmol) of the compound of Example 15A and 0.48 g (5.5 mmol) of morpholine were dissolved in 15 ml of toluene, and the mixture was degassed with argon. 75 mg (0.09 mmol) of [2-(2-aminoethyl)phenyl](chloro)palladium-dicyclohexyl(2',4',6'-triisopropylbiphenyl-2-yl)phosphane/ tert-butyl methyl ether adduct, 44 mg (0.09 mmol) of dicyclohexyl(2',4',6'-triisopropylbiphenyl-2-yl)phosphane and 1.06 g (11.0 mmol) of sodium tert-butoxide were added successively to this solution. The reaction was stirred in a microwave oven (Biotage Initiator, with Dynamic Field Tuning) at 130° C. for 30 min. The reaction was then stirred into 10 ml of saturated aqueous sodium chloride solution and extracted twice with in each case 30 ml of ethyl acetate. The organic phase was washed with pH 4 buffer solution, dried over sodium sulphate and concentrated on a rotary evaporator. The residue was dissolved in 5 ml of tert-butyl methyl ether, and 10 ml of pentane were added. The precipitate formed was filtered off and dried. This gave 1.04 g (68% of theory) of the title compound.

$^1$H NMR (400 MHz, DMSO-$d_6$, δ/ppm): 7.73 (s, 1H), 7.69 (s, 1H), 7.35 (s, 1H), 3.75 (m, 4H), 3.20 (m, 4H).

LC/MS (Method 3): $R_t$=0.91 min; MS (ESIpos): m/z=334 [M+H]$^+$.

Example 19A 3-(2-Hydroxypropan-2-yl)-5-(pentafluoro-$\lambda^6$-sulphanyl)benzoic acid

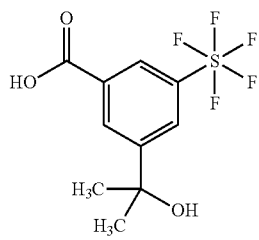 [SMILES: CC(C)(O)c1cc(C(=O)O)cc(S(F)(F)(F)(F)F)c1]

Under argon, 7.6 g (23.3 mmol) of the compound of Example 15A were dissolved in 76 ml of THF, and a few granules of 4 Å molecular sieve were added. The mixture was then cooled to 0° C., and 53.7 ml (69.8 mmol) of a 1.3 M solution of 2-propylmagnesium chloride/lithium chloride complex in THF were slowly added dropwise. After the addition had ended, the reaction mixture was stirred at 0° C. for another 30 min. 2.6 ml (34.9 mmol) of anhydrous acetone were then added, and the reaction was stirred at 0° C. for another 1 h. 90 ml of 1 M hydrochloric acid were then added, and the reaction was allowed to slowly warm to RT over a period of 40 min. The mixture was then extracted three times with ethyl acetate. The combined organic phases were washed with saturated sodium chloride solution, dried over sodium sulphate, filtered and concentrated. The residue was triturated with petroleum ether with a little diethyl ether added, filtered off and dried. This gave 5.8 g (80% of theory) of the title compound as a white solid.

$^1$H NMR (400 MHz, DMSO-$d_6$, δ/ppm): 8.27 (s, 1H), 8.19 (s, 1H), 8.15 (s, 1H), 5.54 (s, 1H), 1.48 (s, 6H).

LC/MS (Method 3): $R_t$=0.89 min; MS (ESIneg): m/z=305 [M−H]$^-$.

Example 20A

3-[1-(tert-Butoxycarbonyl)-3-hydroxyazetidin-3-yl]-5-(pentafluoro-$\lambda^6$-sulphanyl)benzoic acid

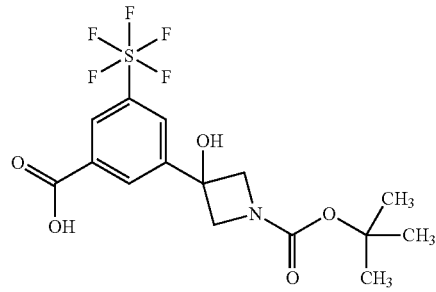 [SMILES: CC(C)(C)OC(=O)N1CC(O)(c2cc(C(=O)O)cc(S(F)(F)(F)(F)F)c2)C1]

Analogously to the procedure for Example 19A, 250 mg (0.76 mmol) of the compound of Example 15A and 0.25 ml (1.15 mmol) of tert-butyl 3-oxoazetidine-1-carboxylate gave, after purification by preparative HPLC (Method 27), 65 mg (20% of theory) of the title compound.

$^1$H NMR (400 MHz, DMSO-$d_6$, δ/ppm): 13.82 (br, 1H), 8.29 (s, 1H), 8.22 (s, 1H), 8.15 (s, 1H), 6.89 (s, 1H), 4.09 (quart, 4H), 1.43 (s, 9H).

LC/MS (Method 3): $R_t$=1.01 min; MS (ESIneg): m/z=418 [M−H]$^-$.

Example 21A 3-tert-Butyl-5-(4-methylpiperazin-1-yl)benzoic acid trifluoroacetate

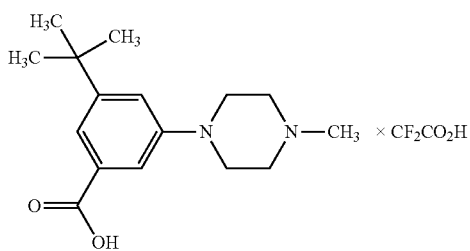

500 mg (1.9 mmol) of 3-bromo-5-tert-butylbenzoic acid and 233 mg (2.3 mmol) of 1-methylpiperazine were initially charged in 12.7 ml of toluene, and the mixture was degassed with argon. 32.2 mg (0.04 mmol) of [2-(2-aminoethyl)phenyl](chloro)palladiumdicyclohexyl(2',4',6'-triisopropylbiphenyl-2-yl)phosphan/tert-butyl methyl ether adduct, 18.5 mg (0.04 mmol) of dicyclohexyl(2',4',6'-triisopropylbiphenyl-2-yl)phosphane and 448.5 mg (4.7 mmol) of sodium tert-butoxide were added successively to this solution. The reaction mixture was stirred in a microwave oven (Biotage Initiator, with Dynamic Field Tuning) at 130° C. for 30 min. The reaction was then filtered whilst still hot and the residue was washed thoroughly with toluene. The combined filtrates were concentrated under reduced pressure and the residue was purified by preparative HPLC (Method 13). This gave 255 mg (34% of theory) of the title compound.

¹H NMR (400 MHz, DMSO-d₆, δ/ppm): 9.94 (br, 1H), 7.49 (s, 1H), 7.34 (s, 1H), 7.26 (s, 1H), 3.91 (br, 2H), 3.53 (br, 2H), 3.17 (br, 2H), 2.99 (br, 2H), 2.88 (s, 3H), 1.29 (s, 9H).

LC/MS (Method 3): $R_t$=0.64 min; MS (ESIpos): m/z=277 (M+H)⁺.

Example 22A 3-tert-Butyl-5-(pyrrolidin-1-ylmethyl)benzoic acid trifluoroacetate

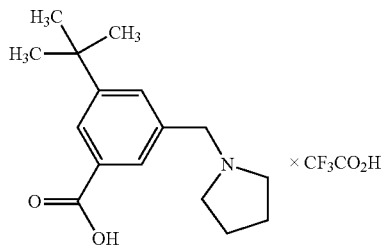

Step 1: 3-tert-Butyl-5-formylbenzoic acid

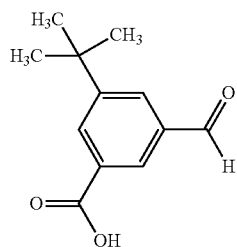

0.38 g (1.7 mmol) of methyl 3-tert-butyl-5-formylbenzoate [for the preparation, see, for example, WO 2008/089034-A2, intermediate K/step 1] were initially charged in 20 ml of water, 0.5 g of lithium hydroxide monohydrate were added and the mixture was stirred at RT for 1 h. The reaction solution was then adjusted to pH 2 with 1 M hydrochloric acid and extracted with ethyl acetate. The organic phase was dried over sodium sulphate, filtered and concentrated on a rotary evaporator. This gave 0.31 g (87% of theory) of the title compound.

¹H NMR (400 MHz, DMSO-d₆, δ/ppm): 13.46-13.20 (m, 1H), 10.10 (s, 1H), 8.28 (s, 1H), 8.25 (s, 1H), 8.19 (s, 1H), 1.36 (s, 9H).

LC/MS (Method 3): $R_t$=0.92 min; MS (ESIpos): m/z=207 (M+H)⁺.

Step 2:
3-tert-Butyl-5-(pyrrolidin-1-ylmethyl)benzoic acid trifluoroacetate

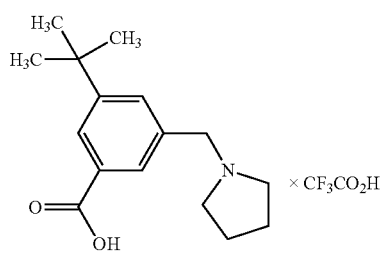

500 mg (2.4 mmol) of the compound of Example 22A/Step 1 were initially charged in 24 ml of methylene chloride, and 258 mg (3.6 mmol) of pyrrolidine, 719 mg (3.4 mmol) of sodium triacetoxyborohydride and 1 ml (17.5 mmol) of acetic acid were added in succession. The reaction was stirred at RT for 2 h. A little water was then added, and the mixture was concentrated. The residue was purified by preparative HPLC (Method 13). This gave 560 mg (62% of theory) of the title compound.

¹H NMR (400 MHz, DMSO-d₆, δ/ppm): 8.00 (s, 1H), 7.96 (s, 1H), 7.83 (s, 1H), 4.43 (s, 2H), 3.11 (br, 2H), 2.02 (br, 2H), 1.89 (br, 2H), 1.33 (s, 9H) [further signals obscured by solvent peaks].

LC/MS (Method 3): $R_t$=0.64 min; MS (ESIpos): m/z=262 (M+H)⁺.

Example 23A

3-Cyano-5-(pentafluoro-$\lambda^6$-sulphanyl)benzoic acid

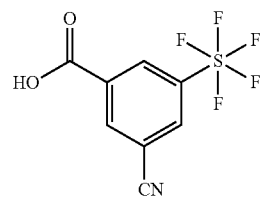 [SMILES: N#Cc1cc(C(=O)O)cc(S(F)(F)(F)(F)F)c1]

200 mg (0.61 mmol) of the compound of Example 15A were dissolved in 2.0 ml of DMF, and the mixture was degassed with argon. After addition of 79 mg (0.67 mmol) of zinc cyanide and 42 mg (0.04 mmol) of tetrakis(triphenylphosphine)palladium(0), the reaction was stirred in a microwave oven (Biotage Initiator, with Dynamic Field Tuning) at 120° C. for 30 min. After cooling, solid components were filtered off and the filtrate was separated into its components by preparative HPLC (Method 15). Concentration of the product fractions and drying of the residue under high vacuum gave 115 mg (88% pure, 61% of theory) of the title compound.

¹H NMR (400 MHz, DMSO-d₆, δ/ppm): 14.18 (br, 1H), 8.89 (t, 1H), 8.60 (t, 1H), 8.50 (t, 1H).

LC/MS (Method 3, ESIneg): $R_t$=0.83 min, m/z=272 [M−H]⁻.

Example 24A

3-Hydroxy-5-(pentafluoro-$\lambda^6$-sulphanyl)benzoic acid

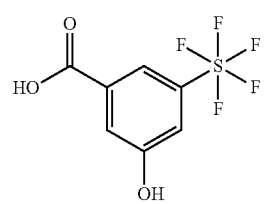 [SMILES: O=C(O)c1cc(O)cc(S(F)(F)(F)(F)F)c1]

2.0 g (6.11 mmol) of the compound of Example 15A were dissolved in 20 ml of dioxane and 2 ml of water, the mixture was degassed with argon, 280 mg (0.31 mmol) of tris(dibenzylideneacetone)dipalladium, 325 mg (0.76 mmol) of 2-di-tert-butylphosphino-2',4',6'-triisopropyl-1,1'-biphenyl and 1.37 g (24.5 mmol) of powdered potassium hydroxide were added and the mixture was stirred at 100° C. for 2 h. The reaction was then stirred into 50 ml of 1 M hydrochloric acid and extracted twice with in each case 50 ml of ethyl acetate. The combined organic phases were washed with saturated sodium chloride solution, dried over sodium sulphate and concentrated under reduced pressure. The residue was suspended in dichloromethane/pentane (9:1), the solid was filtered off and the filter cake was dried under high vacuum. This gave 980 mg (59% of theory) of the title compound.

$^1$H NMR (400 MHz, DMSO-$d_6$, δ/ppm): 13.58 (br, 1H), 10.74 (s, 1H), 7.74 (s, 1H), 7.58 (s, 1H), 7.46 (t, 1H).

LC/MS (Method 3, ESIneg): $R_t$=0.78 min, m/z=263 [M−H]⁻.

Example 25A

3-Methoxy-5-(pentafluoro-$\lambda^6$-sulphanyl)benzoic acid

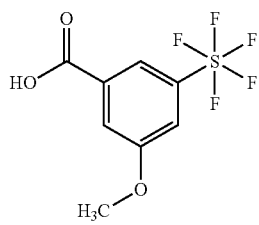 [SMILES: COc1cc(C(=O)O)cc(S(F)(F)(F)(F)F)c1]

150 mg (0.57 mmol) of the compound of Example 24A were dissolved in 1.5 ml of methanol, 0.25 ml (1.14 mmol) of a 25% strength solution of sodium methoxide in methanol and 0.04 ml (0.62 mmol) of methyl iodide were added and the mixture was heated in a microwave oven (Biotage Initiator, with Dynamic Field Tuning) at 120° C. for 30 min. After cooling, the reaction was acidified with 1 M hydrochloric acid and concentrated slightly on a rotary evaporator. The precipitate formed was filtered off, washed with water and dried under high vacuum. This gave 96 mg (94% pure, 57% of theory) of the title compound.

LC/MS (Method 4, ESIneg): $R_t$=0.98 min, m/z=277 [M−H]⁻.

Example 26A 3-(2-Methyl-1H-imidazol-1-yl)-5-(pentafluoro-$\lambda^6$-sulphanyl)benzoic acid

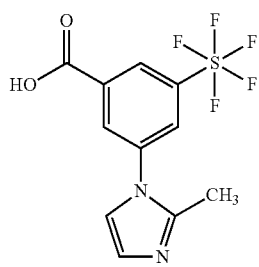 [SMILES: Cc1nccn1-c1cc(C(=O)O)cc(S(F)(F)(F)(F)F)c1]

1.0 g (3.06 mmol) of the compound of Example 15A and 276 mg (3.36 mmol) of 2-methylimidazole were dissolved in 20 ml of DMF and 2 ml of water, and the mixture was degassed with argon. 2.06 g (6.42 mmol) of tetraethylammonium bicarbonate were added carefully, followed by 232 mg (1.22 mmol) of copper(I) iodide and 177 mg (1.22 mmol) of 8-hydroxyquinoline. The mixture was heated in a microwave oven (Biotage Initiator, with Dynamic Field Tuning) at 160° C. for 60 min. The reaction was then filtered, and the filtrate was adjusted at pH 1 with concentrated hydrochloric acid and concentrated under reduced pressure. The residue was separated into its components by preparative HPLC (Method 17). Evaporation of the product fractions and drying of the residue under high vacuum gave 238 mg (94% pure, 22% of theory) of the title compound.

$^1$H NMR (400 MHz, DMSO-$d_6$, δ/ppm): 8.61 (t, 1H), 8.48 (t, 1H), 8.45 (t, 1H), 7.97 (d, 1H), 7.75 (d, 1H), 2.54 (s, 3H).

LC/MS (Method 3, ESIpos): $R_t$=0.57 min, m/z=329 [M+H]⁺.

Example 27A 3-tert-Butyl-5-(2-methyl-1H-imidazol-1-yl)benzoic acid

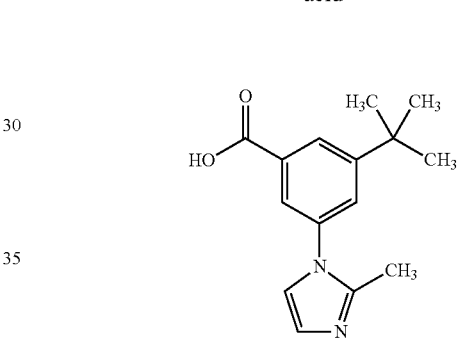

Analogously to the procedure for Example 26A, 500 mg (1.95 mmol) of 3-bromo-5-tert-butyl-benzoic acid and 175 mg (2.14 mmol) of 2-methylimidazole gave 405 mg (56% of theory) of the title compound.

$^1$H NMR (400 MHz, DMSO-$d_6$, δ/ppm): 8.15 (t, 1H), 7.97-7.93 (m, 3H), 7.78 (d, 1H) [further signals obscured by solvent peaks].

LC/MS (Method 3, ESIpos): $R_t$=0.56 min, m/z=259 [M+H]⁺.

Example 28A 3-tert-Butyl-5-(2-hydroxypropan-2-yl)benzoic acid

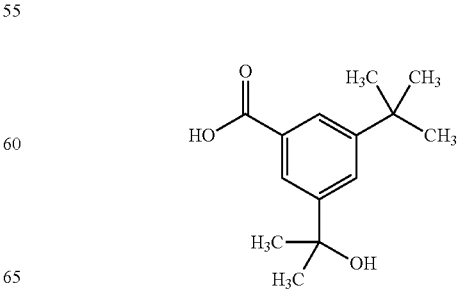

3.0 g (12.7 mmol) of 3-tert-butyl-5-(methoxycarbonyl) benzoic acid were dissolved in 40 ml of abs. THF. With ice bath cooling, 12.7 ml of a 3 M solution of methylmagnesium bromide in THF were added dropwise and the mixture was stirred without cooling for another 1 h. A further 12.7 ml of methylmagnesium bromide solution were then added, and the mixture was stirred at RT for another 1 h. Another 12.7 ml of methylmagnesium bromide solution were then added, and the mixture was stirred at RT for another 72 h. Saturated aqueous ammonium chloride solution was then added, and the mixture was adjusted to pH 1 with concentrated hydrochloric acid. The mixture was extracted with ethyl acetate and the organic phase was concentrated under reduced pressure. The residue was separated into its components by preparative HPLC (Method 15). The product fractions were freed from the solvent on a rotary evaporator and the residue was dried under high vacuum. This gave 1.40 g (47% of theory) of the title compound.

$^1$H NMR (400 MHz, DMSO-$d_6$, δ/ppm): 12.83 (br, 1H), 7.87 (t, 1H), 7.80 (t, 1H), 7.76 (t, 1H), 5.14 (br, 1H), 1.44 (s, 6H), 1.31 (s, 9H).

LC/MS (Method 3, ESIneg): $R_t$=0.84 min, m/z=235 [M–H]$^-$.

Example 29A

3-{2-[(tert-Butoxycarbonyl)amino]ethoxy}-5-(pentafluoro-$\lambda^6$-sulphanyl)benzoic acid

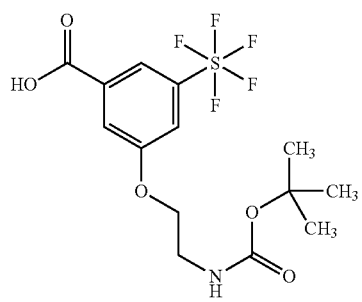 [SMILES: CC(C)(C)OC(=O)NCCOc1cc(C(=O)O)cc(S(F)(F)(F)(F)F)c1]

150 mg (0.57 mmol) of the compound of Example 24A, 140 mg (0.63 mmol) of tert-butyl-(2-bromoethyl)carbamate and 388 mg (1.2 mmol) of caesium carbonate were initially charged in 1.5 ml of DMF and stirred at RT overnight. 1.7 ml of 1 M aqueous sodium hydroxide solution were then added, and the mixture was stirred at RT for another 1 h. The reaction mixture was then acidified slightly with concentrated acetic acid and purified directly by preparative HPLC (Method 18). This gave 63 mg (26% of theory) of the title compound.

LC/MS (Method 3, ESIpos): $R_t$=1.06 min, m/z=408 [M+H]$^+$.

Example 30A

3-{3-[(tert-Butoxycarbonyl)amino]propoxy}-5-(pentafluoro-$\lambda^6$-sulphanyl)benzoic acid

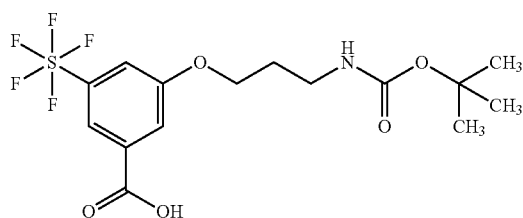 [SMILES: CC(C)(C)OC(=O)NCCCOc1cc(C(=O)O)cc(S(F)(F)(F)(F)F)c1]

Under argon, 1.25 g (4.73 mmol) of the compound of Example 24A were combined with 1.46 g (6.2 mmol) of tert-butyl (3-bromopropyl)carbamate and 4.62 g (14.2 mmol) of caesium carbonate in 25 ml of DMF and stirred at RT until the reaction had gone to completion. The reaction was then acidified with 4 M hydrochloric acid and extracted with ethyl acetate. The organic phase was dried over magnesium sulphate, filtered and concentrated under reduced pressure. The residue was taken up in 25 ml of THF and 12 ml of water and, after addition of 596 mg (14.2 mmol) of lithium hydroxide monohydrate, stirred at 40° C. for 4 h. After the reaction had ended, water and ethyl acetate were added and the mixture was adjusted to pH 2 with 1 M hydrochloric acid. The organic phase was separated off, dried over magnesium sulphate, filtered and concentrated on a rotary evaporator. The crude product was purified by preparative HPLC (Method 19). This gave 1.64 g (92% pure, 76% of theory) of the title compound.

$^1$H NMR (400 MHz, DMSO-$d_6$, δ/ppm): 13.73 (br, 1H), 7.86 (s, 1H), 7.68 (s, 1H), 7.64 (t, 1H), 6.92 (t, 1H), 4.13 (t, 2H), 3.10 (quart, 2H), 1.85 (quint, 2H), 1.36 (s, 9H).

LC/MS (Method 3, ESIpos): $R_t$=1.10 min, m/z=422 [M+H]$^+$.

Example 31A

3-{[1-(tert-Butoxycarbonyl)azetidin-3-yl]oxy}-5-(pentafluoro-$\lambda^6$-sulphanyl)benzoic acid

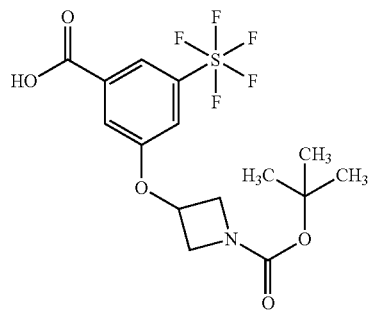 [SMILES: CC(C)(C)OC(=O)N1CC(Oc2cc(C(=O)O)cc(S(F)(F)(F)(F)F)c2)C1]

100 mg (0.38 mmol) of the compound of Example 24A and 104 mg (0.42 mmol) of tert-butyl 3-[(methylsulphonyl)oxy] azetidine-1-carboxylate together with 259 mg (0.80 mmol) of caesium carbonate were initially charged in 1 ml of DMF and stirred at 90° C. overnight. The mixture was then stirred into 10 ml of 0.1 M hydrochloric acid and extracted with ethyl acetate. The organic phase was washed with saturated sodium chloride solution, dried over sodium sulphate, filtered and concentrated under reduced pressure. The residue was purified by preparative HPLC (Method 18). This gave 60 mg (88% pure, 33% of theory) of the title compound.

$^1$H NMR (400 MHz, DMSO-$d_6$, δ/ppm): 13.80 (br, 1H), 7.91 (s, 1H), 7.63 (t, 1H), 7.53 (s, 1H), 5.23 (m, 1H), 4.32 (m, 2H), 3.85 (m, 2H), 1.39 (s, 9H).

LC/MS (Method 3, ESIneg): $R_t$=1.10 min, m/z=418 [M–H]$^-$.

Example 32A 3-(Methylsulphonyl)-5-(pentafluoro-λ⁶-sulphanyl)benzoic acid

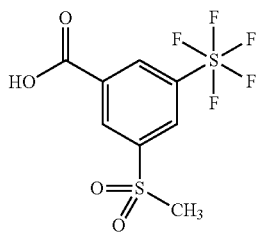 [SMILES: CS(=O)(=O)c1cc(C(=O)O)cc(S(F)(F)(F)(F)F)c1]

A mixture of 250 mg (0.764 mmol) of the compound of Example 15A, 86 mg (0.841 mmol) of sodium methanesulphinate, 19 mg (0.168 mmol) of (S)-proline and 23 mg (0.168 mmol) of potassium carbonate in 3 ml of DMSO/water (4:1) was initially degassed, 16 mg (0.084 mmol) of copper(I) iodide were then added and the mixture was finally, under an argon atmosphere, heated in a microwave oven (Biotage Initiator, with Dynamic Field Tuning) at 150° C. for 30 min. After cooling to RT, the reaction mixture was filtered through a little Celite and then separated into its components by preparative HPLC (Method 9). Concentration of the product fractions and drying of the residue under high vacuum gave 83 mg (33% of theory) of the title compound.

$^1$H NMR (400 MHz, DMSO-$d_6$, δ/ppm): 14.27 (br, 1H), 8.65 (t, 1H), 8.62 (t, 1H), 8.56 (dd, 1H), 3.46 (s, 3H).

LC/MS (Method 3, ESIneg): $R_t$=0.75 min, m/z=325 [M−H]$^-$.

Example 33A

3-Chloro-5-(pentafluoro-λ⁶-sulphanyl)benzoic acid

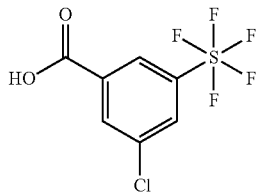 [SMILES: O=C(O)c1cc(Cl)cc(S(F)(F)(F)(F)F)c1]

A solution of 250 mg (0.764 mmol) of the compound of Example 15A in 3 ml of anhydrous DMF was initially degassed, 378 mg (3.82 mmol) of copper(I) chloride and 73 mg (0.382 mmol) of copper(I) iodide were then added and the mixture was finally, under an argon atmosphere, heated in a microwave oven (Biotage Initiator, with Dynamic Field Tuning) at 150° C. for 60 min. After cooling to RT, the reaction mixture was filtered through a little Celite and then separated into its components by preparative HPLC (Method 9). Concentration of the product fractions and drying of the residue under high vacuum gave 127 mg (59% of theory) of the title compound.

$^1$H NMR (400 MHz, DMSO-$d_6$, δ/ppm): 14.04 (br, 1H), 8.40 (t, 1H), 8.22 (dd, 1H), 8.20 (t, 1H).

LC/MS (Method 3, ESIneg): $R_t$=1.02 min, m/z=281/283 [M−H]$^-$.

Example 34A

3-Methyl-5-(pentafluoro-λ⁶-sulphanyl)benzoic acid

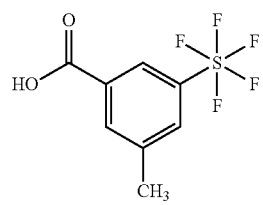 [SMILES: Cc1cc(C(=O)O)cc(S(F)(F)(F)(F)F)c1]

1.15 ml (2.29 mmol) of a 2 M solution of trimethylaluminium in a hexane fraction were added to a solution of 250 mg (0.764 mmol) of the compound of Example 15A and 27 mg (0.023 mmol) of tetrakis(triphenylphosphine)palladium (0) in 2.5 ml of anhydrous THF, and the mixture was then, under an argon atmosphere, heated in a microwave oven (Biotage Initiator, with Dynamic Field Tuning) at 150° C. for 120 min. After cooling to RT, about 10 ml of water were added, and the reaction mixture was extracted three times with in each case about 10 ml of ethyl acetate. The combined organic extracts were washed with saturated sodium chloride solution, dried over anhydrous magnesium sulphate, filtered and then concentrated to dryness on a rotary evaporator. The product was isolated by preparative HPLC (Method 9). Concentration of the product fractions and drying of the residue under high vacuum gave 98 mg (47% of theory, 95% pure) of the title compound.

$^1$H NMR (400 MHz, DMSO-$d_6$, δ/ppm): 13.64 (very broad, 1H), 8.09 (br, 1H), 8.04 (br, 2H), 2.48 (s, 3H).

LC/MS (Method 3, ESIneg): $R_t$=0.97 min, m/z=261 [M−H]$^-$.

Example 35A

3-{[3-(Dimethylamino)propyl](methyl)amino}-5-(trifluoromethyl)benzoic acid dihydrochloride

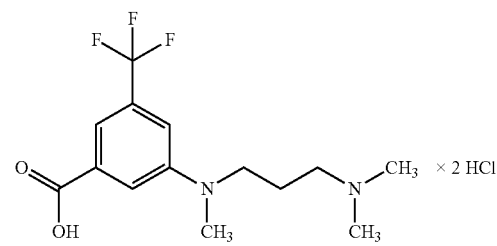 [SMILES: CN(C)CCCN(C)c1cc(C(=O)O)cc(C(F)(F)F)c1]

Step 1: 3-{[3-(Dimethylamino)propyl](methyl)amino}-5-(trifluoromethyl)benzonitrile

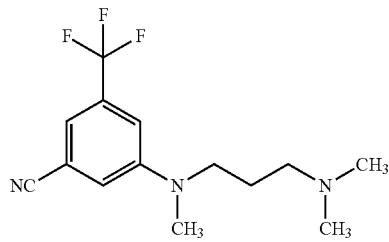 [SMILES: CN(C)CCCN(C)c1cc(C#N)cc(C(F)(F)F)c1]

500 mg (2.64 mmol) of 3-fluoro-5-(trifluoromethyl)benzonitrile, 338 mg (2.91 mmol) of N,N,N'-trimethylpropane-1,3-diamine and 767 mg (5.52 mmol) of potassium carbonate in 5.0 ml of DMSO were stirred at 110° C. for 8 h. The reaction mixture was then separated directly into its components by preparative HPLC (Method 12). The product fractions were freed from the solvent, the residue was suspended in ethyl acetate and the suspension was washed successively with saturated aqueous potassium carbonate solution and saturated aqueous sodium chloride solution. The organic phase was dried over sodium sulphate and concentrated. This gave 290 mg (38% of theory) of the title compound.

$^1$H NMR (400 MHz, DMSO-$d_6$, δ/ppm): 7.38 (s, 1H), 7.31 (s, 1H), 7.21 (s, 1H), 3.44 (t, 2H), 2.97 (s, 3H), 2.18 (t, 3H), 2.12 (s, 6H), 1.62 (quint, 2H).

LC/MS (Method 3, ESIpos): $R_t$=0.72 min, m/z=286 [M+H]$^+$.

Step 2: 3-{[3-(Dimethylamino)propyl](methyl)amino}-5-(trifluoromethyl)benzoic acid dihydrochloride

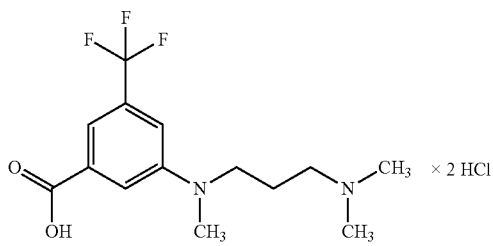 [SMILES: CN(C)CCCN(C)c1cc(C(=O)O)cc(C(F)(F)F)c1]

280 mg (0.98 mmol) of the compound of Example 35A/Step 1 were initially charged in 2.5 ml of semiconcentrated hydrochloric acid and heated in a microwave oven (Biotage Initiator, with Dynamic Field Tuning) at 140° C. for 60 min. After the reaction had ended, the mixture was concentrated and the residue was dried under reduced pressure. This gave 370 mg (99% of theory) of the title compound.

Example 36A

3-Formyl-5-(pentafluoro-$\lambda^6$-sulphanyl)benzoic acid

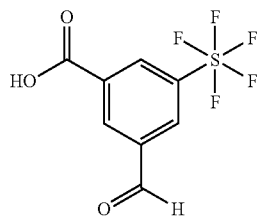 [SMILES: O=Cc1cc(C(=O)O)cc(S(F)(F)(F)(F)F)c1]

With ice bath cooling, 11.5 ml (23 mmol) of a 2 M solution of 2-propylmagnesium chloride in diethyl ether were added dropwise to a solution of 3.0 g (9.17 mmol) of the compound of Example 15A in 1.6 ml of abs. THF. After the addition had ended, stirring was continued without cooling for another 30 min. 1.76 ml (22.9 mmol) of DMF were added with ice bath cooling, and the mixture was stirred without cooling for a further 30 min. 20 ml of 1 M hydrochloric acid were then added, and the mixture was extracted with 100 ml of ethyl acetate. The organic phase was washed with 1 M hydrochloric acid and saturated sodium chloride solution, dried over sodium sulphate, filtered and concentrated to dryness on a rotary evaporator. The residue was suspended in 50 ml of dichloromethane/pentane (1:1) and the solid was filtered off and dried. Any contaminations present were removed by preparative HPLC (Method 22). This gave 780 mg (31% of theory) of the title compound.

$^1$H NMR (400 MHz, DMSO-$d_6$, δ/ppm): 14.06 (br, 1H), 10.17 (s, 1H), 8.66 (s, 1H), 8.64 (s, 1H), 8.52 (s, 1H).

LC/MS (Method 3, ESIneg): $R_t$=0.87 min, m/z=275 [M−H]$^-$.

Example 37A 3-(Hydroxymethyl)-5-(pentafluoro-$\lambda^6$-sulphanyl)benzoic acid

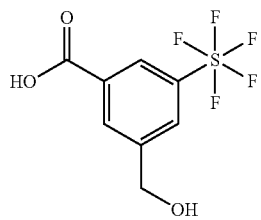 [SMILES: O=C(O)c1cc(CO)cc(S(F)(F)(F)(F)F)c1]

54 mg (0.49 mmol) of 3-hydroxyazetidine hydrochloride, 97 mg (0.46 mmol) of sodium triacetoxyborohydride and 0.13 ml (2.35 mmol) of acetic acid were added in succession to a solution of 90 mg (0.32 mmol) of the compound of Example 36A in 3.2 ml of dichloromethane, and the mixture was stirred at RT for 1 h. A little water was then added, and the mixture was concentrated on a rotary evaporator. The residue was purified by preparative HPLC (Method 18). Evaporation of the appropriate fractions and drying of the residue under high vacuum gave 60 mg (66% of theory) of the title compound as the product of the reaction.

$^1$H NMR (400 MHz, DMSO-$d_6$, δ/ppm): 13.68 (br, 1H), 8.17 (s, 1H), 8.16 (s, 1H), 8.08 (s, 1H), 5.62 (br, 1H), 4.67 (s, 2H).

LC/MS (Method 4, ESIneg): $R_t$=0.78 min, m/z=277 [M−H]$^-$.

Example 38A 3-(Pentafluoro-$\lambda^6$-sulphanyl)-5-(pyrrolidin-1-ylmethyl)benzoic acid trifluoroacetate

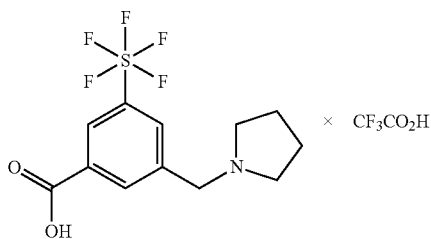 [SMILES: O=C(O)c1cc(CN2CCCC2)cc(S(F)(F)(F)(F)F)c1 ; "CF3CO2H"]

0.03 ml (0.36 mmol) of pyrrolidine and 0.001 ml (0.018 mmol) of acetic acid were added to a solution of 50 mg (0.18 mmol) of the compound of Example 36A in 1.8 ml of abs. THF, and the mixture was stirred at RT for 1 h. 54 mg (0.25 mmol) of sodium triacetoxyborohydride were then added, and the mixture was stirred at RT for 16 h. A little water was then added, and the mixture was concentrated on a rotary evaporator. The residue was purified by preparative HPLC (Method 18). Evaporation of the product fractions and drying of the residue under high vacuum gave 70 mg (87% of theory) of the title compound.

LC/MS (Method 4, ESIpos): $R_t$=0.53 min, m/z=332 [M+H]$^+$.

Example 39A

3-{[(3S)-3-Hydroxypyrrolidin-1-yl]methyl}-5-(pentafluoro-$\lambda^6$-sulphanyl)benzoic acid trifluoroacetate

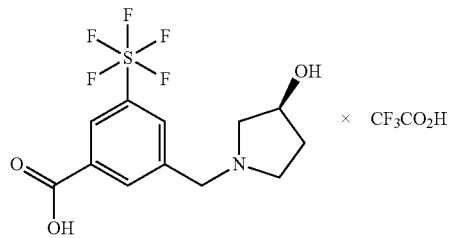 [SMILES: O=C(O)c1cc(CN2CC[C@H](O)C2)cc(S(F)(F)(F)(F)F)c1 ; "CF3CO2H"]

Analogously to the procedure for Example 38A, 100 mg (0.36 mmol) of the compound of Example 36A and 63 mg (0.72 mmol) of (S)-3-hydroxypyrrolidine gave 140 mg (84% of theory) of the title compound.

LC/MS (Method 4, ESIpos): $R_t$=0.48 min, m/z=348 [M+H]$^+$.

Example 40A

3-[(4-Methylpiperazin-1-yl)methyl]-5-(pentafluoro-$\lambda^6$-sulphanyl)benzoic acid trifluoroacetate

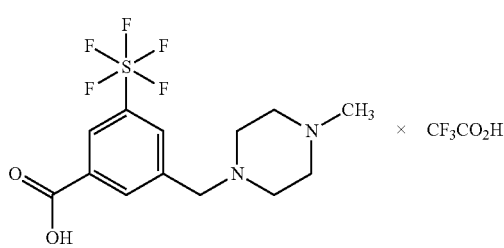 [SMILES: CN1CCN(Cc2cc(C(=O)O)cc(S(F)(F)(F)(F)F)c2)CC1 ; "CF3CO2H"]

Analogously to the procedure for Example 38A, 150 mg (0.54 mmol) of the compound of Example 36A and 109 mg (1.09 mmol) of N-methylpiperazine gave 205 mg (80% of theory) of the title compound.

$^1$H NMR (400 MHz, DMSO-$d_6$, δ/ppm): 13.80 (br, 1H), 9.52 (br, 1H), 8.21 (s, 1H), 8.20 (s, 1H), 8.11 (s, 1H), 3.79 (s, 2H), 3.38 (m, 2H), 3.06 (m, 2H), 2.94 (m, 2H), 2.79 (m, 3H), 2.37 (m, 2H).

LC/MS (Method 3, ESIpos): $R_t$=0.60 min, m/z=361 [M+H]$^+$.

Example 41A

3-Cyano-5-(trifluoromethoxy)benzoic acid

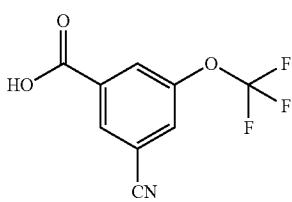 [SMILES: N#Cc1cc(OC(F)(F)F)cc(C(=O)O)c1]

A mixture of 2.0 g (7.02 mmol) of 3-bromo-5-(trifluoromethoxy)benzoic acid, 906 mg (7.72 mmol) of zinc cyanide and 486 mg (0.42 mmol) of tetrakis(triphenylphosphine)palladium(0) in 23 ml of DMF was initially degassed and then, under an atmosphere of argon, heated under reflux for 4 h. A further 243 mg (0.21 mmol) of tetrakis(triphenylphosphine)palladium(0) and 453 mg (3.86 mmol) of zinc cyanide were then added, and the mixture was stirred under reflux for another 16 h. The reaction was then concentrated to a volume of about 5 ml under reduced pressure and stirred into 100 ml of 0.1 M aqueous sodium hydroxide solution. The solid formed was filtered off, the filtrate was adjusted to pH 1 with concentrated hydrochloric acid and the precipitate formed was filtered off again. The filtrate was extracted twice with in each case 50 ml of tert-butyl methyl ether, and the combined organic phases were washed with water and saturated sodium chloride solution, dried over sodium sulphate, filtered and concentrated under reduced pressure. The product was isolated by preparative HPLC (Method 20). Evaporation of the product fractions and drying of the residue under high vacuum gave 75 mg (92% pure, 4% of theory) of the title compound.

¹H NMR (400 MHz, DMSO-d₆, δ/ppm): 13.99 (br, 1H), 8.35 (t, 1H), 8.33 (br, 1H), 8.11 (br, 1H).

LC/MS (Method 4, ESIneg): $R_t$=0.85 min, m/z=230 [M−H]⁻.

Example 42A

3-Cyano-5-(trifluoromethyl)benzoic acid

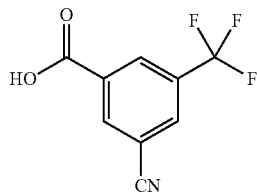 [SMILES: N#Cc1cc(C(=O)O)cc(C(F)(F)F)c1]

A mixture of 2.0 g (7.43 mmol) of 3-bromo-5-(trifluoromethyl)benzoic acid [US 2006/0069261-A1, compound 1.2], 995 mg (8.48 mmol) of zinc cyanide and 859 mg (0.743 mmol) of tetrakis-(triphenylphosphine)palladium(0) in 75 ml of DMF/water (99:1) was initially degassed and then, under an atmosphere of argon, heated at 120° C. for 3 h. After cooling to RT, the mixture was diluted with about 300 ml of water and extracted three times with in each case about 150 ml of ethyl acetate. The combined organic extracts were washed with saturated sodium chloride solution, dried over anhydrous magnesium sulphate, filtered and then concentrated to dryness on a rotary evaporator. The product was isolated by preparative HPLC (Method 9). Evaporation of the product fractions and drying of the residue under high vacuum gave 421 mg (26% of theory) of the title compound.

¹H NMR (400 MHz, DMSO-d₆, δ/ppm): 14.03 (br, 1H), 8.66 (t, 1H), 8.60 (t, 1H), 8.42 (t, 1H).

LC/MS (Method 3, ESIneg): $R_t$=0.82 min, m/z=214 [M−H]⁻.

Example 43A 2-tert-Butyl-6-chloroisonicotinic acid

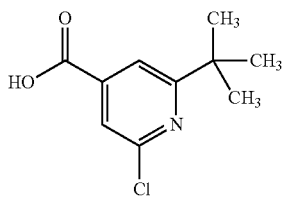

1.0 g (4.39 mmol) of methyl 2-tert-butyl-6-chloroisonicotinate [lit.: O. Isler et al., *Helvetica Chimica Acta* 1955, 38 (4), 1033-1046] in 17 ml of THF and 8.8 ml (8.8 mmol) of 1 M aqueous sodium hydroxide solution were heated under reflux for 30 min. After cooling, the mixture was adjusted to pH 1 with concentrated hydrochloric acid and concentrated almost completely on a rotary evaporator. The solid formed was filtered off, washed with a little water and dried. This gave 870 mg (93% of theory) of the title compound.

LC/MS (Method 3, ESIpos): $R_t$=1.00 min, m/z=214 [M+H]⁺.

Example 44A 2-tert-Butyl-6-(methylamino)isonicotinic acid

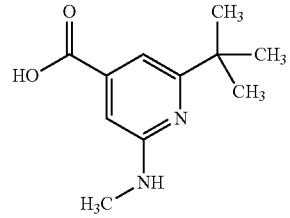

1.0 g (4.39 mmol) of methyl 2-tert-butyl-6-chloroisonicotinate [lit.: O. Isler et al., *Helvetica Chimica Acta* 1955, 38 (4), 1033-1046] and 3.8 ml (43.9 mmol) of a 40% strength aqueous methylamine solution were heated in a microwave oven (Biotage Initiator, with Dynamic Field Tuning) at 160° C. for 6 h. After cooling, the volatile components were removed on a rotary evaporator. The residue was taken up in 4 ml of semiconcentrated hydrochloric acid and once more heated in the microwave at 130° C. for 1 h. The product was then isolated directly by preparative HPLC (Method 12). Evaporation of the product fractions and drying of the residue under high vacuum gave 180 mg (92% pure, 18% of theory) of the title compound.

LC/MS (Method 4, ESIpos): $R_t$=0.39 min, m/z=209 [M+H]⁺.

Example 45A

N-(3-Bromo-4-methylphenyl)-3-(trifluoromethyl)benzamide

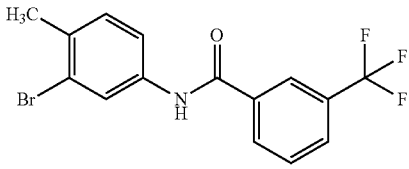 [SMILES: Cc1ccc(NC(=O)c2cccc(C(F)(F)F)c2)cc1Br]

5.51 g (29.6 mmol) of 3-bromo-4-methylaniline were dissolved in 127 ml of dichloromethane, 6.18 g (29.6 mmol) of 3-(trifluoromethyl)benzoyl chloride and 4.54 ml (32.6 mmol) of triethylamine were added and the mixture was stirred at RT for 30 min. All volatile components were removed under reduced pressure and the residue was suspended in 50 ml of methanol. The solid was filtered off and the filtrate was stirred into 100 ml of 1 M hydrochloric acid. The precipitate formed was filtered off, washed with water and dried. This gave 7.05 g (90% pure, 60% of theory) of the title compound.

¹H NMR (400 MHz, DMSO-d₆, δ/ppm): 10.52 (s, 1H), 8.29 (s, 1H), 8.26 (d, 1H), 8.10 (d, 1H), 7.98 (d, 1H), 7.80 (t, 1H), 7.68 (dd, 1H), 7.36 (d, 1H), 2.33 (s, 3H).

LC/MS (Method 1, ESIpos): $R_t$=1.44 min, m/z=360 [M+H]⁺.

Example 46A

N-(3-Bromo-4-methylphenyl)-3-tert-butylbenzamide

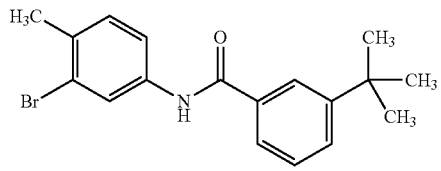 [SMILES: Cc1ccc(NC(=O)c2cccc(C(C)(C)C)c2)cc1Br]

285 mg (1.53 mmol) of 3-bromo-4-methylaniline, 300 mg (1.68 mmol) of 3-tert-butylbenzoic acid and 698 mg (1.83 mmol) of HATU were dissolved in 3 ml of DMF, 0.32 ml (1.83 mmol) of N,N-diisopropylethylamine were added and the mixture was stirred at RT for 16 h. The reaction was then stirred into 20 ml of 0.1 M aqueous sodium hydroxide solution and extracted with ethyl acetate. The organic phase was washed with water and saturated sodium chloride solution, dried over sodium sulphate, filtered and concentrated under reduced pressure. Drying of the residue gave 490 mg (88% of theory) of the title compound.

$^1$H NMR (400 MHz, DMSO-$d_6$, δ/ppm): 10.26 (s, 1H), 8.10 (d, 1H), 7.76 (d, 1H), 7.67 (dd, 1H), 7.63 (d, 1H), 7.46 (t, 1H), 7.33 (d, 1H), 2.33 (s, 3H), 1.34 (s, 9H).

LC/MS (Method 3, ESIpos): $R_t$=1.35 min, m/z=347 [M+H]$^+$.

Example 47A tert-Butyl 4-[3-({4-methyl-3-[6-(1H-pyrazol-4-yl)-1H-imidazo[1,2-b]pyrazol-1-yl]phenyl}-carbamoyl)-5-(pentafluoro-λ$^6$-sulphanyl)phenyl]piperazin-1-carboxylate

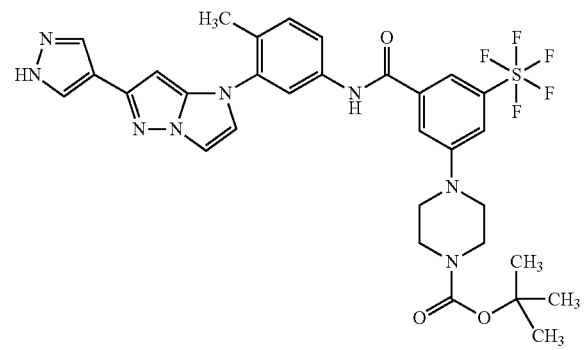 [SMILES: Cc1ccc(NC(=O)c2cc(N3CCN(C(=O)OC(C)(C)C)CC3)cc(S(F)(F)(F)(F)F)c2)cc1-n1ccn2nc(-c3cn[nH]c3)cc12]

The compound from Example 16A (320 mg, 0.74 mmol) was dissolved in 2.3 ml of DMF, HATU (309 mg, 0.81 mmol) and then 4-methylmorpholine (0.32 ml) were added, and the mixture was stirred at RT for 30 min. At −5° C., the compound of Example 7A (103 mg, 0.37 mmol) was then added and the mixture was stirred at RT for 16 h. A few milliliters of concentrated aqueous ammonia solution were then added. The mixture was stirred at RT for 15 min and then extracted with ethyl acetate. The organic phase was washed with conc. sodium chloride solution, dried over sodium sulphate, filtered and concentrated. The crude product was purified by preparative HPLC (Method 28). This gave 210 mg (purity 61%, 50% of theory) of the title compound which was used without further purification for the next synthesis step.

LC/MS (Method 3, ESIpos): $R_t$=1.19 min, m/z=692 [M+H]$^+$.

Example 48A

N-(3-{6-[1-(4-Methoxybenzyl)-1H-pyrazol-4-yl]-1H-imidazo[1,2-b]pyrazol-1-yl}-4-methylphenyl)-3-(4-methylpiperazin-1-yl)-5-(pentafluoro-λ$^6$-sulphanyl)benzamide

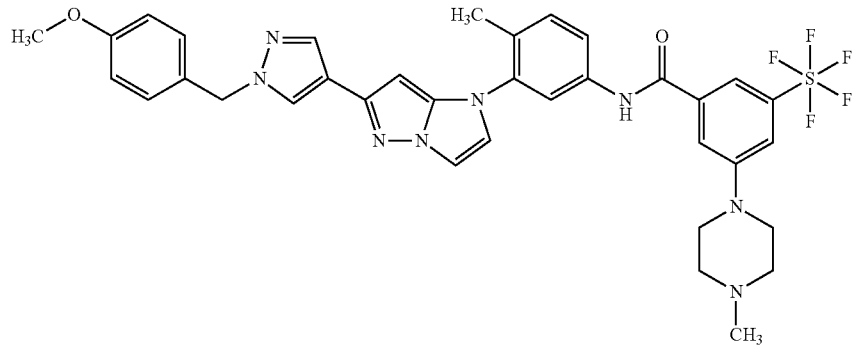 [SMILES: COc1ccc(Cn2cc(-c3cc4n(-c5cc(NC(=O)c6cc(N7CCN(C)CC7)cc(S(F)(F)(F)(F)F)c6)ccc5C)ccn4n3)cn2)cc1]

70 mg (0.14 mmol) of the compound of Example 8A, 62.9 mg (0.14 mmol) of the compound of Example 17A and 62 mg (0.16 mmol) of HATU were dissolved in 0.79 ml of DMF, 0.07 ml (0.41 mmol) of N,N-diisopropylethylamine were added and the mixture was stirred at RT for 1 h. The mixture was then stirred into 10 ml of 0.1 M aqueous sodium hydroxide solution and stirred at RT for 10 min, and the precipitate formed was then filtered off. The solid was washed with water and dried under high vacuum. This gave 94 mg (94% pure, 89% of theory) of the title compound.

$^1$H NMR (400 MHz, DMSO-$d_6$, δ/ppm): 10.52 (s, 1H), 8.05 (s, 1H), 7.90 (d, 1H), 7.77-7.71 (m, 5H), 7.50 (s, 1H), 7.44 (d, 1H), 7.41 (d, 1H), 7.23 (d, 2H), 6.90 (d, 2H), 5.90 (s, 1H), 5.24 (s, 2H), 2.26 (s, 3H), 2.23 (s, 3H) [further signals obscured by solvent peaks].

LC/MS (Method 4, ESIpos): $R_t$=0.86 min, m/z=727 [M+H]$^+$.

Example 49A

N-(3-{6-[1-(4-Methoxybenzyl)-1H-pyrazol-4-yl]-1H-imidazo[1,2-b]pyrazol-1-yl}-4-methylphenyl)-3-(morpholin-4-yl)-5-(pentafluoro-$\lambda^6$-sulphanyl)benzamide

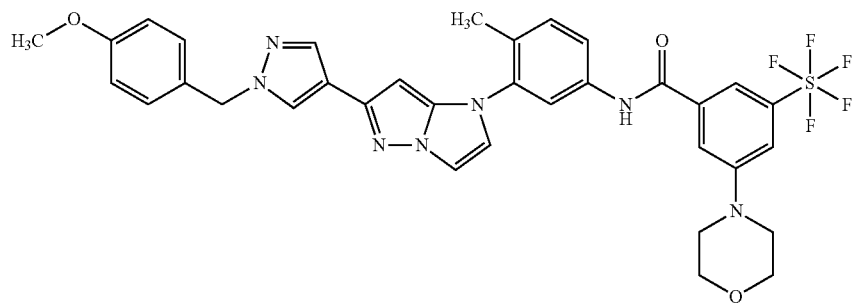 [SMILES: COc1ccc(Cn2cc(-c3cc4n(-c5cc(NC(=O)c6cc(N7CCOCC7)cc(S(F)(F)(F)(F)F)c6)ccc5C)ccn4n3)cn2)cc1]

82 mg (0.16 mmol) of the compound of Example 8A, 59 mg (0.18 mmol) of the compound of Example 18A and 73 mg (0.192 mmol) of HATU were dissolved in 1 ml of DMF. 53 μl (0.48 mmol) of 4-methylmorpholine were then added. After the reaction mixture had been stirred at RT for 16 h, 10 ml of 0.1 M aqueous sodium hydroxide solution were added, whereupon the product precipitated as a solid. The mixture was stirred for another 10 min, and the product was then filtered off with suction, washed with water and dried under high vacuum. This gave 104 mg (70% of theory, 77% pure) of the title compound as a greyish-brown solid.

LC/MS (Method 3, ESIpos): $R_t$=1.21 min, m/z=714 [M+H]$^+$.

Example 50A

N-(3-{6-[1-(4-Methoxybenzyl)-1H-pyrazol-4-yl]-1H-imidazo[1,2-b]pyrazol-1-yl}-4-methylphenyl)-3-(trifluoromethyl)benzamide

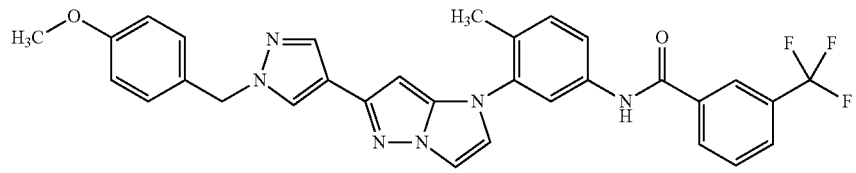 [SMILES: COc1ccc(Cn2cc(-c3cc4n(-c5cc(NC(=O)c6cccc(C(F)(F)F)c6)ccc5C)ccn4n3)cn2)cc1]

55 mg (0.19 mmol) of the compound of Example 5A and 74 mg (0.21 mmol) of the compound of Example 45A were dissolved in 1.24 ml of DMF and 0.12 ml of water, and 126 mg (0.39 mmol) of bis(tetraethylammonium) carbonate were added carefully. The mixture was degassed with argon, and 14.3 mg (0.08 mmol) of copper(I) iodide and 10.9 mg (0.08 mmol) of 8-hydroxyquinoline were then added. The reaction was then heated in a microwave oven (Biotage Initiator, with Dynamic Field Tuning) at 160° C. for 1 h. After cooling, the mixture was poured into 10 ml of water and extracted with ethyl acetate. The organic phase was washed with saturated sodium chloride solution and concentrated under reduced pressure. The residue was purified by preparative HPLC (Method 11). The product fractions were concentrated and the residue was dried under high vacuum. This gave 26 mg (57% pure, 14% of theory) of the title compound which was reacted further in this form.

LC/MS (Method 3, ESIpos): $R_t$=1.14 min, m/z=571 [M+H]$^+$.

Example 51A

N-(3-{6-[1-(4-Methoxybenzyl)-1H-pyrazol-4-yl]-1H-imidazo[1,2-b]pyrazol-1-yl}-4-methylphenyl)-3-(2-methyl-1H-imidazol-1-yl)-5-(trifluoromethyl)benzamide

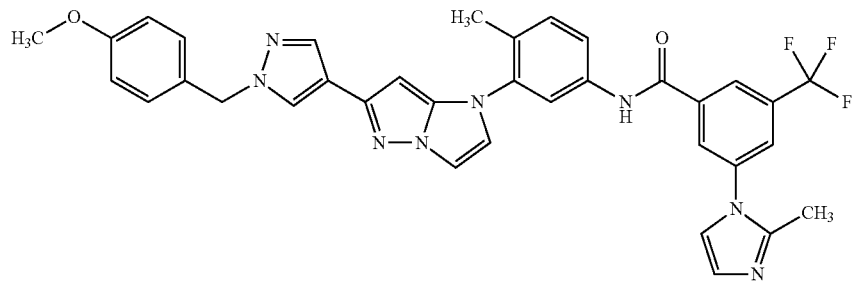 [SMILES: COc1ccc(Cn2cc(-c3cc4n(-c5cc(NC(=O)c6cc(-n7ccnc7C)cc(C(F)(F)F)c6)ccc5C)ccn4n3)cn2)cc1]

60 mg (0.12 mmol) of the compound of Example 8A and 31.6 mg (0.12 mmol) of 3-(2-methyl-1H-imidazol-1-yl)-5-(trifluoromethyl)benzoic acid [lit.: WO 2004/005281-A1, Example 91b] were reacted and worked up analogously to the procedure of Example 48A. This gave 61 mg (77% of theory) of the title compound.

LC/MS (Method 4, ESIpos): $R_t$=0.83 min, m/z=651 [M+H]$^+$.

Example 52A 3-tert-Butyl-N-(3-{6-[1-(4-methoxybenzyl)-1H-pyrazol-4-yl]-1H-imidazo[1,2-b]pyrazol-1-yl}-4-methylphenyl)benzamide

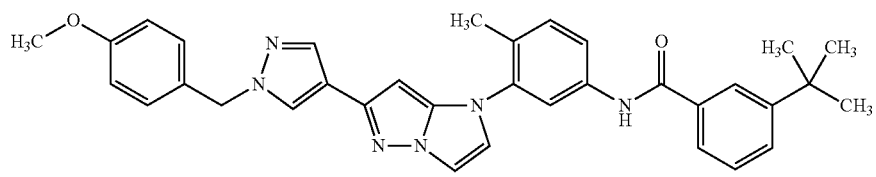 [SMILES: COc1ccc(Cn2cc(-c3cc4n(-c5cc(NC(=O)c6cccc(C(C)(C)C)c6)ccc5C)ccn4n3)cn2)cc1]

Step 1: 3-tert-Butyl-N-(3-{[1-(2,2-diethoxyethyl)-1'-(4-methoxybenzyl)-1H,1'H-3,4'-bipyrazol-5-yl]amino}-4-methylphenyl)benzamide

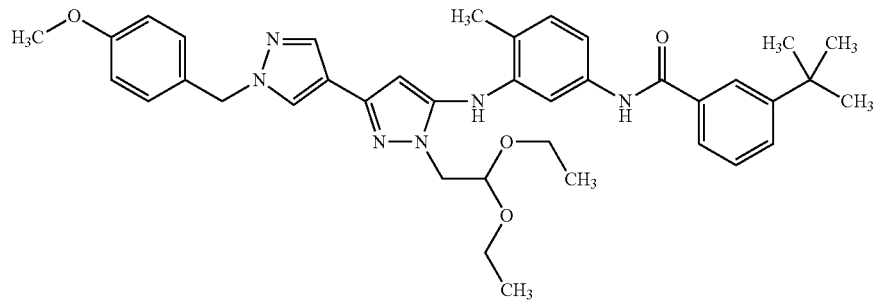 [SMILES: CCOC(Cn1nc(-c2cnn(Cc3ccc(OC)cc3)c2)cc1Nc1cc(NC(=O)c2cccc(C(C)(C)C)c2)ccc1C)OCC]

200 mg (0.44 mmol, purity 85%) of the compound from Example 2A and 199 mg (0.57 mmol) of the compound of Example 46A in 2.18 ml of 1,4-dioxane were degassed with argon. 9.9 mg (0.044 mmol) of palladium(II) acetate, 38.3 mg (0.066 mmol) of xantphos and 431 mg (1.32 mmol) of caesium carbonate were added and the mixture was heated in a microwave oven (Biotage Initiator, with Dynamic Field Tuning) at 150° C. for 30 min. The reaction was then filtered through kieselguhr and the filtrate was concentrated. The residue was subjected to flash-chromatography on silica gel (mobile phase dichloromethane/ethyl acetate 1:1). The product fractions were concentrated under reduced pressure and the residue was dried. This gave 180 mg (63% of theory) of the title compound.

$^1$H NMR (400 MHz, DMSO-$d_6$, δ/ppm): 10.04 (s, 1H), 8.03 (s, 1H), 7.84 (s, 1H), 7.71 (s, 1H), 7.69 (d, 1H), 7.58 (d, 1H), 7.40 (t, 1H), 7.28-7.22 (m, 4H), 7.09 (d, 1H), 6.96 (s, 1H), 6.89 (d, 2H), 6.11 (s, 1H), 5.23 (s, 2H), 4.82 (t, 1H), 4.06 (d, 2H), 3.63 (m, 2H), 3.45 (m, 2H), 2.21 (s, 3H), 1.31 (s, 9H), 1.06 (t, 6H).

LC/MS (Method 3, ESIpos): $R_t$=1.38 min, m/z=651 [M+H]$^+$.

Step 2: 3-tert-Butyl-N-(3-{6-[1-(4-methoxybenzyl)-1H-pyrazol-4-yl]-1H-imidazo[1,2-b]-pyrazol-1-yl}-4-methylphenyl)benzamide

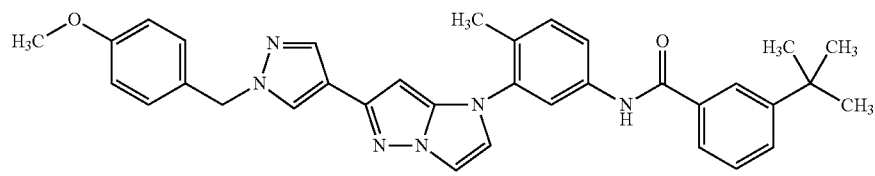 [SMILES: COc1ccc(Cn2cc(-c3cc4n(-c5cc(NC(=O)c6cccc(C(C)(C)C)c6)ccc5C)ccn4n3)cn2)cc1]

150 mg (0.23 mmol) of the compound of Example 52A/Step 1 in 1.2 ml of ethanol and 58 µl (0.12 mmol) of 2 M sulphuric acid were heated in a microwave oven (Biotage Initiator, with Dynamic Field Tuning) at 120° C. for 30 min. The reaction was then concentrated under reduced pressure and the residue was dried. This gave 140 mg (78% pure, 85% of theory) of the title compound which was used without further purification for subsequent reactions.

LC/MS (Method 4, ESIpos): $R_t$=1.27 min, m/z=559 [M+H]$^+$.

Example 53A 3-tert-Butyl-N-(3-{6-[1-(4-methoxybenzyl)-1H-pyrazol-4-yl]-1H-imidazo[1,2-b]pyrazol-1-yl}-4-methylphenyl)-5-(pyrrolidin-1-ylmethyl)benzamide

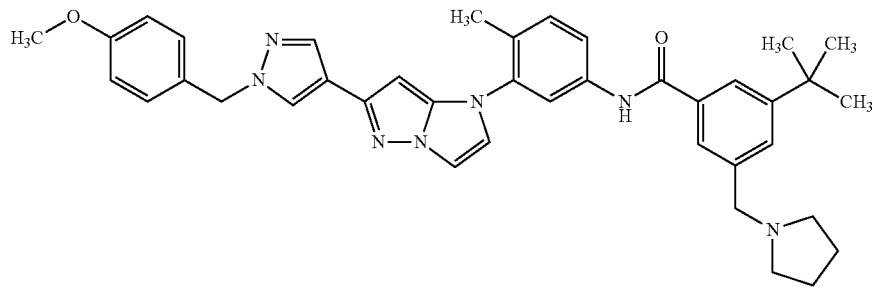 [SMILES: COc1ccc(Cn2cc(-c3cc4n(-c5cc(NC(=O)c6cc(CN7CCCC7)cc(C(C)(C)C)c6)ccc5C)ccn4n3)cn2)cc1]

70 mg (0.14 mmol) of the compound of Example 8A and 51 mg (0.14 mmol) of the compound of Example 22A were reacted analogously to the procedure of Example 48A. This gave 83 mg (88% pure, 83% of theory) of the title compound.

LC/MS (Method 3, ESIpos): $R_t$=0.91 min, m/z=642 [M+H]$^+$.

Example 54A

N-(3-{6-[1-(4-Methoxybenzyl)-1H-pyrazol-4-yl]-3-methyl-1H-imidazo[1,2-b]pyrazol-1-yl}-4-methylphenyl)-3-(4-methylpiperazin-1-yl)-5-(pentafluoro-$\lambda^6$-sulphanyl)benzamide

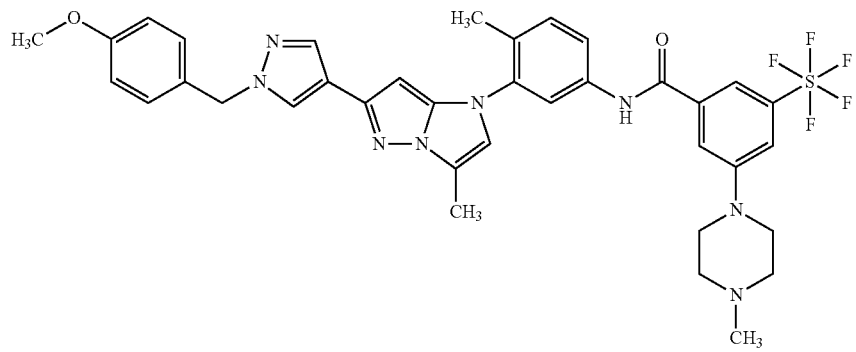 [SMILES: COc1ccc(Cn2cc(-c3cc4n(-c5cc(NC(=O)c6cc(N7CCN(C)CC7)cc(S(F)(F)(F)(F)F)c6)ccc5C)cc(C)n4n3)cn2)cc1]

70 mg (0.17 mmol) of the compound of Example 9A and 78 mg (0.17 mmol) of the compound of Example 17A were reacted and worked up analogously to the procedure of Example 48A. This gave 125 mg (95% of theory) of the title compound.

$^1$H NMR (400 MHz, DMSO-d$_6$, δ/ppm): 10.50 (s, 1H), 8.08 (s, 1H), 7.87 (d, 1H), 7.76 (s, 1H), 7.71 (m, 3H), 7.50 (s, 1H), 7.42 (d, 1H), 7.25 (d, 2H), 7.15 (d, 1H), 6.91 (d, 2H), 5.91 (s, 1H), 5.23 (s, 2H), 3.73 (s, 3H), 2.34 (s, 3H), 2.27 (s, 3H), 2.23 (s, 3H) [further signals obscured by solvent peaks].

LC/MS (Method 3, ESIpos): $R_t$=0.97 min, m/z=741 [M+H]$^+$.

Example 55A

3-Formyl-N-{4-methyl-3-[6-(pyridin-3-yl)-1H-imidazo[1,2-b]pyrazol-1-yl]phenyl}-5-(pentafluoro-λ$^6$-sulphanyl)benzamide

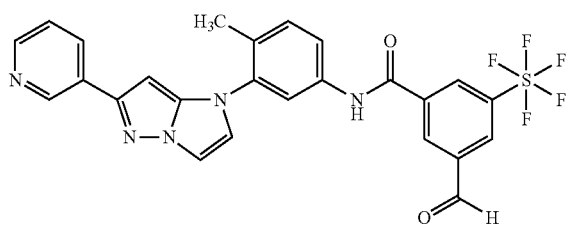 [SMILES: Cc1ccc(NC(=O)c2cc(C=O)cc(S(F)(F)(F)(F)F)c2)cc1-n1ccn2nc(-c3cccnc3)cc12]

320 mg (1.11 mmol) of the compound of Example 6A, 336 mg (1.22 mmol) of the compound of Example 36A and 504 mg (1.33 mmol) of HATU were dissolved in 3.3 ml of DMF, 0.23 ml (1.33 mmol) of N,N-diisopropylethylamine were added and the mixture was stirred at RT for 3 h. The reaction was then stirred into 30 ml of semiconcentrated aqueous sodium bicarbonate solution. After 10 min of stirring at RT, the precipitate formed was filtered off, washed with water and dried. The crude product obtained in this manner was purified by preparative HPLC (Method 12). The product fractions were concentrated, the residue was dissolved in ethyl acetate and the mixture was washed successively with saturated sodium bicarbonate solution and saturated sodium chloride solution. The organic phase was dried over sodium sulphate, filtered and concentrated under reduced pressure. Drying of the residue gave 100 mg (16% of theory) of the title compound.

$^1$H NMR (400 MHz, DMSO-d$_6$, δ/ppm): 10.88 (s, 1H), 10.18 (s, 1H), 9.05 (d, 1H), 8.77 (s, 1H), 8.71 (s, 1H), 8.66 (s, 1H), 8.48 (dd, 1H), 8.19 (dt, 1H), 7.96 (d, 1H), 7.93 (d, 1H), 7.82 (m, 1H), 7.56 (d, 1H), 7.50 (d, 1H), 7.42 (dd, 1H), 6.38 (s, 1H), 2.29 (s, 3H).

LC/MS (Method 3, ESIpos): $R_t$=0.98 min, m/z=548 [M+H]$^+$.

Example 56A

3-Cyano-N-(3-{6-[1-(4-methoxybenzyl)-1H-pyrazol-4-yl]-3-methyl-1H-imidazo[1,2-b]pyrazol-1-yl}-4-methylphenyl)-5-(pentafluoro-λ$^6$-sulphanyl)benzamide

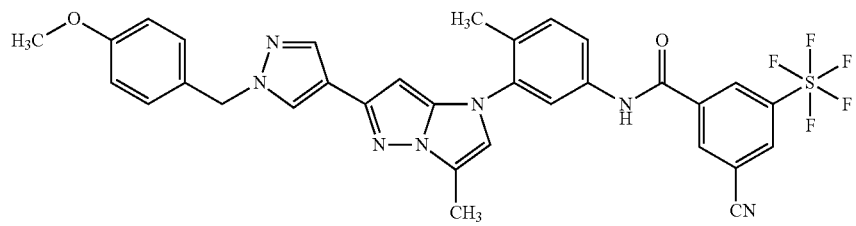 [SMILES: COc1ccc(Cn2cc(-c3cc4n(-c5cc(NC(=O)c6cc(C#N)cc(S(F)(F)(F)(F)F)c6)ccc5C)cc(C)n4n3)cn2)cc1]

100 mg (0.24 mmol) of the compound of Example 9A and 66 mg (0.24 mmol) of the compound of Example 23A were reacted and worked up analogously to the procedure of Example 48A. This gave 153 mg (77% pure, 73% of theory) of the title compound.

LC/MS (Method 1, ESIpos): $R_t$=2.66 min, m/z=576 [M+H]$^+$.

Example 57A 3-tert-Butyl-N-(3-{6-[1-(4-methoxybenzyl)-1H-pyrazol-4-yl]-1H-imidazo[1,2-b]pyrazol-1-yl}-4-methylphenyl)-5-(4-methylpiperazin-1-yl)benzamide

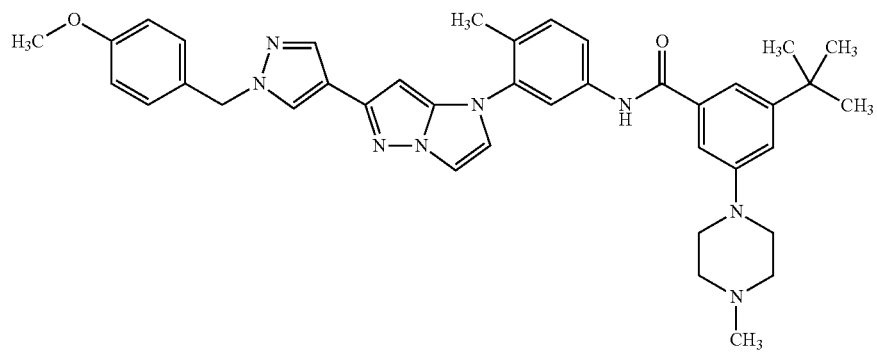 [SMILES: COc1ccc(Cn2cc(-c3cc4n(-c5cc(NC(=O)c6cc(N7CCN(C)CC7)cc(C(C)(C)C)c6)ccc5C)ccn4n3)cn2)cc1]

65 mg (0.13 mmol) of the compound of Example 8A, 50 mg (0.13 mmol) of the compound of Example 21A and 58 mg (0.15 mmol) of HATU were dissolved in 0.73 ml of DMF, 0.07 ml (0.63 mmol) of 4-methylmorpholine was added and the mixture was stirred at RT for 16 h. 10 ml of 0.1 M aqueous sodium hydroxide solution were then added, and the mixture was stirred at RT for another 10 min. The precipitate formed was filtered off, washed with water and dried under high vacuum. This gave 70 mg (76% pure, 64% of theory) of the title compound.

LC/MS (Method 1, ESIpos): $R_t$=1.16 min, m/z=657 [M+H]$^+$.

Example 58A tert-Butyl 3-hydroxy-3-[3-({4-methyl-3-[6-(pyridin-3-yl)-1H-imidazo[1,2-b]pyrazol-1-yl]phenyl}-carbamoyl)-5-(pentafluoro-$\lambda^6$-sulphanyl)phenyl]azetidine-1-carboxylate

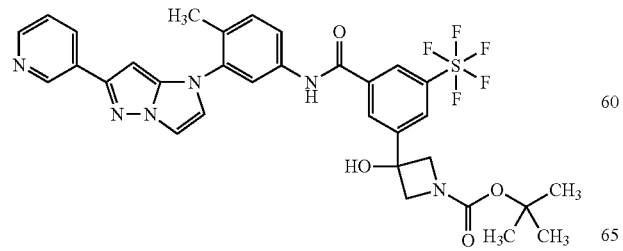

64 mg (0.15 mmol) of the compound of Example 20A and 70 mg (0.18 mmol) of HATU were initially charged in 0.88 ml of DMF, 0.13 ml (1.22 mmol) of 4-methylmorpholine were added and the mixture was stirred at RT for 30 min. At −5° C., 44 mg (0.15 mmol) of the compound of Example 6A were added and the mixture was then stirred at RT for 16 h. Water and 2 M aqueous sodium hydroxide solution were then added, and the mixture was stirred at RT for 15 min. The precipitate formed was filtered off, washed with water and dried. This gave 67 mg (93% pure, 60% of theory) of the title compound.

LC/MS (Method 3, ESIpos): $R_t$=1.07 min, m/z=691 [M+H]$^+$.

Example 59A 1-(2,2-Diethoxyethyl)-3-(pyrazin-2-yl)-1H-pyrazole-5-amine

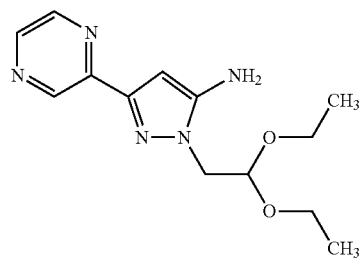

Step 1: Sodium 2-cyano-1-(pyrazin-2-yl)ethenolate

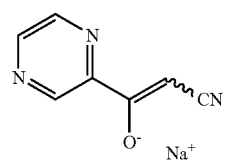 [SMILES: N#CC=C([O-])c1cnccn1 ; [Na+]]

A solution of 1.5 g (10.9 mmol) of methylpyrazine-2-carboxylate and 446 mg (10.9 mmol) of acetonitrile in 16.5 ml of THF was added dropwise to a suspension, heated under reflux, of 434 mg of sodium hydride (60% strength suspension in mineral oil) in 10 ml of THF. The reaction mixture was heated under reflux for 20 h. After cooling, 50 ml of methyl tert-butyl ether were added and the mixture was stirred for 30 minutes. The precipitate formed was filtered off with suction over a frit and dried under oil pump vacuum. This gave 1.77 g (96% of theory) of the title compound which was used without further characterization for the next step.

Step 2: 1-(2,2-Diethoxyethyl)-3-(pyrazin-2-yl)-1H-pyrazole-5-amine

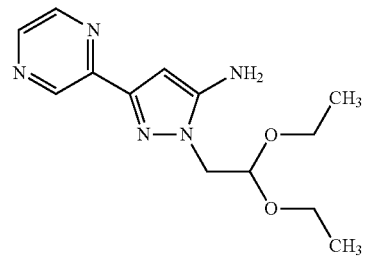

1.76 g (10.4 mmol) of the sodium salt of Example 59A/Step 1 were suspended in 10.5 ml of ethanol, and 1.62 g (10.9 mmol) of (2,2-diethoxyethyl)hydrazine, 0.6 ml (10.4 mmol) of acetic acid and 52 µl of 1 M hydrochloric acid were added in succession. After two hours of heating under reflux, the reaction mixture was cooled to RT and diluted with 200 ml of ethyl acetate. The organic phase was washed in each case once with in each case 30 ml of saturated sodium bicarbonate solution, water and saturated sodium chloride solution, dried over sodium sulphate and, after filtration, concentrated under reduced pressure. The crude product obtained in this manner was purified on a Biotage system (50 g Snap column; mobile phase gradient ethyl acetate/0-10% methanol). This gave 1.17 g (40% of theory) of the title compound.

$^1$H NMR (400 MHz, DMSO-$d_6$, δ/ppm): 9.00 (d, 1H), 8.53 (dd, 1H), 8.43 (d, 1H), 5.87 (s, 1H), 5.31 (s, 2H), 4.84 (t, 1H), 4.02 (d, 2H), 3.63 (dq, 2H), 3.41 (dq, 2H), 1.04 (t, 6H).

LC/MS (Method 7, ESIpos): $R_t$=0.79 min, m/z=278 [M+H]$^+$.

Example 60A

3-{6-[1-(4-Methoxybenzyl)-1H-pyrazol-4-yl]-1H-imidazo[1,2-b]pyrazol-1-yl}-4-methylaniline

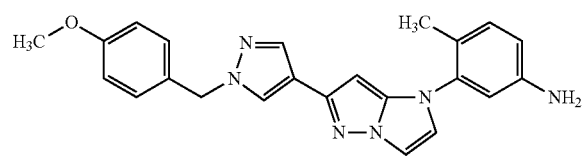

490 mg (1.14 mmol) of the compound of Example 8A/Step 2 were reacted and worked up analogously to Example 9A/Step 3. In this case, the reaction was heated under reflux for 30 min (instead of 1.5 h). This gave 436 mg (77% of theory, 80% pure) of the title compound.

LC/MS (Method 4, ESIpos): $R_t$=0.89 min, m/z=399 [M+H]$^+$.

Example 61A

5-{6-[1-(4-Methoxybenzyl)-1H-pyrazol-4-yl]-1H-imidazo[1,2-b]pyrazol-1-yl}-2,4-dimethylaniline

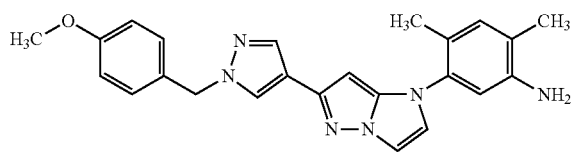

Step 1: 1-(2,2-Diethoxyethyl)-N-(2,4-dimethyl-5-nitrophenyl)-1'-(4-methoxybenzyl)-1H,1'H-3,4'-bi-pyrazole-5-amine

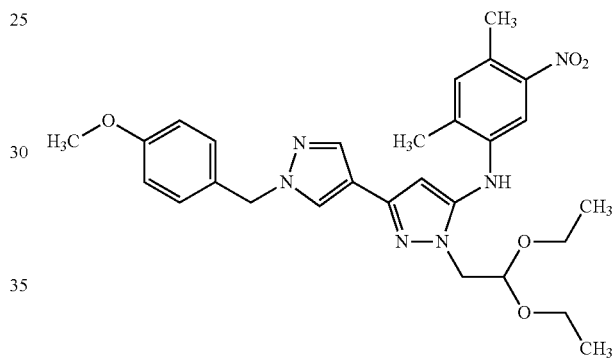

980 mg (2.64 mmol) of the compound of Example 2A were reacted analogously to Example 9A. In deviation from the work-up described therein, here, the mixture was filtered through kieselguhr, the filtrate was concentrated under reduced pressure and the residue was separated into its components by preparative HPLC (Method 35). This gave 1.12 g (66% of theory) of the title compound.

$^1$H NMR (400 MHz, DMSO-$d_6$, δ/ppm): 8.06 (s, 1H), 7.73 (s, 1H), 7.33 (d, 2H), 7.25 (m, 3H), 6.91 (d, 2H), 6.24 (s, 1H), 5.24 (s, 2H), 4.81 (t, 1H), 4.06 (d, 2H), 3.73 (s, 3H), 3.58 (m, 2H), 3.41 (m, 2H), 2.42 (s, 3H), 2.29 (s, 3H), 1.00 (t, 6H).

LC/MS (Method 2, ESIpos): $R_t$=2.68 min, m/z=535 [M+H]$^+$.

Step 2: 1-(2,4-Dimethyl-5-nitrophenyl)-6-[1-(4-methoxybenzyl)-1H-pyrazol-4-yl]-1H-imidazo[1,2-b]pyrazole

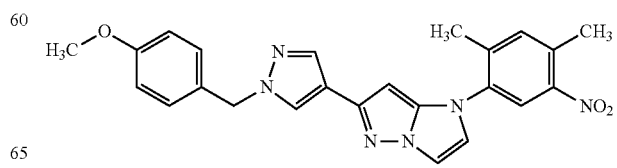

1.12 g (2.10 mmol) of the compound of Example 61A/Step 1 in 21 ml of ethanol with addition of 2.5 ml (5.03 mmol) of 2 M sulphuric acid were heated under reflux for 16 h. After the mixture had cooled, the precipitate formed was filtered off, washed with ethanol and dried. The filter cake was taken up in 20 ml of ethyl acetate, and the solution was washed with in each case 10 ml of saturated aqueous potassium carbonate solution and saturated aqueous sodium chloride solution and dried over sodium sulphate. After filtration, the filtrate was freed from the solvent on a rotary evaporator and the residue was dried under high vacuum. This gave 410 mg (44% of theory) of the title compound.

$^1$H NMR (400 MHz, DMSO-$d_6$, δ/ppm): 8.05 (d, 2H), 7.79 (d, 1H), 7.74 (s, 1H), 7.62 (s, 1H), 7.47 (d, 1H), 7.23 (d, 2H), 6.90 (d, 2H), 5.96 (s, 1H), 5.25 (s, 2H), 3.73 (s, 3H), 2.58 (s, 3H), 2.33 (s, 3H).

LC/MS (Method 3, ESIpos): $R_t$=1.06 min, m/z=443 [M+H]$^+$.

Step 3: 5-{6-[1-(4-Methoxybenzyl)-1H-pyrazol-4-yl]-1H-imidazo[1,2-b]pyrazol-1-yl}-2,4-dimethylaniline

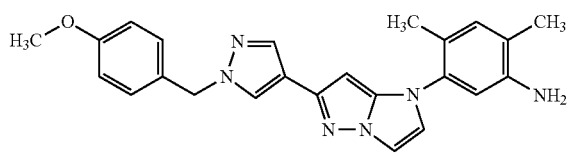

200 mg (0.45 mmol) of the compound of Example 61A/Step 2 were reacted analogously to Example 61A. After the reaction had ended, the mixture was filtered, the filtrate was concentrated under reduced pressure and the residue was separated into its components by preparative HPLC (Method 21). The product-containing fractions were combined, concentrated almost completely under reduced pressure and made alkaline with a little saturated aqueous sodium bicarbonate solution. The resulting precipitate was filtered off, washed with water and dried under high vacuum. This gave 120 mg (64% of theory) of the title compound.

$^1$H NMR (400 MHz, DMSO-$d_6$, δ/ppm): 8.03 (s, 1H), 7.73 (s, 1H), 7.66 (d, 1H), 7.26-7.20 (m, 3H), 6.94-6.88 (m, 3H), 6.63 (s, 1H), 5.78 (s, 1H), 5.24 (s, 2H), 4.96 (s, 2H), 3.72 (s, 3H), 2.07 (s, 3H), 2.03 (s, 3H).

LC/MS (Method 3, ESIpos): $R_t$=0.94 min, m/z=413 [M+H]$^+$.

Example 62A

3-[6-(Pyridin-3-yl)-1H-imidazo[1,2-b]pyrazol-1-yl]aniline

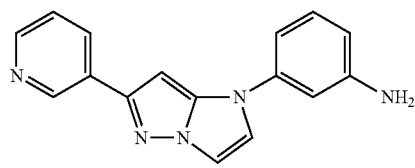 [SMILES: Nc1cccc(-n2ccn3nc(-c4cccnc4)cc23)c1]

Step 1: 1-(2,2-Diethoxyethyl)-N-(3-nitrophenyl)-3-(pyridin-3-yl)-1H-pyrazole-5-amine

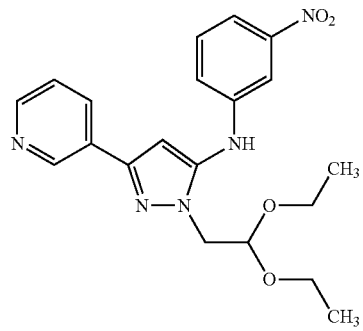 [SMILES: CCOC(Cn1nc(-c2cccnc2)cc1Nc1cccc([N+](=O)[O-])c1)OCC]

Analogously to the process described under Example 6A/Step 1, 1.0 g (3.62 mmol) of the compound of Example 4A and 804 mg (3.98 mmol) of 1-bromo-3-nitrobenzene gave 1.26 g (87% of theory) of the title compound. In this case, chromatographic isolation of the product was by MPLC (mobile phase cyclohexane/ethyl acetate 1:2); subsequent trituration with diisopropyl ether was dispensed with.

$^1$H NMR (400 MHz, CDCl$_3$, δ/ppm): 9.02 (d, 1H), 8.57 (dd, 1H), 8.08 (dt, 1H), 7.80 (t, 1H), 7.74 (dd, 1H), 7.42 (t, 1H), 7.34 (dd, 1H), 7.28-7.25 (m, 2H, partially obscured by the CHCl$_3$ signal), 6.47 (s, 1H), 4.82 (t, 1H), 4.30 (d, 2H), 3.90-3.83 (m, 2H), 3.64-3.56 (m, 2H), 1.28 (t, 6H).

LC/MS (Method 3, ESIpos): $R_t$=0.93 min, m/z=398 [M+H]$^+$.

Step 2: 1-(3-Nitrophenyl)-6-(pyridin-3-yl)-1H-imidazo[1,2-b]pyrazole

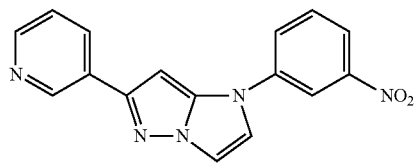

3.8 ml (7.55 mmol) of 2 M sulphuric acid were added to a solution of 1.25 g (3.14 mmol) of the compound of Example 62A/Step 1 in 12.5 ml of ethanol, and the mixture was then heated in a microwave oven (Biotage Initiator, with Dynamic Field Tuning) at 130° C. for 15 minutes. After cooling to RT, the reaction mixture was added with stirring to about 25 ml of saturated aqueous potassium carbonate solution. This mixture was extracted twice with in each case about 50 ml of ethyl acetate and the combined organic phases were washed with saturated sodium chloride solution. After drying over anhydrous magnesium sulphate and filtration, the filtrate was concentrated under reduced pressure and the residue was then dried under high vacuum. This gave 874 mg (82% of theory, 91% pure) of the title compound.

$^1$H NMR (400 MHz, DMSO-$d_6$, δ/ppm): 9.13 (d, 1H), 8.53 (dd, 1H), 8.50 (t, 1H), 8.26 (dt, 1H), 8.22-8.19 (m, 2H), 8.12 (dd, 1H), 8.06 (d, 1H), 7.86 (t, 1H), 7.48 (dd, 1H), 7.07 (s, 1H).

LC/MS (Method 2, ESIpos): $R_t$=1.72 min, m/z=306 [M+H]$^+$.

Step 3: 3-[6-(Pyridin-3-yl)-1H-imidazo[1,2-b]pyrazol-1-yl]aniline

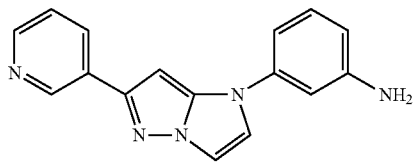 [SMILES: Nc1cccc(-n2ccn3nc(-c4cccnc4)cc23)c1]

Analogously to the process described in Example 9A/Step 3, 855 mg (2.80 mmol) of the compound of Example 62A/Step 2 gave 760 mg (98% of theory) of the title compound. In this case, the reaction time was 30 minutes.

$^1$H NMR (400 MHz, DMSO-d$_6$, δ/ppm): 9.09 (d, 1H), 8.51 (dd, 1H), 8.21 (dt, 1H), 7.91 (d, 1H), 7.80 (d, 1H), 7.46 (dd, 1H), 7.17 (t, 1H), 6.92 (dd, 1H), 6.83 (dd, 1H), 6.80 (s, 1H), 6.49 (dd, 1H), 5.41 (s, broad, 2H).

LC/MS (Method 3, ESIpos): $R_t$=0.57 min, m/z=276 [M+H]$^+$.

Example 63A

3-[6-(Pyridin-3-yl)-1H-imidazo[1,2-b]pyrazol-1-yl]-4-(trifluoromethyl)aniline

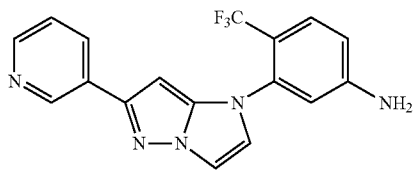

Step 1: 1-(2,2-Diethoxyethyl)-N-[5-nitro-2-(trifluoromethyl)phenyl]-3-(pyridin-3-yl)-1H-pyrazole-5-amine

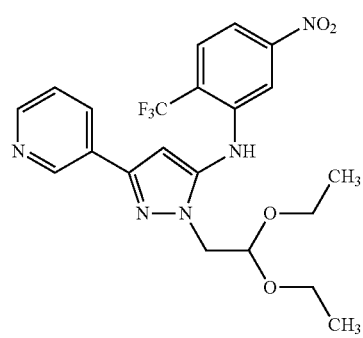

Analogously to Example 13A/Step 1, 1.50 g (5.43 mmol) of the compound of Example 4A and 1.47 g (5.43 mmol) of 2-bromo-4-nitro-1-(trifluoromethyl)benzene gave 2.03 g (75% of theory) of the title compound.

$^1$H NMR (400 MHz, DMSO-d$_6$, δ/ppm): 9.11 (s, 1H), 9.00 (d, 1H), 8.49 (dd, 1H), 8.14 (dt, 1H), 7.77 (d, 1H), 7.39-7.45 (m, 2H), 7.24 (dd, 1H), 6.86 (s, 1H), 4.84 (t, 1H), 4.15 (d, 2H), 3.56 (dq, 2H), 3.36 (dq, 2H), 0.94 (t, 6H).

LC/MS (Method 7, ESIpos): $R_t$=1.24 min, m/z=466 [M+H]$^+$.

Step 2: 1-[5-Nitro-2-(trifluoromethyl)phenyl]-6-(pyridin-3-yl)-1H-imidazo[1,2-b]pyrazole

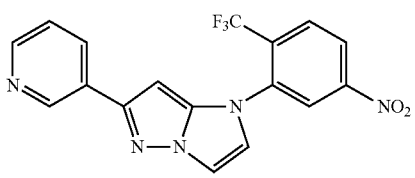

Analogously to Example 13A/Step 2, 2.03 g (4.36 mmol) of the compound of Example 63A/Step 1 gave a crude product which was purified by single chromatography on a Biotage system (50 g Snap column; mobile phase gradient dichloromethane/methanol, from 2% methanol increasing steadily to 8% methanol). This gave 1.17 g (65% of theory) of the title compound.

$^1$H NMR (400 MHz, DMSO-d$_6$, δ/ppm): 9.08 (dd, 1H), 8.51 (dd, 1H), 8.38 (d, 1H), 8.20 (dt, 1H), 8.14-8.18 (m, 2H), 8.11 (d, 1H), 8.08 (d, 1H), 7.45 (ddd, 1H), 7.20 (s, 1H).

LC/MS (Method 7, ESIpos): $R_t$=1.05 min, m/z=374 [M+H]$^+$.

Step 3: 3-[6-(Pyridin-3-yl)-1H-imidazo[1,2-b]pyrazol-1-yl]-4-(trifluoromethyl)aniline

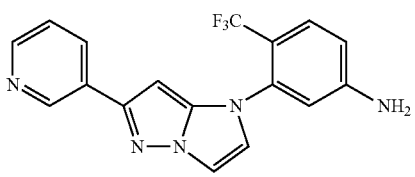

Analogously to Example 13A/Step 3, 1.17 g (3.13 mmol) of the compound of Example 63A/Step 2 gave 866 mg (78% of theory) of the title compound.

$^1$H NMR (400 MHz, DMSO-d$_6$, δ/ppm): 9.05 (dd, 1H), 8.50 (dd, 1H), 8.17 (dt, 1H), 7.95 (d, 1H), 7.87 (d, 1H), 7.41-7.48 (m, 2H), 7.16 (d, 1H), 6.96 (dd, 1H), 6.89 (d, 1H), 5.84 (s, 2H).

LC/MS (Method 7, ESIpos): $R_t$=0.93 min, m/z=344 [M+H]$^+$.

Example 64A

4-Chloro-3-[6-(pyridin-3-yl)-1H-imidazo[1,2-b]pyrazol-1-yl]aniline

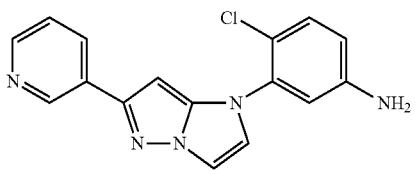 [SMILES: O=[N+]([O-])c1ccc(Cl)c(-n2ccn3nc(-c4cccnc4)cc23)c1]

Step 1: N-(2-Chloro-5-nitrophenyl)-1-(2,2-diethoxy-ethyl)-3-(pyridin-3-yl)-1H-pyrazole-5-amine

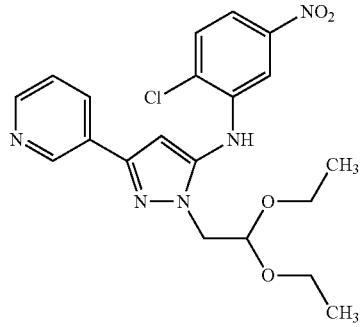

Analogously to the process described in Example 9A/Step 1, 1.0 g (3.62 mmol) of the compound of Example 4A and 941 mg (3.98 mmol) of 1-bromo-2-chloro-5-nitrobenzene gave 1.26 g (80% of theory) of the title compound. In this case, the reaction time in the microwave reactor was 1 h at a temperature of 140° C. Chromatographic isolation of the product was by MPLC (mobile phase cyclohexane/ethyl acetate 1:2).

$^1$H NMR (400 MHz, CDCl$_3$, δ/ppm): 9.04 (d, 1H), 8.58 (dd, 1H), 8.09 (dt, 1H), 8.04 (d, 1H), 7.68 (dd, 1H), 7.53-7.50 (m, 2H), 7.36 (dd, 1H), 6.55 (s, 1H), 4.81 (t, 1H), 4.30 (d, 2H), 3.88-3.80 (m, 2H), 3.66-3.58 (m, 2H), 1.26 (t, 6H).

LC/MS (Method 3, ESIpos): R$_t$=1.08 min, m/z=432/434 [M+H]$^+$.

Step 2: 1-(2-Chloro-5-nitrophenyl)-6-(pyridin-3-yl)-1H-imidazo[1,2-b]pyrazole

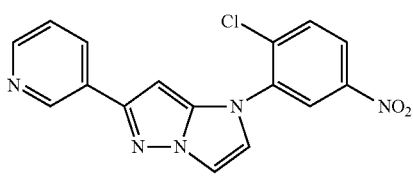

4 ml (8 mmol) of 2 M sulphuric acid were added to a solution of 1.44 g (3.33 mmol) of the compound of Example 64A/Step 1 in 14 ml of ethanol, and the mixture was then heated in a microwave oven (Biotage Initiator, with Dynamic Field Tuning) at 130° C. for 60 minutes. After cooling to RT, the reaction mixture was added with stirring to about 50 ml of saturated aqueous sodium bicarbonate solution. This mixture was extracted twice with in each case about 50 ml of ethyl acetate and the combined organic phases were washed with saturated sodium chloride solution. After drying over anhydrous magnesium sulphate and filtration, the filtrate was concentrated under reduced pressure. From the residue obtained in this manner, the product was isolated by MPLC (silica gel, dichloromethane/methanol 50:1). This gave 160 mg (14% of theory) of the title compound.

$^1$H NMR (400 MHz, DMSO-d$_6$, δ/ppm): 9.05 (d, 1H), 8.53 (d, 1H), 8.50 (dd, 1H), 8.34 (dd, 1H), 8.19 (dt, 1H), 8.08 (d, 1H), 8.01 (d, 1H), 7.69 (d, 1H), 7.43 (dd, 1H), 6.47 (s, 1H).

LC/MS (Method 4, ESIpos): R$_t$=0.77 min, m/z=340/342 [M+H]$^+$.

Step 3: 4-Chloro-3-[6-(pyridin-3-yl)-1H-imidazo[1,2-b]pyrazol-1-yl]aniline

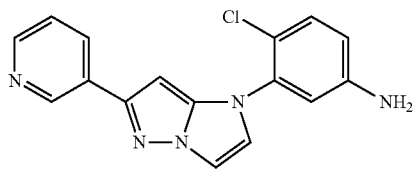

Analogously to the process described in Example 9A/Step 3, 310 mg (0.912 mmol) of the compound of Example 64A/Step 2 gave, after a reaction time of 60 minutes, 267 mg (73% pure, 68% of theory) of a mixture which consisted of the title compound and the compound from Example 62A in a ratio of 73:27. This mixture was used without further purification for subsequent reactions.

$^1$H NMR (400 MHz, CDCl$_3$, δ/ppm, for the title compound): 9.05 (d, 1H), 8.53 (dd, 1H), 8.16 (dt, 1H), 7.48 (d, 1H), 7.34-7.29 (m, 2H), 7.08 (d, 1H), 6.82 (d, 1H), 6.67 (dd, 1H), 6.12 (s, 1H), 3.91 (s, broad, 2H).

LC/MS (Method 3, ESIpos): R$_t$=0.66 min, m/z=310/312 [M+H]$^+$.

Example 65A 3,4-Dimethyl-5-[6-(pyridin-3-yl)-1H-imidazo[1,2-b]pyrazol-1-yl]aniline

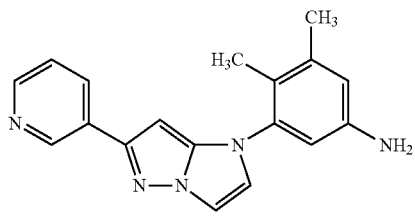 [SMILES: Cc1cc(N)cc(-n2ccn3nc(-c4cccnc4)cc23)c1C]

Step 1: 1-(2,2-Diethoxyethyl)-N-(2,3-dimethyl-5-nitrophenyl)-3-(pyridin-3-yl)-1H-pyrazole-5-amine

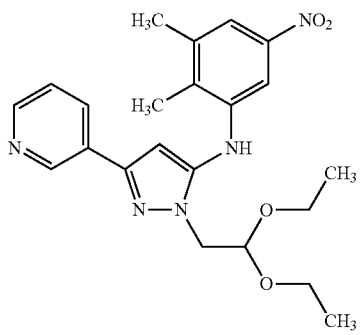 [SMILES: CCOC(Cn1nc(-c2cccnc2)cc1Nc1cc([N+](=O)[O-])cc(C)c1C)OCC]

Analogously to Example 13A/Step 1, two batches of 100 mg (0.36 mmol) and of 1.50 g (5.43 mmol), respectively, of the compound of Example 4A and 92 mg (0.40 mmol) and 1.37 g (5.97 mmol), respectively, of 1-bromo-2,3-dimethyl-5-nitrobenzene gave a total of 1.31 g (23% of theory) of the title compound.

¹H NMR (400 MHz, DMSO-d₆, δ/ppm): 8.99 (d, 1H), 8.47 (dd, 1H), 8.13 (dt, 1H), 7.54-7.60 (m, 2H), 7.36-7.42 (m, 2H), 6.62 (s, 1H), 4.87 (t, 1H), 4.13 (d, 2H), 3.58 (dq, 2H), 3.41 (dq, 2H), 2.35 (s, 3H), 2.23 (s, 3H), 0.98 (t, 6H).

LC/MS (Method 7, ESIpos): $R_t$=1.34 min, m/z=426 [M+H]⁺.

Step 2: 1-(2,3-Dimethyl-5-nitrophenyl)-6-(pyridin-3-yl)-1H-imidazo[1,2-b]pyrazole

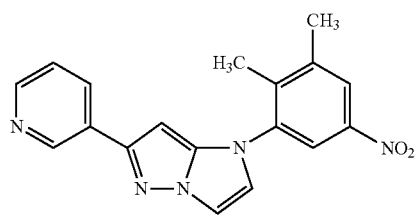 [SMILES: Cc1cc([N+](=O)[O-])cc(-n2ccn3nc(-c4cccnc4)cc23)c1C]

Analogously to Example 13A/Step 2, 1.31 g (3.08 mmol) of the compound of Example 65A/Step 1 gave a crude product which was purified by single chromatography on a Biotage system (50 g Snap column; mobile phase gradient dichloromethane/methanol, from 0% methanol increasing steadily to 10% methanol). This gave 670 mg (63% of theory) of the title compound.

¹H NMR (400 MHz, DMSO-d₆, δ/ppm): 9.00 (dd, 1H), 8.45 (dd, 1H), 8.19 (d, 1H), 8.14 (dt, 1H), 8.10 (d, 1H), 7.92 (dd, 1H), 7.55 (d, 1H), 7.38 (ddd, 1H), 6.35 (s, 1H), 2.23 (s, 3H).

LC/MS (Method 7, ESIpos): $R_t$=0.93 min, m/z=334 [M+H]⁺.

Step 3: 3,4-Dimethyl-5-[6-(pyridin-3-yl)-1H-imidazo[1,2-b]pyrazol-1-yl]aniline

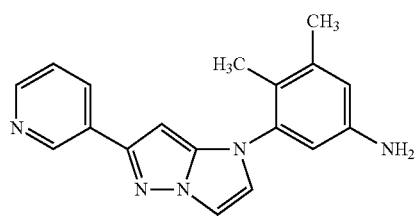

Analogously to Example 13A/Step 3, 670 mg (2.01 mmol) of the compound of Example 65A/Step 2 gave 524 mg (86% of theory) of the title compound.

¹H NMR (400 MHz, DMSO-d₆, δ/ppm): 9.00 (dd, 1H), 8.43 (dd, 1H), 8.14 (dt, 1H), 7.78 (dd, 1H), 7.36 (ddd, 1H), 7.32 (d, 1H), 6.50 (d, 1H), 6.42 (d, 1H), 6.19 (d, 1H), 5.08 (s, 2H), 2.17 (s, 3H), 1.90 (s, 3H).

LC/MS (Method 7, ESIpos): $R_t$=0.73 min, m/z=304 [M+H]⁺.

Example 66A

3-Fluoro-4-methyl-5-[6-(pyridin-3-yl)-1H-imidazo[1,2-b]pyrazol-1-yl]aniline

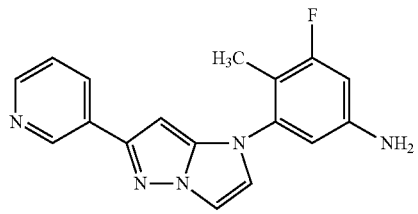 [SMILES: Cc1c(F)cc(N)cc1-n1ccn2nc(-c3cccnc3)cc12]

Step 1: N-(3-Fluoro-2-methyl-5-nitrophenyl)-1-(2,2-diethoxyethyl)-3-(pyridin-3-yl)-1H-pyrazole-5-amine

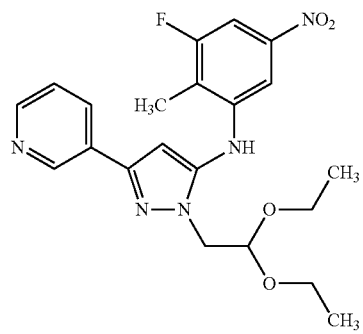

Analogously to Example 13A/Step 1, 1.5 g (5.43 mmol) of the compound of Example 4A and 1.4 g (5.97 mmol) of 1-bromo-3-fluoro-2-methyl-5-nitrobenzene gave 1.19 g (50% of theory) of the title compound.

¹H NMR (400 MHz, DMSO-d₆, δ/ppm): 9.00 (d, 1H), 8.49 (dd, 1H), 8.14 (dt, 1H), 7.89 (s, 1H), 7.50 (dd, 1H), 7.41 (ddd, 1H), 7.28-7.31 (m, 1H), 6.78 (s, 1H), 4.87 (t, 1H), 4.14 (d, 2H), 3.51-3.61 (m, 2H), 3.35-3.45 (m, 2H), 2.24 (d, 3H), 0.96 (t, 6H).

LC/MS (Method 7, ESIpos): $R_t$=1.25 min, m/z=430 [M+H]⁺.

Step 2: 1-(3-Fluoro-2-methyl-5-nitrophenyl)-6-(pyridin-3-yl)-1H-imidazo[1,2-b]pyrazole

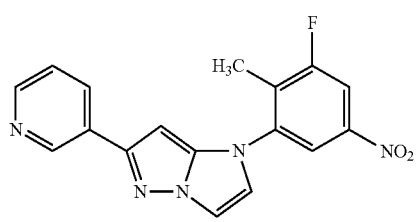 [SMILES: Cc1c(F)cc([N+](=O)[O-])cc1-n1ccn2nc(-c3cccnc3)cc12]

Analogously to Example 13A/Step 2, 1.19 g (2.77 mmol) of the compound of Example 66A/Step 1 gave a crude product which was purified by single chromatography on a Biotage system (25 g Snap column; mobile phase gradient hexane/ethyl acetate, from 0% ethyl acetate increasing steadily to 100% ethyl acetate, then ethyl acetate/methanol, proportion of methanol increasing slowly from 0 to 80%). This gave 587 mg (60% of theory) of the title compound.

$^1$H NMR (400 MHz, DMSO-d$_6$, δ/ppm): 9.01 (d, 1H), 8.46 (dd, 1H), 8.12-8.24 (m, 3H), 7.97 (dd, 1H), 7.64 (d, 1H), 7.39 (ddd, 1H), 6.48 (s, 1H), 2.30 (d, 3H).

LC/MS (Method 7, ESIpos): R$_t$=0.92 min, m/z=338 [M+H]$^+$.

Step 3: 3-Fluoro-4-methyl-5-[6-(pyridin-3-yl)-1H-imidazo[1,2-b]pyrazol-1-yl]aniline

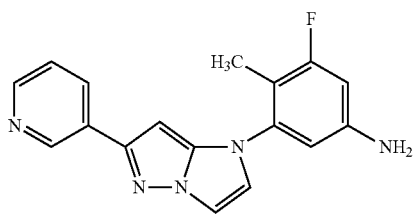

Analogously to Example 13A/Step 3, 570 mg (1.69 mmol) of the compound of Example 66A/Step 2 gave 520 mg (100% of theory) of the title compound.

$^1$H NMR (400 MHz, DMSO-d$_6$, δ/ppm): 9.01 (d, 1H), 8.44 (dd, 1H), 8.15 (dt, 1H), 7.83 (d, 1H), 7.43 (d, 1H), 7.37 (dd, 1H), 6.46 (s, 1H), 6.41 (dd, 1H), 6.31 (s, 1H), 5.52 (s, 2H), 1.95 (d, 3H).

LC/MS (Method 7, ESIpos): R$_t$=0.79 min, m/z=308 [M+H]$^+$.

Example 67A

3-Chloro-4-methyl-5-[6-(pyridin-3-yl)-1H-imidazo[1,2-b]pyrazol-1-yl]anilin

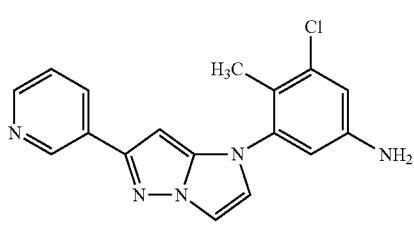

Step 1: N-(3-Chloro-2-methyl-5-nitrophenyl)-1-(2,2-diethoxyethyl)-3-(pyridin-3-yl)-1H-pyrazole-5-amine

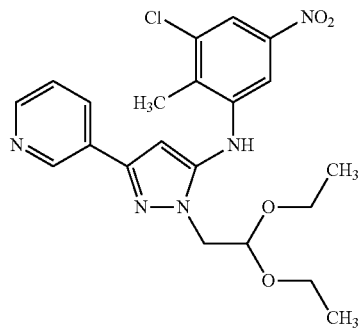 [SMILES: CCOC(Cn1nc(-c2cccnc2)cc1Nc1cc([N+](=O)[O-])cc(Cl)c1C)OCC]

Analogously to Example 13A/Step 1, 1.0 g (3.62 mmol) of the compound of Example 4A and 1.0 g (3.98 mmol) of 1-bromo-3-chloro-2-methyl-5-nitrobenzene gave 670 mg (42% of theory) of the title compound. The starting material 1-bromo-3-chloro-2-methyl-5-nitrobenzene can be prepared from 2-chloro-1-methyl-4-nitrobenzene by a process described in U.S. Pat. No. 5,877,191 for the preparation of 3-bromo-5-fluoro-4-methyl-1-nitrobenzene.

$^1$H NMR (400 MHz, DMSO-d$_6$, δ/ppm): 9.00 (d, 1H), 8.49 (dd, 1H), 8.14 (dt, 1H), 7.88 (s, 1H), 7.71 (d, 1H), 7.35-7.45 (m, 2H), 6.76 (s, 1H), 4.87 (t, 1H), 4.13 (d, 2H), 3.50-3.63 (m, 2H), 3.33-3.46 (m, 2H), 2.39 (s, 3H), 0.96 (t, 6H).

LC/MS (Method 7, ESIpos): R$_t$=1.40 min, m/z=446/448 [M+H]$^+$.

Step 2: 1-(3-Chloro-2-methyl-5-nitrophenyl)-6-(pyridin-3-yl)-1H-imidazo[1,2-b]pyrazole

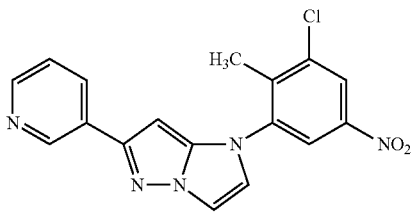 [SMILES: Cc1c(Cl)cc([N+](=O)[O-])cc1-n1ccn2nc(-c3cccnc3)cc12]

Analogously to Example 13A/Step 2, 670 mg (1.50 mmol) of the compound of Example 67A/Step 1 gave a crude product which was purified by single chromatography on a Biotage system (25 g Snap column; mobile phase gradient hexane/ethyl acetate, from 0% ethyl acetate increasing steadily to 100% ethyl acetate, then ethyl acetate/methanol, proportion of methanol increasing slowly from 0 to 80%). This gave 309 mg (52% of theory) of the title compound.

$^1$H NMR (400 MHz, DMSO-d$_6$, δ/ppm): 9.01 (d, 1H), 8.45 (dd, 1H), 8.40 (d, 1H), 8.27 (d, 1H), 8.15 (dt, 1H), 7.96 (d, 1H), 7.62 (d, 1H), 7.39 (dd, 1H), 6.46 (s, 1H), 2.39 (s, 3H).

LC/MS (Method 7, ESIpos): $R_t$=1.00 min, m/z=354/356 [M+H]$^+$.

Step 3: 3-Chloro-4-methyl-5-[6-(pyridin-3-yl)-1H-imidazo[1,2-b]pyrazol-1-yl]aniline

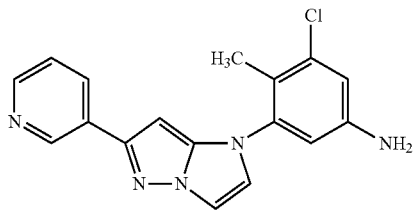

Analogously to Example 13A/Step 3, 253 mg (0.72 mmol) of the compound of Example 67A/Step 2 gave 249 mg (97% of theory) of the title compound.

$^1$H NMR (400 MHz, DMSO-d$_6$, δ/ppm): 9.01 (d, 1H), 8.44 (dd, 1H), 8.15 (dt, 1H), 7.83 (d, 1H), 7.42 (d, 1H), 7.37 (dd, 1H), 6.73 (d, 1H), 6.58 (d, 1H), 6.30 (s, 1H), 5.51 (s, 2H), 2.04 (s, 3H).

LC/MS (Method 7, ESIpos): $R_t$=0.86 min, m/z=324/326 [M+H]$^+$.

Example 68A 2,4-Dimethyl-3-[6-(pyridin-3-yl)-1H-imidazo[1,2-b]pyrazol-1-yl]aniline

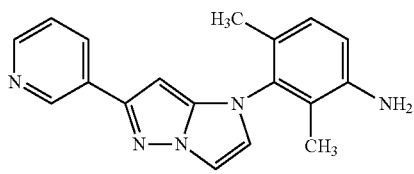

Step 1: 1-(2,2-Diethoxyethyl)-N-(2,6-dimethyl-3-nitrophenyl)-3-(pyridin-3-yl)-1H-pyrazole-5-amine

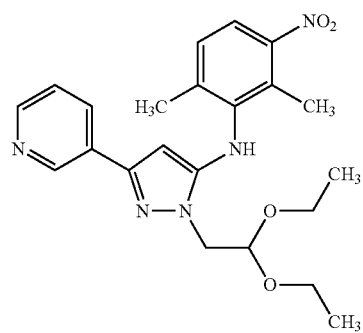 [SMILES: CCOC(Cn1nc(-c2cccnc2)cc1Nc1c(C)ccc([N+](=O)[O-])c1C)OCC]

Analogously to Example 13A/Step 1, a test reaction with 1.0 g (3.62 mmol) and the main reaction with 2.0 g (7.24 mmol), respectively, of the compound of Example 4A and 916 mg (3.98 mmol) and 1.83 g (7.96 mmol), respectively, of 4-bromo-1,3-dimethyl-2-nitrobenzene gave a total of 3.15 g (75% of theory) of the title compound.

$^1$H NMR (400 MHz, DMSO-d$_6$, δ/ppm): 8.83 (d, 1H), 8.39 (dd, 1H), 7.95-8.00 (m, 1H), 7.70 (d, 1H), 7.40 (s, 1H), 7.34 (d, 1H), 7.29 (dd, 1H), 5.46 (s, 1H), 4.97 (t, 1H), 4.24 (d, 2H), 3.62-3.73 (m, 2H), 3.44-3.54 (m, 2H), 2.27 (s, 3H), 2.25 (s, 3H), 1.06 (t, 6H).

LC/MS (Method 6, ESIpos): $R_t$=1.15 min, m/z=426 [M+H]$^+$.

Step 2: 1-(2,6-Dimethyl-3-nitrophenyl)-6-(pyridin-3-yl)-1H-imidazo[1,2-b]pyrazole

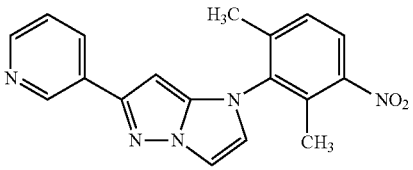

Analogously to Example 13A/Step 2, two batches of in each case 1.58 g (3.70 mmol) of the compound of Example 68A/Step 1 gave a crude product which was initially purified on a Biotage system (100 g Snap column; mobile phase gradient hexane/ethyl acetate, from 0% ethyl acetate increasing steadily to 100% ethyl acetate, then ethyl acetate/methanol, proportion of methanol increasing slowly from 0 to 80%). A second purification was then carried out by preparative HPLC (Method 16). This gave 534 mg (22% of theory) of the title compound.

$^1$H NMR (400 MHz, DMSO-d$_6$, δ/ppm): 8.99 (dd, 1H), 8.44 (dd, 1H), 8.13 (dt, 1H), 8.03 (d, 1H), 7.92 (dd, 1H), 7.55 (d, 1H), 7.44 (d, 1H), 7.37 (ddd, 1H), 6.23 (d, 1H), 2.14 (s, 3H), 2.13 (s, 3H).

LC/MS (Method 6, ESIpos): $R_t$=0.93 min, m/z=334 [M+H]$^+$.

Step 3: 2,4-Dimethyl-3-[6-(pyridin-3-yl)-1H-imidazo[1,2-b]pyrazol-1-yl]aniline

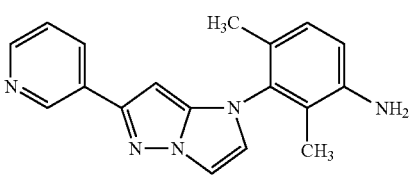

Analogously to Example 13A/Step 3, 530 mg (1.59 mmol) of the compound of Example 68A/Step 2 gave 507 mg (99% of theory) of the title compound.

$^1$H NMR (400 MHz, DMSO-d$_6$, δ/ppm): 8.99 (dd, 1H), 8.42 (dd, 1H), 8.13 (dt, 1H), 7.80 (dd, 1H), 7.35 (ddd, 1H), 7.25 (d, 1H), 6.91 (d, 1H), 6.69 (d, 1H), 6.08 (d, 1H), 4.96 (s, 2H), 1.86 (s, 3H), 1.72 (s, 3H).

LC/MS (Method 6, ESIpos): R$_t$=0.74 min, m/z=304 [M+H]$^+$.

Example 69A

2-Methyl-3-[6-(pyridin-3-yl)-1H-imidazo[1,2-b]pyrazol-1-yl]aniline

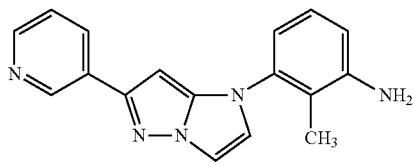

Step 1: 1-(2,2-Diethoxyethyl)-N-(2-methyl-3-nitrophenyl)-3-(pyridin-3-yl)-1H-pyrazole-5-amine

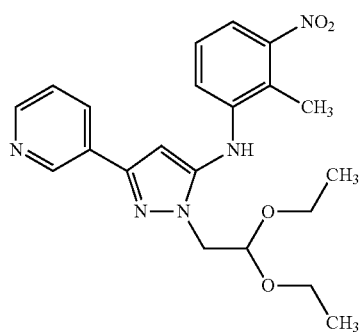 [SMILES: CCOC(Cn1nc(-c2cccnc2)cc1Nc1cccc([N+](=O)[O-])c1C)OCC]

Analogously to the process described in Example 64A/Step 1, 1.0 g (3.62 mmol) of the compound of Example 4A and 860 mg (3.98 mmol) of 2-bromo-6-nitrotoluene gave 1.45 g (97% of theory) of the title compound.

$^1$H NMR (400 MHz, CDCl$_3$, δ/ppm): 9.00 (d, 1H), 8.56 (dd, 1H), 8.08 (dt, 1H), 7.35-7.31 (m, 3H), 7.22 (t, 1H), 6.80 (s, 1H), 6.37 (s, 1H), 4.82 (t, 1H), 4.27 (d, 2H), 3.88-3.80 (m, 2H), 3.66-3.58 (m, 2H), 2.38 (s, 3H), 1.26 (t, 6H).

LC/MS (Method 3, ESIpos): R$_t$=1.02 min, m/z=412 [M+H]$^+$.

Step 2: 1-(2-Methyl-3-nitrophenyl)-6-(pyridin-3-yl)-1H-imidazo[1,2-b]pyrazole

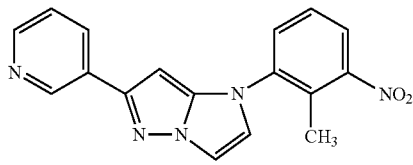

Analogously to the process described in Example 64A/Step 2, 1.43 g (3.47 mmol) of the compound of Example 69A/Step 1 gave 1.09 g (95% of theory) of the title compound. In this case, the reaction time in the microwave was 15 min at 130° C. Here, chromatographic purification of the product could be dispensed with.

$^1$H NMR (400 MHz, DMSO-d$_6$, δ/ppm): 9.06 (d, 1H), 8.49 (dd, 1H), 8.19 (dt, 1H), 8.06 (d, 1H), 7.97 (d, 1H), 7.88 (d, 1H), 7.66 (t, 1H), 7.61 (d, 1H), 7.42 (dd, 1H), 6.44 (s, 1H), 2.35 (s, 3H).

LC/MS (Method 4, ESIpos): R$_t$=0.76 min, m/z=320 [M+H]$^+$.

Step 3: 2-Methyl-3-[6-(pyridin-3-yl)-1H-imidazo[1,2-b]pyrazol-1-yl]aniline

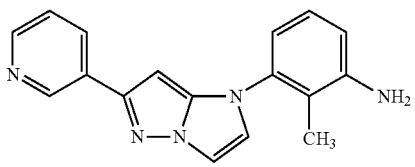

Analogously to the process described in Example 9A/Step 3, 1.08 g (3.38 mmol) of the compound of Example 69A/Step 2 gave 940 mg (93% of theory, 97% pure) of the title compound. In this case, the reaction time was 30 minutes.

$^1$H NMR (400 MHz, CDCl$_3$, δ/ppm): 9.04 (d, 1H), 8.52 (dd, 1H), 8.15 (dt, 1H), 7.49 (d, 1H), 7.32 (dd, 1H), 7.14 (t, 1H), 6.90 (d, 1H), 6.80 (d, 1H), 6.77 (d, 1H), 5.96 (s, 1H), 3.86 (broad, 2H), 2.06 (s, 3H).

LC/MS (Method 3, ESIpos): R$_t$=0.63 min, m/z=290 [M+H]$^+$.

Example 70A

2-Fluoro-3-[6-(pyridin-3-yl)-1H-imidazo[1,2-b]pyrazol-1-yl]aniline

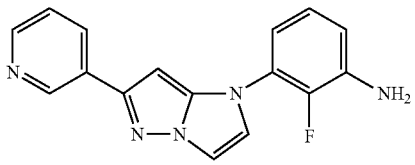 [SMILES: Nc1cccc(-n2ccn3nc(-c4cccnc4)cc23)c1F]

Step 1: 1-(2,2-Diethoxyethyl)-N-(2-fluoro-3-nitrophenyl)-3-(pyridin-3-yl)-1H-pyrazole-5-amine

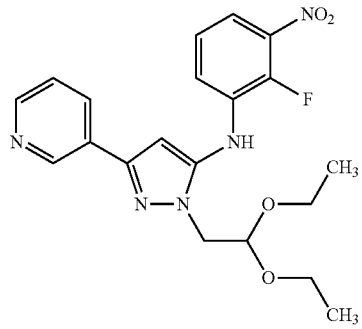 [SMILES: CCOC(Cn1nc(-c2cccnc2)cc1Nc1cccc([N+](=O)[O-])c1F)OCC]

Analogously to the process described in Example 64A/Step 1, 1.0 g (3.62 mmol) of the compound of Example 4A and 876 mg (3.98 mmol) of 1-bromo-2-fluoro-3-nitrobenzene gave 1.11 g (73% of theory) of the title compound.

¹H NMR (400 MHz, CDCl₃, δ/ppm): 9.00 (d, 1H), 8.56 (dd, 1H), 8.09 (dt, 1H), 7.54-7.48 (m, 3H), 7.34 (t, 1H), 7.17 (t, 1H), 6.44 (s, 1H), 4.81 (t, 1H), 4.31 (d, 2H), 3.89-3.81 (m, 2H), 3.65-3.57 (m, 2H), 1.28 (t, 6H).

LC/MS (Method 3, ESIpos): $R_t$=1.00 min, m/z=416 [M+H]⁺.

Step 2: 1-(2-Fluoro-3-nitrophenyl)-6-(pyridin-3-yl)-1H-imidazo[1,2-b]pyrazole

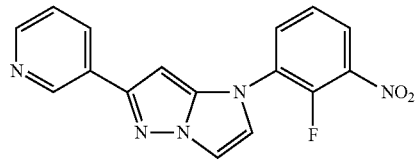 [SMILES: O=[N+]([O-])c1cccc(-n2ccn3nc(-c4cccnc4)cc23)c1F]

Analogously to the process described in Example 69A/Step 2, 1.10 g (2.65 mmol) of the compound of Example 70A/Step 1 gave 570 mg (63% of theory) of the title compound. For purification, the product was then triturated with a little acetonitrile at RT.

¹H NMR (400 MHz, DMSO-d₆, δ/ppm): 9.07 (d, 1H), 8.51 (dd, 1H), 8.21 (dt, 1H), 8.18 (d, 1H), 8.15 (d, 1H), 8.04 (d, 1H), 7.74 (dd, 1H), 7.63 (td, 1H), 7.45 (dd, 1H), 6.66 (d, 1H).

LC/MS (Method 4, ESIpos): $R_t$=0.73 min, m/z=324 [M+H]⁺.

Step 3: 2-Fluoro-3-[6-(pyridin-3-yl)-1H-imidazo[1,2-b]pyrazol-1-yl]aniline

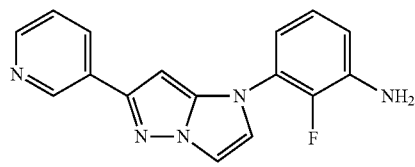

Analogously to the process described in Example 69A/Step 3, 560 mg (1.73 mmol) of the compound of Example 70A/Step 2 gave 490 mg (96% of theory) of the title compound.

¹H NMR (400 MHz, DMSO-d₆, δ/ppm): 9.07 (d, 1H), 8.49 (dd, 1H), 8.20 (dt, 1H), 7.92 (d, 1H), 7.57 (dd, 1H), 7.43 (dd, 1H), 7.03 (td, 1H), 6.81 (dd, 1H), 6.77 (dd, 1H), 6.49 (s, 1H), 5.56 (s, broad, 2H).

LC/MS (Method 3, ESIpos): $R_t$=0.60 min, m/z=294 [M+H]⁺.

Example 71A

2-Amino-6-[6-(pyridin-3-yl)-1H-imidazo[1,2-b]pyrazol-1-yl]phenol

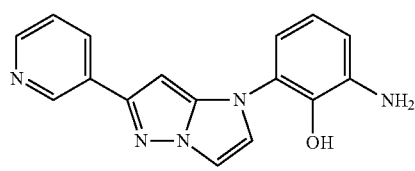

Step 1: 2-(Benzyloxy)-1-bromo-3-nitrobenzene

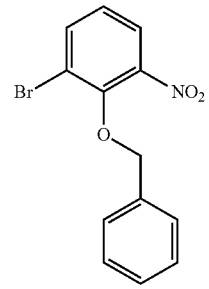 [SMILES: O=[N+]([O-])c1cccc(Br)c1OCc1ccccc1]

A mixture of 5.22 g (23.9 mmol) of 2-bromo-6-nitrophenol, 3.0 ml (25.1 mmol) of benzyl bromide and 3.64 g (26.3 mmol) of potassium carbonate in 50 ml of acetonitrile was heated under reflux for 2 h. After cooling to RT, the solid was filtered off and the filtrate was freed from the solvent on a rotary evaporator. The residue obtained was dissolved in ethyl acetate and washed successively with water and saturated sodium chloride solution. After drying over anhydrous magnesium sulphate, the mixture was filtered and the filtrate was concentrated on a rotary evaporator. The residue that remained was dried under high vacuum. This gave 7.53 g (99% of theory) of the title compound.

¹H NMR (400 MHz, CDCl₃, δ/ppm): 7.84 (dd, 1H), 7.79 (dd, 1H), 7.57-7.53 (m, 2H), 7.44-7.36 (m, 3H), 7.16 (t, 1H), 5.20 (s, 2H).

LC/MS (Method 4, ESIpos): $R_t$=1.26 min, no ionization.

Step 2: N-[2-(Benzyloxy)-3-nitrophenyl]-1-(2,2-diethoxyethyl)-3-(pyridin-3-yl)-1H-pyrazole-5-amine

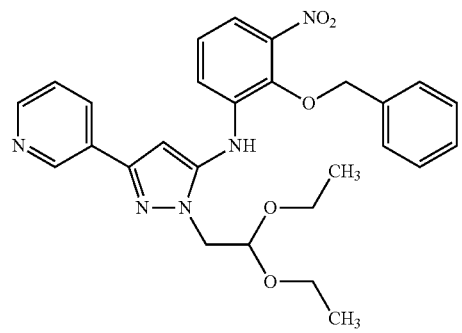 [SMILES: CCOC(Cn1nc(-c2cccnc2)cc1Nc1cccc([N+](=O)[O-])c1OCc1ccccc1)OCC]

Analogously to the process described in Example 64A/Step 1, 1.0 g (3.62 mmol) of the compound of Example 4A and 1.23 g (3.98 mmol) of the compound of Example 71A/Step 1 gave 1.44 g of the title compound (63% of theory, content 80%, contamination: debenzylated product). Here, chromatographic purification was carried out using the mobile phase cyclohexane/ethyl acetate 1:1.

LC/MS (Method 2, ESIpos): $R_t$=2.54 min, m/z=504 [M+H]$^+$.

Step 3: 2-Nitro-6-[6-(pyridin-3-yl)-1H-imidazo[1,2-b]pyrazol-1-yl]phenol

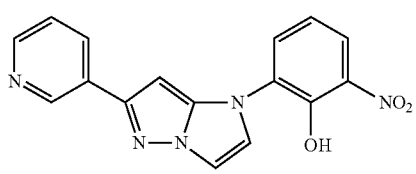 [SMILES: O=[N+]([O-])c1cccc(-n2ccn3nc(-c4cccnc4)cc23)c1O]

2.7 ml (5.45 mmol) of 2 M sulphuric acid were added to a solution of 1.43 g (2.27 mmol, content 80%) of the compound from Example 71A/Step 2 in 10 ml of ethanol and the mixture was then heated in a microwave oven (Biotage Initiator, with Dynamic Field Tuning) at 130° C. for 20 min. After cooling to RT, the reaction mixture was added with stirring to about 50 ml of saturated aqueous sodium bicarbonate solution. This mixture was extracted twice with in each case about 50 ml of ethyl acetate and the combined organic phases were washed with saturated sodium chloride solution. After drying over anhydrous magnesium sulphate and filtration, the filtrate was concentrated under reduced pressure. The residue that remained was triturated with acetonitrile. The insoluble material was filtered off with suction and dried under high vacuum. This gave 75 mg (10% of theory) of the title compound. The filtrate obtained was processed further, see Step 4 below.

$^1$H NMR (400 MHz, CDCl$_3$, δ/ppm): 9.06 (s, 1H), 8.55 (d, 1H), 8.19-8.15 (m, 2H), 7.89 (d, 1H), 7.54 (d, 1H), 7.36-7.33 (m, 2H), 7.18 (t, 1H), 6.22 (s, 1H).

LC/MS (Method 3, ESIpos): $R_t$=0.68 min, m/z=322 [M+H]$^+$.

Step 4: 1-[2-(Benzyloxy)-3-nitrophenyl]-6-(pyridin-3-yl)-1H-imidazo[1,2-b]pyrazole

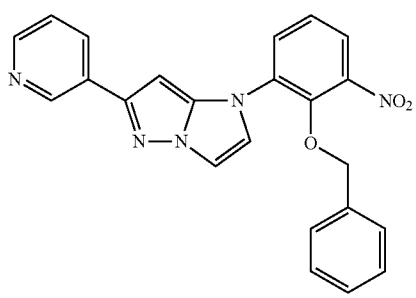 [SMILES: O=[N+]([O-])c1cccc(-n2ccn3nc(-c4cccnc4)cc23)c1OCc1ccccc1]

The filtrate obtained in Step 3 above was freed from the solvent on a rotary evaporator and the residue that remained was purified by preparative HPLC (Method 9) gereinigt. Evaporation of the product fractions and drying of the residue under high vacuum gave 263 mg (28% of theory) of the title compound.

$^1$H NMR (400 MHz, CDCl$_3$, δ/ppm): 9.05 (d, 1H), 8.57 (dd, 1H), 8.15 (dt, 1H), 7.82-7.78 (m, 2H), 7.52 (d, 1H), 7.40 (t, 1H), 7.36 (dd, 1H), 7.25-7.21 (m, 3H, partially obscured by the CHCl$_3$ signal), 7.15-7.12 (m, 2H), 6.19 (s, 1H), 4.83 (s, 2H).

LC/MS (Method 3, ESIpos): $R_t$=0.92 min, m/z=412 [M+H]$^+$.

Step 5: 2-Amino-6-[6-(pyridin-3-yl)-1H-imidazo[1,2-b]pyrazol-1-yl]phenol

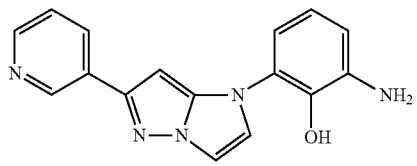 [SMILES: Nc1cccc(-n2ccn3nc(-c4cccnc4)cc23)c1O]

Variant A: Preparation Starting with the Compound from Example 71A/Step 3:

Analogously to the process described in Example 9A/Step 3, 72 mg (0.224 mmol) of the compound of Example 71A/Step 3 gave 57 mg (87% of theory) of the title compound. In this case, the reaction time was 1 h.

Variant B: Preparation Starting with the Compound from Example 71A/Step 4:

Analogously to the process described in Example 9A/Step 3, 260 mg (0.632 mmol) of the compound of Example 71A/Step 4 gave 200 mg (86% of theory, 80% pure) of the title compound. In this case, the reaction time was 1 h.

$^1$H NMR (400 MHz, DMSO-d$_6$, δ/ppm): 9.04 (d, 1H), 8.47 (dd, 1H), 8.18 (dt, 1H), 7.80 (d, 1H), 7.46 (d, 1H), 7.41 (dd, 1H), 6.76 (t, 1H), 6.69-6.64 (m, 2H), 6.32 (s, 1H), 3.50 (broad, 1H).

LC/MS (Method 3, ESIpos): $R_t$=0.56 min, m/z=292 [M+H]$^+$.

Example 72A

4-Methyl-3-[6-(pyrazin-2-yl)-1H-imidazo[1,2-b]pyrazol-1-yl]aniline

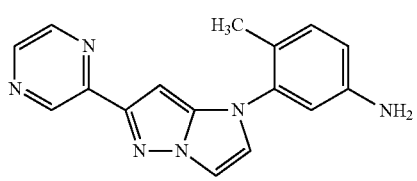 [SMILES: Cc1ccc(N)cc1-n1ccn2nc(-c3cnccn3)cc12]

Step 1: 1-(2,2-Diethoxyethyl)-N-(2-methyl-5-nitrophenyl)-3-(pyrazin-2-yl)-1H-pyrazole-5-amine

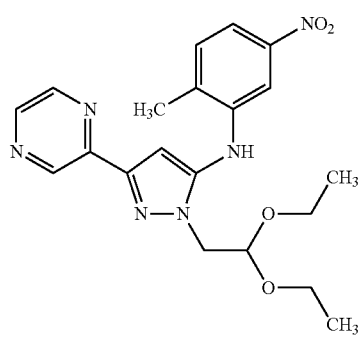

Analogously to Example 13A/Step 1, 1.16 g (4.18 mmol) of the compound of Example 59A and 994 mg (4.60 mmol) of 2-Bromo-4-nitrotoluene gave 1.64 g (86% of theory) of the title compound.

¹H NMR (400 MHz, DMSO-d₆, δ/ppm): 9.14 (d, 1H), 8.61 (dd, 1H), 8.54 (d, 1H), 7.63 (s, 1H), 7.60 (dd, 1H), 7.48 (d, 1H), 7.40 (d, 1H), 6.71 (s, 1H), 4.88 (t, 1H), 4.20 (d, 2H), 3.53-3.62 (m, 2H), 3.36-3.46 (m, 2H), 2.35 (s, 3H), 0.97 (t, 6H).

LC/MS (Method 7, ESIpos): R$_t$=1.29 min, m/z=413 [M+H]⁺.

Step 2: 1-(2-Methyl-5-nitrophenyl)-6-(pyrazin-2-yl)-1H-imidazo[1,2-b]pyrazole

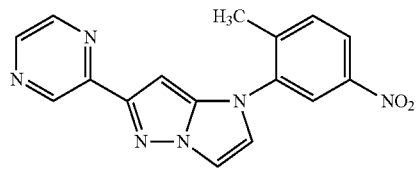

Analogously to Example 13A/Step 2, 1.63 g (3.95 mmol) of the compound of Example 72A/Step 1 gave a crude product which was purified by single chromatography on a Biotage system (25 g Snap column; mobile phase gradient dichloromethane/methanol, from 2% methanol increasing steadily to 8% methanol). This gave 346 mg (25% of theory) of the title compound.

¹H NMR (400 MHz, DMSO-d₆, δ/ppm): 9.16 (d, 1H), 8.58 (dd, 1H), 8.51 (d, 1H), 8.28 (d, 1H), 8.21 (dd, 1H), 7.99 (dd, 1H), 7.73 (d, 1H), 7.70 (d, 1H), 6.41 (d, 1H), 5.72 (s, 2H), 2.39 (s, 3H).

LC/MS (Method 7, ESIpos): R$_t$=1.02 min, m/z=321 [M+H]⁺.

Step 3: 4-Methyl-3-[6-(pyrazin-2-yl)-1H-imidazo[1,2-b]pyrazol-1-yl]aniline

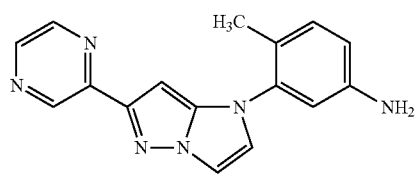 [SMILES: Cc1ccc([N+](=O)[O-])cc1-n1ccn2nc(-c3cnccn3)cc12]

Analogously to Example 13A/Step 3, 343 mg (1.07 mmol) of the compound of Example 72A/Step 2 gave 255 mg (65% of theory) of the title compound.

¹H NMR (400 MHz, DMSO-d₆, δ/ppm): 9.14 (d, 1H), 8.57 (dd, 1H), 8.49 (d, 1H), 7.85 (dd, 1H), 7.48 (d, 1H), 7.02 (d, 1H), 6.62 (d, 1H), 6.55 (dd, 1H), 6.24 (d, 1H), 5.19 (br. s, 2H), 2.05 (s, 3H).

LC/MS (Method 7, ESIpos): R$_t$=0.81 min, m/z=291 [M+H]⁺.

Example 73A

3-Cyano-5-(1-hydroxycyclobutyl)benzoic acid

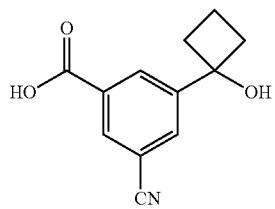 [SMILES: N#Cc1cc(C(=O)O)cc(C2(O)CCC2)c1]

Step 1: Methyl 3-carbamoyl-5-iodobenzoate

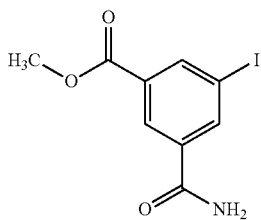

20 ml of 1 M hydrochloric acid were added to a solution of 3.88 g (11.8 mmol) of sodium 3-iodo-5-(methoxycarbonyl)benzoate [J. H. Ackermann et al., *J. Med. Chem.* 1966, 9 (1), 165-168] in 100 ml of water. After 10 min, the mixture was extracted three times with in each case about 100 ml of ethyl acetate. The combined organic extracts were washed with saturated sodium chloride solution and dried over anhydrous magnesium sulphate. After filtration, the solvent was removed on a rotary evaporator. The residue that remained was dissolved in 75 ml of dichloromethane, and 5.2 ml (59.1 mmol) of oxalyl chloride and a small drop of DMF were added at RT. After 1 h of stirring at RT, all volatile components were removed on a rotary evaporator. The residue was then dissolved in 50 ml of dioxane and, at a temperature of about 0° C., slowly added dropwise to 44 ml of a 25% strength aqueous ammonia solution. After the dropwise addition had ended, the cooling bath was removed and stirring was continued at RT for 30 min. The precipitated product was then filtered off with suction, washed with cold water and dried under high vacuum. This gave 3.02 g (81% of theory, 97% pure) of the title compound.

¹H NMR (400 MHz, DMSO-d₆, δ/ppm): 8.47 (dd, 1H), 8.44 (dd, 1H), 8.35 (dd, 1H), 8.25 (s, broad, 1H), 7.63 (s, broad, 1H), 3.89 (s, 3H).

LC/MS (Method 4, ESIpos): R$_t$=0.75 min, m/z=306 [M+H]$^+$.

Step 2: Methyl 3-cyano-5-iodobenzoate

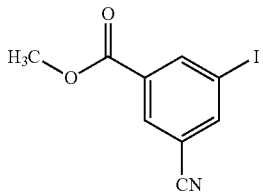

At a temperature of about 0° C., a solution of 2.8 ml (16.5 mmol) of trifluoromethanesulphonic anhydride in 50 ml of dichloromethane was added dropwise to a solution of 2.80 g (9.18 mmol) of the compound of Example 73A/Step 1 and 8 ml (45.9 mmol) of N,N-diisopropylethylamine in 150 ml of dichloromethane. After a reaction time of 30 min at 0° C., 50 ml of saturated aqueous sodium bicarbonate solution were added and the mixture was stirred vigorously at RT for 10 min. The organic phase was separated off, dried over anhydrous magnesium sulphate, filtered and freed from the solvent on a rotary evaporator. The crude product obtained in this manner was purified by filtration with suction (about 200 g of silica gel, mobile phase cyclohexane/ethyl acetate 3:1). This gave 2.24 g (85% of theory) of the title compound.
$^1$H NMR (400 MHz, CDCl$_3$, δ/ppm): 8.59 (dd, 1H), 8.28 (dd, 1H), 8.15 (dd, 1H), 3.97 (s, 3H).
GC/MS (Method 8, EIpos): R$_t$=5.62 min, m/z=287 [M]$^+$.

Step 3: Methyl 3-cyano-5-(1-hydroxycyclobutyl)benzoate

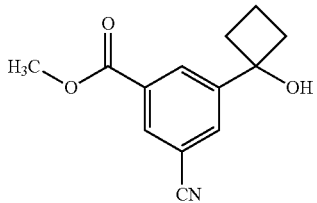 [SMILES: COC(=O)c1cc(C#N)cc(C2(O)CCC2)c1]

At a temperature of −40° C., 1.1 ml (1.46 mmol) of a 1.3 M solution of isopropylmagnesium chloride/lithium chloride complex in THF were added dropwise to a solution of 400 mg (1.39 mmol) of the compound of Example 73A/Step 2 in 10 ml of anhydrous THF. After the dropwise addition had ended, the mixture was stirred at −40° C. to −30° C. for another 1.5 h, and the temperature was then lowered to −78° C. At −78° C., this solution was then slowly added dropwise to a solution of 209 μl (2.79 mmol) of cyclobutanone in 4 ml of anhydrous THF. Ten minutes after the addition had ended and after further stirring at −78° C., the reaction mixture was warmed initially to 0° C. and then, after a further 45 min, to RT. After 1 h of stirring at RT, 250 ml of water were added at about −20° C. The mixture was extracted three times with in each case 100 ml of ethyl acetate. The combined organic extracts were washed with saturated sodium chloride solution, dried over anhydrous magnesium sulphate, filtered and freed from the solvent on a rotary evaporator. The product was isolated from the residue obtained in this manner by MPLC (about 50 g of silica gel, mobile phase gradient cyclohexane/ethyl acetate 10:1→4:1). This gave 94 mg (29% of theory) of the title compound.
$^1$H NMR (400 MHz, CDCl$_3$, δ/ppm): 8.41 (dd, 1H), 8.23 (dd, 1H), 8.01 (dd, 1H), 3.97 (s, 3H), 2.60-2.52 (m, 2H), 2.47-2.39 (m, 3H), 2.18-2.08 (m, 1H), 1.87-1.76 (m, 1H).
GC/MS (Method 8, EIpos): R$_t$=6.60 min, m/z=213 [M−H$_2$O]$^+$.

Step 4: 3-Cyano-5-(1-hydroxycyclobutyl)benzoic acid

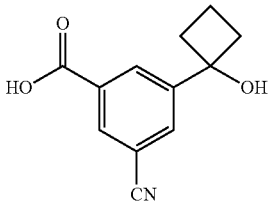 [SMILES: N#Cc1cc(C(=O)O)cc(C2(O)CCC2)c1]

85 mg (0.368 mmol) of the compound of Example 73A/Step 3 were dissolved in a mixture of 1 ml of methanol and 1 ml of THF, and a solution of 19 mg (0.441 mmol) of lithium hydroxide monohydrate in 1 ml of water was added at RT. After the reaction mixture had been stirred for 1 h, in each case 50 ml of water and ethyl acetate and 2 ml of 1 M hydrochloric acid were added and the mixture was stirred vigorously. After phase separation, the aqueous phase was extracted once more with 50 ml of ethyl acetate. The combined organic extracts were washed with saturated sodium chloride solution, dried over anhydrous magnesium sulphate, filtered and freed from the solvent on a rotary evaporator. This gave 78 mg (95% of theory, 97% pure) of the title compound.
$^1$H NMR (400 MHz, DMSO-d$_6$, δ/ppm): 13.53 (broad, 1H), 8.33 (dd, 1H), 8.17 (dd, 1H), 8.14 (dd, 1H), 5.90 (s, broad, 1H), 2.45-2.39 (m, 2H), 2.34-2.27 (m, 2H), 2.02-1.93 (m, 1H), 1.77-1.69 (m, 1H).
LC/MS (Method 3, ESIneg): R$_t$=0.68 min, m/z=216 [M−H]$^-$, 433 [2M−H]$^-$.

Example 74A 3-(Methoxymethyl)-5-(pentafluoro-λ$^6$-sulphanyl)benzoic acid

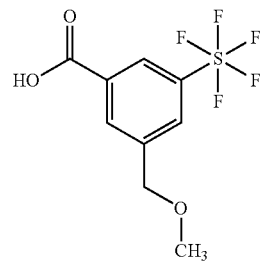 [SMILES: COCc1cc(C(=O)O)cc(S(F)(F)(F)(F)F)c1]

108 mg (2.70 mmol) of sodium hydride (as a 60% strength suspension in mineral oil) were deoiled with pentane and then suspended in 5 ml of anhydrous THF. At 0° C., a solution of 250 mg (0.899 mmol) of the compound of Example 37A in 2.5 ml of anhydrous THF was slowly added dropwise to this suspension. After 30 min of stirring at 0° C., 170 μl (2.70 mmol) of iodomethane were added and the cooling bath was removed. Since, according to analytical HPLC, conversion was still incomplete after 6 h at RT, the mixture was once more cooled to 0° C., and a further 560 μl (9.0 mmol) of iodomethane and 36 mg (0.897 mmol) of sodium hydride (60% strength suspension in mineral oil) were added in succession. After 2 h of stirring at RT, about 75 ml of water were added carefully and the reaction mixture was acidified by addition of 1 M hydrochloric acid. The mixture was extracted three times with in each case about 25 ml of ethyl acetate. The combined organic extracts were washed successively with in each case about 30 ml of water and saturated sodium chloride solution. After drying over anhydrous magnesium sulphate, filtration and removal of the solvent on a rotary evaporator, the residue obtained was triturated with pentane. The crude product obtained in this manner was purified by preparative HPLC (Method 32). Pooling of the product fractions, removal of the solvent on a rotary evaporator and drying under high vacuum gave 153 mg (58% of theory) of the title compound.

$^1$H NMR (400 MHz, DMSO-$d_6$, δ/ppm): 13.75 (broad, 1H), 8.20 (s, 1H), 8.16 (s, 1H), 8.09 (s, 1H), 4.60 (s, 1H), 3.36 (s, 3H).

LC/MS (Method 3, ESIneg): $R_t$=0.94 min, m/z=291 [M−H]$^-$.

Example 75A

3-Cyano-N-(3-{6-[1-(4-methoxybenzyl)-1H-pyrazol-4-yl]-1H-imidazo[1,2-b]pyrazol-1-yl}-4-methylphenyl)-5-(pentafluoro-λ$^6$-sulphanyl)benzamide

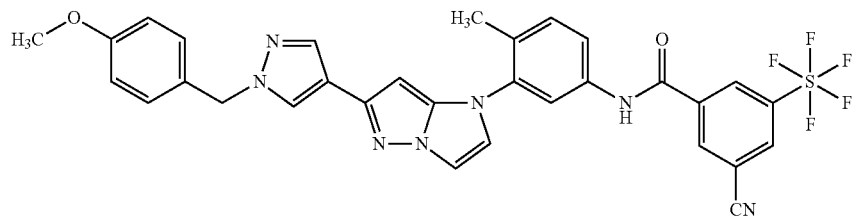 [SMILES: COc1ccc(Cn2cc(-c3cc4n(-c5cc(NC(=O)c6cc(C#N)cc(S(F)(F)(F)(F)F)c6)ccc5C)ccn4n3)cn2)cc1]

80 mg (0.16 mmol) of the compound of Example 60A and 66 mg (0.24 mmol) of the compound of Example 23A were reacted with one another analogously to Example 48A. In deviation from the work-up described therein, here, the mixture was separated directly into its components by preparative HPLC (Method 21). The product-containing fractions were concentrated under reduced pressure and the residue was dried under high vacuum. This gave 84 mg (64% of theory, 80% pure) of the title compound.

LC/MS (Method 4, ESIpos): $R_t$=1.21 min, m/z=654 [M+H]$^+$.

Example 76A

3-Cyano-N-(5-{6-[1-(4-methoxybenzyl)-1H-pyrazol-4-yl]-1H-imidazo[1,2-b]pyrazol-1-yl}-2,4-dimethylphenyl)-5-(pentafluoro-λ$^6$-sulphanyl)benzamide

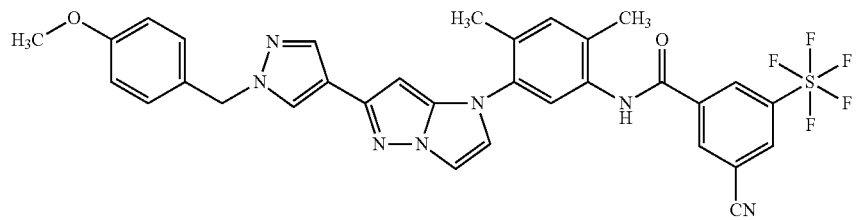 [SMILES: COc1ccc(Cn2cc(-c3cc4n(-c5cc(NC(=O)c6cc(C#N)cc(S(F)(F)(F)(F)F)c6)c(C)cc5C)ccn4n3)cn2)cc1]

105 mg (0.26 mmol) of the compound of Example 61A and 82 mg (0.24 mmol) of the compound of Example 23A were reacted with one another analogously to Example 48A. In deviation from the work-up described therein, here, the mixture was separated directly into its components by preparative HPLC (Method 21). The product-containing fractions were concentrated under reduced pressure and the residue was dried under high vacuum. This gave 125 mg (71% of theory) of the title compound.

$^1$H NMR (400 MHz, DMSO-$d_6$, δ/ppm): 10.40 (s, 1H), 8.86 (s, 1H), 8.73 (s, 1H), 8.66 (s, 1H), 8.04 (s, 1H), 7.75 (d, 1H), 7.74 (s, 1H), 7.48 (s, 1H), 7.37 (d, 2H), 7.23 (d, 2H), 6.90 (d, 2H), 5.85 (s, 1H), 5.24 (s, 2H), 3.72 (s, 3H), 2.30 (s, 3H), 2.24 (s, 3H).

LC/MS (Method 4, ESIpos): $R_t$=1.20 min, m/z=668 [M+H]$^+$.

Example 77A

N-{2,4-Dimethyl-5-[6-(pyridin-3-yl)-1H-imidazo[1,2-b]pyrazol-1-yl]phenyl}-3-formyl-5-(pentafluoro-$\lambda^6$-sulphanyl)benzamide

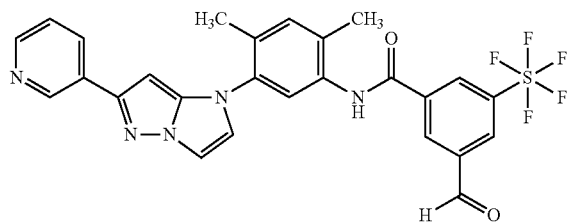 [SMILES: Cc1cc(C)c(-n2ccn3nc(-c4cccnc4)cc23)cc1NC(=O)c1cc(C=O)cc(S(F)(F)(F)(F)F)c1]

214 mg (0.659 mmol, 85% pure) of the compound from Example 36A and 301 mg (0.791 mmol) of HATU were dissolved in 2.3 ml of anhydrous DMF, and 140 μl (0.791 mmol) of N,N-diisopropylethylamine were added. After 30 min, 200 mg (0.659 mmol) of the compound of Example 11A were added. After the reaction mixture had been stirred at RT for 1.5 h, about 50 ml of water were added and the mixture was extracted three times with in each case about 50 ml of ethyl acetate. The combined organic extracts were washed with saturated sodium chloride solution, dried over anhydrous magnesium sulphate, filtered and freed from the solvent on a rotary evaporator. The crude product obtained in this manner was purified by MPLC (30 g of silica gel, mobile phase gradient cyclohexane/ethyl acetate 1:1→1:5). Evaporation of the product fractions and drying of the residue under high vacuum gave 160 mg (36% of theory, 85% pure) of the title compound.

LC/MS (Method 3, ESIpos): $R_t$=0.98 min, m/z=562 [M+H]$^+$.

Example 78A 1-(2,2-Diethoxyethyl)-3-(pyrimidin-5-yl)-1H-pyrazole-5-amine

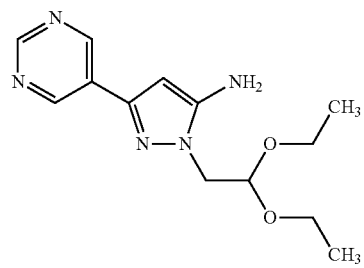 [SMILES: CCOC(Cn1nc(-c2cncnc2)cc1N)OCC]

Analogously to Example 59A/Steps 1 and 2, 5.0 g (32.9 mmol) of ethyl 5-pyrimidinecarboxylate gave 3.01 g of the title compound (27% of theory over the two steps).

$^1$H NMR (400 MHz, DMSO-$d_6$, δ/ppm): 9.01 (s, 2H), 5.85 (s, 1H), 5.71 (s, 1H), 5.33 (s, 2H), 4.82 (t, 1H), 4.00 (d, 2H), 3.53-3.67 (m, 2H), 3.41 (dd, 2H), 1.04 (t, 6H).

LC/MS (Method 7, ESIpos): $R_t$=0.75 min, m/z=278 [M+H]$^+$.

Example 79A 1-(2,2-Diethoxyethyl)-3-(pyridazin-4-yl)-1H-pyrazole-5-amine

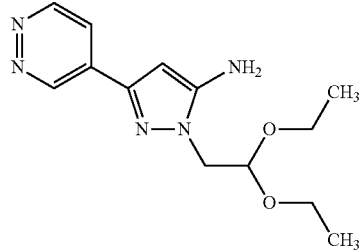 [SMILES: CCOC(Cn1nc(-c2ccnnc2)cc1N)OCC]

Analogously to Example 59A/Steps 1 and 2, 5.0 g (32.9 mmol) of ethyl pyridazine-4-carboxylate gave 4.5 g of the title compound (49% of theory over the two steps).

$^1$H NMR (400 MHz, DMSO-$d_6$, δ/ppm): 9.46 (dd, 1H), 9.10 (dd, 1H), 7.79 (dd, 1H), 5.94 (s, 1H), 5.42 (s, 2H), 4.83 (t, 1H), 4.02 (d, 2H), 3.55-3.68 (m, 2H), 3.33-3.46 (m, 3H), 1.03 (t, 6H).

LC/MS (Method 7, ESIpos): $R_t$=0.75 min, m/z=278 [M+H]$^+$.

Example 80A 1-(2,2-Diethoxyethyl)-3-(pyridazin-3-yl)-1H-pyrazole-5-amine

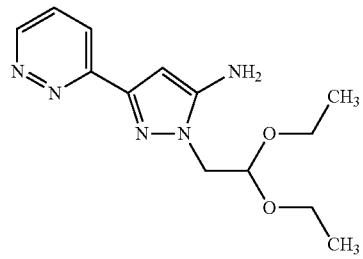

Analogously to Example 59A/Steps 1 and 2, 2.5 g (16.4 mmol) of ethyl pyridazine-3-carboxylate gave 1.09 g of the title compound (24% of theory over the two steps).

$^1$H NMR (400 MHz, DMSO-$d_6$, δ/ppm): 9.05 (dd, 1H), 7.97 (dd, 1H), 7.60 (dd, 1H), 6.00 (s, 1H), 5.32 (s, 2H), 4.83 (t, 1H), 4.02 (d, 2H), 3.57-3.68 (m, 2H), 3.36-3.46 (m, 2H), 1.04 (t, 6H).

LC/MS (Method 7, ESIpos): $R_t$=0.76 min, m/z=278 [M+H]$^+$.

Example 81A 1-(2,2-Diethoxyethyl)-3-(1,3-thiazol-5-yl)-1H-pyrazole-5-amine

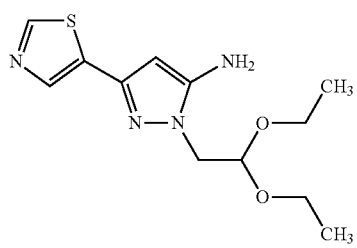 [SMILES: CCOC(Cn1nc(-c2cncs2)cc1N)OCC]

Step 1: Sodium 2-cyano-1-(1,3-thiazol-5-yl)ethenolate

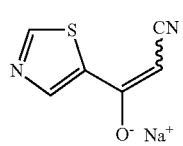

A solution of 1.5 g (10.5 mmol) of methyl 1,3-thiazole-5-carboxylate and 430 mg (10.8 mmol) of acetonitrile in 15 ml of THF was added dropwise to a suspension of 419 mg of sodium hydride (60% strength suspension in mineral oil) in 16 ml of THF which was heated under reflux. The reaction mixture was heated under reflux for 20 h. After cooling, 50 ml of methyl tert-butyl ether were added and the mixture was stirred for 30 minutes. The resulting precipitate was filtered off with suction through a frit and dried under oil pump vacuum. This gave 1.71 g (94% of theory) of the title compound which was combined with the product (3.48 g, 95% of theory) from a second batch starting with 3.0 g (21 mmol) of methyl 1,3-thiazole-5-carboxylate. This material was used without further characterization for the next step.

Step 2: 1-(2,2-Diethoxyethyl)-3-(1,3-thiazol-5-yl)-1H-pyrazole-5-amine

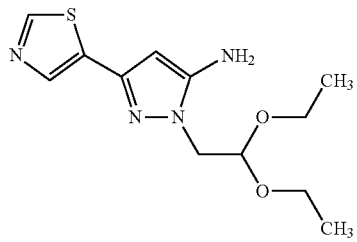 [SMILES: CCOC(Cn1nc(-c2cncs2)cc1N)OCC]

5.19 g (29.8 mmol) of the sodium salt of Example 81A/Step 1 were suspended in 30 ml of ethanol, and 4.64 g (31.3 mmol) of (2,2-diethoxyethyl)hydrazine, 1.7 ml (29.8 mmol) of acetic acid and 149 µl 1 M hydrochloric acid were added in succession. After two hours of heating under reflux, the reaction mixture was cooled to RT and diluted with 400 ml of ethyl acetate. The organic phase was washed in each case once with in each case 50 ml of saturated sodium bicarbonate solution, water and saturated sodium chloride solution, dried over sodium sulphate and, after filtration, concentrated under reduced pressure. The crude product obtained in this manner was purified on a Biotage system (100 g Snap column; mobile phase gradient ethyl acetate/0-8% methanol). This gave 2.93 g (34% of theory) of the title compound.

$^1$H NMR (400 MHz, DMSO-$d_6$, δ/ppm): 8.88 (s, 1H), 8.02 (s, 1H), 5.65 (s, 1H), 5.28 (s, 2H), 4.76 (t, 1H), 3.93 (d, 2H), 3.53-3.68 (m, 2H), 3.31-3.46 (m, 2H), 1.03 (t, 6H).

LC/MS (Method 7, ESIpos): $R_t$=0.85 min, m/z=283 [M+H]$^+$.

Example 82A

6-Amino-3-methyl-2-[6-(pyridin-3-yl)-1H-imidazo[1,2-b]pyrazol-1-yl]phenol

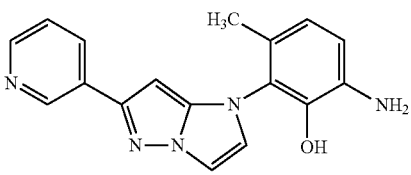 [SMILES: Cc1ccc(N)c(O)c1-n1ccn2nc(-c3cccnc3)cc12]

Step 1: Methyl 2-bromo-3-hydroxy-4-nitrobenzoate

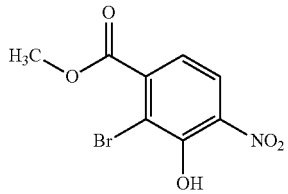

At −78° C., a solution of 1 ml (20.3 mmol) of bromine in 5 ml of dichloromethane was slowly added dropwise to a solution of 4.3 ml (40.6 mmol) of tert-butylamine in 35 ml of dichloromethane. After the addition of bromine had ended, the mixture was stirred at −78° C. for a further hour, and a solution of 4.0 g (20.3 mmol) of methyl 3-hydroxy-4-nitrobenzoate in 5 ml of dichloromethane was then added. Over the course of about 16 h, the reaction mixture was then slowly warmed to RT. This resulted in the precipitation of a solid which was filtered off with suction and stirred with in each case about 25 ml of dichloromethane and 2 M hydrochloric acid. The dichloromethane phase was separated off, dried over magnesium sulphate, filtered and concentrated ("residue 1"). The filtrate of the reaction mixture obtained above was concentrated on a rotary evaporator ("residue 2"). Residue 1 was purified in 5 portions and residue 2 in 2 portions by preparative HPLC (Method 33). The product fractions were, separated as residue 1 and 2, combined, concentrated and dried under high vacuum. Residue 1 gave 1.79 g (31% of theory) of a mixture of the title compound and the isomeric methyl 2-bromo-5-hydroxy-4-nitrobenzoate in a ratio of 85:15; residue 2 gave 0.77 g (13% of theory) of the same mixture, but in a ratio of 73:27.

$^1$H NMR (400 MHz, DMSO-$d_6$, δ/ppm): 8.03 (d, 1H), 7.28 (d, 1H), 3.89 (s, 3H).

Step 2: Methyl 3-(benzyloxy)-2-bromo-4-nitrobenzoate

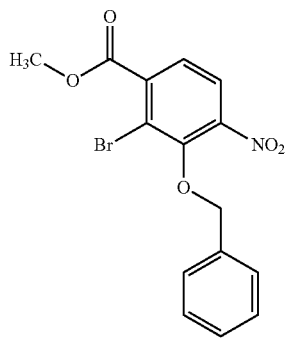 [SMILES: COC(=O)c1ccc([N+](=O)[O-])c(OCc2ccccc2)c1Br]

1.79 g (6.48 mmol) of the compound of Example 82A/Step 1 (product mixture of "residue 1") together with 0.81 ml (6.80 mmol) of benzyl bromide and 0.99 g (7.12 mmol) of potassium carbonate in 30 ml of acetonitrile were heated under reflux for 2 h. After cooling to RT, the solid was filtered off and the filtrate was concentrated under reduced pressure. The residue that remained was taken up in about 75 ml of ethyl acetate and washed successively with water and saturated aqueous sodium chloride solution. After drying over magnesium sulphate, the mixture was filtered and the filtrate was evaporated to dryness. The title compound was isolated by MPLC (silica gel, mobile phase cyclohexane/ethyl acetate 5:1). This gave 1.95 g (82% of theory) of the title compound.

$^1$H NMR (400 MHz, CDCl$_3$, δ/ppm): 7.79 (d, 1H), 7.57-7.53 (m, 3H), 7.43-7.37 (m, 3H), 5.21 (s, 2H), 3.99 (s, 3H).

LC/MS (Method 3, ESIneg): R$_t$=1.20 min, m/z=364/366 [M–H]$^-$ ($^{79}$Br/$^{81}$Br).

Step 3: [3-(Benzyloxy)-2-bromo-4-nitrophenyl]methanol

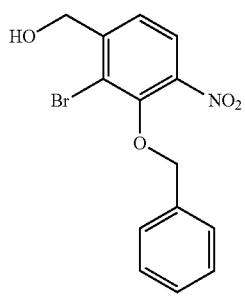 [SMILES: O=[N+]([O-])c1ccc(CO)c(Br)c1OCc1ccccc1]

At –78° C., 2.9 ml (2.93 mmol) of a 1 M solution of lithium aluminium hydride in THF were added dropwise to a solution of 1.95 g (5.32 mmol) of the compound of Example 82A/Step 2 in 40 ml of anhydrous THF. After the addition had ended, the cooling bath was removed, the reaction mixture was warmed to RT and stirring was continued at RT for another 1 h. About 5 ml of saturated aqueous ammonium chloride solution were then added carefully. The mixture was diluted with ethyl acetate and dried over magnesium sulphate. After filtration and evaporation of the solvent, the residue obtained was purified by MPLC (silica gel, mobile phase cyclohexane/ethyl acetate 5:1). This gave 1.12 g (62% of theory) of the title compound.

$^1$H NMR (400 MHz, DMSO-d$_6$, δ/ppm): 8.04 (d, 1H), 7.56 (d, 1H), 7.50 (d, 2H), 7.44-7.37 (m, 3H), 5.75 (t, 1H), 5.11 (s, 2H), 4.59 (d, 2H).

Step 4: 2-(Benzyloxy)-3-bromo-4-(bromomethyl)-1-nitrobenzene

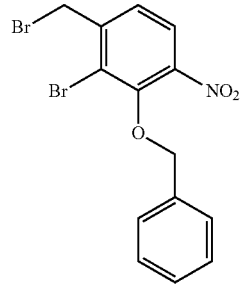 [SMILES: O=[N+]([O-])c1ccc(CBr)c(Br)c1OCc1ccccc1]

1.02 g (3.02 mmol) of the compound of Example 82A/Step 3 were dissolved in 18 ml of THF, and 0.95 g (3.62 mmol) of triphenylphosphine was added. Once this had gone into solution, 1.20 g (3.62 mmol) of tetrabromomethane were added and the reaction mixture was stirred at RT for about 20 h. This resulted in the formation of a fine white precipitate. Precipitation was brought to completion by addition of 50 ml of cyclohexane. The mixture was subsequently filtered and the filtrate was evaporated to dryness on a rotary evaporator. From this residue, the product was isolated by MPLC (silica gel, mobile phase cyclohexane/ethyl acetate 10:1). This gave 1.01 g (83% of theory) of the title compound.

$^1$H NMR (400 MHz, DMSO-d$_6$, δ/ppm): 8.01 (d, 1H), 7.68 (d, 1H), 7.49 (d, 2H), 7.45-7.39 (m, 3H), 5.12 (s, 2H), 4.83 (s, 2H).

Step 5: 2-(Benzyloxy)-3-bromo-4-methyl-1-nitrobenzene

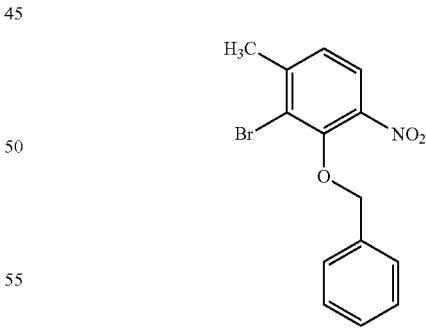

At –78° C., 0.75 ml (0.75 mmol) of a 1 M solution of lithium aluminium hydride in THF was added to a solution of 1.0 g (2.50 mmol) of the compound of Example 82A/Step 4 in 25 ml of anhydrous THF. After the addition had ended, the cooling bath was removed, the reaction mixture was warmed to RT and stirring was continued at RT for another 1 h. Since, according to TLC, the reaction was still incomplete, the reaction was once more cooled to –78° C. and a further 0.75 ml (0.75 mmol) of the 1 M solution of lithium aluminium hydride in THF was added. After warming to RT, the mixture was once more stirred at RT for another 1 h, and about 5 ml of saturated aqueous ammonium chloride solution were then added carefully. The mixture was diluted with ethyl acetate and dried over magnesium sulphate. After filtration and evaporation of the solvent, the residue obtained was purified by MPLC (silica gel, mobile phase cyclohexane/ethyl acetate 10:1). Concentration of the product fractions and drying of the residue under high vacuum gave 622 mg (77% of theory) of the title compound.

$^1$H NMR (400 MHz, DMSO-$d_6$, δ/ppm): 7.93 (d, 1H), 7.50 (d, 2H), 7.45-7.39 (m, 4H), 5.10 (s, 2H), 2.54 (s, 3H).

MS (DCI, NH$_3$): m/z=339/341 [M−H]$^-$ ($^{79}$Br/$^{81}$Br).

Step 6: N-[2-(Benzyloxy)-6-methyl-3-nitrophenyl]-1-(2,2-diethoxyethyl)-3-(pyridin-3-yl)-1H-pyrazole-5-amine and 2-{[1-(2,2-diethoxyethyl)-3-(pyridin-3-yl)-1H-pyrazol-5-yl]amino}-3-methyl-6-nitrophenol

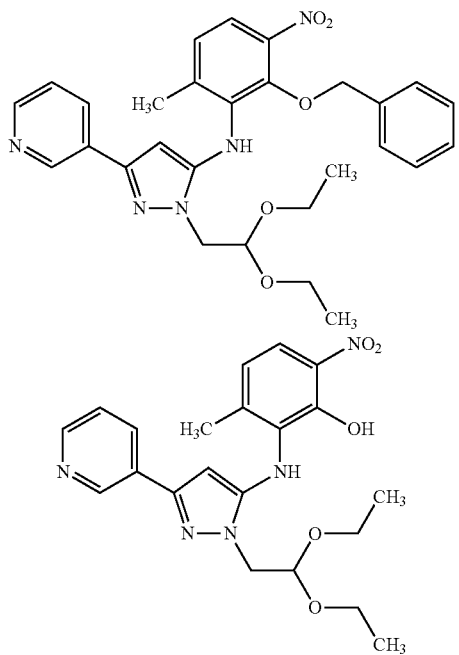

452 mg (1.64 mmol) of the compound of Example 82A/Step 5 together with 580 mg (1.80 mmol) of the compound of Example 4A, 37 mg (0.164 mmol) of palladium(II) acetate, 142 mg (0.245 mmol) of xantphos [4,5-bis(diphenylphosphino)-9,9-dimethylxanthene] and 1.6 g (4.91 mmol) of caesium carbonate in 10 ml of 1,4-dioxane were heated in a microwave oven (Biotage Initiator, with Dynamic Field Tuning) at 140° C. for 1 h. The mixture was then filtered through kieselguhr and the filtrate was concentrated on a rotary evaporator. The crude product obtained in this manner was purified by MPLC on silica gel (mobile phase gradient cyclohexane/ethyl acetate 10:1→1:1). The product fractions were combined and freed from the solvent on a rotary evaporator. This gave 230 mg (27% of theory) of a mixture of the two title compounds which was used as such for the subsequent reaction.

LC/MS (Method 3, ESIpos): R$_t$=1.13 min, m/z=518 [M+H]$^+$ (benzyl ether);

LC/MS (Method 3, ESIpos): R$_t$=0.97 min, m/z=428 [M+H]$^+$ (phenol).

Step 7: 1-[2-(Benzyloxy)-6-methyl-3-nitrophenyl]-6-(pyridin-3-yl)-1H-imidazo[1,2-b]pyrazole and 3-methyl-6-nitro-2-[6-(pyridin-3-yl)-1H-imidazo[1,2-b]pyrazol-1-yl]phenol

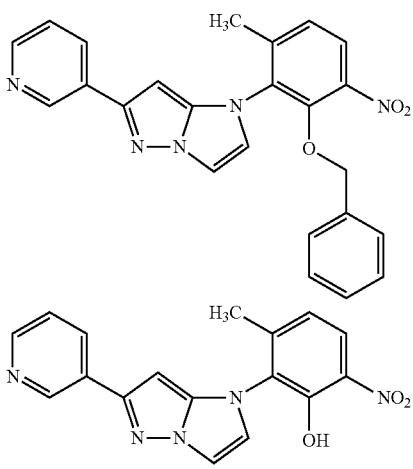

A solution of 230 mg (0.444 mmol) of the product mixture from Example 82A/Step 6 in 2 ml of ethanol and 533 µl (1.07 mmol) of 2 M sulphuric acid was heated in a microwave oven (Biotage Initiator, with Dynamic Field Tuning) at 130° C. for 30 min. The reaction was then diluted with 4 ml of DMF and, in 2 portions, separated into its components by preparative HPLC (Method 36). This operation also resulted in the separation of the benzyl ether and the phenol product. The respective product fractions were then combined, and the solvent was subsequently removed on a rotary evaporator. Final drying under high vacuum gave 23 mg (12% of theory) of the benzyl ether and 63 mg (42% of theory) of the phenol.

1-[2-(Benzyloxy)-6-methyl-3-nitrophenyl]-6-(pyridin-3-yl)-1H-imidazo[1,2-b]pyrazole:

LC/MS (Method 3, ESIpos): R$_t$=0.95 min, m/z=426 [M+H]$^+$.

3-Methyl-6-nitro-2-[6-(pyridin-3-yl)-1H-imidazo[1,2-b]pyrazol-1-yl]phenol:

LC/MS (Method 3, ESIpos): R$_t$=0.73 min, m/z=336 [M+H]$^+$.

Step 8: 6-Amino-3-methyl-2-[6-(pyridin-3-yl)-1H-imidazo[1,2-b]pyrazol-1-yl]phenol

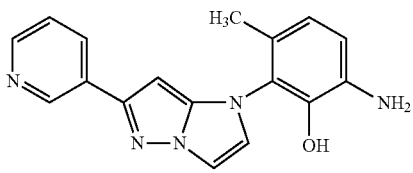 [SMILES: Cc1ccc(N)c(O)c1-n1ccn2nc(-c3cccnc3)cc12]

The benzyl ether product and the phenol product from Example 82A/Step 7 were re-combined. 85 mg (0.253 mmol) of this mixture were dissolved in 1.7 ml of ethanol and 0.8 ml of water. 80 mg (1.27 mmol) of ammonium formate and 3.3 mg of palladium (10% on activated carbon, 0.003 mmol) were added. The mixture was then heated under reflux for about 20 h. Since the reaction was still incomplete after this time, the mixture was filtered and 10 mg of fresh palladium (10% on activated carbon, 0.01 mmol) were added to the filtrate. The mixture was then hydrogenated at RT under an atmosphere of 1 bar of hydrogen for about 40 h. The reaction mixture was then filtered through a little silica gel and the filtrate was evaporated to dryness. The residue was purified by preparative HPLC (Method 37). Concentration of the product fractions and drying under high vacuum gave 40 mg (51% of theory) of the title compound.

LC/MS (Method 3, ESIpos): $R_t$=0.54 min, m/z=306 [M+H]$^+$.

Example 83A

3-[7-Fluoro-6-(pyridin-3-yl)-1H-imidazo[1,2-b]pyrazol-1-yl]-4-methylaniline

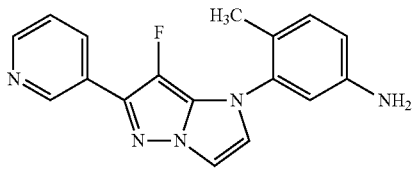 [SMILES: Cc1ccc([N+](=O)[O-])cc1-n1ccn2nc(-c3cccnc3)c(F)c12]

Step 1: 7-Fluoro-1-(2-methyl-5-nitrophenyl)-6-(pyridin-3-yl)-1H-imidazo[1,2-b]pyrazole

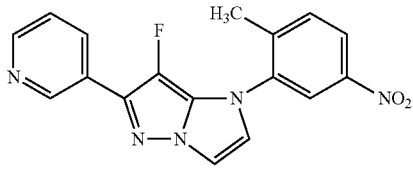

At 0° C., 1.91 g (5.40 mmol) of 1-chloromethyl-4-fluoro-1,4-diazabicyclo[2.2.2]octane-bis(tetrafluoroborate) were added to a suspension of 1.15 g (3.60 mmol) of the compound of Example 6A/Step 2 in 34.5 ml of acetonitrile, and the mixture was stirred at this temperature for 45 min. A clear solution was formed. About 100 ml of water and 100 ml of ethyl acetate were then added, and the reaction mixture was made weakly alkaline with saturated aqueous sodium bicarbonate solution. After phase separation, the aqueous phase was extracted two more times with ethyl acetate. The combined organic extracts were washed successively with water and saturated sodium chloride solution. After drying over magnesium sulphate, the mixture was filtered and the filtrate was concentrated on a rotary evaporator to dryness. The residue that remained was purified by MPLC on about 70 g of silica gel using a mobile phase gradient dichloromethane/ethyl acetate/methanol 1:1:0→1:2:0→10:0:1. Pooling of the product fractions, evaporation of the solvent and drying of the residue under high vacuum gave 400 mg (32% of theory) of the title compound.

$^1$H NMR (400 MHz, DMSO-d$_6$, δ/ppm): 8.98 (dd, 1H), 8.56 (dd, 1H), 8.37 (d, 1H), 8.27 (dd, 1H), 8.14 (dt, 1H), 7.98 (dd, 1H), 7.79 (d, 1H), 7.70 (d, 1H), 7.50 (dd, 1H), 2.47 (s, 3H).

LC/MS (Method 3, ESIpos): $R_t$=0.90 min, m/z=338 [M+H]$^+$.

Step 2: 3-[7-Fluoro-6-(pyridin-3-yl)-1H-imidazo[1,2-b]pyrazol-1-yl]-4-methylaniline

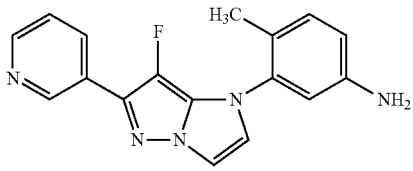 [SMILES: Cc1ccc(N)cc1-n1ccn2nc(-c3cccnc3)c(F)c12]

400 mg (1.18 mmol) of the compound of Example 83A/Step 1 were dissolved in 8 ml of ethanol and 0.8 ml of water. 374 mg (5.93 mmol) of ammonium formate and 15 mg (0.014 mmol) of palladium (10% on activated carbon) were added. The mixture was heated under reflux for 2.5 h. After cooling to RT, the mixture was filtered through a little Celite and most of the solvent was removed on a rotary evaporator. The residue that remained was taken up in dichloromethane, solid magnesium sulphate was added and the mixture was stirred and, after a while, filtered. The filtrate was concentrated and, in 2 portions, separated into its components by preparative HPLC (Method 37). The product fractions were combined and concentrated. The residue was dissolved in a little methanol and passed through a bicarbonate cartridge (from Polymerlabs, Stratospheres SPE, PL-HCO$_3$ MP SPE, capacity 0.9 mmol). Re-concentration and drying under high vacuum gave 191 mg (52% of theory) of the title compound.

$^1$H NMR (400 MHz, CDCl$_3$, δ/ppm): 9.15 (m, 1H), 8.55 (dd, 1H), 8.19 (dt, 1H), 7.38 (m, 1H), 7.36 (dd, 1H), 7.13 (d, 1H), 6.89 (d, 1H), 6.70-6.68 (m, 2H), 2.22 (s, 3H).

LC/MS (Method 3, ESIpos): $R_t$=0.68 min, m/z=308 [M+H]$^+$.

Example 84A

4-Chloro-2-methyl-5-[6-(pyridin-3-yl)-1H-imidazo[1,2-b]pyrazol-1-yl]aniline

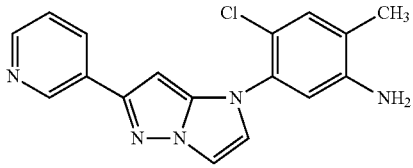

Step 1: N-(2-Chloro-4-methyl-5-nitrophenyl)-1-(2,2-diethoxyethyl)-3-(pyridin-3-yl)-1H-pyrazole-5-amine

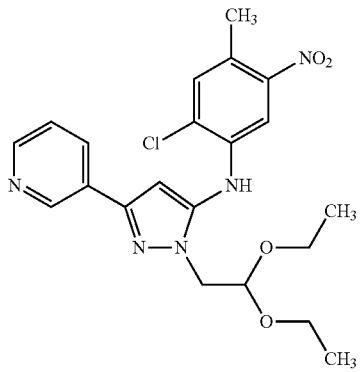

Analogously to Example 13A/Step 1, from two reactions (273 mg and 1.58 g; 6.72 mmol in total) of the compound of Example 4A and 250 mg and 1.45 g (7.4 mmol in total) of 1-bromo-2-chloro-4-methyl-5-nitrobenzene gave, after 2 h of heating under reflux, a crude product which was purified by double chromatography on a Biotage system (in each case 50 g Snap column; mobile phase gradient hexane/ethyl acetate, from 20% ethyl acetate increasing rapidly to 100% ethyl acetate, then ethyl acetate/methanol, increasing slowly to 100% methanol). This gave 1.96 g (69% of theory) of the title compound.

$^1$H NMR (400 MHz, DMSO-$d_6$, δ/ppm): 8.99 (d, 1H), 8.48 (dd, 1H), 8.13 (dt, 1H), 7.86 (s, 1H), 7.61 (s, 1H), 7.45 (s, 1H), 7.41 (ddd, 1H), 6.84 (s, 1H), 4.83 (t, 1H), 4.15 (d, 2H), 3.60 (dq, 2H), 3.43 (dq, 2H), 2.39 (s, 3H), 0.99 (t, 6H).

LC/MS (Method 7, ESIpos): $R_t$=1.31 min, m/z=446/448 [M+H]$^+$ ($^{35}$Cl/$^{37}$Cl).

Step 2: 1-(2-Chloro-4-methyl-5-nitrophenyl)-6-(pyridin-3-yl)-1H-imidazo[1,2-b]pyrazole

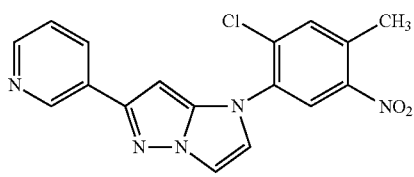 [SMILES: Cc1cc(Cl)c(-n2ccn3nc(-c4cccnc4)cc23)cc1N]

Analogously to Example 13A/Step 2, 2.32 g (5.2 mmol) of the compound prepared in Example 84A/Step 1 gave, after double chromatography on a Biotage system (in each case 50 g Snap column; mobile phase gradient hexane/ethyl acetate, from 20% ethyl acetate increasing rapidly to 100% ethyl acetate, then ethyl acetate/methanol, increasing slowly to 100% methanol), 420 mg (10% of theory) of the title compound.

$^1$H NMR (400 MHz, DMSO-$d_6$, δ/ppm): 9.00 (d, 1H), 8.46 (dd, 1H), 8.30 (s, 1H), 8.14 (dt, 1H), 7.97 (s, 1H), 7.94 (d, 1H), 7.59 (d, 1H), 7.39 (dd, 1H), 6.40 (s, 1H), 2.57 (s, 3H).

LC/MS (Method 7, ESIpos): $R_t$=0.96 min, m/z=354/356 [M+H]$^+$ ($^{35}$Cl/$^{37}$Cl).

Step 3: 4-Chloro-2-methyl-5-[6-(pyridin-3-yl)-1H-imidazo[1,2-b]pyrazol-1-yl]aniline

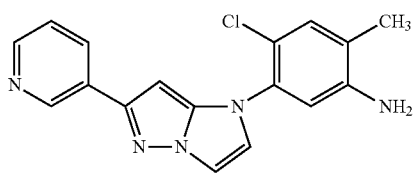 [SMILES: Cc1cc(Cl)c(-n2ccn3nc(-c4cccnc4)cc23)cc1[N+](=O)[O-]]

Analogously to Example 13A/Step 3, 420 mg (1.2 mmol) of the compound prepared in Example 84A/Step 2 gave 395 mg (102% of theory) of the title compound as a crude product which was still very impure and which was used without further purification in subsequent reactions.

LC/MS (Method 7, ESIpos): $R_t$=0.85 min, m/z=324/326 [M+H]$^+$ ($^{35}$Cl/$^{37}$Cl).

Example 85A

4-Methyl-3-[6-(pyrimidin-5-yl)-1H-imidazo[1,2-b]pyrazol-1-yl]aniline

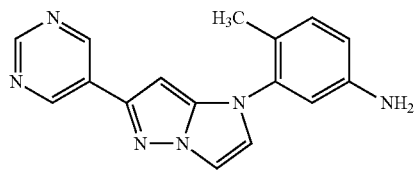

Step 1: 1-(2,2-Diethoxyethyl)-N-(2-methyl-5-nitrophenyl)-3-(pyrimidin-5-yl)-1H-pyrazole-5-amine

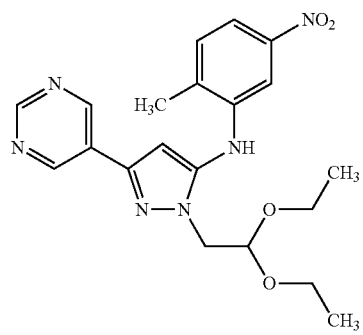

Analogously to Example 13A/Step 1, 2.22 g (8.01 mmol) of the compound of Example 78A and 1.90 g (8.81 mmol) of 2-bromo-4-nitrotoluene gave, after 3 h of heating under reflux, a crude product which was purified by chromatography on a Biotage system (100 g Snap column; mobile phase gradient ethyl acetate/0-8% methanol). This gave 1.93 g (49% of theory) of the title compound.

$^1$H NMR (400 MHz, DMSO-$d_6$, δ/ppm): 9.18 (s, 2H), 9.10 (s, 1H), 7.58-7.64 (m, 2H), 7.48 (d, 1H), 7.40 (d, 1H), 6.84 (s, 1H), 4.87 (t, 1H), 4.17 (d, 2H), 3.52-3.63 (m, 2H), 3.35-3.45 (m, 2H), 2.35 (s, 3H), 0.97 (t, 6H).

LC/MS (Method 7, ESIpos): $R_t$=1.22 min, m/z=413 [M+H]$^+$.

Step 2: 1-(2-Methyl-5-nitrophenyl)-6-(pyrimidin-5-yl)-1H-imidazo[1,2-b]pyrazole

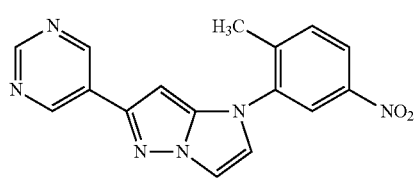 [SMILES: Cc1ccc([N+](=O)[O-])cc1-n1ccn2nc(-c3cncnc3)cc12]

Analogously to Example 13A/Step 2, 1.93 g (4.7 mmol) of the compound prepared in Example 85A/Step 1 gave, after chromatography on a Biotage system (50 g Snap column;

mobile phase gradient methylene chloride/0-7% methanol), 180 mg (11% of theory) of the title compound.

$^1$H NMR (400 MHz, DMSO-d$_6$, δ/ppm): 9.18 (s, 2H), 9.07 (s, 1H), 8.28 (d, 1H), 8.24 (dd, 1H), 7.98 (d, 1H), 7.76 (d, 1H), 7.66 (d, 1H), 6.53 (s, 1H), 2.39 (s, 3H).

LC/MS (Method 7, ESIpos): R$_t$=0.95 min, m/z=321 [M+H]$^+$.

Step 3: 4-Methyl-3-[6-(pyrimidin-5-yl)-1H-imidazo[1,2-b]pyrazol-1-yl]aniline

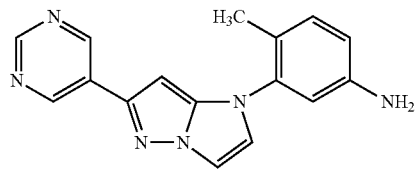

Analogously to Example 13A/Step 3, 169 mg (0.53 mmol) of the compound prepared in Example 85A/Step 2 gave 113 mg (63% of theory, purity about 85%) of the title compound as a crude product which was not purified any further.

$^1$H NMR (400 MHz, DMSO-d$_6$, δ/ppm): 9.17 (s, 2H), 9.05 (s, 1H), 7.83 (dd, 1H), 7.43 (d, 1H), 7.03 (d, 1H), 6.54-6.61 (m, 2H), 6.38 (d, 1H), 5.19 (s, 2H), 2.03 (s, 3H).

LC/MS (Method 7, ESIpos): R$_t$=0.77 min, m/z=291 [M+H]$^+$.

Example 86A 2,4-Dimethyl-5-[6-(pyrimidin-5-yl)-1H-imidazo[1,2-b]pyrazol-1-yl]aniline

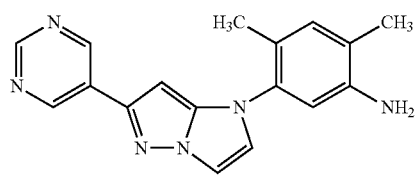 [SMILES: Cc1cc(C)c([N+](=O)[O-])cc1-n1ccn2nc(-c3cncnc3)cc12]

Step 1: 1-(2,2-Diethoxyethyl)-N-(2,4-dimethyl-5-nitrophenyl)-3-(pyrimidin-5-yl)-1H-pyrazole-5-amine

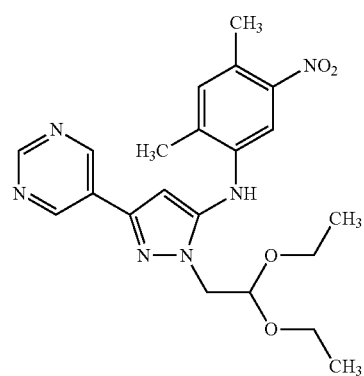

Analogously to Example 13A/Step 1, 3.01 g (10.8 mmol) of the compound of Example 78A and 2.75 g (11.9 mmol) of 5-bromo-2,4-dimethylnitrobenzene gave, after 3 h of heating under reflux, a crude product which was purified by chromatography on a Biotage system (100 g Snap column; mobile phase gradient ethyl acetate/0-8% methanol). This gave 3.70 g (65% of theory) of the title compound.

$^1$H NMR (400 MHz, DMSO-d$_6$, δ/ppm): 9.16 (s, 2H), 9.09 (s, 1H), 7.49 (s, 1H), 7.35 (s, 1H), 7.26 (s, 1H), 6.73 (s, 1H), 4.87 (t, 1H), 4.16 (d, 2H), 3.51-3.65 (m, 2H), 3.34-3.47 (m, 2H), 2.39 (s, 3H), 2.28 (s, 3H), 0.98 (t, 6H).

LC/MS (Method 7, ESIpos): R$_t$=1.31 min, m/z=427 [M+H]$^+$.

Step 2: 1-(2,4-Dimethyl-5-nitrophenyl)-6-(pyrimidin-5-yl)-1H-imidazo[1,2-b]pyrazole

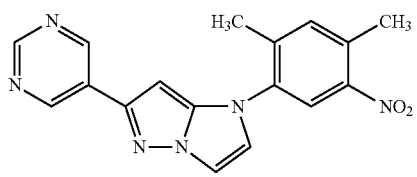

Analogously to Example 13A/Step 2, two reactions of in each case 1.85 g (4.3 mmol) of the compound prepared in Example 86A/Step 1 gave a combined crude product which was purified by chromatography on a Biotage system (100 g Snap column; mobile phase gradient methylene chloride/0-7% methanol). This gave 502 mg (17% of theory) of the title compound.

$^1$H NMR (400 MHz, DMSO-d$_6$, δ/ppm): 9.17 (s, 2H), 9.07 (s, 1H), 8.09 (s, 1H), 7.95 (d, 1H), 7.59-7.63 (m, 2H), 6.50 (s, 1H), 2.55 (s, 3H), 2.31 (s, 3H).

LC/MS (Method 7, ESIpos): R$_t$=1.06 min, m/z=335 [M+H]$^+$.

Step 3: 2,4-Dimethyl-5-[6-(pyrimidin-5-yl)-1H-imidazo[1,2-b]pyrazol-1-yl]aniline

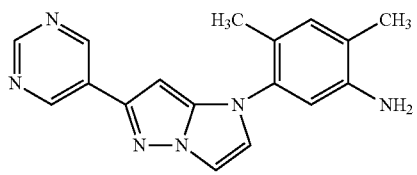

Analogously to Example 13A/Step 3, 498 mg (1.49 mmol) of the compound prepared in Example 86A/Step 2 gave 331 mg (62% of theory, purity about 85%) of the title compound as a crude product which was used without further purification.

$^1$H NMR (400 MHz, DMSO-d$_6$, δ/ppm): 9.17 (s, 2H), 9.05 (s, 1H), 7.82 (d, 1H), 7.40 (d, 1H), 6.93 (s, 1H), 6.63 (s, 1H), 6.35 (s, 1H), 4.96 (s, 2H), 2.05 (s, 3H), 2.00 (s, 3H).

LC/MS (Method 7, ESIpos): R$_t$=0.90 min, m/z=305 [M+H]$^+$.

Example 87A

4-Methyl-3-[6-(pyridazin-4-yl)-1H-imidazo[1,2-b]pyrazol-1-yl]aniline

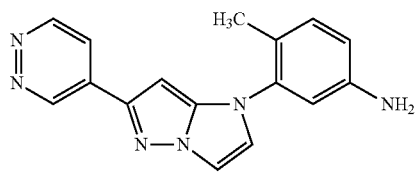

Step 1: 1-(2,2-Diethoxyethyl)-N-(2-methyl-5-nitrophenyl)-3-(pyridazin-4-yl)-1H-pyrazole-5-amine

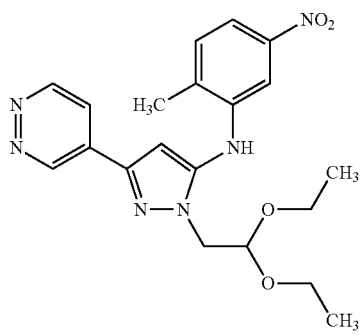 [SMILES: CCOC(Cn1nc(-c2ccnnc2)cc1Nc1cc([N+](=O)[O-])ccc1C)OCC]

Analogously to Example 13A/Step 1, 4.5 g (16.2 mmol) of the compound of Example 79A and 3.86 g (17.8 mmol) of 2-bromo-4-nitrotoluene gave, after 3 h of heating under reflux, a crude product which was purified by chromatography on a Biotage system (100 g Snap column; mobile phase gradient ethyl acetate/0-8% methanol). This gave 5.52 g (82% of theory) of the title compound.

$^1$H NMR (400 MHz, DMSO-d$_6$, δ/ppm): 9.62 (dd, 1H), 9.20 (dd, 1H), 7.96 (dd, 1H), 7.65 (s, 1H), 7.62 (dd, 1H), 7.47 (d, 1H), 7.41 (d, 1H), 6.95 (s, 1H), 4.88 (t, 1H), 4.20 (d, 2H), 3.52-3.62 (m, 2H), 3.35-3.46 (m, 2H), 2.35 (s, 3H), 0.97 (t, 6H).

LC/MS (Method 7, ESIpos): R$_t$=1.19 min, m/z=413 [M+H]$^+$.

Step 2: 1-(2-Methyl-5-nitrophenyl)-6-(pyridazin-4-yl)-1H-imidazo[1,2-b]pyrazole

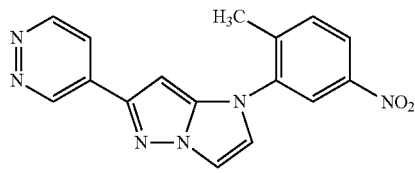 [SMILES: Cc1ccc([N+](=O)[O-])cc1-n1ccn2nc(-c3ccnnc3)cc12]

Analogously to Example 13A/Step 2, two reactions of in each case 2.76 g (6.7 mmol) of the compound prepared in Example 87A/Step 1 gave a combined crude product which was purified by chromatography on a Biotage system (100 g Snap column; mobile phase gradient methylene chloride/0-7% methanol). This gave 1.56 g (36% of theory) of the title compound.

$^1$H NMR (400 MHz, DMSO-d$_6$, δ/ppm): 9.63 (dd, 1H), 9.17 (dd, 1H), 8.29 (d, 1H), 8.24 (dd, 1H), 8.01 (d, 1H), 7.96 (dd, 1H), 7.76 (d, 1H), 7.71 (d, 1H), 6.68 (s, 1H), 2.38 (s, 3H).

LC/MS (Method 7, ESIpos): R$_t$=0.91 min, m/z=321 [M+H]$^+$.

Step 3: 4-Methyl-3-[6-(pyridazin-4-yl)-1H-imidazo[1,2-b]pyrazol-1-yl]aniline

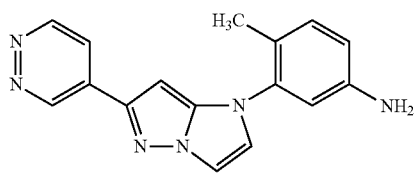

Analogously to Example 13A/Step 3, two reactions of 500 mg (1.56 mmol) and 1.06 g (3.31 mmol), respectively, of the compound prepared in Example 87A/Step 2 gave, in total, 1.14 g (80% of theory) of the title compound as a crude product which was not purified any further.

$^1$H NMR (400 MHz, DMSO-d$_6$, δ/ppm): 9.63 (dd, 1H), 9.15 (dd, 1H), 7.95-7.98 (m, 1H), 7.87 (dd, 1H), 7.49 (d, 1H), 7.04 (d, 1H), 6.56-6.61 (m, 2H), 6.53 (s, 1H), 5.20 (s, 2H), 2.03 (s, 3H).

LC/MS (Method 7, ESIpos): R$_t$=0.81 min, m/z=291 [M+H]$^+$.

Example 88A 2,4-Dimethyl-5-[6-(pyridazin-3-yl)-1H-imidazo[1,2-b]pyrazol-1-yl]aniline

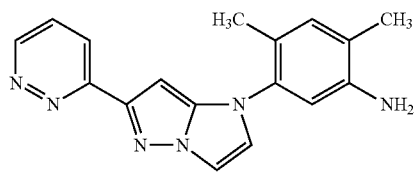

Step 1: 1-(2,2-Diethoxyethyl)-N-(2,4-dimethyl-5-nitrophenyl)-3-(pyridazin-3-yl)-1H-pyrazole-5-amine

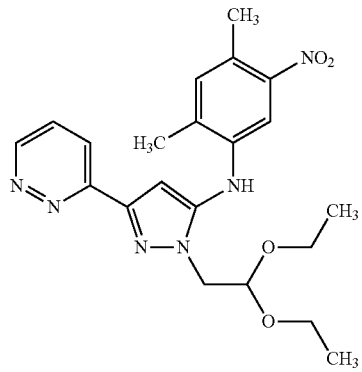

Analogously to Example 13A/Step 1, 1.09 g (3.93 mmol) of the compound of Example 80A and 996 mg (4.33 mmol) of 5-bromo-2,4-dimethylnitrobenzene gave, after 3 h of heating under reflux, a crude product which was purified by chromatography on a Biotage system (100 g Snap column; mobile phase gradient ethyl acetate/0-8% methanol). This gave 1.38 g (77% of theory) of the title compound.

$^1$H NMR (400 MHz, DMSO-$d_6$, δ/ppm): 9.13 (dd, 1H), 8.11 (dd, 1H), 7.70 (dd, 1H), 7.52 (s, 1H), 7.37 (s, 1H), 7.27 (s, 1H), 6.72 (s, 1H), 4.87 (t, 1H), 4.19 (d, 2H), 3.53-3.64 (m, 2H), 3.36-3.46 (m, 2H), 2.41 (s, 3H), 2.30 (s, 3H), 0.98 (t, 6H).

LC/MS (Method 7, ESIpos): $R_t$=1.28 min, m/z=427 [M+H]$^+$.

Step 2: 1-(2,4-Dimethyl-5-nitrophenyl)-6-(pyridazin-3-yl)-1H-imidazo[1,2-b]pyrazole

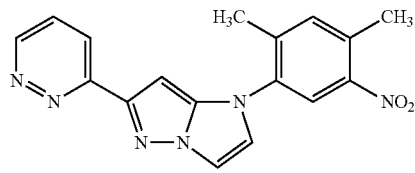 [SMILES: Cc1cc(C)c([N+](=O)[O-])cc1-n1ccn2nc(-c3cccnn3)cc12]

Analogously to Example 13A/Step 2, 1.38 g (3.24 mmol) of the compound prepared in Example 88A/Step 1 gave, after chromatography on a Biotage system (100 g Snap column; mobile phase gradient methylene chloride/0-7% methanol), 277 mg (23% of theory) of the title compound.

$^1$H NMR (400 MHz, DMSO-$d_6$, δ/ppm): 9.11 (dd, 1H), 8.09-8.16 (m, 2H), 7.97 (d, 1H), 7.69 (dd, 1H), 7.65 (d, 1H), 7.60 (s, 1H), 6.52 (s, 1H), 2.55 (s, 3H), 2.33 (s, 3H).

LC/MS (Method 7, ESIpos): $R_t$=1.01 min, m/z=335 [M+H]$^+$.

Step 3: 2,4-Dimethyl-5-[6-(pyridazin-3-yl)-1H-imidazo[1,2-b]pyrazol-1-yl]aniline

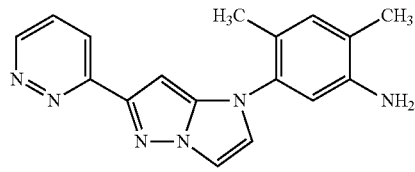 [SMILES: Cc1cc(C)c(-n2ccn3nc(-c4cccnn4)cc23)cc1N]

Analogously to Example 13A/Step 3, 272 mg (0.81 mmol) of the compound prepared in Example 88A/Step 2 gave 182 mg (63% of theory, about 85% pure) of the title compound as a crude product which was not purified any further.

$^1$H NMR (400 MHz, DMSO-$d_6$, δ/ppm): 9.09 (dd, 1H), 8.11 (dd, 1H), 7.84 (d, 1H), 7.68 (dd, 1H), 7.45 (d, 1H), 6.94 (s, 1H), 6.67 (s, 1H), 6.34 (s, 1H), 4.97 (s, 2H), 2.06 (s, 3H), 2.05 (s, 3H).

LC/MS (Method 7, ESIpos): $R_t$=0.85 min, m/z=305 [M+H]$^+$.

Example 89A

4-Methyl-3-[6-(1,3-thiazol-5-yl)-1H-imidazo[1,2-b]pyrazol-1-yl]aniline

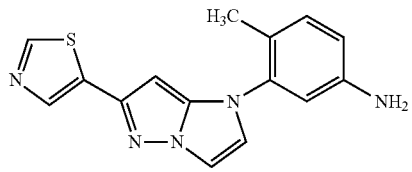

Step 1: 1-(2,2-Diethoxyethyl)-N-(2-methyl-5-nitrophenyl)-3-(1,3-thiazol-5-yl)-1H-pyrazole-5-amine

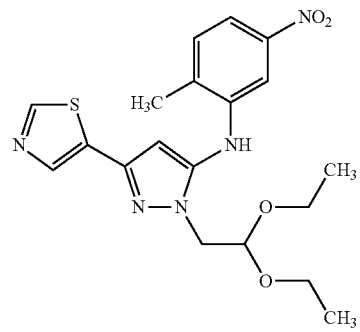 [SMILES: CCOC(Cn1nc(-c2cncs2)cc1Nc1cc([N+](=O)[O-])ccc1C)OCC]

Under nitrogen, 2.93 g (10.4 mmol) of the compound of Example 81A together with 2.47 g (11.4 mmol) of 2-bromo-4-nitrotoluene, 233 mg (1.04 mmol) of palladium(II) acetate, 901 mg (1.56 mmol) of xantphos [4,5-bis(diphenylphosphino)-9,9-dimethylxanthene] and 10.2 g (31.1 mmol) of caesium carbonate in 43 ml of 1,4-dioxane were heated under reflux for 3 h. After cooling, the mixture was filtered through Celite, the filter cake was washed with ethyl acetate and the filtrate was concentrated under reduced pressure. The crude product obtained in this manner was purified on a Biotage system (100 g Snap column; mobile phase gradient ethyl acetate/0-8% methanol). This gave 3.26 g (75% of theory) of the title compound.

$^1$H NMR (400 MHz, DMSO-$d_6$, δ/ppm): 8.99 (s, 1H), 8.21 (s, 1H), 7.60 (dd, 1H), 7.57 (s, 1H), 7.47 (d, 1H), 7.39 (d, 1H), 6.61 (s, 1H), 4.80 (t, 1H), 4.11 (d, 2H), 3.51-3.61 (m, 2H), 3.35-3.44 (m, 2H), 2.33 (s, 3H), 0.96 (t, 6H).

LC/MS (Method 7, ESIpos): $R_t$=1.31 min, m/z=418 [M+H]$^+$.

Step 2: 1-(2-Methyl-5-nitrophenyl)-6-(1,3-thiazol-5-yl)-1H-imidazo[1,2-b]pyrazole

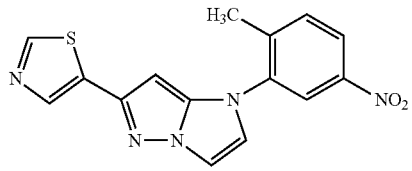 [SMILES: Cc1ccc([N+](=O)[O-])cc1-n1ccn2nc(-c3cncs3)cc12]

0.9 ml (1.77 mmol) of 2 M sulphuric acid was added to a solution of 308 mg (0.82 mmol) of the compound of Example 89A/Step 1 in 2.6 ml of ethanol, and the mixture was then heated in a microwave reactor at 125° C. for 20 min. After cooling, the reaction mixture was combined with two further reactions of in each case 1.63 g (3.9 mmol) of the compound of Example 89A/Step 1 and diluted with 350 ml of ethyl acetate. The organic phase was washed once with 30 ml of saturated sodium bicarbonate solution and once with saturated sodium chloride solution. After drying over sodium sulphate and filtration, the mixture was concentrated under reduced pressure. The crude product obtained in this manner was purified on a Biotage system (100 g Snap column; mobile phase gradient methylene chloride/0-7% methanol). This gave 1.94 g (69% of theory) of the title compound.

$^1$H NMR (400 MHz, DMSO-$d_6$, δ/ppm): 8.97 (s, 1H), 8.26 (d, 1H), 8.22 (dd, 1H), 8.20 (d, 1H), 7.89 (d, 1H), 7.75 (d, 1H), 7.60 (d, 1H), 6.31 (s, 1H), 2.38 (s, 3H).

LC/MS (Method 7, ESIpos): $R_t$=1.04 min, m/z=326 [M+H]$^+$.

Step 3: 4-Methyl-3-[6-(1,3-thiazol-5-yl)-1H-imidazo[1,2-b]pyrazol-1-yl]aniline

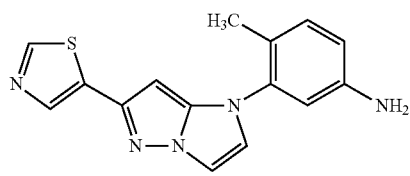 [SMILES: Cc1ccc(N)cc1-n1ccn2nc(-c3cncs3)cc12]

13 mg of palladium (10% on activated carbon) were added to a solution of 132 mg (0.41 mmol) of the compound of Example 89A/Step 2 in a mixture of 3.2 ml of ethanol and 0.01 ml of water. After addition of 128 mg (2.3 mmol) of ammonium formate, the reaction mixture was heated under reflux for 1 h. After cooling, the mixture was filtered off through Celite, the filter cake was washed with ethyl acetate and the filtrate was diluted with 200 ml of ethyl acetate. The organic phase was washed once with 30 ml of water and once with 30 ml of saturated sodium chloride solution. After drying over sodium sulphate and filtration, the filtrate was concentrated under reduced pressure. The crude product obtained in this manner still contained starting material and was therefore reacted once more under analogous conditions with a further 1.81 g (5.56 mmol) of the compound of Example 89A/Step 2. Since the crude product resulting from this reaction likewise still contained starting material, this material was reacted once more, where in this case only half the amount of palladium catalyst was used. The crude product obtained in this manner was finally purified on a Biotage system (500 g Snap column; mobile phase gradient hexane/60-100% ethyl acetate, then ethyl acetate/0-15% methanol). This gave 904 mg (49% of theory) of the title compound.

$^1$H NMR (400 MHz, DMSO-$d_6$, δ/ppm): 8.94 (s, 1H), 8.20 (s, 1H), 7.75 (d, 1H), 7.38 (d, 1H), 7.02 (d, 1H), 6.53-6.60 (m, 2H), 6.14 (s, 1H), 5.18 (s, 2H), 2.03 (s, 3H).

LC/MS (Method 7, ESIpos): $R_t$=0.85 min, m/z=296 [M+H]$^+$.

Example 90A 3-(4,4-Difluoropiperidin-1-yl)benzoic acid

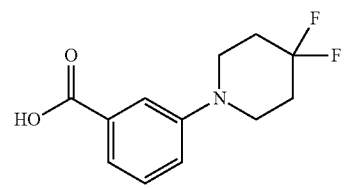 [SMILES: O=C(O)c1cccc(N2CCC(F)(F)CC2)c1]

Step 1: Methyl 3-(4,4-difluoropiperidin-1-yl)benzoate

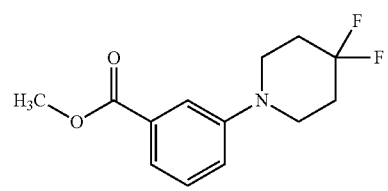 [SMILES: COC(=O)c1cccc(N2CCC(F)(F)CC2)c1]

In a microwave reaction vessel, a solution of 500 mg (2.33 mmol) of methyl 3-bromobenzoate and 366 mg (2.33 mmol) of 4,4-difluoropiperidine hydrochloride in 15 ml of dioxane was deoxygenated by passing through argon. 52 mg (0.233 mmol) of palladium(II) acetate, 202 mg (0.349 mmol) of 4,5-bis(diphenylphosphino)-9,9-dimethylxanthene (xantphos) and 2.27 g (6.98 mmol) of caesium carbonate were then added. The microwave vessel was closed with a crimp closure and, with magnetic stirring, heated in a microwave oven (Biotage Initiator, with Dynamic Field Tuning) at 120-140° C. for 1.5 hours. After the reaction had ended the reaction mixture was filtered through a little kieselguhr and then evaporated to dryness. The residue was separated into its components by preparative HPLC (Method 33). Evaporation of the product fractions and drying of the residue under high vacuum gave 342 mg (57% of theory) of the title compound.

$^1$H NMR (400 MHz, DMSO-$d_6$, δ/ppm): 7.52-7.50 (m, 1H), 7.40-7.35 (m, 2H), 7.32-7.28 (m, 1H), 3.83 (s, 3H), 3.38 (m, 4H), 2.06 (m, 4H).

LC/MS (Method 3, ESIpos): $R_t$=1.09 min, m/z=256 [M+H]$^+$.

Step 2: 3-(4,4-Difluoropiperidin-1-yl)benzoic acid

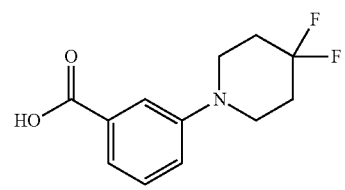 [SMILES: O=C(O)c1cccc(N2CCC(F)(F)CC2)c1]

335 mg (1.31 mmol) of the compound of Example 90A/Step 1 were dissolved in 13 ml of methanol, and 3.9 ml (3.94 mmol) of 1 M aqueous sodium hydroxide solution were added. After the reaction mixture had been stirred at RT for 7 h, the methanol was removed on a rotary evaporator and the aqueous residue that remained was, with ice cooling, acidified with 1 M hydrochloric acid. Part of the product precipitated out and was filtered off with suction, washed with water until neutral and dried under high vacuum (280 mg, 88% of theory). A second fraction of the product was obtained by extraction of the aqueous mother liquor with ethyl acetate and evaporation and drying of the organic extract (32 mg, 10% of theory). Thus, 312 mg (98% of theory) of the title compound were obtained in total.

$^1$H NMR (400 MHz, DMSO-d$_6$, δ/ppm): 7.51 (m, 1H), 7.39 (dt, 1H), 7.35 (t, 1H), 7.27 (ddd, 1H), 3.37 (m, 4H), 2.06 (m, 4H).

LC/MS (Method 3, ESIpos): R$_t$=0.90 min, m/z=242 [M+H]$^+$.

Example 91A 3-(1,1,1-Trifluoro-2-methylpropan-2-yl)benzoic acid

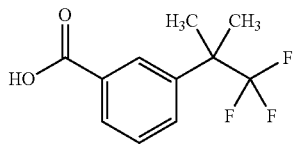 [SMILES: CC(C)(c1cccc(C(=O)O)c1)C(F)(F)F]

Step 1:
2-(3-Bromophenyl)-1,1,1-trifluoropropan-2-ol

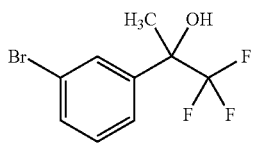

Under argon and with stirring, 22.7 ml (22.7 mmol) of a 1 M solution of methylmagnesium bromide in diethyl ether were added dropwise at 0° C. to a solution of 5.22 g (20.6 mmol) of 1-(3-bromophenyl)-2,2,2-trifluoroethanone in 40 ml of anhydrous THF. After the addition had ended, the reaction mixture was stirred at 0° C. for another 30 min. Then—still at 0° C.—excess Grignard reagent was hydrolyzed by careful addition of water. The mixture was then adjusted to a pH of about 5 by addition of 2 M hydrochloric acid. The phases were separated and the aqueous phase was extracted twice with in each case about 20 ml of diethyl ether. The combined organic phases were dried over magnesium sulphate, filtered and evaporated to dryness on a rotary evaporator. This gave 5.32 g (95% of theory) of the title compound.

$^1$H NMR (400 MHz, DMSO-d$_6$, δ/ppm): 7.76 (s, 1H), 7.58 (d, 2H), 7.38 (t, 1H), 6.77 (s, 1H), 1.69 (s, 3H).

GC/MS (Method 8, EIpos): R$_t$=3.62 min, m/z=268/270 [M]$^+$, 199/201 [M-CF$_3$]$^+$ ($^{79}$Br/$^{81}$Br).

Step 2: 2-(3-Bromophenyl)-1,1,1-trifluoropropan-2-yl-methanesulphonate

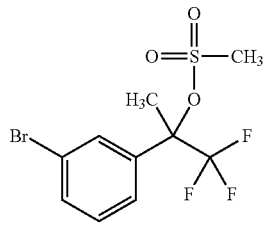 [SMILES: CC(OS(C)(=O)=O)(c1cccc(Br)c1)C(F)(F)F]

Under argon and with stirring, a solution of 3.15 g (11.7 mmol) of the compound of Example 91A/Step 1 in 20 ml of anhydrous THF was added dropwise at RT to a suspension of 937 mg (23.4 mmol) of sodium hydride (60% in mineral oil) in 30 ml of anhydrous THF. After the dropwise addition had ended, the mixture was stirred at RT for another 1 h. The mixture was then warmed to 40° C. After 30 min—still at 40° C.—a solution of 1.8 ml (23.4 mmol) of methanesulphonyl chloride in 5 ml of anhydrous THF was added dropwise. The reaction mixture was then stirred at this temperature for 1 h and then cooled to RT. 50 ml of water and then 50 ml of saturated aqueous sodium bicarbonate solution were added carefully and dropwise. The phases were separated, and the aqueous phase was extracted twice with in each case about 100 ml of ethyl acetate. The combined organic phases were dried over magnesium sulphate, filtered and evaporated to dryness on a rotary evaporator. The crude product obtained in this manner was purified by trituration with a little hexane at RT. Filtration and drying under reduced pressure gave 3.70 g (91% of theory) of the title compound.

$^1$H NMR (400 MHz, DMSO-d$_6$, δ/ppm): 7.81 (s, 1H), 7.71 (d, 1H), 7.69 (d, 1H), 7.47 (t, 1H), 3.44 (s, 3H), 2.27 (s, 3H).

GC/MS (Method 8, EIpos): R$_t$=5.34 min, m/z=346/348 [M]$^+$, 250/252 [M-CH$_3$SO$_3$H]$^+$ ($^{79}$Br/$^{81}$Br).

Step 3: 1-Bromo-3-(1,1,1-trifluoro-2-methylpropan-2-yl)benzene

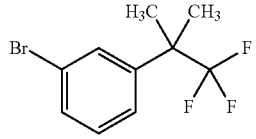

Under argon and with stirring, 11.5 ml (23.0 mmol) of a 2 M solution of trimethylaluminium in toluene were added dropwise at 0° C. to a solution of 4.0 g (11.5 mmol) of the compound of Example 91A/Step 2 in 20 ml of dichloromethane. After the dropwise addition had ended, the ice/water bath was removed and stirring was continued at RT for another 1.5 h. Subsequently, 40 ml of saturated aqueous sodium bicarbonate solution and then 12 ml of saturated aqueous sodium chloride solution were added carefully and dropwise. The resulting precipitated organic salts were filtered off through a little kieselguhr. The filter cake was washed twice with dichloromethane. The combined filtrates were washed with saturated sodium chloride solution and dried over magnesium sulphate. Evaporation of the solvent on a rotary evaporator gave 2.9 g (84% of theory) of the title compound.

$^1$H NMR (400 MHz, DMSO-$d_6$, δ/ppm): 7.69 (s, 1H), 7.57 (d, 2H), 7.38 (t, 1H), 1.55 (s, 6H).

GC/MS (Method 8, EIpos): $R_t$=3.14 min, m/z=266/268 [M]$^+$, 197/199 [M-CF$_3$]$^+$ ($^{79}$Br/$^{81}$Br).

Step 4:
3-(1,1,1-Trifluoro-2-methylpropan-2-yl)benzoic acid

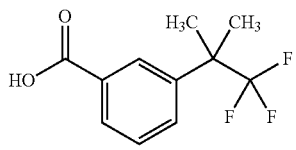 [SMILES: CC(C)(c1cccc(C(=O)O)c1)C(F)(F)F]

Under argon and with stirring, 824 µl (2.06 mmol) of a 2.5 M solution of n-butyllithium in a hexane fraction was added dropwise at 0° C. to a solution of 500 mg (1.87 mmol) of the compound of Example 91A/Step 3 in 15 ml of anhydrous diethyl ether. After the dropwise addition had ended, the mixture was stirred at 0° C. for another 1 h, and dry carbon dioxide gas was then introduced into the apparatus. After a further hour at 0° C., the reaction mixture was warmed to RT and about 50 ml of water were added. The phases were separated, and the ether phase was extracted once with water. The combined aqueous phases were then acidified by addition of 1 M hydrochloric acid and then extracted three times with in each case about 50 ml of ethyl acetate. The combined organic extracts were dried over magnesium sulphate and evaporated to dryness on a rotary evaporator. Drying of the residue under high vacuum gave 95 mg (21% of theory) of the title compound.

$^1$H NMR (400 MHz, DMSO-$d_6$, δ/ppm): 13.07 (broad, 1H), 8.08 (s, 1H), 7.93 (d, 1H), 7.82 (d, 1H), 7.55 (t, 1H), 1.59 (s, 6H).

LC/MS (Method 3, ESIneg): $R_t$=0.96 min, m/z=231 [M−H]$^-$.

Example 92A 3-(2-Hydroxypropan-2-yl)benzoic acid

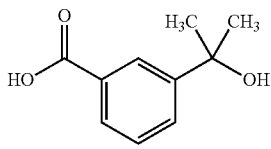

Under argon and at −78° C., 4 ml (9.95 mmol) of a 2.5 M solution of n-butyllithium in a hexane fraction were added dropwise to a solution of 1.0 g (4.97 mmol) of 3-bromobenzoic acid in 20 ml of anhydrous THF. After 20 min, 730 µl (9.95 mmol) of acetone were added dropwise at the same temperature. The reaction mixture was stirred at −78° C. for a further hour and then allowed to warm to RT over the course of about 1 h. The reaction mixture was then hydrolysed by careful addition of a few drops of saturated aqueous ammonium chloride solution. The mixture was diluted with 200 ml of water and extracted five times with in each case about 25 ml of ethyl acetate. The combined organic extracts were washed with saturated aqueous sodium chloride solution, dried over magnesium sulphate, filtered and freed from the solvent on a rotary evaporator. The residue obtained was purified in four portions by preparative HPLC (Method 36). Pooling of the product fractions, evaporation and drying under high vacuum gave 356 mg (39% of theory) of the title compound.

$^1$H NMR (400 MHz, DMSO-$d_6$, δ/ppm): 12.85 (broad, 1H), 8.08 (t, 1H), 7.78 (dt, 1H), 7.69 (dt, 1H), 7.42 (t, 1H), 5.14 (s, 1H), 1.44 (s, 6H).

LC/MS (Method 3, ESIneg): $R_t$=0.62 min, m/z=179 [M−H]$^-$.

Example 93A 3-(Pentafluoro-λ$^6$-sulphanyl)-5-(piperidin-1-yl)benzoic acid

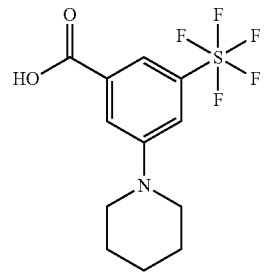 [SMILES: O=C(O)c1cc(N2CCCCC2)cc(S(F)(F)(F)(F)F)c1]

Step 1: Methyl 3-bromo-5-(pentafluoro-λ$^6$-sulphanyl)benzoate

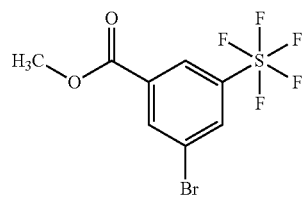 [SMILES: COC(=O)c1cc(Br)cc(S(F)(F)(F)(F)F)c1]

5.0 g (15.3 mmol) of the compound of Example 15A were dissolved in 150 ml of methanol and 2.2 ml (30.6 mmol) of thionyl chloride were added dropwise at RT. The reaction mixture was then heated under reflux for 4 h. After cooling to RT, the major part of the solvent except for a residual volume of about 50 ml was removed on a rotary evaporator. The residue was diluted with ethyl acetate and washed successively with water, saturated sodium bicarbonate solution and saturated sodium chloride solution. After drying over magnesium sulphate, the mixture was filtered and concentrated. The crude product obtained in this manner was purified by filtration with suction over about 50 g of silica gel with dichloromethane as mobile phase. Re-concentration gave 5.06 g (97% of theory) of the title compound.

$^1$H NMR (400 MHz, DMSO-$d_6$, δ/ppm): 8.51 (t, 1H), 8.35 (s, 1H), 8.27 (dd, 1H), 3.92 (s, 3H).

LC/MS (Method 3, ESIpos): $R_t$=1.27 min, no ionization.

Step 2: 3-(Pentafluoro-λ⁶-sulphanyl)-5-(piperidin-1-yl)benzoic acid

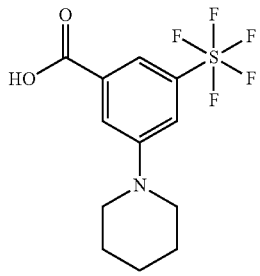 [SMILES: O=C(O)c1cc(N2CCCCC2)cc(S(F)(F)(F)(F)F)c1]

A mixture of 200 mg (0.586 mmol) of the compound of Example 93A/Step 1, 70 µl (0.704 mmol) of piperidine, 27 mg (0.029 mmol) of tris(dibenzylideneacetone)dipalladium, 42 mg (0.088 mmol) of 2-dicyclohexylphosphino-2',4',6'-triisopropylbiphenyl and 141 mg (1.47 mmol) of sodium tert-butoxide in 6 ml of toluene was heated in a microwave oven (Biotage Initiator, with Dynamic Field Tuning) at 80° C. for 90 min. After cooling to RT, about 20 ml of water were added and the mixture was extracted three times with in each case about 20 ml of ethyl acetate. The combined organic extracts were washed with saturated aqueous sodium chloride solution, dried over magnesium sulphate, filtered and freed from the solvent on a rotary evaporator. The residue obtained was separated into its components by preparative HPLC (Method 33). This gave two fractions: 41 mg (21% of theory) of the title compound and 27 mg (13% of theory) of the corresponding methyl ester.

LC/MS (Method 3, ESIpos): $R_t$=1.28 min, m/z=332 [M+H]⁺.

Example 94A 3-(4-Cyanopiperidin-1-yl)-5-(pentafluoro-λ⁶-sulphanyl)benzoic acid

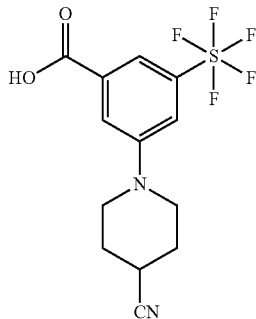 [SMILES: N#CC1CCN(c2cc(C(=O)O)cc(S(F)(F)(F)(F)F)c2)CC1]

Analogously to the process described in Example 93A/Step 2, 400 mg (1.17 mmol) of the compound of Example 93A/Step 1 and 155 mg (1.41 mmol) of 4-cyanopiperidine gave 158 mg (37% of theory) of the title compound and 104 mg (23% of theory) of the corresponding methyl ester.

¹H NMR (400 MHz, DMSO-d₆, δ/ppm): 13.61 (broad, 1H), 7.67-7.65 (m, 2H), 7.59 (t, 1H), 3.54-3.48 (m, 2H), 3.24-3.17 (m, 2H), 3.12-3.05 (m, 1H), 2.04-1.96 (m, 2H), 1.87-1.78 (m, 2H).

LC/MS (Method 3, ESIpos): $R_t$=0.99 min, m/z=357 [M+H]⁺.

Example 95A 3-(4-Methoxypiperidin-1-yl)-5-(pentafluoro-λ⁶-sulphanyl)benzoic acid

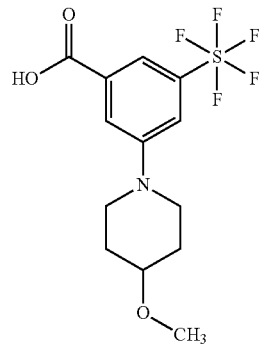 [SMILES: COC1CCN(c2cc(C(=O)O)cc(S(F)(F)(F)(F)F)c2)CC1]

Analogously to the process described in Example 93A/Step 2, 200 mg (0.586 mmol) of the compound of Example 93A/Step 1 and 81 mg (0.704 mmol) of 4-methoxypiperidine gave 49 mg (23% of theory) of the title compound and 23 mg (10% of theory) of the corresponding methyl ester.

LC/MS (Method 3, ESIpos): $R_t$=1.06 min, m/z=362 [M+H]⁺.

Example 96A 3-(3-Methoxyazetidin-1-yl)-5-(pentafluoro-λ⁶-sulphanyl)benzoic acid

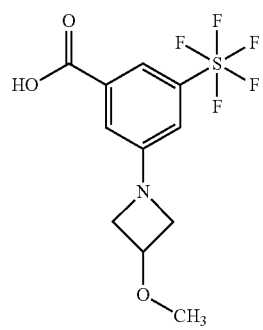 [SMILES: COC1CN(c2cc(C(=O)O)cc(S(F)(F)(F)(F)F)c2)C1]

Step 1: Methyl 3-(3-methoxyazetidin-1-yl)-5-(pentafluoro-λ⁶-sulphanyl)benzoate

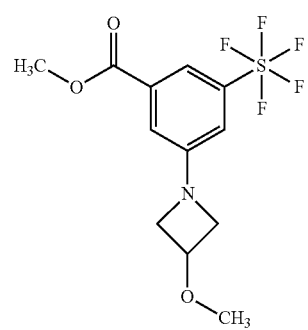 [SMILES: COC(=O)c1cc(N2CC(OC)C2)cc(S(F)(F)(F)(F)F)c1]

Analogously to the process described in Example 93A/Step 2, 220 mg (0.645 mmol) of the compound of Example 93A/Step 1 and 120 mg (0.967 mmol) of 3-methoxyazetidine hydrochloride gave 88 mg (37% of theory) of the title compound and 35 mg (16% of theory) of the corresponding benzoic acid.

$^1$H NMR (400 MHz, DMSO-d$_6$, δ/ppm): 7.54 (m, 1H), 7.14 (m, 1H), 7.04 (t, 1H), 4.37-4.32 (m, 1H), 4.18 (dd, 2H), 3.88 (s, 3H), 3.78 (dd, 2H), 3.25 (s, 3H).

LC/MS (Method 3, ESIpos): R$_t$=1.21 min, m/z=348 [M+H]$^+$.

Step 2: 3-(3-Methoxyazetidin-1-yl)-5-(pentafluoro-λ$^6$-sulphanyl)benzoic acid

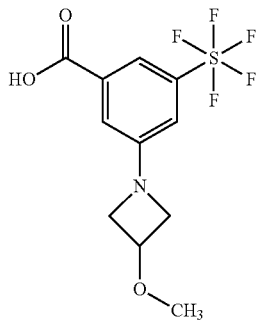 [SMILES: COC1CN(c2cc(C(=O)O)cc(S(F)(F)(F)(F)F)c2)C1]

80 mg (0.230 mmol) of the compound of Example 96A/Step 1 were dissolved in 3 ml of methanol and with 691 μl (0.691 mmol) of 1 M aqueous sodium hydroxide solution were added. The reaction mixture was stirred initially at RT for about 18 h and then at 50° C. for 10 h. The reaction mixture was then acidified by addition of 1 M hydrochloric acid. The mixture was extracted three times with in each case about 10 ml of ethyl acetate. The combined organic extracts were washed with saturated aqueous sodium chloride solution, dried over magnesium sulphate, filtered and freed from the solvent on a rotary evaporator. Drying of the residue under high vacuum gave 78 mg (96% of theory) of the title compound.

$^1$H NMR (400 MHz, DMSO-d$_6$, δ/ppm): 13.49 (broad, 1H), 7.54 (m, 1H), 7.15 (m, 1H), 7.00 (t, 1H), 4.37-4.32 (m, 1H), 4.17 (dd, 2H), 3.77 (dd, 2H), 3.25 (s, 3H).

LC/MS (Method 3, ESIpos): R$_t$=1.02 min, m/z=334 [M+H]$^+$.

Example 97A 3-(2-tert-Butoxy-2-oxoethyl)-5-(pentafluoro-λ$^6$-sulphanyl)benzoic acid

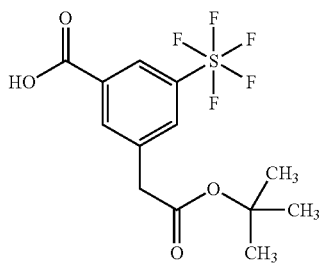 [SMILES: CC(C)(C)OC(=O)Cc1cc(C(=O)O)cc(S(F)(F)(F)(F)F)c1]

Step 1: Methyl 3-(2-tert-butoxy-2-oxoethyl)-5-(pentafluoro-λ$^6$-sulphanyl)benzoate

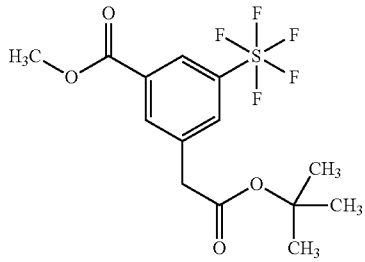 [SMILES: COC(=O)c1cc(CC(=O)OC(C)(C)C)cc(S(F)(F)(F)(F)F)c1]

Under argon, 2.40 g (36.6 mmol) of zinc dust were initially charged in 20 ml of anhydrous diethyl ether and with 265 μl (2.09 mmol) of chlorotrimethylsilane were added. After 15 min of stirring at RT, the mixture was heated under reflux. The heating bath was then removed, and 5.4 ml (36.6 mmol) of tert-butyl bromoacetate were added dropwise such that the mixture remained at the boil. After the dropwise addition had ended, the mixture was, with the aid of the heating bath, heated under reflux for a further 1 h. The organozinc solution obtained in this manner was then allowed to cool to RT.

Under argon, a solution of 2.5 g (7.33 mmol) of the compound of Example 93A/Step 1 in 15 ml of anhydrous THF was added to 9 ml of the organozinc solution prepared above [corresponds to about 14.7 mmol of bromo(2-tert-butoxy-2-oxoethyl)zinc]. 104 mg (0.147 mmol) of 1,2,3,4,5-pentaphenyl-1'-(di-tert-butylphosphino)ferrocene (Q-Phos) and 84 mg (0.147 mmol) of bis-(dibenzylideneacetone)palladium were then added, and the mixture was stirred at RT for 16 h. Since at this stage the reaction was still incomplete, the remaining organozinc solution was added and the resulting mixture was heated at 60° C. for 20 h. After cooling to RT, the mixture was diluted with 400 ml of ethyl acetate. The mixture was washed successively with in each case about 200 ml of water and saturated aqueous sodium chloride solution. The mixture was dried over magnesium sulphate and filtered, and the solvent was removed on a rotary evaporator. The crude product obtained in this manner was purified by filtration with suction through about 120 g of silica gel using the mobile phase petroleum ether/dichloromethane 2:1→1:3. Evaporation of the product fractions and drying of the residue under high vacuum gave 1.21 g (43% of theory) of the title compound.

$^1$H NMR (400 MHz, CDCl$_3$, δ/ppm): 8.33 (t, 1H), 8.10 (s, 1H), 7.88 (t, 1H), 3.96 (s, 3H), 3.65 (s, 2H), 1.45 (s, 9H).

GC/MS (Method 8, EIpos): R$_t$=5.37 min, m/z=289 [M-87]$^+$.

Step 2: 3-(2-tert-Butoxy-2-oxoethyl)-5-(pentafluoro-λ$^6$-sulphanyl)benzoic acid

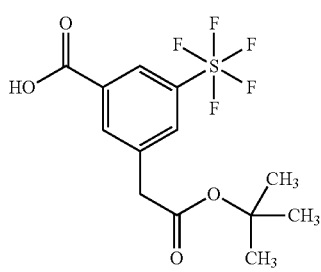 [SMILES: CC(C)(C)OC(=O)Cc1cc(C(=O)O)cc(S(F)(F)(F)(F)F)c1]

At RT, 25.7 ml (6.43 mmol) of 0.25 M aqueous lithium hydroxide solution were added to a solution of 1.21 g (3.22 mmol) of the compound of Example 97A/Step 1 in 28 ml of THF. After 2 h at RT, the reaction mixture was poured into 250 ml of water and adjusted with acetic acid to a weakly acidic pH. The mixture was quickly extracted three times with in each case about 75 ml of ethyl acetate. The combined organic extracts were washed once with saturated aqueous sodium chloride solution, dried over magnesium sulphate, filtered and freed from the solvent on a rotary evaporator. At RT, the crude product obtained in this manner was stirred in 20 ml of pentane/diisopropyl ether 20:1 for 20 min. The solid was filtered off with suction, washed with pentane and dried under high vacuum. This gave 845 mg (72% of theory) of the title compound.

$^1$H NMR (400 MHz, DMSO-$d_6$, δ/ppm): 13.68 (broad, 1H), 8.18 (dd, 1H), 8.13 (s, 1H), 8.11 (dd, 1H), 3.87 (s, 2H), 1.41 (s, 9H).

LC/MS (Method 3, ESIneg): $R_t$=1.12 min, m/z=361 [M−H]$^-$.

Example 98A

3-[(2-Methoxyethoxy)methyl]-5-(pentafluoro-$\lambda^6$-sulphanyl)benzoic acid

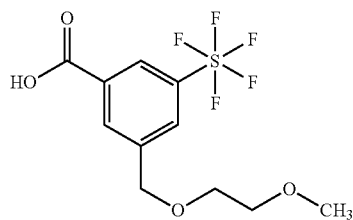

Step 1: 2-Methoxyethyl 3-[(2-methoxyethoxy)methyl]-5-(pentafluoro-$\lambda^6$-sulphanyl)benzoate

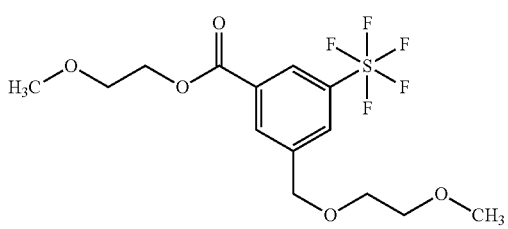

At 0° C., 86 mg (2.16 mmol) of sodium hydride (60% strength suspension in mineral oil) were added to a solution of 200 mg (0.719 mmol) of the compound of Example 37A in 5.7 ml of anhydrous DMF, and the mixture was then warmed to RT. 300 mg (2.16 mmol) of 2-bromoethyl methyl ether were then added, and the reaction mixture was stirred at 60° C. for about 16 h. After cooling to RT, 1 ml of methanol was added. In two portions, the reaction mixture was then separated into its components by preparative HPLC (Method 33). The product fractions were combined and concentrated on a rotary evaporator and the residue was dried under high vacuum. This gave 58 mg (20% of theory) of the title compound. In addition, 138 mg (57% of theory) of 2-methoxyethyl 3-(hydroxymethyl)-5-(pentafluoro-$\lambda^6$-sulphanyl)benzoate were isolated, which were then reacted once more in the manner described above with 2-bromoethyl methyl ether to give a further 30 mg of the title compound.

$^1$H NMR (400 MHz, CDCl$_3$, δ/ppm): 8.34 (t, 1H), 8.17 (s, 1H), 7.97 (s, 1H), 4.67 (s, 2H), 4.52 (m, 2H), 3.74 (m, 2H), 3.69 (m, 2H), 3.61 (m, 2H), 3.43 (s, 3H), 3.41 (s, 3H).

LC/MS (Method 3, ESIpos): $R_t$=1.12 min, m/z=395 [M+H]$^+$.

Step 2: 3-[(2-Methoxyethoxy)methyl]-5-(pentafluoro-$\lambda^6$-sulphanyl)benzoic acid

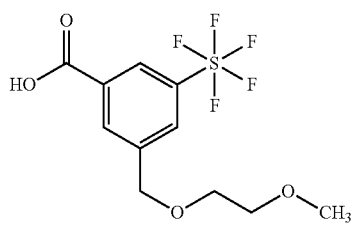 [SMILES: COCCOCc1cc(C(=O)O)cc(S(F)(F)(F)(F)F)c1]

85 mg (0.194 mmol) of the compound of Example 98A/Step 1 were dissolved in 2 ml of THF and 204 µl (0.204 mmol) of a 1 M solution of lithium hydroxide in water were added. The reaction mixture was then stirred initially at RT for 1 h and then at 5-8° C. for about 16 h. After warming to RT, 2 ml of water and 14 µl (0.242 mmol) of glacial acetic acid were added and the reaction mixture was then separated into its components by preparative HPLC (Method 36). The product fractions were combined and concentrated on a rotary evaporator and the residue was dried under high vacuum. This gave 60 mg (92% of theory) of the title compound.

$^1$H NMR (400 MHz, DMSO-$d_6$, δ/ppm): 13.70 (broad, 1H), 8.20 (t, 1H), 8.17 (s, 1H), 7.11 (t, 1H), 4.68 (s, 2H), 4.63 (m, 2H), 3.51 (m, 2H), 3.26 (s, 3H).

LC/MS (Method 3, ESIneg): $R_t$=0.96 min, m/z=335 [M−H]$^-$.

Example 99A 3-(3-Bromophenyl)-3-methyloxetane

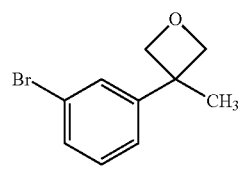

Step 1: Diethyl (3-bromophenyl)malonate

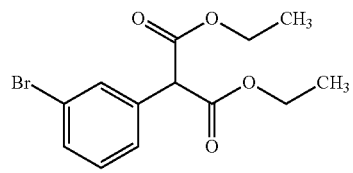 [SMILES: CCOC(=O)C(C(=O)OCC)c1cccc(Br)c1]

Preparation of ethyl 3-bromophenylacetate:

2.5 ml of conc. sulphuric acid were added to a solution of 25 g (116 mmol) of 3-bromophenylacetic acid in 170 ml of ethanol. The mixture was heated under reflux for 20 h. After cooling, the mixture was concentrated under reduced pressure and the residue was dissolved in 800 ml of ethyl acetate. The organic phase was washed three times with in each case 50 ml of saturated aqueous sodium bicarbonate solution and twice with in each case 50 ml of saturated aqueous sodium chloride solution, dried over sodium sulphate and, after filtration, concentrated under reduced pressure. The residue obtained in this manner was purified by column chromatography on silica gel using the mobile phase hexane/0-20% ethyl acetate. This gave 27.8 g (98% of theory) of ethyl 3-bromophenylacetate.

Preparation of the Title Compound:

At 150° C., a solution of 27.8 g (114 mmol) of ethyl 3-bromophenylacetate in 100 ml of toluene was added dropwise over a period of 30 minutes to a suspension of 13.7 g (343 mmol) of sodium hydride (60% strength suspension in mineral oil) in 299 ml of toluene and 54 g (457 mmol) of diethyl carbonate, and the mixture was then heated under reflux for 3 h. After cooling, the reaction mixture was poured into ice water and extracted three times with in each case 250 ml of ethyl acetate. The combined organic phases were washed once with 100 ml of saturated sodium chloride solution, dried over sodium sulphate and, after filtration, concentrated under reduced pressure. The residue obtained in this manner was purified by column chromatography on silica gel using the mobile phase hexane/0-20% ethyl acetate. This gave 31.8 g (88% of theory) of the title compound.

$^1$H NMR (400 MHz, DMSO-$d_6$, δ/ppm): 7.56 (t, 1H), 7.52 (dt, 1H), 7.34-7.39 (m, 1H), 7.32 (d, 1H), 5.00 (s, 1H), 4.06-4.18 (m, 4H), 1.14 (t, 6H).

LC/MS (Method 7, ESIneg): $R_t$=1.32 min, m/z=315 [M−H]$^-$.

Step 2: 3-(3-Bromophenyl)-3-methyloxetane

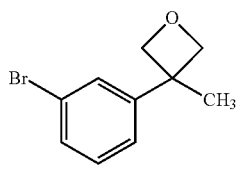

Methylation:

At RT, 6.55 g (121 mmol) of sodium methoxide were added to a solution of 31.8 g (101 mmol) of the compound of Example 99A/Step 1 in 220 ml of ethanol. After complete dissolution, 7.54 ml (121 mmol) of iodomethane were added dropwise and the mixture was stirred at RT for 24 h. The reaction mixture was then concentrated under reduced pressure and the residue was taken up in 800 ml of ethyl acetate. The organic phase was washed twice with in each case 50 ml of water and once with saturated sodium chloride solution, dried over sodium sulphate and, after filtration, concentrated under reduced pressure. Since the crude product obtained in this manner still contained starting material, the crude product was reacted three more times in the manner described above, in each case using only 1.5 g (24.1 mmol) of sodium methoxide and 1.5 g (27.8 mmol) of iodomethane. The crude product finally obtained was purified by column chromatography on silica gel using the mobile phase hexane/0-20% ethyl acetate. This gave 25.7 g of a mixture of methyl and ethyl esters with diethyl (3-bromophenyl)(methyl)malonate as main component.

Reduction:

At 0° C., 988 mg (3.0 mmol) of the diester prepared above, dissolved in 100 ml of THF, were added dropwise to a solution of 171 mg (4.5 mmol) of lithium aluminium hydride in 200 ml of THF. The mixture was stirred initially at RT for 30 min and then at 40° C. for 4 h. The mixture was then cooled to 0° C., and 20 ml of saturated aqueous sodium bicarbonate solution were added carefully. The mixture was filtered through Celite and then extracted with ethyl acetate. The organic phase was dried over sodium sulphate and, after filtration, concentrated under reduced pressure. Purification of the crude product was carried out together with that of the crude product of a second analogous reaction with 21 g (44.8 mmol) of the diester prepared above, by column chromatography on silica gel using the mobile phase hexane/ethyl acetate 8:1→1:2. This gave 9.0 g (76% of theory) of 2-(3-bromophenyl)-2-methylpropane-1,3-diol.

Preparation of the Title Compound:

428 mg (1.63 mmol) of triphenylphosphine were added to a solution of 200 mg (0.82 mmol) of the diol prepared above in 5.0 ml of toluene. After 10 min of stirring at RT, 374 mg (1.22 mmol) of ziram (zinc dimethyldithiocarbamate) were added and 284 mg (1.63 mmol) of diethyl azodicarboxylate as a 40% strength solution in toluene were added dropwise. The reaction mixture was then stirred at RT for 18 h. After filtration over Celite, the filtrate was concentrated under reduced pressure. This crude product was combined with those of two further reactions (200 mg and 1.1 g of diol, respectively) and purified by column chromatography on silica gel using the mobile phase hexane/0-10% ethyl acetate. The 700 mg of still impure material obtained in this manner were re-purified in identical fashion together with the material obtained from four further reactions (one reaction of 1.1 g of diol and three reactions of in each case 2.33 g of diol). This gave 5.0 g (69% of theory) of the title compound.

$^1$H NMR (400 MHz, DMSO-$d_6$, δ/ppm): 7.37-7.43 (m, 2H), 7.29 (t, 1H), 7.19-7.24 (m, 1H), 4.74 (d, 2H), 4.48 (d, 2H), 1.57 (s, 3H).

Working Examples

Example 1

N-{4-Methyl-3-[6-(1H-pyrazol-4-yl)-1H-imidazo[1,2-b]pyrazol-1-yl]phenyl}-3-(pentafluoro-λ$^6$-sulphanyl)-5-(piperazin-1-yl)benzamide

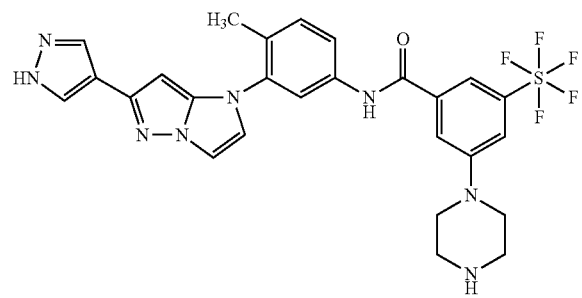 [SMILES: Cc1ccc(NC(=O)c2cc(N3CCNCC3)cc(S(F)(F)(F)(F)F)c2)cc1-n1ccn2nc(-c3cn[nH]c3)cc12]

210 mg (0.19 mmol, purity 61%) of the compound from Example 47A were stirred in 4.4 ml of a 25% strength solution of trifluoroacetic acid in methylene chloride at RT for 30 min. The mixture was then concentrated under reduced pressure. The residue was dissolved in a little methanol and added to semiconcentrated aqueous sodium bicarbonate solution. After 15 min of stirring at RT, 15 ml of ethyl acetate were added. The precipitate formed was filtered off, and the organic phase of the filtrate was separated off, washed with water, dried over sodium sulphate, filtered and concentrated. Drying of the residue under reduced pressure gave 41 mg (37% of theory) of the title compound.

$^1$H NMR (400 MHz, DMSO-$d_6$, δ/ppm): 12.85 (br. s, 1H), 10.55 (s, 1H), 8.01 (br. s, 1H), 7.90 (d, 1H), 7.78 (m, 3H), 7.75 (d, 1H), 7.72 (s, 1H), 7.55 (s, 1H), 7.45 (d, 1H), 7.41 (d, 1H), 5.92 (s, 1H), 3.38 (m, 4H), 3.06 (m, 4H), 2.27 (s, 3H).

LC/MS (Method 3, ESIpos): $R_t$=0.75 min, m/z=593 [M+H]$^+$.

Example 2

3-(4-Methylpiperazin-1-yl)-N-{4-methyl-3-[6-(1H-pyrazol-4-yl)-1H-imidazo[1,2-b]pyrazol-1-yl]-phenyl}-5-(pentafluoro-λ$^6$-sulphanyl)benzamide

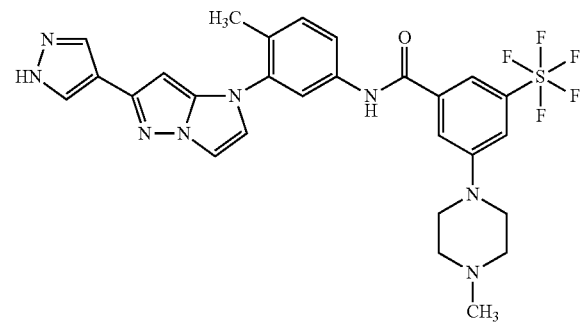 [SMILES: Cc1ccc(NC(=O)c2cc(N3CCN(C)CC3)cc(S(F)(F)(F)(F)F)c2)cc1-n1ccn2nc(-c3cn[nH]c3)cc12]

At 80° C., 90 mg (0.12 mmol) of the compound of Example 48A were stirred in 0.61 ml of trifluoroacetic acid for 3 h. The reaction was then concentrated and the residue was purified by preparative HPLC (Method 18). The product fractions were concentrated, and the residue was dissolved in ethyl acetate and washed successively with saturated potassium carbonate solution and saturated sodium chloride solution. The organic phase was dried over sodium sulphate, filtered and concentrated under reduced pressure. Drying of the residue under high vacuum gave 40 mg (53% of theory) of the title compound.

$^1$H NMR (400 MHz, DMSO-$d_6$, δ/ppm): 12.85 (br, 1H), 10.53 (s, 1H), 8.01 (br, 1H), 7.90 (d, 1H), 7.81-7.71 (m, 5H), 7.51 (s, 1H), 7.45 (d, 1H), 7.41 (d, 1H), 5.92 (s, 1H), 2.27 (s, 3H) [further signals obscured by solvent peaks].

LC/MS (Method 3, ESIpos): $R_t$=0.75 min, m/z=607 [M+H]$^+$.

Example 3

N-{4-Methyl-3-[6-(1H-pyrazol-4-yl)-1H-imidazo[1,2-b]pyrazol-1-yl]phenyl}-3-(morpholin-4-yl)-5-(pentafluoro-λ$^6$-sulphanyl)benzamide

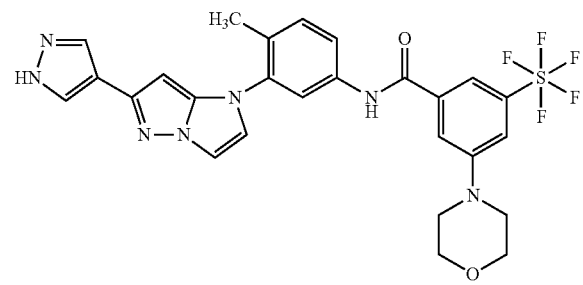 [SMILES: Cc1ccc(NC(=O)c2cc(N3CCOCC3)cc(S(F)(F)(F)(F)F)c2)cc1-n1ccn2nc(-c3cn[nH]c3)cc12]

At 80° C., 98 mg (0.14 mmol) of the compound of Example 49A were stirred in 0.56 ml of trifluoroacetic acid for 3 h. The reaction was then concentrated, the residue was dissolved in ethyl acetate and the solution was washed with saturated sodium bicarbonate solution. The organic phase was dried over sodium sulphate, filtered and concentrated under reduced pressure. After drying of the residue under high vacuum, the crude product was purified by preparative HPLC (Method 29). The product fractions were combined and concentrated, and the residue was taken up in ethyl acetate and washed with saturated sodium bicarbonate solution. The organic phase was dried over sodium sulphate, filtered and concentrated under reduced pressure. Drying under high vacuum gave a first product fraction (39 mg). A second product fraction of a further 19 mg was obtained from the combined mixed fractions of the HPLC separation by concentrating these fractions followed by re-purification by the same method by preparative HPLC. This gave a total of 58 mg (69% of theory) of the title compound.

$^1$H NMR (400 MHz, DMSO-$d_6$, δ/ppm): 12.85 (br. s, 1H), 10.53 (s, 1H), 8.01 (br. s, 1H), 7.90 (d, 1H), 7.81-7.75 (m, 4H), 7.71 (s, 1H), 7.52 (t, 1H), 7.45 (d, 1H), 7.41 (d, 1H), 5.92 (s, 1H), 3.76 (m, 4H), 2.27 (s, 3H) [further signals obscured by solvent peaks].

LC/MS (Method 4, ESIpos): $R_t$=1.04 min, m/z=594 [M+H]$^+$.

Example 4

3-(2-Hydroxypropan-2-yl)-N-{4-methyl-3-[6-(1H-pyrazol-4-yl)-1H-imidazo[1,2-b]pyrazol-1-yl]-phenyl}-5-(pentafluoro-λ$^6$-sulphanyl)benzamide

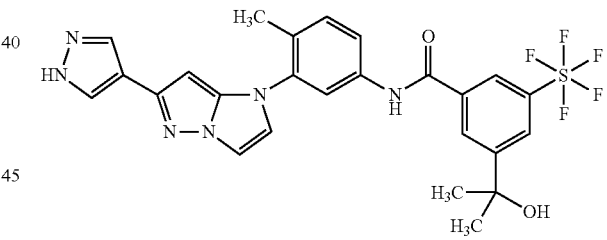

The compound from Example 7A (2.63 g, 9.45 mmol) was dissolved in 55 ml of DMF. HATU (7.91 g, 20.8 mmol) and N-methylmorpholine (8.31 ml, 75.6 mmol) were added, and the mixture was stirred at RT for 30 min. The mixture was then cooled to −5° C. and the compound from Example 19A (5.79 g, 18.9 mmol) was added. The mixture was stirred for a further 45 min, concentrated aqueous ammonia solution was then added and the mixture was stirred for another 15 min. The mixture was then extracted with ethyl acetate, and the organic extract was washed with conc. sodium chloride solution, dried over sodium sulphate and concentrated. The crude product was purified by preparative HPLC [column: Waters Sunfire C-18.5 μm, 250 mm×20 mm; ternary gradient water/acetonitrile/1% TFA in water: 0-6.7 min 45:50:5, ramp, 6.9-9.0 min 0:95:5]. This gave 3.86 g (72% of theory) of the title compound.

¹H NMR (400 MHz, DMSO-d₆, δ/ppm): 10.64 (s, 1H), 8.28 (d, 2H), 8.17 (s, 1H), 7.92 (m, 3H), 7.79 (d, 1H), 7.76 (d, 1H), 7.46 (d, 1H), 7.43 (d, 1H), 5.95 (s, 1H), 2.27 (s, 3H), 1.51 (s, 6H).

LC/MS (Method 4, ESIpos): $R_t$=1.04 min, m/z=594 [M+H]⁺.

Example 5

N-{4-Methyl-3-[6-(1H-pyrazol-4-yl)-1H-imidazo[1,2-b]pyrazol-1-yl]phenyl}-3-(trifluoromethyl)-benzamide

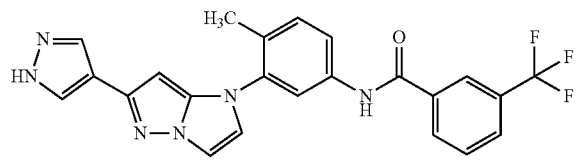 [SMILES: Cc1ccc(NC(=O)c2cccc(C(F)(F)F)c2)cc1-n1ccn2nc(-c3cn[nH]c3)cc12]

At 80° C., 25 mg (0.025 mmol, 57% pure) of the compound from Example 50A were stirred in 0.5 ml of trifluoroacetic acid for 6 h. After concentration of the mixture under reduced pressure, the residue was purified by preparative HPLC (Method 11). This gave 6.0 mg (53% of theory) of the title compound.

¹H NMR (400 MHz, DMSO-d₆, δ/ppm): 10.62 (s, 1H), 8.30 (s, 1H), 8.27 (d, 1H), 7.98 (d, 1H), 7.95 (d, 1H), 7.91 (s, 2H), 7.82-7.77 (m, 3H), 7.45 (d, 1H), 7.43 (d, 1H), 5.94 (s, 1H), 2.27 (s, 3H).

LC/MS (Method 3, ESIpos): $R_t$=0.94 min, m/z=451 [M+H]⁺.

Example 6

3-(2-Methyl-1H-imidazol-1-yl)-N-{4-methyl-3-[6-(1H-pyrazol-4-yl)-1H-imidazo[1,2-b]pyrazol-1-yl]phenyl}-5-(trifluoromethyl)benzamide

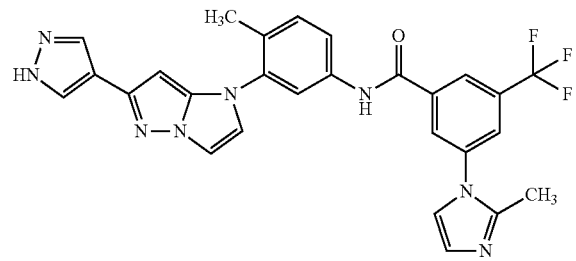 [SMILES: Cc1ccc(NC(=O)c2cc(-n3ccnc3C)cc(C(F)(F)F)c2)cc1-n1ccn2nc(-c3cn[nH]c3)cc12]

60 mg (0.09 mmol) of the compound of Example 51A were reacted and worked up analogously to the procedure of Example 2. This gave 20 mg (40% of theory) of the title compound.

¹H NMR (400 MHz, DMSO-d₆, δ/ppm): 12.85 (s, 1H), 10.66 (s, 1H), 8.35 (s, 1H), 8.32 (s, 1H), 8.16 (s, 1H), 8.02 (s, 1H), 7.93 (d, 1H), 7.79 (m, 3H), 7.50 (d, 1H), 7.47 (d, 1H), 7.42 (d, 1H), 6.99 (d, 1H), 5.92 (s, 1H), 2.36 (s, 3H), 2.27 (s, 3H).

LC/MS (Method 1, ESIpos): $R_t$=0.91 min, m/z=531 [M+H]⁺.

Example 7

3-tert-Butyl-N-{4-methyl-3-[6-(1H-pyrazol-4-yl)-1H-imidazo[1,2-b]pyrazol-1-yl]phenyl}-benzamide

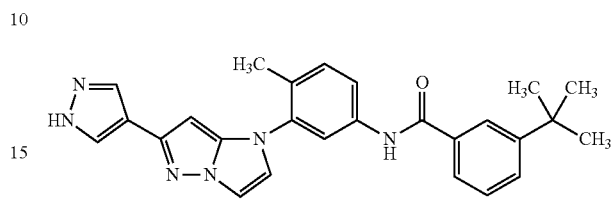

140 mg (0.2 mmol) of the compound of Example 52A were reacted analogously to the procedure of Example 2. Here, purification of the crude product was by preparative HPLC according to Method 11. This gave 38 mg (44% of theory) of the title compound.

¹H NMR (400 MHz, DMSO-d₆, δ/ppm): 10.36 (s, 1H), 7.95 (d, 1H), 7.91 (m, 3H), 7.80-7.77 (m, 3H), 7.63 (d, 1H), 7.48-7.41 (m, 3H), 5.94 (s, 1H), 2.26 (s, 3H), 1.33 (s, 9H).

LC/MS (Method 3, ESIpos): $R_t$=1.02 min, m/z=439 [M+H]⁺.

Example 8

3-tert-Butyl-5-(4-methylpiperazin-1-yl)-N-{4-methyl-3-[6-(1H-pyrazol-4-yl)-1H-imidazo[1,2-b]-pyrazol-1-yl]phenyl}benzamide

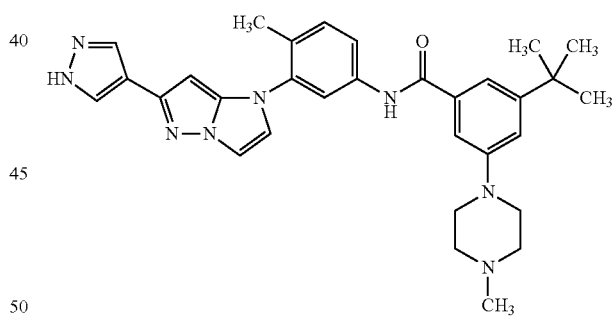

68 mg (76% pure, 79 μmol) of the compound of Example 57A were initially charged in 0.32 ml of trifluoroacetic acid and stirred at 80° C. for 3 h. The mixture was then purified directly by preparative HPLC (Method 29). The product fractions were concentrated under reduced pressure and the residue was taken up in ethyl acetate and washed with saturated aqueous sodium bicarbonate solution. The organic phase was dried over sodium sulphate, filtered and concentrated under reduced pressure. This gave 41 mg (97% of theory) of the title compound.

¹H NMR (400 MHz, DMSO-d₆, δ/ppm): 12.84 (br. s, 1H), 10.25 (s, 1H), 8.01 (br. s, 1H), 7.92 (d, 1H), 7.84-7.74 (m, 3H), 7.44-7.39 (m, 2H), 7.37 (s, 1H), 7.27 (s, 1H), 7.14 (s, 1H), 5.92 (s, 1H), 3.23 (m, 4H), 2.31 (m, 2H), 2.25 (s, 3H), 1.31 (s, 9H) [further signals obscured by solvent peaks].

Example 9

3-tert-Butyl-N-{4-methyl-3-[6-(1H-pyrazol-4-yl)-1H-imidazo[1,2-b]pyrazol-1-yl]phenyl}-5-(pyrrolidin-1-ylmethyl)benzamide

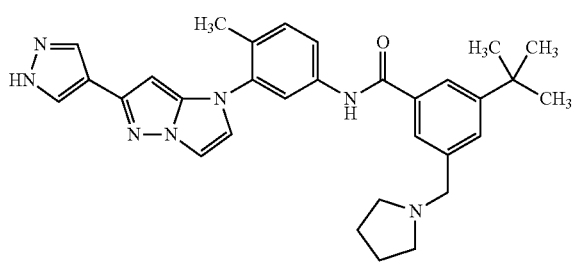 [SMILES: Cc1ccc(NC(=O)c2cc(CN3CCCC3)cc(C(C)(C)C)c2)cc1-n1ccn2nc(-c3cn[nH]c3)cc12]

80 mg (0.13 mmol) of the compound of Example 53A were reacted analogously to the procedure of Example 2. This gave 27 mg (39% of theory) of the title compound.

$^1$H NMR (400 MHz, DMSO-d$_6$, δ/ppm): 12.84 (br, 1H), 10.36 (s, 1H), 8.02 (s, 1H), 7.94 (d, 1H), 7.81-7.77 (m, 3H), 7.71 (s, 1H), 7.54 (s, 1H), 7.42 (m, 2H), 5.93 (s, 1H), 3.65 (br, 2H), 2.46 (br, 2H), 2.26 (s, 3H), 1.71 (br, 4H), 1.33 (s, 9H) [further signals obscured by solvent peaks].

LC/MS (Method 3, ESIpos): R$_t$=0.76 min, m/z=522 [M+H]$^+$.

Example 10

N-{4-Methyl-3-[3-methyl-6-(1H-pyrazol-4-yl)-1H-imidazo[1,2-b]pyrazol-1-yl]phenyl}-3-(pentafluoro-λ$^6$-sulphanyl)-5-(piperazin-1-yl)benzamide

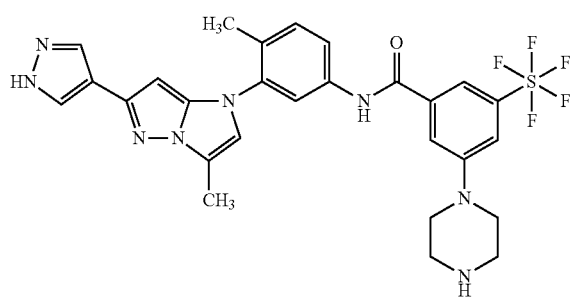 [SMILES: Cc1ccc(NC(=O)c2cc(N3CCNCC3)cc(S(F)(F)(F)(F)F)c2)cc1-n1cc(C)n2nc(-c3cn[nH]c3)cc12]

65 mg (0.16 mmol) of the compound of Example 9A, 68 mg (0.158 mmol) of the compound of Example 16A and 72 mg (0.19 mmol) of HATU were initially charged in 0.9 ml of DMF, 0.033 ml (0.19 mmol) of N,N-diisopropylethylamine were added and the mixture was stirred at RT for 1 h. The reaction was then stirred into 10 ml of 0.1 M aqueous sodium hydroxide solution. After 10 min of further stirring at RT, the precipitate formed was filtered off, washed with water and dried. The intermediate obtained in this manner was dissolved in 0.5 ml of trifluoroacetic acid and stirred at 80° C. for 6 h. The mixture was then concentrated under reduced pressure and the residue was purified by double preparative HPLC (Method 18). This gave 18 mg (19% of theory) of the title compound.

$^1$H NMR (400 MHz, DMSO-d$_6$, δ/ppm): 12.84 (br, 1H), 10.51 (s, 1H), 8.10-7.80 (br, 2H), 7.88 (d, 1H), 7.74-7.69 (m, 3H), 7.46 (t, 1H), 7.43 (d, 1H), 7.15 (d, 1H), 5.93 (s, 1H), 3.22 (m, 4H), 2.84 (m, 4H), 2.41 (s, 3H), 2.27 (s, 3H).

LC/MS (Method 3, ESIpos): R$_t$=0.77 min, m/z=607 [M+H]$^+$.

Example 11

N-{4-Methyl-3-[3-methyl-6-(1H-pyrazol-4-yl)-1H-imidazo[1,2-b]pyrazol-1-yl]phenyl}-3-(4-methylpiperazin-1-yl)-5-(pentafluoro-λ$^6$-sulphanyl)benzamide

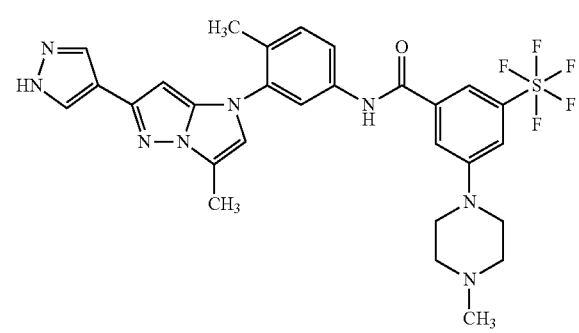 [SMILES: Cc1ccc(NC(=O)c2cc(N3CCN(C)CC3)cc(S(F)(F)(F)(F)F)c2)cc1-n1cc(C)n2nc(-c3cn[nH]c3)cc12]

115 mg (0.16 mmol) of the compound of Example 54A were reacted and worked up analogously to the procedure of Example 2. This gave 64 mg (65% of theory) of the title compound.

$^1$H NMR (400 MHz, DMSO-d$_6$, δ/ppm): 12.85 (br, 1H), 10.51 (s, 1H), 8.05-7.78 (br, 2H), 7.89 (d, 1H), 7.74-7.71 (m, 3H), 7.50 (s, 1H), 7.43 (d, 1H), 7.14 (d, 1H), 5.93 (s, 1H), 2.41 (s, 3H), 2.27 (s, 3H), 2.23 (s, 3H) [further signals obscured by solvent peaks].

LC/MS (Method 3, ESIpos): R$_t$=0.82 min, m/z=621 [M+H]$^+$.

Example 12

3-Cyano-N-{4-methyl-3-[3-methyl-6-(1H-pyrazol-4-yl)-1H-imidazo[1,2-b]pyrazol-1-yl]phenyl}-5-(pentafluoro-λ$^6$-sulphanyl)benzamide

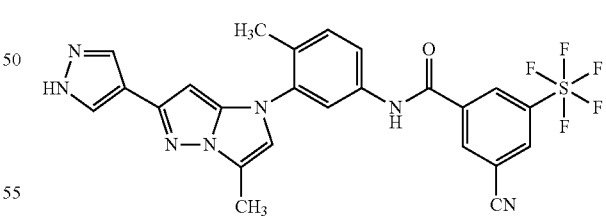

At 90° C., 115 mg (0.23 mmol) of the compound of Example 56A were stirred in 1.5 ml of trifluoroacetic acid for 60 min. The reaction was then concentrated under reduced pressure and the residue was purified by preparative HPLC (Method 21). The product fractions were combined, concentrated almost completely under reduced pressure and made alkaline with a little saturated aqueous sodium bicarbonate solution. The resulting precipitate was filtered off, washed with water and dried under high vacuum. This gave 60 mg (46% of theory) of the title compound.

$^1$H NMR (400 MHz, DMSO-d$_6$, δ/ppm): 12.85 (br, 1H), 10.76 (s, 1H), 8.85 (s, 1H), 8.74 (s, 1H), 8.66 (s, 1H), 8.05-7.78 (br, 2H), 7.90 (d, 1H), 7.73 (dd, 1H), 7.46 (d, 1H), 7.16 (d, 1H), 5.93 (s, 1H), 2.41 (s, 3H), 2.29 (s, 3H).

LC/MS (Method 3, ESIpos): R$_t$=1.07 min, m/z=548 [M+H]$^+$.

Example 13

3-Methoxy-N-{4-methyl-3-[3-methyl-6-(1H-pyrazol-4-yl)-1H-imidazo[1,2-b]pyrazol-1-yl]-phenyl}-5-(pentafluoro-λ$^6$-sulphanyl)benzamide

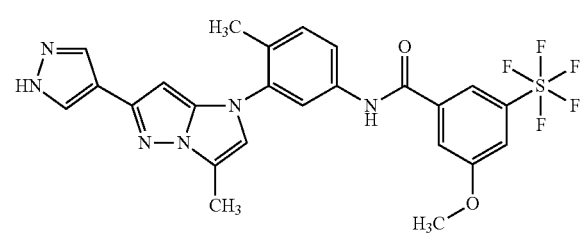 [SMILES: COc1cc(C(=O)Nc2ccc(C)c(-n3cc(C)n4nc(-c5cn[nH]c5)cc34)c2)cc(S(F)(F)(F)(F)F)c1]

60 mg (0.15 mmol) of the compound of Example 9A and 40 mg (0.15 mmol) of the compound of Example 25A were reacted analogously to the procedure of Example 10, except that here the reaction was stirred with trifluoroacetic acid at 80° C. only for 3 h (instead of 6 h). This gave 36 mg (43% of theory) of the title compound.

$^1$H NMR (400 MHz, DMSO-d$_6$, δ/ppm): 12.84 (br, 1H), 10.59 (s, 1H), 8.04 (s, 1H), 7.99 (s, 1H), 7.90 (d, 1H), 7.83 (s, 1H), 7.80 (s, 1H), 7.73 (dd, 1H), 7.63 (s, 1H), 7.43 (d, 1H), 7.15 (s, 1H), 5.93 (s, 1H), 3.94 (s, 3H), 2.41 (s, 3H), 2.28 (s, 3H).

LC/MS (Method 4, ESIpos): R$_t$=1.10 min, m/z=553 [M+H]$^+$.

Example 14

3-(2-Methyl-1H-imidazol-1-yl)-N-{4-methyl-3-[3-methyl-6-(1H-pyrazol-4-yl)-1H-imidazo[1,2-b]-pyrazol-1-yl]phenyl}-5-(trifluoromethyl)benzamide

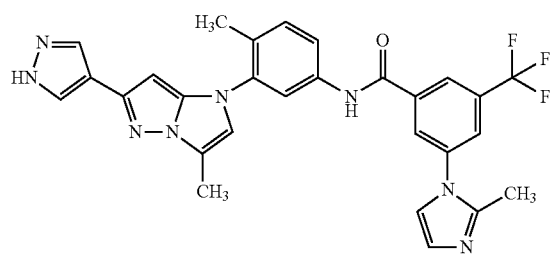 [SMILES: Cc1ccc(NC(=O)c2cc(-n3ccnc3C)cc(C(F)(F)F)c2)cc1-n1cc(C)n2nc(-c3cn[nH]c3)cc12]

70 mg (0.17 mmol) of the compound of Example 9A and 50 mg (0.19 mmol) of 3-(2-methyl-1H-imidazol-1-yl)-5-(trifluoromethyl)benzoic acid [lit.: WO 2004/005281-A1, Example 91b] were reacted analogously to the procedure of Example 13. This gave 58 mg (71% of theory) of the title compound.

$^1$H NMR (400 MHz, DMSO-d$_6$, δ/ppm): 12.84 (br, 1H), 10.63 (s, 1H), 8.35 (s, 1H), 8.32 (s, 1H), 8.16 (s, 1H), 8.04 (s, 1H), 7.92 (d, 1H), 7.80 (s, 1H), 7.75 (dd, 1H), 7.50 (d, 1H), 7.45 (d, 1H), 7.15 (d, 1H), 6.99 (d, 1H), 5.93 (s, 1H), 2.41 (s, 3H), 2.35 (s, 3H), 2.28 (s, 3H).

LC/MS (Method 4, ESIpos): R$_t$=0.73 min, m/z=545 [M+H]$^+$.

Example 15

N-{4-Methyl-3-[6-(pyridin-3-yl)-1H-imidazo[1,2-b]pyrazol-1-yl]phenyl}-3-(pentafluoro-λ$^6$-sulphanyl)benzamide

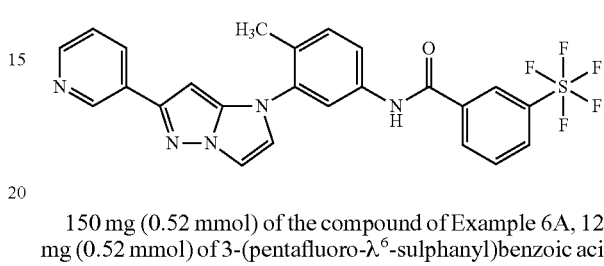

150 mg (0.52 mmol) of the compound of Example 6A, 128 mg (0.52 mmol) of 3-(pentafluoro-λ$^6$-sulphanyl)benzoic acid and 237 mg (0.62 mmol) of HATU were initially charged in 1.8 ml of DMF, 0.11 ml (0.62 mmol) of N,N-diisopropylethylamine were added and the reaction was stirred at RT for 1 h. The reaction was then stirred into 15 ml of 0.1 M aqueous sodium hydroxide solution. After a further 10 min of stirring at RT, the precipitate formed was filtered off, washed with water and dried. This gave 235 mg (83% of theory) of the title compound.

$^1$H NMR (400 MHz, DMSO-d$_6$, δ/ppm): 10.69 (s, 1H), 9.06 (s, 1H), 8.48 (d, 1H), 8.41 (s, 1H), 8.28 (s, 1H), 8.20-8.16 (m, 2H), 7.96 (d, 1H), 7.92 (d, 1H), 7.84-7.79 (m, 2H), 7.55 (d, 1H), 7.48 (d, 1H), 7.41 (dd, 1H), 6.37 (s, 1H), 2.28 (s, 3H).

LC/MS (Method 2, ESIpos): R$_t$=2.24 min, m/z=520 [M+H]$^+$.

Example 16

3-(2-Methyl-1H-imidazol-1-yl)-N-{4-methyl-3-[6-(pyridin-3-yl)-1H-imidazo[1,2-b]pyrazol-1-yl]-phenyl}-5-(pentafluoro-λ$^6$-sulphanyl)benzamide

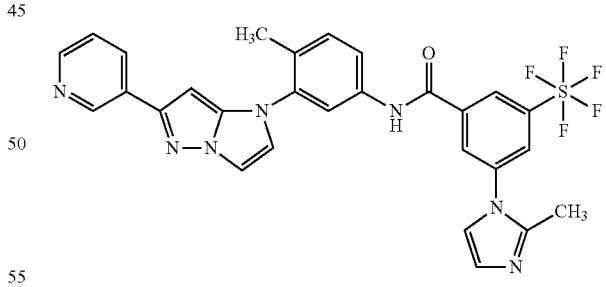

50 mg (0.17 mmol) of the compound of Example 6A, 57 mg (0.17 mmol) of the compound of Example 26A and 79 mg (0.207 mmol) of HATU were initially charged in 0.6 ml of DMF, 36 μl (0.207 mmol) of N,N-diisopropylethylamine were added and the mixture was stirred at RT for 16 h. The reaction was then stirred into 10 ml of 0.1 M aqueous sodium hydroxide solution. After a further 10 min of stirring at RT, the precipitate formed was filtered off, washed with water and dried. This gave 66 mg (62% of theory) of the title compound.

$^1$H NMR (400 MHz, DMSO-d$_6$, δ/ppm): 10.70 (s, 1H), 9.05 (s, 1H), 8.47 (m, 2H), 8.36 (s, 2H), 8.19 (d, 1H), 7.94 (m, 2H), 7.80 (d, 1H), 7.55 (d, 1H), 7.49 (m, 2H), 7.42 (m, 2H), 6.99 (s, 1H), 6.36 (s, 1H), 2.35 (s, 3H), 2.28 (s, 3H).

LC/MS (Method 1, ESIpos): $R_t$=1.86 min, m/z=600 [M+H]$^+$.

Example 17

N-{4-Methyl-3-[6-(pyridin-3-yl)-1H-imidazo[1,2-b]pyrazol-1-yl]phenyl}-3-(pentafluoro-$\lambda^6$-sulphanyl)-5-(piperazin-1-yl)benzamide

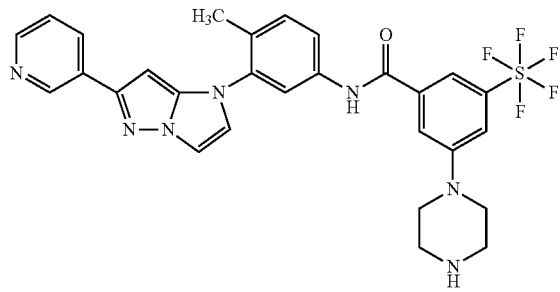 [SMILES: Cc1ccc(NC(=O)c2cc(N3CCNCC3)cc(S(F)(F)(F)(F)F)c2)cc1-n1ccn2nc(-c3cccnc3)cc12]

120 mg (0.42 mmol) of the compound of Example 6A and 179 mg (0.42 mmol) of the compound of Example 16A were reacted and worked up analogously to the procedure of Example 16. In this manner, 260 mg (89% of theory) of the Boc-protected intermediate tert-butyl 4-[3-({4-methyl-3-[6-(pyridin-3-yl)-1H-imidazo[1,2-b]pyrazol-1-yl]phenyl}carbamoyl)-5-(pentafluoro-$\lambda^6$-sulphanyl)-phenyl]piperazine-1-carboxylate were obtained. This compound was dissolved in 3 ml of 1,4-dioxane and 1 ml of methanol, 0.31 ml (1.24 mmol) of a 4 M solution of hydrogen chloride in 1,4-dioxane was added and the mixture was stirred at 80° C. for 1 h. The mixture was then concentrated under reduced pressure and the residue was purified by preparative HPLC (Method 18). The product fractions were concentrated and the residue was dissolved in ethyl acetate and washed successively with saturated potassium carbonate solution and saturated sodium chloride solution. The organic phase was dried over sodium sulphate, filtered and concentrated under reduced pressure. Drying of the residue gave 155 mg (62% of theory) of the title compound.

$^1$H NMR (400 MHz, DMSO-d$_6$, δ/ppm): 10.54 (s, 1H), 9.06 (d, 1H), 8.48 (dd, 1H), 8.19 (m, 1H), 7.92 (m, 2H), 7.78 (dd, 1H), 7.72 (s, 1H), 7.69 (s, 1H), 7.55 (d, 1H), 7.47 (m, 2H), 7.41 (dd, 1H), 6.37 (s, 1H), 3.22 (m, 4H), 2.85 (m, 4H), 2.27 (s, 3H).

LC/MS (Method 1, ESIpos): $R_t$=0.96 min, m/z=604 [M+H]$^+$.

Example 18

3-(4-Methylpiperazin-1-yl)-N-{4-methyl-3-[6-(pyridin-3-yl)-1H-imidazo[1,2-b]pyrazol-1-yl]-phenyl}-5-(pentafluoro-$\lambda^6$-sulphanyl)benzamide

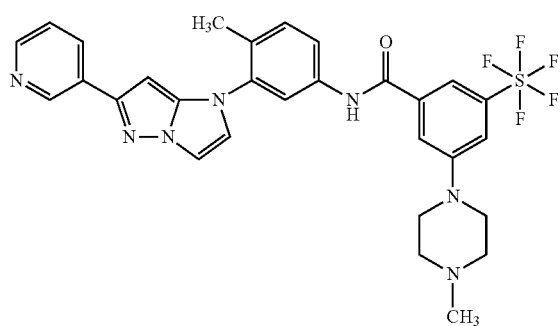 [SMILES: Cc1ccc(NC(=O)c2cc(N3CCN(C)CC3)cc(S(F)(F)(F)(F)F)c2)cc1-n1ccn2nc(-c3cccnc3)cc12]

50 mg (0.17 mmol) of the compound of Example 6A and 79.6 mg (0.17 mmol) of the compound of Example 17A were reacted and worked up analogously to the procedure of Example 16. This gave 82 mg (77% of theory) of the title compound.

$^1$H NMR (400 MHz, DMSO-d$_6$, δ/ppm): 10.55 (s, 1H), 9.06 (d, 1H), 8.48 (d, 1H), 8.19 (m, 1H), 7.93 (m, 2H), 7.79 (m, 1H), 7.73 (s, 1H), 7.71 (s, 1H), 7.50-7.47 (m, 2H), 7.41 (dd, 1H), 6.37 (s, 1H), 3.22 (m, 4H), 2.85 (m, 4H), 2.28 (s, 3H), 2.23 (s, 3H) [further signals obscured by solvent peaks].

LC/MS (Method 3, ESIpos): $R_t$=0.76 min, m/z=618 [M+H]$^+$.

Example 19

N-{4-Methyl-3-[6-(pyridin-3-yl)-1H-imidazo[1,2-b]pyrazol-1-yl]phenyl}-3-(morpholin-4-yl)-5-(pentafluoro-$\lambda^6$-sulphanyl)benzamide

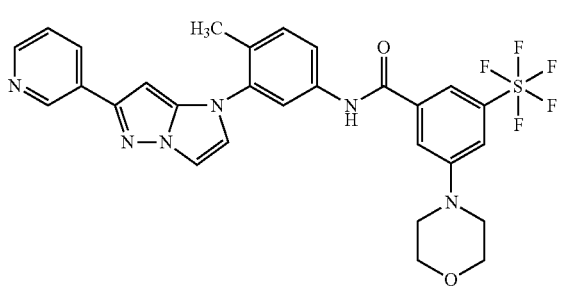 [SMILES: Cc1ccc(NC(=O)c2cc(N3CCOCC3)cc(S(F)(F)(F)(F)F)c2)cc1-n1ccn2nc(-c3cccnc3)cc12]

50 mg (0.17 mmol) of the compound of Example 6A, 58 mg (0.17 mmol) of the compound of Example 18A and 79 mg (0.21 mmol) of HATU were dissolved in 1.0 ml of DMF, 38 μl (0.35 mmol) of 4-methylmorpholine were added and the mixture was stirred at RT for 16 h. 10 ml of 0.1 M aqueous sodium hydroxide solution were then added, and the mixture was stirred at RT for another 10 min. The precipitate formed was filtered off, washed with water and dried under high vacuum. This crude product was then purified by preparative HPLC (Method 29). The product fractions were concentrated under reduced pressure and the residue was taken up in ethyl acetate and with saturated sodium bicarbonate solution. The organic phase was dried over sodium sulphate, filtered and concentrated under reduced pressure. This gave 55 mg (53% of theory) of the title compound.

$^1$H NMR (400 MHz, DMSO-d$_6$, δ/ppm): 10.56 (s, 1H), 9.05 (d, 1H), 8.48 (dd, 1H), 8.19 (dt, 1H), 7.93 (t, 2H), 7.81-7.76 (m, 2H), 7.72 (s, 1H), 7.55 (d, 1H), 7.53 (s, 1H), 7.48 (d, 1H), 7.42 (dd, 1H), 6.37 (s, 1H), 3.77 (t, 4H), 2.28 (s, 3H).

LC/MS (Method 3, ESIpos): $R_t$=1.03 min, m/z=605 [M+H]$^+$.

Example 20

3-Hydroxy-N-{4-methyl-3-[6-(pyridin-3-yl)-1H-imidazo[1,2-b]pyrazol-1-yl]phenyl}-5-(pentafluoro-$\lambda^6$-sulphanyl)benzamide

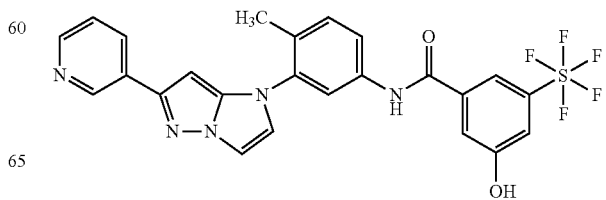

300 mg (1.04 mmol) of the compound of Example 6A, 301 mg (1.14 mmol) of the compound of Example 24A and 473 mg (1.24 mmol) of HATU were initially charged in 3.6 ml of DMF, 0.36 ml (2.07 mmol) of N,N-diisopropylethylamine was added and the mixture was stirred at RT for two days. The reaction was then directly separated into its components by preparative HPLC (Method 18). This gave 180 mg (31% of theory) of the title compound.

$^1$H NMR (400 MHz, DMSO-d$_6$, δ/ppm): 10.73 (s, 1H), 10.60 (s, 1H), 9.05 (d, 1H), 8.48 (dd, 1H), 8.19 (m, 1H), 7.95 (d, 1H), 7.92 (d, 1H), 7.86 (s, 1H), 7.79 (dd, 1H), 7.65 (s, 1H), 7.55 (d, 1H), 7.48-7.40 (m, 3H), 6.37 (s, 1H), 2.28 (s, 3H).

LC/MS (Method 3, ESIpos): R$_t$=0.92 min, m/z=536 [M+H]$^+$.

Example 21

3-Methoxy-N-{4-methyl-3-[6-(pyridin-3-yl)-1H-imidazo[1,2-b]pyrazol-1-yl]phenyl}-5-(pentafluoro-λ$^6$-sulphanyl)benzamide

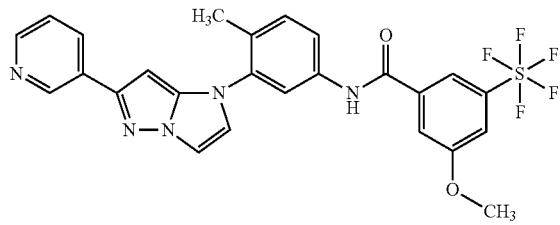 [SMILES: COc1cc(C(=O)Nc2ccc(C)c(-n3ccn4nc(-c5cccnc5)cc34)c2)cc(S(F)(F)(F)(F)F)c1]

30 mg (0.10 mmol) of the compound of Example 6A and 29 mg (0.10 mmol) of the compound of Example 25A were reacted and worked up analogously to the procedure of Example 16. This gave 32 mg (55% of theory) of the title compound.

$^1$H NMR (400 MHz, DMSO-d$_6$, δ/ppm): 10.63 (s, 1H), 9.06 (d, 1H), 8.48 (d, 1H), 8.19 (m, 1H), 8.00 (s, 1H), 7.94 (d, 1H), 7.92 (d, 1H), 7.84 (s, 1H), 7.79 (dd, 1H), 7.63 (s, 1H), 7.55 (d, 1H), 7.48 (d, 1H), 7.42 (dd, 1H), 6.37 (s, 1H), 3.94 (s, 3H), 2.28 (s, 3H).

LC/MS (Method 3, ESIpos): R$_t$=1.08 min, m/z=550 [M+H]$^+$.

Example 22

3-(2-Aminoethoxy)-N-{4-methyl-3-[6-(pyridin-3-yl)-1H-imidazo[1,2-b]pyrazol-1-yl]phenyl}-5-(pentafluoro-λ$^6$-sulphanyl)benzamide

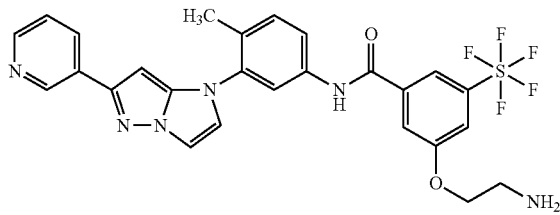 [SMILES: Cc1ccc(NC(=O)c2cc(OCCN)cc(S(F)(F)(F)(F)F)c2)cc1-n1ccn2nc(-c3cccnc3)cc12]

40 mg (0.14 mmol) of the compound of Example 6A and 62 mg (0.15 mmol) of the compound of Example 29A were reacted and worked up analogously to the procedure of Example 16. In this manner, 81 mg (86% of theory) of the Boc-protected intermediate tert-butyl {2-[3-({4-methyl-3-[6-(pyridin-3-yl)-1H-imidazo[1,2-b]pyrazol-1-yl]phenyl}carbamoyl)-5-(pentafluoro-λ$^6$-sulphanyl)phenoxy]ethyl}carbamate were obtained. This compound was stirred in 1 ml of dichloromethane and 0.5 ml of trifluoroacetic acid at RT for 2 h. The mixture was then concentrated under reduced pressure and the residue was purified by preparative HPLC (Method 18). The product-containing fractions were combined and concentrated under reduced pressure, and the residue was dissolved in ethyl acetate and washed successively with saturated potassium carbonate solution and saturated sodium chloride solution. The organic phase was dried over sodium sulphate, filtered and concentrated under reduced pressure. Drying of the residue gave 61 mg (76% of theory) of the title compound.

$^1$H NMR (400 MHz, DMSO-d$_6$, δ/ppm): 10.63 (s, 1H), 9.05 (d, 1H), 8.48 (dd, 1H), 8.19 (m, 1H), 7.99 (s, 1H), 7.95 (d, 1H), 7.92 (d, 1H), 7.84 (s, 1H), 7.79 (dd, 1H), 7.63 (t, 1H), 7.55 (d, 1H), 7.48 (d, 1H), 7.41 (dd, 1H), 6.37 (s, 1H), 4.11 (t, 2H), 2.91 (t, 2H), 2.28 (s, 3H).

LC/MS (Method 4, ESIpos): R$_t$=0.71 min, m/z=579 [M+H]$^+$.

Example 23

3-(3-Aminopropoxy)-N-{4-methyl-3-[6-(pyridin-3-yl)-1H-imidazo[1,2-b]pyrazol-1-yl]phenyl}-5-(pentafluoro-λ$^6$-sulphanyl)benzamide

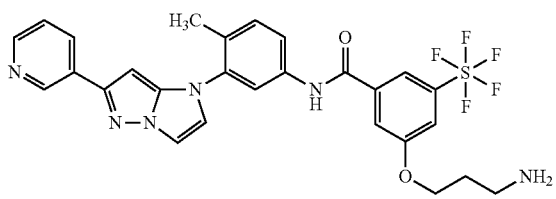 [SMILES: Cc1ccc(NC(=O)c2cc(OCCCN)cc(S(F)(F)(F)(F)F)c2)cc1-n1ccn2nc(-c3cccnc3)cc12]

50 mg (0.17 mmol) of the compound of Example 6A and 73 mg (0.17 mmol) of the compound of Example 30A were reacted and worked up analogously to the procedure of Example 16. In this manner, 118 mg (98% of theory) of the Boc-protected intermediate tert-butyl {3-[3-({4-methyl-3-[6-(pyridin-3-yl)-1H-imidazo[1,2-b]pyrazol-1-yl]phenyl}carbamoyl)-5-(pentafluoro-λ$^6$-sulphanyl)phenoxy]propyl}carbamate were obtained. This compound was dissolved in 3 ml of 1,4-dioxane and 1 ml of methanol, 0.13 ml (0.52 mmol) of a 4 M solution of hydrogen chloride in 1,4-dioxane was added and the mixture was stirred at 80° C. for 1 h. The mixture was then concentrated under reduced pressure and the residue was purified by preparative HPLC (Method 18). The product-containing fractions were combined and concentrated under reduced pressure, and the residue was dissolved in ethyl acetate and washed successively with saturated potassium carbonate solution and saturated sodium chloride solution. The organic phase was dried over sodium sulphate, filtered and concentrated under reduced pressure. Drying of the residue gave 41 mg (38% of theory) of the title compound.

$^1$H NMR (400 MHz, DMSO-d$_6$, δ/ppm): 10.61 (br, 1H), 9.05 (d, 1H), 8.48 (dd, 1H), 8.19 (m, 1H), 7.98 (s, 1H), 7.95 (d, 1H), 7.92 (d, 1H), 7.84 (s, 1H), 7.80 (dd, 1H), 7.63 (t, 1H), 7.55 (d, 1H), 7.48 (d, 1H), 7.42 (dd, 1H), 6.37 (s, 1H), 4.22 (t, 2H), 2.71 (t, 2H), 2.28 (s, 3H), 1.83 (m, 2H).

LC/MS (Method 3, ESIpos): $R_t$=0.76 min, m/z=593 [M+H]$^+$.

Example 24

3-(Azetidin-3-yloxy)-N-{4-methyl-3-[6-(pyridin-3-yl)-1H-imidazo[1,2-b]pyrazol-1-yl]phenyl}-5-(pentafluoro-$\lambda^6$-sulphanyl)benzamide

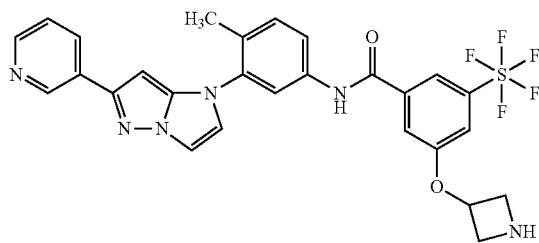 [SMILES: Cc1ccc(NC(=O)c2cc(OC3CNC3)cc(S(F)(F)(F)(F)F)c2)cc1-n1ccn2nc(-c3cccnc3)cc12]

37.6 mg (0.13 mmol) of the compound of Example 6A and 60 mg (0.14 mmol) of the compound of Example 31A were reacted analogously to the procedure of Example 16, except that here, the isolation of the intermediate, the Boc-protected compound tert-butyl 3-[3-({4-methyl-3-[6-(pyridin-3-yl)-1H-imidazo[1,2-b]pyrazol-1-yl]phenyl}carbamoyl)-5-(pentafluoro-$\lambda^6$-sulphanyl)phenoxy]azetidin-1-carboxylate, was carried out by preparative HPLC (Method 11). In this manner, 42 mg (47% of theory) of the Boc-protected intermediate were obtained. This compound was dissolved in 1 ml of methylene chloride, 0.5 ml of trifluoroacetic acid was added and the mixture was stirred at RT for 2 h. The mixture was then concentrated under reduced pressure and the residue was purified by preparative HPLC (Method 18). After concentration of the product-containing fractions, the residue was dissolved in ethyl acetate and washed successively with saturated potassium carbonate solution and saturated sodium chloride solution. The organic phase was dried over sodium sulphate, filtered and concentrated under reduced pressure. Drying of the residue gave 24 mg (90% pure, 28% of theory) of the title compound.

$^1$H NMR (400 MHz, DMSO-d$_6$, δ/ppm): 10.64 (br, 1H), 9.05 (d, 1H), 8.48 (dd, 1H), 8.19 (m, 1H), 8.01 (s, 1H), 7.94 (d, 1H), 7.92 (d, 1H), 7.79 (d, 1H), 7.67 (s, 1H), 7.55 (d, 1H), 7.47 (m, 2H), 7.42 (dd, 1H), 6.37 (s, 1H), 5.22 (quint, 1H), 3.80 (t, 2H), 3.52 (t, 1H), 2.28 (s, 3H), 1.83 (m, 1H).

LC/MS (Method 4, ESIpos): $R_t$=0.73 min, m/z=591 [M+H]$^+$.

Example 25

N-{4-Methyl-3-[6-(pyridin-3-yl)-1H-imidazo[1,2-b]pyrazol-1-yl]phenyl}-3-(pentafluoro-$\lambda^6$-sulphanyl)-5-(pyrrolidin-3-yloxy)benzamide

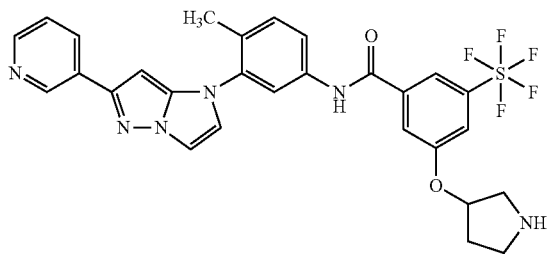 [SMILES: Cc1ccc(NC(=O)c2cc(OC3CCNC3)cc(S(F)(F)(F)(F)F)c2)cc1-n1ccn2nc(-c3cccnc3)cc12]

150 mg (0.28 mmol) of the compound of Example 20, 89 mg (0.34 mmol) of tert-butyl 3-[(methyl-sulphonyl)oxy]pyrrolidine-1-carboxylate [lit. e.g.: P. Kocalka et al., *Tetrahedron* 2006, 62 (24), 5763-5774] and 201 mg (0.62 mmol) of caesium carbonate in 3 ml of DMF were heated at 90° C. for 6 h. The reaction was then stirred into 15 ml of 0.1 M aqueous sodium hydroxide solution and the mixture was stirred at RT for another 10 min. The precipitate formed was filtered off, washed with water and dried under reduced pressure. The intermediate obtained in this manner was stirred in 3 ml of dichloromethane and 1 ml of trifluoroacetic acid at RT for 1 h. The mixture was then concentrated under reduced pressure and the residue was purified by preparative HPLC (Method 18). After concentration of the product-containing fractions, the residue was dissolved in ethyl acetate and washed successively with saturated potassium carbonate solution and saturated sodium chloride solution. The organic phase was dried over sodium sulphate, filtered and concentrated under reduced pressure. Drying of the residue gave 101 mg (90% pure, 60% of theory) of the title compound.

$^1$H NMR (400 MHz, DMSO-d$_6$, δ/ppm): 10.70 (br, 1H), 9.05 (s, 1H), 8.48 (d, 1H), 8.19 (d, 1H), 7.99 (s, 1H), 7.94 (s, 1H), 7.92 (d, 1H), 7.81 (s, 1H), 7.55 (m, 2H), 7.47 (s, 1H), 7.41 (dd, 1H), 6.37 (s, 1H), 5.09 (br, 1H), 3.07 (dd, 1H), 2.89 (m, 2H), 2.79 (m, 1H), 2.28 (s, 3H), 2.05 (m, 1H), 1.78 (m, 1H).

LC/MS (Method 3, ESIpos): $R_t$=0.76 min, m/z=605 [M+H]$^+$.

Example 26

N-{4-Methyl-3-[6-(pyridin-3-yl)-1H-imidazo[1,2-b]pyrazol-1-yl]phenyl}-3-(methylsulphonyl)-5-(pentafluoro-$\lambda^6$-sulphanyl)benzamide

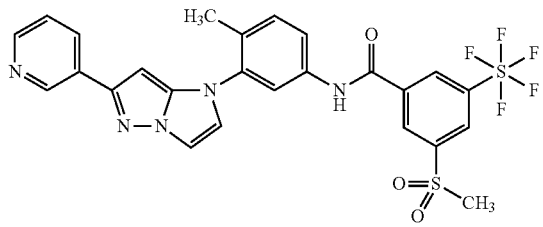 [SMILES: Cc1ccc(NC(=O)c2cc(S(C)(=O)=O)cc(S(F)(F)(F)(F)F)c2)cc1-n1ccn2nc(-c3cccnc3)cc12]

66 mg (0.228 mmol) of the compound of Example 6A and 74 mg (0.228 mmol) of the compound of Example 32A were dissolved in 1.5 ml of anhydrous DMF, and 104 mg (0.273 mmol) of HATU and 48 µl (0.273 mmol) of N,N-diisopropylethylamine were added in succession. The reaction mixture was stirred at RT for 4 h and then separated completely into its components by preparative HPLC (Method 9). The product fractions were combined and concentrated to dryness on a rotary evaporator. This gave the title compound in the form of its formic acid salt. For conversion into the salt-free form, the formate was dissolved in about 5 ml of methanol and passed over a bicarbonate cartridge (from Polymerlabs, Stratospheres SPE, PL-HCO$_3$ MP SPE, capacity 0.9 mmol). After re-evaporation, the residue was triturated with a little diisopropyl ether at RT. Filtration with suction and drying of the solid under high vacuum gave 72.6 mg (53% of theory) of the title compound.

$^1$H NMR (400 MHz, CDCl$_3$, δ/ppm): 9.73 (br. s, 1H), 8.97 (s, 1H), 8.69-8.68 (m, 2H), 8.49 (d, 1H), 8.44 (s, 1H), 8.08 (d, 1H), 7.80 (s, 1H), 7.73 (dd, 1H), 7.47 (d, 1H), 7.38 (d, 1H), 7.31 (dd, 1H), 6.95 (d, 1H), 5.94 (s, 1H), 3.12 (s, 3H), 2.31 (s, 3H).

LC/MS (Method 4, ESIpos): $R_t$=0.97 min, m/z=598 [M+H]$^+$.

Example 27

3-Chloro-N-{4-methyl-3-[6-(pyridin-3-yl)-1H-imidazo[1,2-b]pyrazol-1-yl]phenyl}-5-(pentafluoro-$\lambda^6$-sulphanyl)benzamide

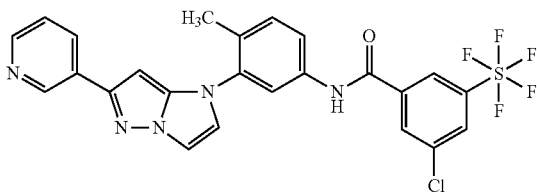 [SMILES: Cc1ccc(NC(=O)c2cc(Cl)cc(S(F)(F)(F)(F)F)c2)cc1-n1ccn2nc(-c3cccnc3)cc12]

Analogously to the process described in Example 26, 80 mg (0.276 mmol) of the compound of Example 6A and 78 mg (0.276 mmol) of the compound of Example 33A gave 101 mg (66% of theory) of the title compound.

$^1$H NMR (400 MHz, CDCl$_3$, δ/ppm): 9.00 (d, 1H), 8.85 (br. s, 1H), 8.50 (dd, 1H), 8.22 (s, 1H), 8.11 (dt, 1H), 8.08 (s, 1H), 7.91 (t, 1H), 7.81 (s, 1H), 7.63 (dd, 1H), 7.48 (d, 1H), 7.39 (d, 1H), 7.32 (dd, 1H), 6.95 (d, 1H), 5.96 (s, 1H), 2.31 (s, 3H).

LC/MS (Method 4, ESIpos): R$_t$=1.15 min, m/z=554/556 [M+H]$^+$.

Example 28

3-Cyano-N-{4-methyl-3-[6-(pyridin-3-yl)-1H-imidazo[1,2-b]pyrazol-1-yl]phenyl}-5-(pentafluoro-$\lambda^6$-sulphanyl)benzamide

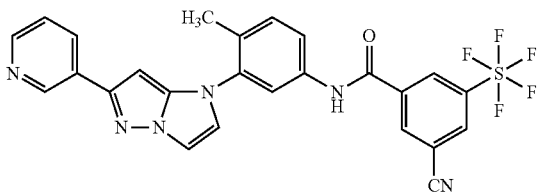 [SMILES: Cc1ccc(NC(=O)c2cc(C#N)cc(S(F)(F)(F)(F)F)c2)cc1-n1ccn2nc(-c3cccnc3)cc12]

1.00 g (3.46 mmol) of the compound of Example 6A, 944 mg (3.46 mmol) of the compound of Example 23A and 1.58 g (4.15 mmol) of HATU were dissolved in 12.1 ml of anhydrous DMF, and 0.72 ml (4.15 mmol) of N,N-diisopropylethylamine was added. The reaction mixture was stirred at RT for 1 h and then stirred into 120 ml of 0.1 M aqueous sodium hydroxide solution. After a further 10 min of stirring at RT, the precipitate formed was filtered off and dried. This crude product was then separated into its components by preparative HPLC (Method 23). The product fractions were combined and concentrated to dryness on a rotary evaporator. The product obtained was suspended in a mixture of 10 ml of acetonitrile and 10 ml of water, made alkaline with a little saturated sodium bicarbonate solution and stirred at RT for 10 min. The solid was filtered off, washed with water and dried. This gave 1.12 g (69% of theory) of the title compound.

$^1$H NMR (400 MHz, DMSO-d$_6$, δ/ppm): 10.80 (s, 1H), 9.05 (d, 1H), 8.86 (s, 1H), 8.75 (s, 1H), 8.66 (s, 1H), 8.49 (d, 1H), 8.19 (dt, 1H), 7.94 (dd, 2H), 7.79 (dd, 1H), 7.56 (d, 1H), 7.50 (d, 1H), 7.42 (dd, 1H), 6.37 (s, 1H), 2.29 (s, 3H).

LC/MS (Method 3, ESIpos): R$_t$=1.01 min, m/z=545 [M+H]$^+$.

Example 29

N-{4-Methyl-3-[6-(pyridin-3-yl)-1H-imidazo[1,2-b]pyrazol-1-yl]phenyl}-5-(pentafluoro-$\lambda^6$-sulphanyl)isophthalamide

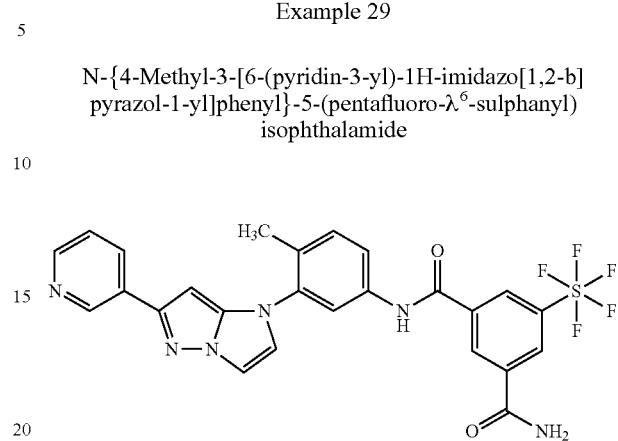

In the preparation and work-up of Example 28, the title compound was isolated as a by-product. The appropriate fractions from the HPLC separation (according to Method 23) were combined and evaporated to dryness on a rotary evaporator. The product obtained was then suspended in a mixture of 2 ml of acetonitrile and 2 ml of water, made alkaline with a little saturated sodium bicarbonate solution and stirred at RT for 10 min. The solid was filtered off, washed with water and dried. This gave 154 mg of the title compound.

$^1$H NMR (400 MHz, DMSO-d$_6$, δ/ppm): 10.80 (s, 1H), 9.05 (d, 1H), 8.77 (s, 1H), 8.55 (d, 2H), 8.48 (dd, 1H), 8.46 (br, 1H), 8.19 (dt, 1H), 7.96 (d, 1H), 7.93 (d, 1H), 7.86 (br, 1H), 7.81 (dd, 1H), 7.56 (d, 1H), 7.49 (d, 1H), 7.42 (dd, 1H), 6.37 (s, 1H), 2.28 (s, 3H).

LC/MS (Method 4, ESIpos): R$_t$=0.87 min, m/z=563 [M+H]$^+$.

Example 30

3-Methyl-N-{4-methyl-3-[6-(pyridin-3-yl)-1H-imidazo[1,2-b]pyrazol-1-yl]phenyl}-5-(pentafluoro-$\lambda^6$-sulphanyl)benzamide

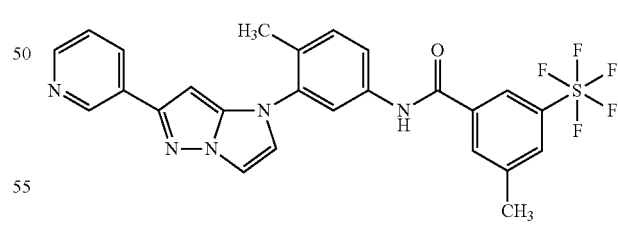

Analogously to the process described in Example 26, 80 mg (0.276 mmol) of the compound of Example 6A and 73 mg (0.276 mmol) of the compound of Example 34A gave 101 mg (61% of theory, 90% pure) of the title compound.

$^1$H NMR (400 MHz, CDCl$_3$, δ/ppm): 9.02 (d, 1H), 8.51 (br. s, 1H), 8.51 (dd, 1H), 8.13 (dt, 1H), 8.09 (s, 1H), 7.86-7.84 (m, 2H), 7.73 (s, 1H), 7.60 (dd, 1H), 7.49 (d, 1H), 7.38 (d, 1H), 7.31 (dd, 1H), 6.95 (d, 1H), 5.99 (s, 1H), 2.49 (s, 3H), 2.30 (s, 3H).

LC/MS (Method 4, ESIpos): R$_t$=1.10 min, m/z=534 [M+H]$^+$.

Example 31

3-(Hydroxymethyl)-N-{4-methyl-3-[6-(pyridin-3-yl)-1H-imidazo[1,2-b]pyrazol-1-yl]phenyl}-5-(pentafluoro-λ$^6$-sulphanyl)benzamide

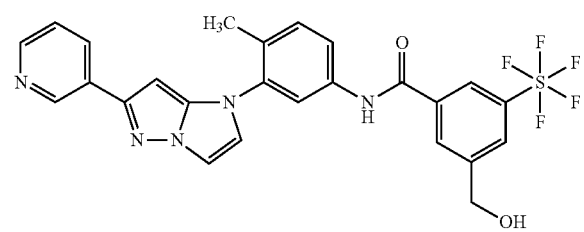 [SMILES: Cc1ccc(NC(=O)c2cc(CO)cc(S(F)(F)(F)(F)F)c2)cc1-n1ccn2nc(-c3cccnc3)cc12]

62 mg (0.21 mmol) of the compound of Example 6A and 60 mg (0.21 mmol) of the compound of Example 37A were reacted and worked up analogously to the procedure of Example 16. The product obtained in this manner was repurified by preparative HPLC (Method 15). The product-containing fractions were combined and concentrated under reduced pressure, and the residue was dissolved in ethyl acetate and washed successively with saturated potassium carbonate solution and saturated sodium chloride solution. The organic phase was dried over sodium sulphate, filtered and concentrated under reduced pressure. Drying of the residue gave 40 mg (48% of theory) of the title compound.

$^1$H NMR (400 MHz, DMSO-d$_6$, δ/ppm): 10.70 (s, 1H), 9.05 (d, 1H), 8.48 (dd, 1H), 8.29 (s, 1H), 8.22 (s, 1H), 8.19 (dt, 1H), 8.05 (s, 1H), 7.95 (d, 1H), 7.92 (d, 1H), 7.81 (dd, 1H), 7.56 (d, 1H), 7.48 (d, 1H), 7.42 (dd, 1H), 6.37 (s, 1H), 5.65 (t, 1H), 4.69 (d, 2H), 2.28 (s, 3H).

LC/MS (Method 3, ESIpos): R$_t$=0.95 min, m/z=550 [M+H]$^+$.

Example 32

3-(2-Hydroxypropan-2-yl)-N-{4-methyl-3-[6-(pyridin-3-yl)-1H-imidazo[1,2-b]pyrazol-1-yl]-phenyl}-5-(pentafluoro-λ$^6$-sulphanyl)benzamide

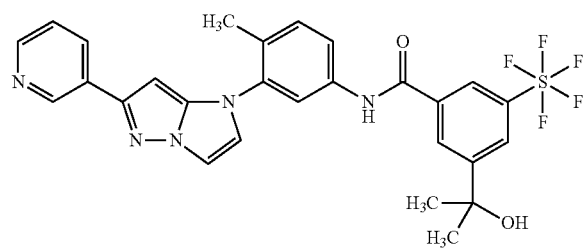 [SMILES: Cc1ccc(NC(=O)c2cc(C(C)(C)O)cc(S(F)(F)(F)(F)F)c2)cc1-n1ccn2nc(-c3cccnc3)cc12]

50 mg (0.17 mmol) of the compound of Example 6A and 52.9 mg (0.17 mmol) of the compound of Example 19A were reacted and worked up analogously to the procedure of Example 19. This gave 49 mg (49% of theory) of the title compound.

$^1$H NMR (400 MHz, DMSO-d$_6$, δ/ppm): 10.65 (s, 1H), 9.05 (d, 1H), 8.48 (dd, 1H), 8.29 (s, 1H), 8.27 (s, 1H), 8.21-8.14 (m, 2H), 7.94 (d, 1H), 7.92 (d, 1H), 7.79 (dd, 1H), 7.55 (d, 1H), 7.48 (d, 1H), 7.42 (dd, 1H), 6.37 (s, 1H), 5.54 (s, 1H), 2.28 (s, 3H), 1.51 (s, 6H).

LC/MS (Method 3, ESIpos): R$_t$=0.97 min, m/z=578 [M+H]$^+$.

Example 33

N-{4-Methyl-3-[6-(pyridin-3-yl)-1H-imidazo[1,2-b]pyrazol-1-yl]phenyl}-3-(pentafluoro-λ$^6$-sulphanyl)-5-(pyrrolidin-1-ylmethyl)benzamide

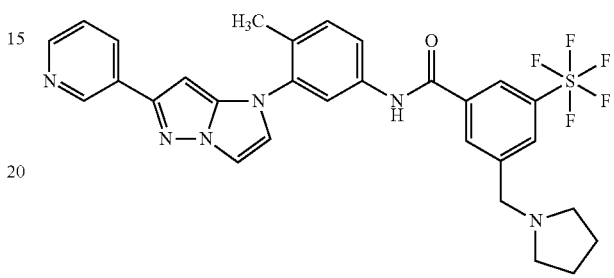

45 mg (0.16 mmol) of the compound of Example 6A and 70 mg (0.16 mmol) of the compound of Example 38A were reacted analogously to the procedure of Example 16, except that here the reaction was, after the reaction had ended, directly separated into its components by preparative HPLC (Method 15). The product-containing fractions were combined and concentrated under reduced pressure, and the residue was dissolved in ethyl acetate and washed successively with saturated potassium carbonate solution and saturated sodium chloride solution. The organic phase was dried over sodium sulphate, filtered and concentrated under reduced pressure. Drying of the residue gave 48 mg (51% of theory) of the title compound.

$^1$H NMR (400 MHz, DMSO-d$_6$, δ/ppm): 10.68 (s, 1H), 9.05 (d, 1H), 8.48 (dd, 1H), 8.32 (s, 1H), 8.21 (s, 1H), 8.19 (m, 1H), 8.03 (s, 1H), 7.95 (d, 1H), 7.93 (d, 1H), 7.80 (dd, 1H), 7.56 (d, 1H), 7.48 (d, 1H), 7.41 (dd, 1H), 6.37 (s, 1H), 3.79 (br, 2H), 2.28 (s, 3H), 1.73 (br, 4H) [further signals obscured by solvent peaks].

LC/MS (Method 4, ESIpos): R$_t$=0.80 min, m/z=603 [M+H]$^+$.

Example 34

3-{[(3S)-3-Hydroxypyrrolidin-1-yl]methyl}-N-{4-methyl-3-[6-(pyridin-3-yl)-1H-imidazo[1,2-b]-pyrazol-1-yl]phenyl}-5-(pentafluoro-λ$^6$-sulphanyl)benzamide

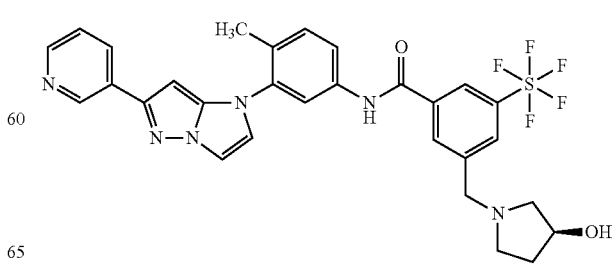

Analogously to the procedure for Example 33, 44 mg (0.15 mmol) of the compound of Example 6A and 70 mg (0.15 mmol) of the compound of Example 39A gave 38 mg (39% of theory) of the title compound.

$^1$H NMR (400 MHz, DMSO-d$_6$, δ/ppm): 10.69 (br, 1H), 9.05 (d, 1H), 8.48 (d, 1H), 8.32 (s, 1H), 8.19 (m, 2H), 8.00 (s, 1H), 7.94 (d, 1H), 7.92 (d, 1H), 7.78 (d, 1H), 7.55 (d, 1H), 7.46 (d, 1H), 7.41 (dd, 1H), 6.37 (s, 1H), 4.75 (br, 1H), 4.21 (m, 1H), 3.75 (quart, 2H), 2.70 (quart, 1H), 2.63 (quart, 1H), 2.45 (m, 1H), 2.35 (dd, 1H), 2.27 (s, 3H), 2.01 (m, 1H), 1.57 (m, 1H).

LC/MS (Method 4, ESIpos): R$_t$=0.75 min, m/z=619 [M+H]$^+$.

Example 35

N-{4-Methyl-3-[6-(pyridin-3-yl)-1H-imidazo[1,2-b]pyrazol-1-yl]phenyl}-3-(pentafluoro-λ$^6$-sulphanyl)-5-(piperazin-1-ylmethyl)benzamide

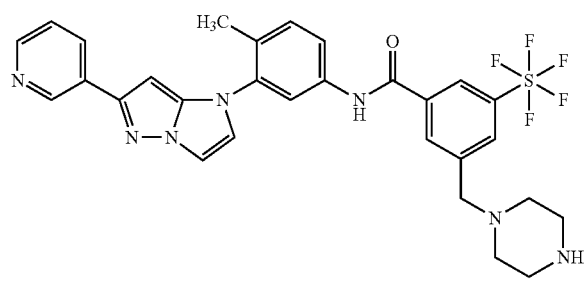 [SMILES: Cc1ccc(NC(=O)c2cc(CN3CCNCC3)cc(S(F)(F)(F)(F)F)c2)cc1-n1ccn2nc(-c3cccnc3)cc12]

90 mg (0.16 mmol) of the compound of Example 55A and 34 mg (0.18 mmol) of tert-butyl piperazine-1-carboxylate were dissolved in 3.2 ml of dichloromethane, 52 mg (0.25 mmol) of sodium triacetoxyborohydride were added and the mixture was stirred at RT for 3 h. 3 ml of water were then added, and the mixture was extracted with 6 ml of ethyl acetate. The organic phase was washed with saturated sodium chloride solution, dried over sodium sulphate, filtered and concentrated under reduced pressure. The residue was then stirred in 2 ml of dichloromethane and 1 ml of trifluoroacetic acid at RT for 2 h. The reaction was then concentrated on a rotary evaporator and the residue was separated into its components by preparative HPLC (Method 24). The product-containing fractions were combined and concentrated under reduced pressure and the residue dried under high vacuum. This gave 11 mg (11% of theory) of the title compound.

$^1$H NMR (400 MHz, DMSO-d$_6$, δ/ppm): 10.67 (s, 1H), 9.05 (d, 1H), 8.48 (dd, 1H), 8.32 (s, 1H), 8.21-8.17 (m, 2H), 8.03 (s, 1H), 7.95 (d, 1H), 7.92 (d, 1H), 7.80 (dd, 1H), 7.55 (d, 1H), 7.48 (d, 1H), 7.41 (dd, 1H), 6.37 (s, 1H), 3.63 (s, 2H), 2.71 (br, 4H), 2.34 (br, 4H), 2.28 (s, 3H).

LC/MS (Method 3, ESIneg): R$_t$=0.77 min, m/z=616 [M-H]$^-$.

Example 36

3-[(4-Methylpiperazin-1-yl)methyl]-N-{4-methyl-3-[6-(pyridin-3-yl)-1H-imidazo[1,2-b]pyrazol-1-yl]phenyl}-5-(pentafluoro-λ$^6$-sulphanyl)benzamide

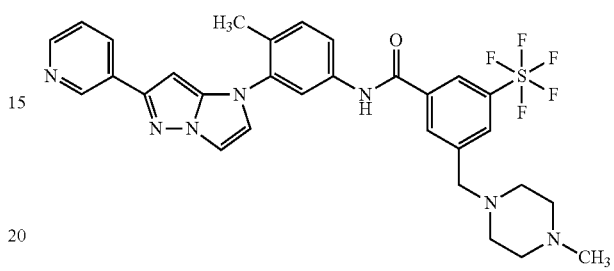

Analogously to the procedure for Example 33, 60 mg (0.18 mmol) of the compound of Example 6A and 85 mg (0.18 mmol) of the compound of Example 40A gave 73 mg (65% of theory) of the title compound.

$^1$H NMR (400 MHz, DMSO-d$_6$, δ/ppm): 10.68 (s, 1H), 9.06 (s, 1H), 8.48 (d, 1H), 8.32 (s, 1H), 8.19 (m, 2H), 8.03 (s, 1H), 7.95 (d, 1H), 7.93 (d, 1H), 7.80 (d, 1H), 7.56 (d, 1H), 7.48 (d, 1H), 7.41 (dd, 1H), 6.38 (s, 1H), 3.66 (s, 2H), 2.50-2.20 (br, 8H), 2.28 (s, 3H), 2.15 (s, 3H).

LC/MS (Method 3, ESIpos): R$_t$=0.74 min, m/z=632 [M+H]$^+$.

Example 37

3-(3-Hydroxyazetidin-3-yl)-N-{4-methyl-3-[6-(pyridin-3-yl)-1H-imidazo[1,2-b]pyrazol-1-yl]-phenyl}-5-(pentafluoro-λ$^6$-sulphanyl)benzamide bis(trifluoroacetate)

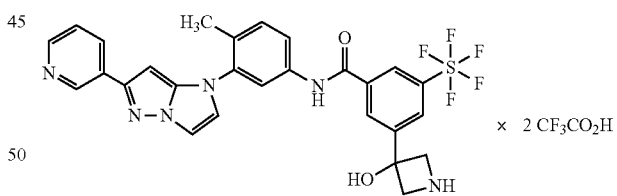

65 mg (0.09 mmol) of the compound of Example 58A were dissolved in 0.5 ml of 1,4-dioxane, 2.0 ml of a 4 M solution of hydrogen chloride in dioxane were added and the mixture was stirred at RT for 30 min. The mixture was then concentrated under reduced pressure, the residue was dissolved in a little methanol and stirred into semiconcentrated aqueous sodium bicarbonate solution and the mixture was stirred at RT for another 15 min. The solid formed was filtered off, washed with water and dried. The product obtained in this manner was re-purified by preparative HPLC (Method 30). This gave 33 mg (43% of theory) of the title compound.

$^1$H NMR (400 MHz, DMSO-d$_6$, δ/ppm): 10.77 (s, 1H), 9.29 (br. s, 1H), 9.12 (s, 1H), 8.82 (br, 1H), 8.58 (d, 1H), 8.45 (m, 2H), 8.40 (d, 1H), 8.25 (t, 1H), 7.97 (m, 2H), 7.79 (dd, 1H), 7.63-7.57 (m, 2H), 7.51 (d, 1H), 7.15 (s, 1H), 6.44 (s, 1H), 4.48 (m, 2H), 4.13 (m, 2H), 2.29 (s, 3H).

LC/MS (Method 3, ESIpos): $R_t$=0.74 min, m/z=591 [M+H]$^+$.

Example 38

3-Cyano-N-{4-methyl-3-[6-(pyridin-3-yl)-1H-imidazo[1,2-b]pyrazol-1-yl]phenyl}-5-(trifluoromethoxy)benzamide

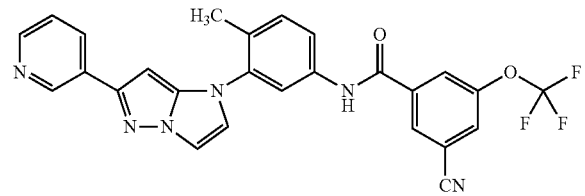 [SMILES: Cc1ccc(NC(=O)c2cc(C#N)cc(OC(F)(F)F)c2)cc1-n1ccn2nc(-c3cccnc3)cc12]

Analogously to the procedure for Example 33, 50 mg (0.17 mmol) of the compound of Example 6A and 40 mg (0.18 mmol) of the compound of Example 41A were reacted with one another. After purification of the crude product by preparative HPLC, the product-containing fractions were concentrated to a small residual volume and made alkaline with a little saturated aqueous sodium bicarbonate solution. The precipitate formed was filtered off, washed with water and dried. This gave 56 mg (65% of theory) of the title compound.

$^1$H NMR (400 MHz, DMSO-d$_6$, δ/ppm): 10.69 (s, 1H), 9.05 (d, 1H), 8.49 (m, 2H), 8.31 (s, 1H), 8.22 (s, 1H), 8.19 (dt, 1H), 7.95 (d, 1H), 7.93 (d, 1H), 7.79 (dd, 1H), 7.56 (d, 1H), 7.49 (d, 1H), 7.42 (dd, 1H), 6.37 (s, 1H), 2.28 (s, 3H).

LC/MS (Method 3, ESIpos): $R_t$=0.98 min, m/z=503 [M+H]$^+$.

Example 39

N-{4-Methyl-3-[6-(pyridin-3-yl)-1H-imidazo[1,2-b]pyrazol-1-yl]phenyl}-3-(trifluoromethyl)-benzamide

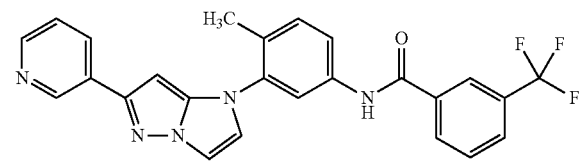 [SMILES: Cc1ccc(NC(=O)c2cccc(C(F)(F)F)c2)cc1-n1ccn2nc(-c3cccnc3)cc12]

19 mg (0.1 mmol) of 3-(trifluoromethyl)benzoic acid were initially charged in a well of a 96-well multititre plate. 27.1 mg (0.1 mmol) of the compound of Example 6A and 41.7 mg (0.13 mmol) of N-[(1H-benzotriazol-1-yloxy)(dimethylamino)methylene]-N-methylmethanaminium tetrafluoroborate (TBTU), in each case dissolved in 0.3 ml of DMF, and 26 mg (0.2 mmol) of N,N-diisopropylethylamine were added. The multititre plate was covered and shaken at RT for 18 h. The mixture was then filtered and the filtrate was purified directly by preparative LC/MS using one of the methods below:

Method A:

MS instrument: Waters, HPLC instrument: Waters; column: Phenomenex Luna 5μ C18(2) 100 A, AXIA Tech. 50 mm×21.2 mm; mobile phase A: water+0.05% formic acid, mobile phase B: methanol+0.05% formic acid, with gradient; flow rate: 40 ml/min; UV detection (DAD): 210-400 nm.

Method B:

MS instrument: Waters, HPLC instrument: Waters; column: Phenomenex Luna 5μ C18(2) 100 A, AXIA Tech. 50 mm×21.2 mm; mobile phase A: water+0.05% Triethylamine, mobile phase B: methanol+0.05% Triethylamine, with gradient; flow rate: 40 ml/min; UV detection (DAD): 210-400 nm.

The product-containing fractions were concentrated under reduced pressure using a centrifugal dryer. The residues of the individual fractions were each dissolved in 0.6 ml of DMSO and the solutions were then combined. The solvent was then evaporated completely in the centrifugal dryer. This gave 28.5 mg (62% of theory) of the title compound.

LC/MS (Method 31, ESIpos): $R_t$=1.25 min, m/z=462 [M+H]$^+$, purity 100%.

Example 40

3-(2-Methyl-1H-imidazol-1-yl)-N-{4-methyl-3-[6-(pyridin-3-yl)-1H-imidazo[1,2-b]pyrazol-1-yl]-phenyl}-5-(trifluoromethyl)benzamide

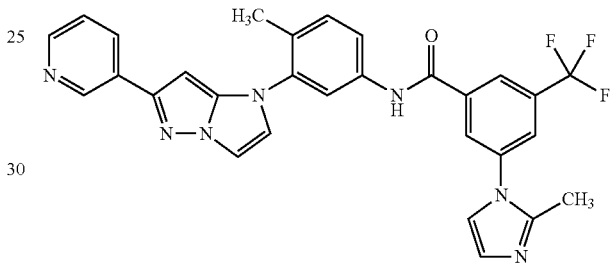

35 mg (0.12 mmol) of the compound of Example 6A and 33 mg (0.12 mmol) of 3-(2-methyl-1H-imidazol-1-yl)-5-(trifluoromethyl)benzoic acid [lit.: WO 2004/005281 A1, Example 91b] were reacted and worked up analogously to the procedure of Example 16. This gave 53 mg (81% of theory) of the title compound.

$^1$H NMR (400 MHz, DMSO-d$_6$, δ/ppm): 10.67 (s, 1H), 9.05 (d, 1H), 8.48 (d, 1H), 8.36 (s, 1H), 8.32 (s, 1H), 8.18 (m, 1H), 8.16 (s, 1H), 7.96 (d, 1H), 7.92 (d, 1H), 7.81 (d, 1H), 7.55 (d, 1H), 7.49 (m, 2H), 7.41 (dd, 1H), 6.99 (s, 1H), 6.37 (s, 1H), 2.35 (s, 3H), 2.28 (s, 3H).

LC/MS (Method 3, ESIpos): $R_t$=0.69 min, m/z=542 [M+H]$^+$.

Example 41

3-(4-Methylpiperazin-1-yl)-N-{4-methyl-3-[6-(pyridin-3-yl)-1H-imidazo[1,2-b]pyrazol-1-yl]-phenyl}-5-(trifluoromethyl)benzamide

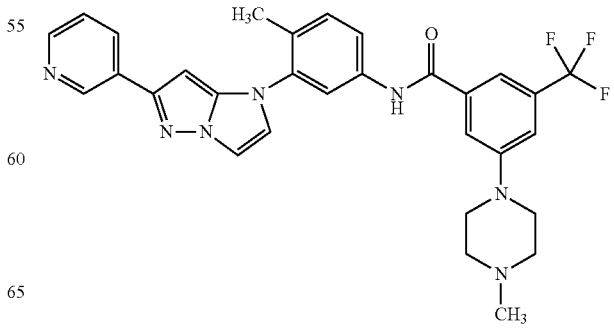

40 mg (0.14 mmol) of the compound of Example 6A and 44 mg (0.14 mmol) of 3-(4-methylpiperazin-1-yl)-5-(trifluoromethyl)benzoic acid [lit.: WO 2004/029038-A1, Example 14.2] were reacted and worked up analogously to the procedure of Example 33. This gave 43 mg (53% of theory) of the title compound.

$^1$H NMR (400 MHz, DMSO-$d_6$, δ/ppm): 10.50 (s, 1H), 9.05 (d, 1H), 8.48 (dd, 1H), 8.19 (dt, 1H), 7.94 (d, 1H), 7.92 (d, 1H), 7.80 (dd, 1H), 7.70 (s, 1H), 7.61 (s, 1H), 7.55 (d, 1H), 7.46 (d, 1H), 7.41 (dd, 1H), 7.38 (s, 1H), 6.37 (s, 1H), 2.47 (m, 4H), 2.27 (s, 3H), 2.23 (s, 3H) [further signals obscured by solvent peaks].

LC/MS (Method 4, ESIpos): $R_t$=0.70 min, m/z=560 [M+H]$^+$.

Example 42

3-{[3-(Dimethylamino)propyl](methyl)amino}-N-{4-methyl-3-[6-(pyridin-3-yl)-1H-imidazo-[1,2-b]pyrazol-1-yl]phenyl}-5-(trifluoromethyl)benzamide

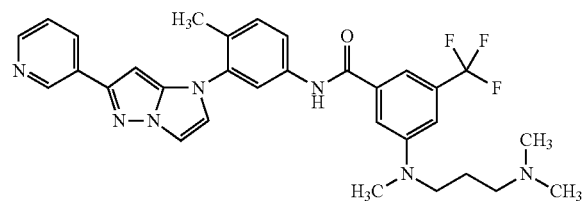 [SMILES: Cc1ccc(NC(=O)c2cc(N(C)CCCN(C)C)cc(C(F)(F)F)c2)cc1-n1ccn2nc(-c3cccnc3)cc12]

40 mg (0.14 mmol) of the compound of Example 6A and 57 mg (0.15 mmol) of the compound of Example 35A were reacted and worked up analogously to the procedure of Example 33, except that here 3 equivalents of N,N-diisopropylethylamine were used for the reaction. This gave 22 mg (90% pure, 25% of theory) of the title compound.

$^1$H NMR (400 MHz, DMSO-$d_6$, δ/ppm): 10.47 (s, 1H), 9.05 (d, 1H), 8.48 (dd, 1H), 8.19 (dt, 1H), 7.95 (d, 1H), 7.92 (d, 1H), 7.80 (dd, 1H), 7.55 (d, 1H), 7.47-7.40 (m, 4H), 7.13 (s, 1H), 6.37 (s, 1H), 3.47 (t, 2H), 3.00 (s, 3H), 2.27 (s, 3H), 2.21 (t, 2H), 2.11 (s, 6H), 1.65 (quint, 2H).

LC/MS (Method 3, ESIpos): $R_t$=0.79 min, m/z=576 [M+H]$^+$.

Example 43

N-{4-Methyl-3-[6-(pyridin-3-yl)-1H-imidazo[1,2-b]pyrazol-1-yl]phenyl}-3,5-bis(trifluoromethyl)-benzamide

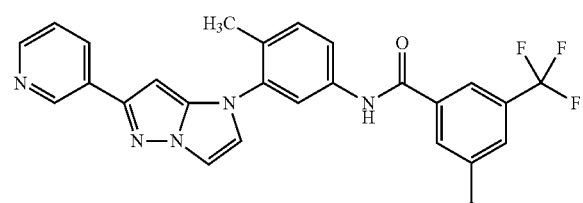

By the process described in Example 39, the compound from Example 6A and 3,5-bis(trifluoromethyl)benzoic acid gave 17.8 mg (34% of theory) of the title compound.

LC/MS (Method 31, ESIpos): $R_t$=1.36 min, m/z=530 [M+H]$^+$, purity 100%.

Example 44

3-Cyano-N-{4-methyl-3-[6-(pyridin-3-yl)-1H-imidazo[1,2-b]pyrazol-1-yl]phenyl}-5-(trifluoromethyl)benzamide

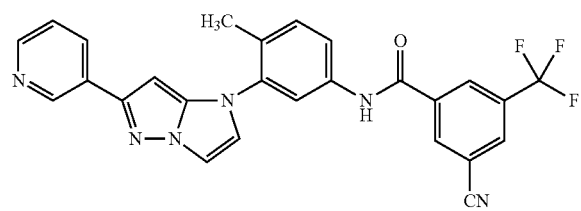 [SMILES: Cc1ccc(NC(=O)c2cc(C#N)cc(C(F)(F)F)c2)cc1-n1ccn2nc(-c3cccnc3)cc12]

Analogously to the process described in Example 26, 80 mg (0.276 mmol) of the compound of Example 6A and 60 mg (0.276 mmol) of the compound of Example 42A gave 72 mg (54% of theory) of the title compound. In this case, the reaction time was 18 h, and subsequent trituration of the product with diisopropyl ether could be dispensed with.

$^1$H NMR (400 MHz, CDCl$_3$, δ/ppm): 9.38 (br. s, 1H), 8.98 (s, 1H), 8.50-8.46 (m, 3H), 8.11 (d, 1H), 8.05 (s, 1H), 7.84 (s, 1H), 7.70 (dd, 1H), 7.48 (d, 1H), 7.40 (d, 1H), 7.32 (dd, 1H), 6.96 (d, 1H), 5.97 (s, 1H), 2.31 (s, 3H).

LC/MS (Method 3, ESIpos): $R_t$=0.99 min, m/z=487 [M+H]$^+$.

Example 45

4-Fluoro-N-{4-methyl-3-[6-(pyridin-3-yl)-1H-imidazo[1,2-b]pyrazol-1-yl]phenyl}-3-(trifluoromethyl)benzamide

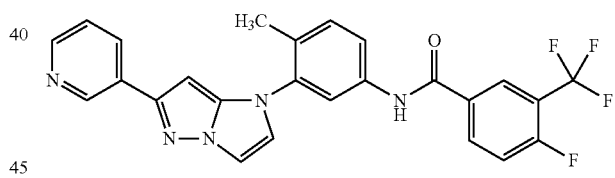

By the process described in Example 39, the compound from Example 6A and 4-fluoro-3-(trifluoromethyl)benzoic acid gave 32.2 mg (67% of theory) of the title compound.

LC/MS (Method 31, ESIpos): $R_t$=1.27 min, m/z=480 [M+H]$^+$, purity 100%.

Example 46

2-Fluoro-N-{4-methyl-3-[6-(pyridin-3-yl)-1H-imidazo[1,2-b]pyrazol-1-yl]phenyl}-3-(trifluoromethyl)benzamide

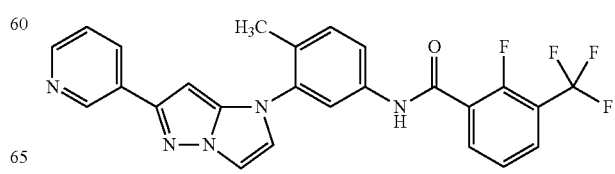

By the process described in Example 39, the compound from Example 6A and 2-fluoro-3-(trifluoromethyl)benzoic acid gave 20.6 mg (43% of theory) of the title compound.

LC/MS (Method 31, ESIpos): $R_t$=1.24 min, m/z=480 [M+H]$^+$, purity 100%.

Example 47

3-tert-Butyl-5-(2-methyl-1H-imidazol-1-yl)-N-{4-methyl-3-[6-(pyridin-3-yl)-1H-imidazo[1,2-b]-pyrazol-1-yl]phenyl}benzamide

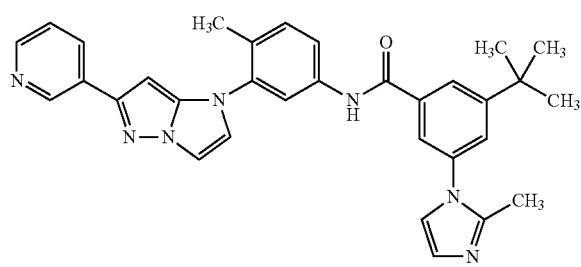 [SMILES: Cc1ccc(NC(=O)c2cc(-n3ccnc3C)cc(C(C)(C)C)c2)cc1-n1ccn2nc(-c3cccnc3)cc12]

50 mg (0.17 mmol) of the compound of Example 6A and 64 mg (0.17 mmol) of the compound of Example 27A were reacted and worked up analogously to the procedure of Example 16. This gave 65 mg (97% pure, 69% of theory) of the title compound.

$^1$H NMR (400 MHz, DMSO-d$_6$, δ/ppm): 10.48 (s, 1H), 9.05 (d, 1H), 8.48 (d, 1H), 8.19 (d, 1H), 8.00 (s, 1H), 7.96 (d, 1H), 7.92 (d, 1H), 7.84 (s, 1H), 7.80 (d, 1H), 7.69 (s, 1H), 7.55 (d, 1H), 7.47 (d, 1H), 7.41 (m, 1H), 7.40 (s, 1H), 6.95 (s, 1H), 6.37 (s, 1H), 2.32 (s, 3H), 2.27 (s, 3H), 1.37 (s, 9H).

LC/MS (Method 3, ESIpos): $R_t$=0.84 min, m/z=530 [M+H]$^+$.

Example 48

3-tert-Butyl-5-(4-methylpiperazin-1-yl)-N-{4-methyl-3-[6-(pyridin-3-yl)-1H-imidazo[1,2-b]-pyrazol-1-yl]phenyl}benzamide

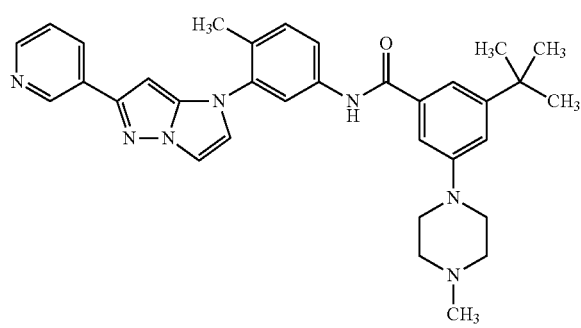 [SMILES: Cc1ccc(NC(=O)c2cc(N3CCN(C)CC3)cc(C(C)(C)C)c2)cc1-n1ccn2nc(-c3cccnc3)cc12]

35 mg (0.12 mmol) of the compound of Example 6A and 47 mg (0.12 mmol) of the compound of Example 21A were reacted and worked up analogously to the procedure of Example 16. This gave 25 mg (95% pure, 38% of theory) of the title compound.

$^1$H NMR (400 MHz, DMSO-d$_6$, δ/ppm): 10.26 (s, 1H), 9.05 (d, 1H), 8.48 (dd, 1H), 8.19 (dt, 1H), 7.94 (d, 1H), 7.91 (d, 1H), 7.79 (dd, 1H), 7.54 (d, 1H), 7.44 (d, 1H), 7.41 (m, 1H), 7.36 (s, 1H), 7.27 (s, 1H), 7.13 (s, 1H), 6.37 (s, 1H), 3.21 (t, 4H), 2.47 (t, 4H), 2.26 (s, 3H), 2.23 (s, 3H), 1.31 (s, 9H).

LC/MS (Method 4, ESIneg): $R_t$=0.72 min, m/z=546 [M−H]$^-$.

Example 49

3-tert-Butyl-5-(2-hydroxypropan-2-yl)-N-{4-methyl-3-[6-(pyridin-3-yl)-1H-imidazo[1,2-b]-pyrazol-1-yl]phenyl}benzamide

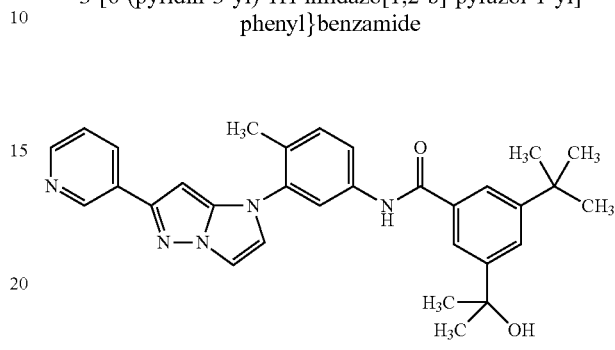

40 mg (0.14 mmol) of the compound of Example 6A and 33 mg (0.14 mmol) of the compound of Example 28A were reacted and worked up analogously to the procedure of Example 33. This gave 31 mg (44% of theory) of the title compound.

$^1$H NMR (400 MHz, DMSO-d$_6$, δ/ppm): 10.33 (s, 1H), 9.06 (d, 1H), 8.48 (dd, 1H), 8.19 (dt, 1H), 7.95 (d, 1H), 7.92 (d, 1H), 7.83-7.78 (m, 2H), 7.76 (s, 1H), 7.73 (s, 1H), 7.55 (d, 1H), 7.45 (d, 1H), 7.41 (dd, 1H), 6.37 (s, 1H), 5.14 (s, 1H), 2.27 (s, 3H), 1.47 (s, 6H), 1.34 (s, 9H).

LC/MS (Method 3, ESIpos): $R_t$=0.95 min, m/z=508 [M+H]$^+$.

Example 50

3-tert-Butyl-5-cyano-N-{4-methyl-3-[6-(pyridin-3-yl)-1H-imidazo[1,2-b]pyrazol-1-yl]phenyl}-benzamide

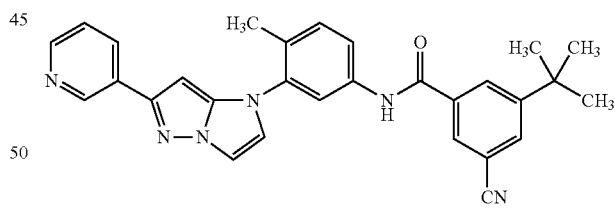

144 mg (0.38 mmol) of HATU and 81 mg (0.63 mmol) of N,N-diisopropylethylamine were added to a solution of 91 mg (0.31 mmol) of the compound of Example 6A and 173 mg (purity 37%, 0.31 mmol) of 3-tert-butyl-5-cyanobenzoic acid [lit.: WO 2008/021388 A1, intermediate E, page 164] in 2.0 ml of DMSO. The reaction was stirred at 25° C. for 16 h. The reaction mixture was then diluted with ethyl acetate and the phases were separated. The organic phase was washed twice with in each case 50 ml of saturated sodium bicarbonate solution and then dried over sodium sulphate. After filtration, the mixture was concentrated under reduced pressure and the residue obtained in this manner was purified by double chromatography on a Biotage system (first run: 25 g Snap column, mobile phase gradient ethyl acetate/hexane, starting with 20% ethyl acetate, then increasing rapidly to 100% ethyl acetate, then ethyl acetate/methanol, from 0% methanol increasing steadily to 50% methanol; second run: 10 g Snap column, mobile phase gradient ethyl acetate/hexane, starting with 20% ethyl acetate, then increasing rapidly to 100% ethyl acetate, then ethyl acetate/methanol, from 0% methanol increasing steadily to 50% methanol). This gave 17.8 mg (11% of theory) of the title compound.

$^1$H NMR (300 MHz, CDCl$_3$, δ/ppm): 9.03 (s, 1H), 8.51 (d, 1H), 8.09-8.18 (m, 3H), 7.93 (s, 1H), 7.88 (s, 1H), 7.84 (s, 1H), 7.56 (d, 1H), 7.50 (d, 1H), 7.40 (d, 1H), 7.32 (dd, 1H), 6.96 (d, 1H), 6.02 (s, 1H), 2.32 (s, 3H), 1.37 (s, 9H).

LC/MS (Method 6, ESIpos): R$_t$=1.23 min, m/z=475 [M+H]$^+$.

Example 51

3-tert-Butyl-N-{4-methyl-3-[6-(pyridin-3-yl)-1H-imidazo[1,2-b]pyrazol-1-yl]phenyl}-5-(pyrrolidin-1-ylmethyl)benzamide

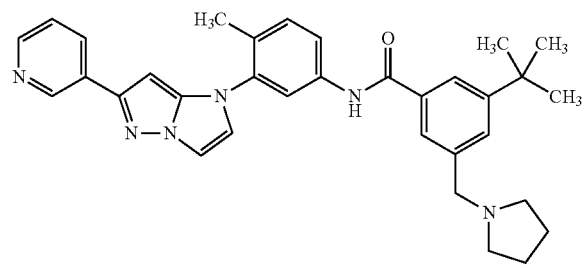 [SMILES: Cc1ccc(NC(=O)c2cc(CN3CCCC3)cc(C(C)(C)C)c2)cc1-n1ccn2nc(-c3cccnc3)cc12]

35 mg (0.12 mmol) of the compound of Example 6A and 47 mg (0.12 mmol) of the compound of Example 22A were reacted and worked up analogously to the procedure of Example 16. This gave 55 mg (95% pure, 81% of theory) of the title compound.

$^1$H NMR (400 MHz, DMSO-d$_6$, δ/ppm): 10.36 (s, 1H), 9.06 (d, 1H), 8.48 (dd, 1H), 8.19 (dt, 1H), 7.96 (d, 1H), 7.91 (d, 1H), 7.83-7.78 (m, 2H), 7.71 (s, 1H), 7.55 (d, 1H), 7.53 (s, 1H), 7.45 (d, 1H), 7.41 (dd, 1H), 6.37 (s, 1H), 3.63 (s, 2H), 2.45 (br, 4H), 2.27 (s, 3H), 1.70 (br, 4H), 1.33 (s, 9H).

LC/MS (Method 3, ESIneg): R$_t$=0.76 min, m/z=531 [M−H]$^−$.

Example 52

3,5-Dimethyl-N-{4-methyl-3-[6-(pyridin-3-yl)-1H-imidazo[1,2-b]pyrazol-1-yl]phenyl}benzamide

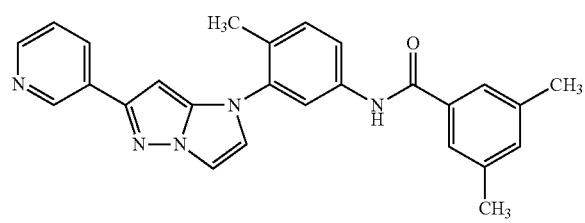 [SMILES: Cc1cc(C)cc(C(=O)Nc2ccc(C)c(-n3ccn4nc(-c5cccnc5)cc34)c2)c1]

By the process described in Example 39, the compound from Example 6A and 3,5-dimethylbenzoic acid gave 9.6 mg (22% of theory) of the title compound.

LC/MS (Method 31, ESIpos): R$_t$=1.23 min, m/z=422 [M+H]$^+$, purity 95%.

Example 53

2-Hydroxy-N-{4-methyl-3-[6-(pyridin-3-yl)-1H-imidazo[1,2-b]pyrazol-1-yl]phenyl}-5-(propan-2-yl)benzamide

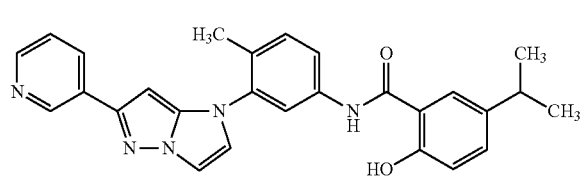 [SMILES: Cc1ccc(NC(=O)c2cc(C(C)C)ccc2O)cc1-n1ccn2nc(-c3cccnc3)cc12]

By the process described in Example 39, the compound from Example 6A and 2-hydroxy-5-isopropylbenzoic acid gave 9.2 mg (18% of theory) of the title compound.

LC/MS (Method 31, ESIpos): R$_t$=1.32 min, m/z=452 [M+H]$^+$, purity 89%.

Example 54

3'-Cyano-N-{4-methyl-3-[6-(pyridin-3-yl)-1H-imidazo[1,2-b]pyrazol-1-yl]phenyl}biphenyl-3-carboxamide

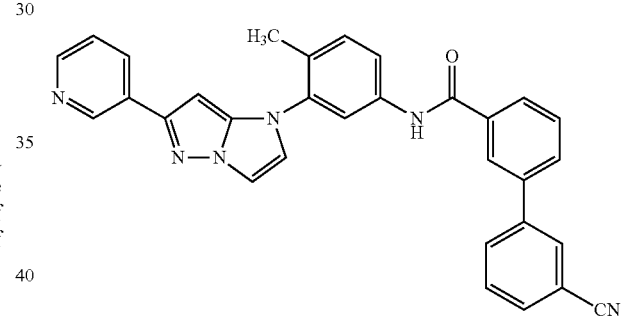

By the process described in Example 39, the compound from Example 6A and 3'-cyanobiphenyl-3-carboxylic acid gave 9.1 mg (18% of theory) of the title compound.

LC/MS (Method 31, ESIpos): R$_t$=1.28 min, m/z=495 [M+H]$^+$, purity 100%.

Example 55

N-{4-Methyl-3-[6-(pyridin-3-yl)-1H-imidazo[1,2-b]pyrazol-1-yl]phenyl}-3-(1H-pyrazol-1-yl)-benzamide

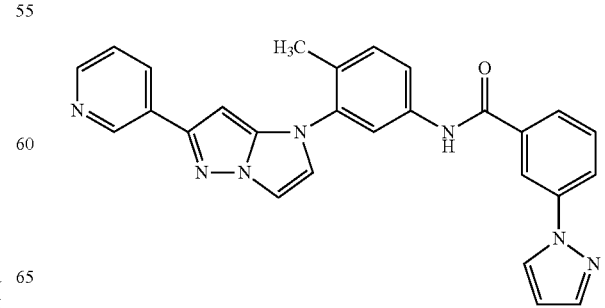

By the process described in Example 39, the compound from Example 6A and 3-(1H-pyrazol-1-yl)benzoic acid gave 31.7 mg (69% of theory) of the title compound.

LC/MS (Method 31, ESIpos): $R_t$=1.14 min, m/z=460 [M+H]$^+$, purity 100%.

Example 56

N-{4-Methyl-3-[6-(pyridin-3-yl)-1H-imidazo[1,2-b]pyrazol-1-yl]phenyl}-3-(pyrrolidin-1-yl)-benzamide

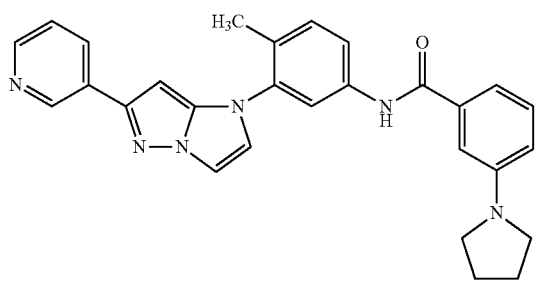 [SMILES: Cc1ccc(NC(=O)c2cccc(N3CCCC3)c2)cc1-n1ccn2nc(-c3cccnc3)cc12]

By the process described in Example 39, the compound from Example 6A and 3-(pyrrolidin-1-yl)-benzoic acid gave 26.3 mg (57% of theory) of the title compound.

LC/MS (Method 31, ESIpos): $R_t$=1.26 min, m/z=463 [M+H]$^+$, purity 100%.

Example 57

2-Chloro-N-{4-methyl-3-[6-(pyridin-3-yl)-1H-imidazo[1,2-b]pyrazol-1-yl]phenyl}-5-(pyrrolidin-1-yl)benzamide

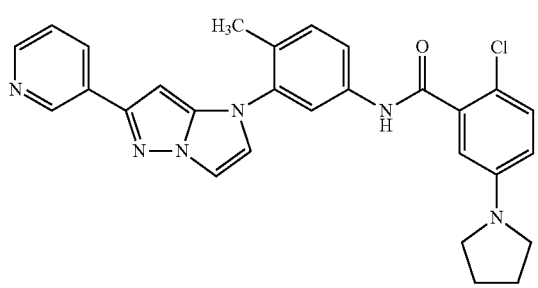 [SMILES: Cc1ccc(NC(=O)c2cc(N3CCCC3)ccc2Cl)cc1-n1ccn2nc(-c3cccnc3)cc12]

By the process described in Example 39, the compound from Example 6A and 2-chloro-5-(pyrrolidin-1-yl)benzoic acid gave 15.2 mg (31% of theory) of the title compound.

LC/MS (Method 31, ESIpos): $R_t$=1.28 min, m/z=497 [M+H]$^+$, purity 100%.

Example 58

4-Chloro-N-{4-methyl-3-[6-(pyridin-3-yl)-1H-imidazo[1,2-b]pyrazol-1-yl]phenyl}-3-(piperidin-1-yl)benzamide

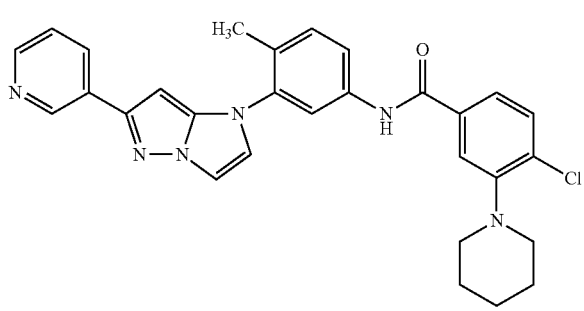 [SMILES: Cc1ccc(NC(=O)c2ccc(Cl)c(N3CCCCC3)c2)cc1-n1ccn2nc(-c3cccnc3)cc12]

By the process described in Example 39, the compound from Example 6A and 4-chloro-3-(piperidin-1-yl)benzoic acid gave 23.2 mg (45% of theory) of the title compound.

LC/MS (Method 31, ESIpos): $R_t$=1.39 min, m/z=511 [M+H]$^+$, purity 100%.

Example 59

3-(Dimethylamino)-N-{4-methyl-3-[6-(pyridin-3-yl)-1H-imidazo[1,2-b]pyrazol-1-yl]phenyl}-benzamide

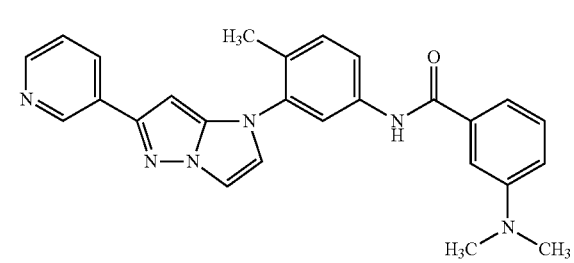 [SMILES: Cc1ccc(NC(=O)c2cccc(N(C)C)c2)cc1-n1ccn2nc(-c3cccnc3)cc12]

By the process described in Example 39, the compound from Example 6A and 3-(dimethylamino)benzoic acid gave 26.1 mg (60% of theory) of the title compound.

LC/MS (Method 31, ESIpos): $R_t$=1.14 min, m/z=437 [M+H]$^+$, purity 100%.

Example 60

N-{4-Methyl-3-[6-(pyridin-3-yl)-1H-imidazo[1,2-b]pyrazol-1-yl]phenyl}-3-(propan-2-yloxy)-benzamide

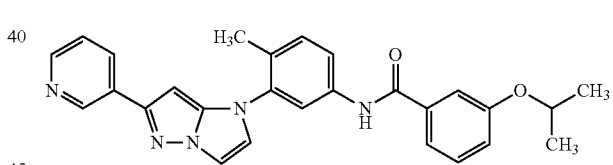

By the process described in Example 39, the compound from Example 6A and 3-isopropoxybenzoic acid gave 41.2 mg (69% of theory) of the title compound.

LC/MS (Method 31, ESIpos): $R_t$=1.23 min, m/z=452 [M+H]$^+$, purity 76%.

Example 61

N-{4-Methyl-3-[6-(pyridin-3-yl)-1H-imidazo[1,2-b]pyrazol-1-yl]phenyl}-3-propoxybenzamide

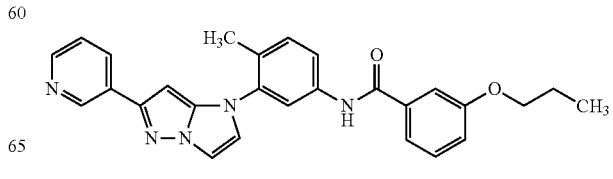

By the process described in Example 39, the compound from Example 6A and 3-propoxybenzoic acid gave 40.3 mg (67% of theory) of the title compound.

LC/MS (Method 31, ESIpos): $R_t$=1.26 min, m/z=452 [M+H]$^+$, purity 75%.

Example 62

3-(2-Methylpropoxy)-N-{4-methyl-3-[6-(pyridin-3-yl)-1H-imidazo[1,2-b]pyrazol-1-yl]phenyl}-benzamide

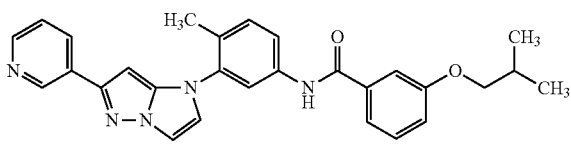 [SMILES: Cc1ccc(NC(=O)c2cccc(OCC(C)C)c2)cc1-n1ccn2nc(-c3cccnc3)cc12]

By the process described in Example 39, the compound from Example 6A and 3-isobutoxybenzoic acid gave 26.9 mg (58% of theory) of the title compound.

LC/MS (Method 31, ESIpos): $R_t$=1.32 min, m/z=466 [M+H]$^+$, purity 100%.

Example 63

3,5-Dimethoxy-N-{4-methyl-3-[6-(pyridin-3-yl)-1H-imidazo[1,2-b]pyrazol-1-yl]phenyl}benzamide

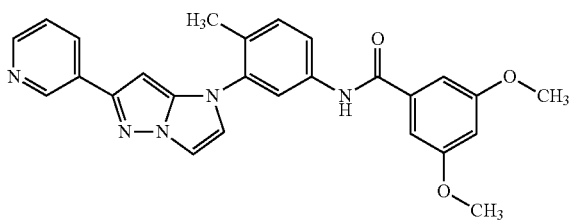 [SMILES: COc1cc(OC)cc(C(=O)Nc2ccc(C)c(-n3ccn4nc(-c5cccnc5)cc34)c2)c1]

By the process described in Example 39, the compound from Example 6A and 3,5-dimethoxybenzoic acid gave 18.3 mg (40% of theory) of the title compound.

LC/MS (Method 31, ESIpos): $R_t$=1.17 min, m/z=454 [M+H]$^+$, purity 100%.

Example 64

2-tert-Butyl-N-{4-methyl-3-[6-(pyridin-3-yl)-1H-imidazo[1,2-b]pyrazol-1-yl]phenyl}isonicotinamide

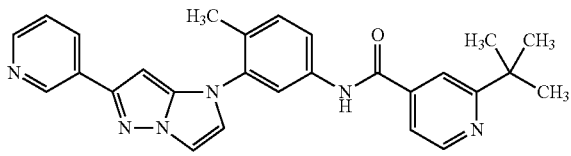 [SMILES: Cc1ccc(NC(=O)c2ccnc(C(C)(C)C)c2)cc1-n1ccn2nc(-c3cccnc3)cc12]

60 mg (0.21 mmol) of the compound of Example 6A and 37 mg (0.21 mmol) of 2-tert-butyliso-nicotinic acid were reacted and worked up analogously to the procedure of Example 33, except that in this case the reaction time was 16 h. This gave 13 mg (96% pure, 13% of theory) of the title compound.

$^1$H NMR (400 MHz, DMSO-d$_6$, δ/ppm): 10.63 (br, 1H), 9.05 (d, 1H), 8.69 (d, 1H), 8.48 (d, 1H), 8.19 (d, 1H), 7.95 (s, 1H), 7.91 (d, 1H), 7.86 (s, 1H), 7.76 (d, 1H), 7.68 (d, 1H), 7.54 (d, 1H), 7.44 (d, 1H), 7.41 (m, 1H), 6.36 (s, 1H), 2.27 (s, 3H), 1.36 (s, 9H).

LC/MS (Method 4, ESIneg): $R_t$=0.92 min, m/z=449 [M–H]$^-$.

Example 65

2-tert-Butyl-6-chloro-N-{4-methyl-3-[6-(pyridin-3-yl)-1H-imidazo[1,2-b]pyrazol-1-yl]phenyl}isonicotinamide

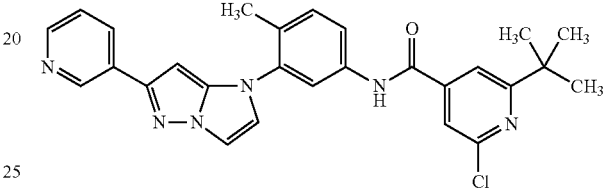

50 mg (0.17 mmol) of the compound of Example 6A and 37 mg (0.17 mmol) of the compound of Example 43A were reacted analogously to the procedure of Example 15, except that here only 6 ml of 0.1 M aqueous sodium hydroxide solution (instead of 15 ml) were used for work-up. The product obtained was re-purified by preparative HPLC (column: Reprosil-Pur C18, 10 µm, 250 mm×30 mm; mobile phase: methanol/water with 0.05% TFA, with gradient). The product-containing fractions were combined and concentrated under reduced pressure, and the residue was dissolved in ethyl acetate and washed successively with saturated potassium carbonate solution and saturated sodium chloride solution. The organic phase was dried over sodium sulphate, filtered and concentrated under reduced pressure. Drying of the residue gave 44 mg (97% pure, 51% of theory) of the title compound.

$^1$H NMR (400 MHz, DMSO-d$_6$, δ/ppm): 10.68 (br, 1H), 9.05 (d, 1H), 8.48 (d, 1H), 8.19 (d, 1H), 7.93 (m, 2H), 7.84 (s, 1H), 7.82 (s, 1H), 7.78 (dd, 1H), 7.55 (d, 1H), 7.49 (d, 1H), 7.42 (dd, 1H), 6.37 (s, 1H), 2.28 (s, 3H), 1.35 (s, 9H).

LC/MS (Method 4, ESIpos): $R_t$=1.15 min, m/z=485 [M+H]$^+$.

Example 66

2-tert-Butyl-6-(methylamino)-N-{4-methyl-3-[6-(pyridin-3-yl)-1H-imidazo[1,2-b]pyrazol-1-yl]-phenyl}isonicotinamide

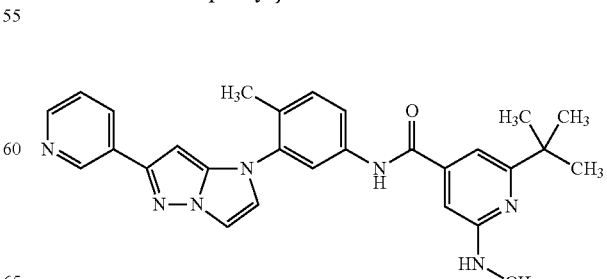

60 mg (0.21 mmol) of the compound of Example 6A and 43 mg (0.21 mmol) of the compound of Example 44A were reacted analogously to the procedure of Example 33, except that in this case the reaction time was 16 h. This gave 31 mg (31% of theory) of the title compound.

$^1$H NMR (400 MHz, DMSO-d$_6$, δ/ppm): 10.40 (s, 1H), 9.05 (d, 1H), 8.48 (dd, 1H), 8.19 (dt, 1H), 7.93 (d, 1H), 7.91 (d, 1H), 7.77 (dd, 1H), 7.54 (d, 1H), 7.45 (d, 1H), 7.41 (dd, 1H), 6.89 (s, 1H), 6.67 (s, 1H), 6.60 (quart, 1H), 6.37 (s, 1H), 2.82 (d, 3H), 2.27 (s, 3H), 1.30 (s, 9H).

LC/MS (Method 3, ESIneg): R$_t$=0.78 min, m/z=478 [M−H]$^−$.

Example 67

N-{4-Methyl-3-[6-(pyridin-3-yl)-1H-imidazo[1,2-b] pyrazol-1-yl]phenyl}-2-(pyrrolidin-1-yl)-pyridine-4-carboxamide

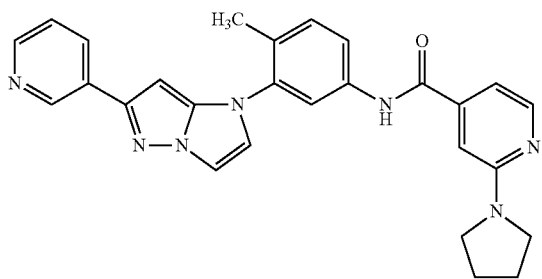 [SMILES: Cc1ccc(NC(=O)c2ccnc(N3CCCC3)c2)cc1-n1ccn2nc(-c3cccnc3)cc12]

By the process described in Example 39, the compound from Example 6A and 2-(pyrrolidin-1-yl)-pyridine-4-carboxylic acid gave 8.6 mg (19% of theory) of the title compound.

LC/MS (Method 31, ESIpos): R$_t$=0.82 min, m/z=462 [M+H]$^+$, purity 100%.

Example 68

N-{4-Methyl-3-[6-(pyridin-3-yl)-1H-imidazo[1,2-b] pyrazol-1-yl]phenyl}-2-(piperidin-1-yl)-pyridine-4-carboxamide

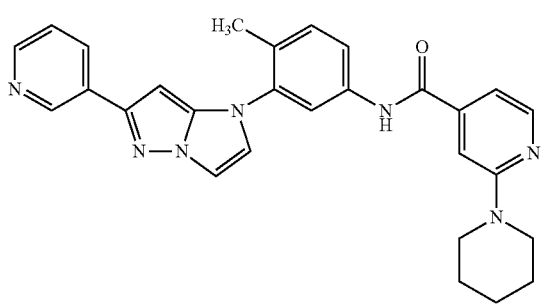 [SMILES: Cc1ccc(NC(=O)c2ccnc(N3CCCCC3)c2)cc1-n1ccn2nc(-c3cccnc3)cc12]

By the process described in Example 39, the compound from Example 6A and 2-(piperidin-1-yl)-pyridine-4-carboxylic acid gave 30.0 mg (63% of theory) of the title compound.

LC/MS (Method 31, ESIpos): R$_t$=0.98 min, m/z=478 [M+H]$^+$, purity 100%.

Example 69

N-{4-Methyl-3-[6-(pyridin-3-yl)-1H-imidazo[1,2-b] pyrazol-1-yl]phenyl}-2-(morpholin-4-yl)-pyridine-4-carboxamide

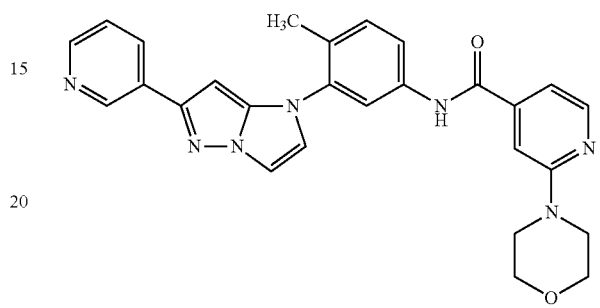

By the process described in Example 39, the compound from Example 6A and 2-(morpholin-4-yl)-pyridine-4-carboxylic acid gave 10.9 mg (23% of theory) of the title compound.

LC/MS (Method 31, ESIneg): R$_t$=1.01 min, m/z=478 [M−H]$^−$, purity 100%.

Example 70

N-{4-Fluoro-5-[6-(pyridin-3-yl)-1H-imidazo[1,2-b] pyrazol-1-yl]phenyl}-3-(pentafluoro-λ$^6$-sulphanyl) benzamide

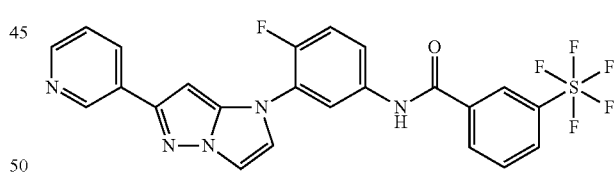

Analogously to the procedure of Example 50, 70 mg (0.24 mmol) of the compound of Example 13A and 59 mg (0.24 mmol) of 3-(pentafluoro-λ$^6$-sulphanyl)benzoic acid gave a crude product which, in deviation from Example 50, was, after the first purification run on a Biotage system, purified further by preparative thick-layer chromatography (mobile phase ethyl acetate/methanol 9:1). This gave 39 mg (27% of theory) of the title compound.

$^1$H NMR (300 MHz, CDCl$_3$, δ/ppm): 9.09 (d, 1H), 8.53 (dd, 1H), 8.37 (s, 1H), 8.32 (t, 1H), 8.24 (dd, 1H), 8.15 (dt, 1H), 8.07 (d, 1H), 7.97 (dd, 1H), 7.64 (t, 1H), 7.51 (d, 1H), 7.40-7.46 (m, 1H), 7.30-7.36 (m, 2H), 7.28 (t, 1H), 6.34 (s, 1H).

Example 71

3-Cyano-N-{4-fluoro-5-[6-(pyridin-3-yl)-1H-imidazo[1,2-b]pyrazol-1-yl]phenyl}-3-(pentafluoro-λ⁶-sulphanyl)benzamide

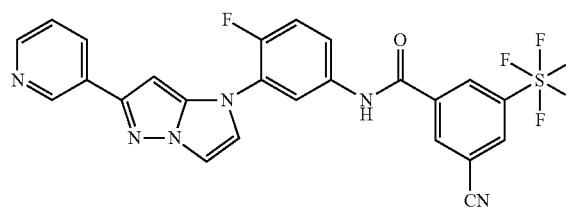

Analogously to the procedure of Example 50, 80 mg (0.27 mmol) of the compound of Example 13A and 74 mg (0.27 mmol) of the compound of Example 23A gave a crude product which, in deviation from Example 50, was, in the second run, also purified on the Biotage system using a 25 g Snap column (instead of 10 g). This gave 38 mg (25% of theory) of the title compound.

¹H NMR (300 MHz, DMSO-$d_6$, δ/ppm): 10.85 (s, 1H), 9.03 (d, 1H), 8.84 (t, 1H), 8.72 (s, 1H), 8.64 (t, 1H), 8.48 (dd, 1H), 8.13-8.21 (m, 2H), 7.96 (d, 1H), 7.74 (ddd, 1H), 7.63 (t, 1H), 7.56 (dd, 1H), 7.41 (dd, 1H), 6.54 (s, 1H).

LC/MS (Method 5, ESIpos): $R_t$=1.17 min, m/z=549 [M+H]⁺.

Example 72

N-{4-Methoxy-3-[6-(pyridin-3-yl)-1H-imidazo[1,2-b]pyrazol-1-yl]phenyl}-3-(pentafluoro-λ⁶-sulphanyl)benzamide

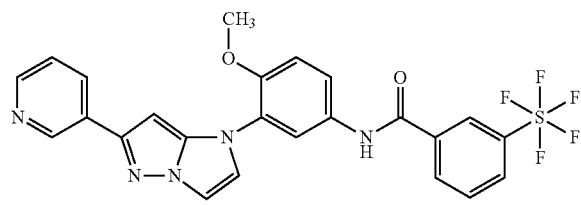 [SMILES: COc1ccc(NC(=O)c2cccc(S(F)(F)(F)(F)F)c2)cc1-n1ccn2nc(-c3cccnc3)cc12]

45 mg (0.15 mmol) of the compound of Example 10A and 37 mg (0.15 mmol) of 3-(pentafluoro-λ⁶-sulphanyl)benzoic acid were reacted and worked up analogously to the procedure of Example 16. This gave 72 mg (91% of theory) of the title compound.

¹H NMR (400 MHz, DMSO-$d_6$, δ/ppm): 10.63 (s, 1H), 9.05 (d, 1H), 8.49 (dd, 1H), 8.42 (s, 1H), 8.29 (d, 1H), 8.21-8.14 (m, 2H), 8.03 (d, 1H), 7.88 (d, 1H), 7.85-7.77 (m, 2H), 7.57 (d, 1H), 7.43 (dd, 1H), 7.34 (d, 1H), 6.43 (s, 1H), 3.91 (s, 3H).

LC/MS (Method 5, ESIpos): $R_t$=1.17 min, m/z=524 [M+H]⁺.

Example 73

N-{2,4-Dimethyl-5-[6-(pyridin-3-yl)-1H-imidazo[1,2-b]pyrazol-1-yl]phenyl}-3-(pentafluoro-λ⁶-sulphanyl)benzamide

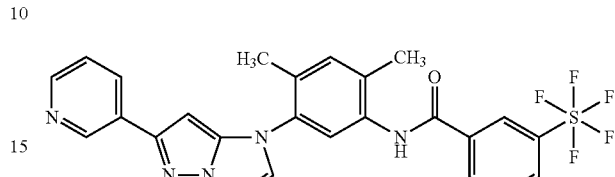

45 mg (87% pure, 0.13 mmol) of the compound of Example 11A and 32 mg (0.153 mmol) of 3-(pentafluoro-λ⁶-sulphanyl)benzoic acid were reacted and worked up analogously to the procedure of Example 38. This gave 36 mg (96% pure, 50% of theory) of the title compound.

¹H NMR (400 MHz, DMSO-$d_6$, δ/ppm): 10.32 (s, 1H), 9.04 (s, 1H), 8.48 (d, 1H), 8.42 (s, 1H), 8.29 (d, 1H), 8.17 (m, 2H), 7.90 (d, 1H), 7.81 (t, 1H), 7.51 (s, 1H), 7.49 (d, 1H), 7.43-7.37 (m, 2H), 6.31 (s, 1H), 2.30 (s, 3H), 2.26 (s, 3H).

LC/MS (Method 3, ESIpos): $R_t$=1.03 min, m/z=534 [M+H]⁺.

Example 74

3-Cyano-N-{2,4-dimethyl-5-[6-(pyridin-3-yl)-1H-imidazo[1,2-b]pyrazol-1-yl]phenyl}-5-(pentafluoro-λ⁶-sulphanyl)benzamide

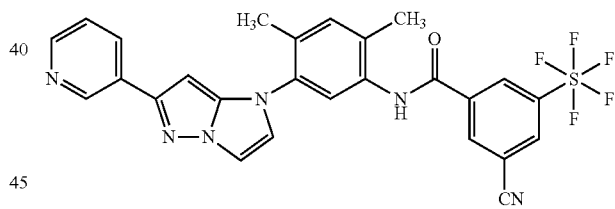

Variant A:

60 mg (87% pure, 0.17 mmol) of the compound of Example 11A and 55 mg (85% pure, 0.17 mmol) of the compound of Example 23A were reacted and worked up analogously to the procedure of Example 38. This gave 38 mg (40% of theory) of the title compound.

¹H NMR (400 MHz, DMSO-$d_6$, δ/ppm): 10.42 (s, 1H), 9.04 (d, 1H), 8.86 (s, 1H), 8.74 (s, 1H), 8.66 (s, 1H), 8.50 (dd, 1H), 8.17 (dt, 1H), 7.90 (d, 1H), 7.53 (s, 1H), 7.49 (d, 1H), 7.43-7.38 (m, 2H), 6.31 (s, 1H), 2.31 (s, 3H), 2.26 (s, 3H).

LC/MS (Method 3, ESIpos): $R_t$=1.00 min, m/z=559 [M+H]⁺.

Variant B:

5.75 g (18.9 mmol) of the compound of Example 11A and 5.18 g (18.9 mmol) of the compound of Example 23A were dissolved in 30 ml of DMF, and 8.65 g (22.7 mmol) of HATU and 6.6 ml (37.9 mmol) of N,N-diisopropylethylamine were added in succession. After 4 h of stirring at RT, the reaction mixture was stirred into about 120 ml of cold, saturated aqueous sodium bicarbonate solution. The mixture was then extracted three times with in each case about 100 ml of ethyl acetate. The combined organic extracts were dried over magnesium sulphate, filtered and concentrated under reduced pressure. The residue obtained was purified by MPLC (350 g of silica gel, mobile phase dichloromethane/methanol 100:1→50:1). Evaporation of the product fractions gave a product of a purity of about 95%. Further purification was achieved by recrystallization from a solvent mixture consisting of 100 ml of isopropanol and 80 ml of water. Filtration at RT and drying of the solid under high vacuum gave 9.01 g (84% of theory) of the title compound.

$^1$H NMR (400 MHz, DMSO-$d_6$, δ/ppm): 10.42 (s, 1H), 9.04 (d, 1H), 8.86 (s, 1H), 8.74 (s, 1H), 8.66 (s, 1H), 8.48 (dd, 1H), 8.17 (dt, 1H), 7.90 (d, 1H), 7.53 (s, 1H), 7.49 (d, 1H), 7.42 (dd, 1H), 7.40 (s, 1H), 6.31 (s, 1H), 2.31 (s, 3H), 2.26 (s, 3H).

LC/MS (Method 3, ESIpos): $R_t$=1.06 min, m/z=559 [M+H]$^+$.

Example 75

3-Cyano-N-{2-fluoro-4-methyl-5-[6-(pyridin-3-yl)-1H-imidazo[1,2-b]pyrazol-1-yl]phenyl}-5-(pentafluoro-λ$^6$-sulphanyl)benzamide

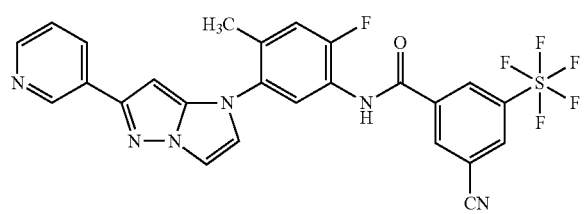 [SMILES: Cc1cc(F)c(NC(=O)c2cc(C#N)cc(S(F)(F)(F)(F)F)c2)cc1-n1ccn2nc(-c3cccnc3)cc12]

55 mg (0.18 mmol) of the compound of Example 12A and 58 mg (85% pure, 0.18 mmol) of the compound of Example 23A were reacted and worked up analogously to the procedure of Example 38. This gave 43 mg (42% of theory) of the title compound.

$^1$H NMR (400 MHz, DMSO-$d_6$, δ/ppm): 10.77 (s, 1H), 9.04 (d, 1H), 8.87 (s, 1H), 8.72 (s, 1H), 8.67 (s, 1H), 8.48 (dd, 1H), 8.18 (dt, 1H), 7.92 (d, 1H), 7.84 (d, 1H), 7.54-7.50 (m, 2H), 7.42 (d, 1H), 6.35 (s, 1H), 2.29 (s, 3H).

LC/MS (Method 3, ESIpos): $R_t$=0.98 min, m/z=563 [M+H]$^+$.

Example 76

N-{2-Methyl-5-[6-(pyridin-3-yl)-1H-imidazo[1,2-b]pyrazol-1-yl]phenyl}-3-(pentafluoro-λ$^6$-sulphanyl)benzamide

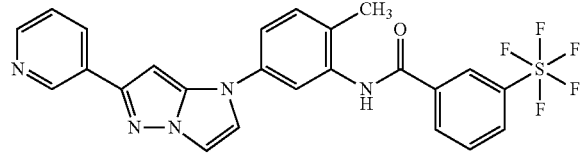 [SMILES: Cc1ccc(-n2ccn3nc(-c4cccnc4)cc23)cc1NC(=O)c1cccc(S(F)(F)(F)(F)F)c1]

Analogously to the procedure of Example 50, 100 mg (0.35 mmol) of the compound of Example 14A and 86 mg (0.35 mmol) of 3-(pentafluoro-λ$^6$-sulphanyl)benzoic acid gave a crude product which, in deviation from Example 50, was, after the first purification run on the Biotage system, purified further initially by preparative thick-layer chromatography (mobile phase ethyl acetate/methanol 95:5) and then by preparative HPLC (Method 15). The 7 mg of product obtained in this manner were dissolved in a little ethyl acetate and washed successively with 15 ml of saturated sodium bicarbonate solution and saturated sodium chloride solution. The organic phase was dried over sodium sulphate and, after filtration, concentrated under reduced pressure. This gave 5.6 mg (2.6% of theory) of the title compound.

$^1$H NMR (300 MHz, CDCl$_3$, δ/ppm): 9.11 (br. s, 1H), 8.54 (d, 1H), 8.40 (d, 1H), 8.35 (s, 1H), 8.19 (d, 1H), 8.04 (d, 1H), 7.99 (dd, 1H), 7.85 (s, 1H), 7.67 (t, 1H), 7.51 (d, 1H), 7.30-7.43 (m, 4H), 6.47 (s, 1H), 2.41 (s, 3H).

LC/MS (Method 5, ESIpos): $R_t$=1.15 min, m/z=520 [M+H]$^+$.

Example 77

3-Cyano-N-{2-methyl-5-[6-(pyridin-3-yl)-1H-imidazo[1,2-b]pyrazol-1-yl]phenyl}-3-(pentafluoro-λ$^6$-sulphanyl)benzamide

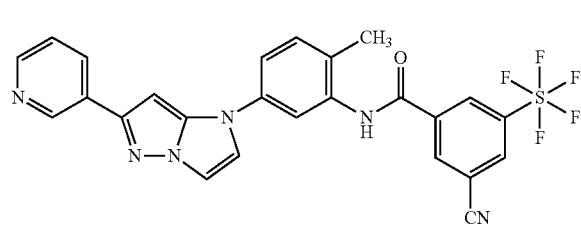 [SMILES: Cc1ccc(-n2ccn3nc(-c4cccnc4)cc23)cc1NC(=O)c1cc(C#N)cc(S(F)(F)(F)(F)F)c1]

315 mg (0.83 mmol) of HATU and 179 mg (1.38 mmol) of N,N-diisopropylethylamine were added to a solution of 189 mg (0.69 mmol) of the compound of Example 14A and 200 mg (0.69 mmol) of 3-cyano-5-(pentafluoro-λ$^6$-sulphanyl)benzoic acid from Example 23A in 4.4 ml of DMSO. The reaction was stirred at 25° C. for 16 h. A further 60 mg (0.22 mmol) of 3-cyano-5-(pentafluoro-λ$^6$-sulphanyl)benzoic acid, 150 mg (0.41 mmol) of HATU and 74 mg (0.57 mmol) of N,N-diisopropylethylamine were then added, and the mixture was warmed at 40° C. for several hours. After cooling, the reaction mixture was added to water and extracted with ethyl acetate. The organic phase was washed twice with in each case 50 ml of saturated sodium bicarbonate solution and once with saturated sodium chloride solution and dried over sodium sulphate. After filtration, the mixture was concentrated under reduced pressure and the residue obtained in this manner was purified by chromatography on a Biotage system (25 g Snap column; mobile phase gradient ethyl acetate/hexane, starting with 20% ethyl acetate, then increasing rapidly to 100% ethyl acetate, then ethyl acetate/methanol, from 0% methanol increasing steadily to 50% methanol). The product obtained in this manner was taken up in ethyl acetate and washed three times with in each case 25 ml sodium bicarbonate solution and once with saturated sodium chloride solution and dried over sodium sulphate. After filtration, the mixture was concentrated under reduced pressure. This gave 60 mg (15% of theory) of the title compound.

$^1$H NMR (300 MHz, DMSO-$d_6$, δ/ppm): 10.47 (s, 1H), 9.06 (d, 1H), 8.84 (s, 1H), 8.75 (s, 1H), 8.69 (s, 1H), 8.48 (dd, 1H), 8.19 (dt, 1H), 7.93 (d, 1H), 7.91 (d, 1H), 7.75 (d, 1H), 7.58 (dd, 1H), 7.39-7.48 (m, 2H), 6.85 (s, 1H), 2.27 (s, 3H).

LC/MS (Method 5, ESIpos): R$_t$=1.15 min, m/z=545 [M+H]$^+$.

Example 78

3-Bromo-5-tert-butyl-N-{2-methyl-5-[6-(pyridin-3-yl)-1H-imidazo[1,2-b]pyrazol-1-yl]phenyl}-3-(pentafluoro-λ$^6$-sulphanyl)benzamide

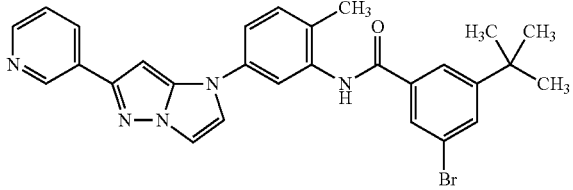 [SMILES: Cc1ccc(-n2ccn3nc(-c4cccnc4)cc23)cc1NC(=O)c1cc(Br)cc(C(C)(C)C)c1]

Analogously to the procedure of Example 77, 200 mg (0.69 mmol) of the compound of Example 14A and 248 mg (0.96 mmol) of 3-bromo-5-tert-butylbenzoic acid gave a crude product which was initially purified by chromatography on a Biotage system, as described above. This gave 145 mg (40% of theory) of the title compound which was used without further purification for the subsequent reaction, and 60 mg of still impure material which was purified by further separation by preparative HPLC (Method 16). This gave a further 14 mg (3.6% of theory) of the title compound.

$^1$H NMR (300 MHz, CDCl$_3$, δ/ppm): 9.13 (d, 1H), 8.55 (dd, 1H), 8.48 (d, 1H), 8.20 (dt, 1H), 7.90 (s, 1H), 7.79 (s, 1H), 7.74 (t, 2H), 7.51 (d, 1H), 7.30-7.40 (m, 3H), 7.25 (dd, 1H), 6.50 (s, 1H), 2.41 (s, 3H), 1.38 (s, 9H).

LC/MS (Method 5, ESIpos): R$_t$=1.32 min, m/z=528/530 [M+H]$^+$.

Example 79

3-Cyano-5-tert-butyl-N-{2-methyl-5-[6-(pyridin-3-yl)-1H-imidazo[1,2-b]pyrazol-1-yl]phenyl}-3-(pentafluoro-λ$^6$-sulphanyl)benzamide

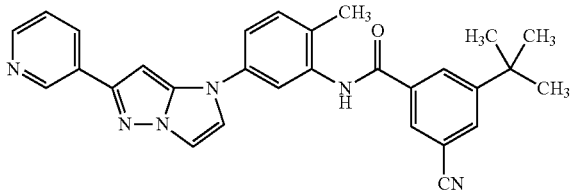 [SMILES: Cc1ccc(-n2ccn3nc(-c4cccnc4)cc23)cc1NC(=O)c1cc(C#N)cc(C(C)(C)C)c1]

35.5 mg (0.30 mmol) of zinc cyanide and 19 mg (0.016 mmol) of tetrakis(triphenyl-phosphine)palladium(0) were added to a solution of 145 mg (0.28 mmol) of the compound of Example 78 in 5.0 ml DMF (degassed under argon) and the mixture was heated under reflux for 2 h. After cooling, ethyl acetate was added to the reaction mixture and the organic phase was washed successively with saturated sodium bicarbonate solution and saturated sodium chloride solution. After drying over sodium sulphate and filtration, the filtrate was concentrated under reduced pressure. The residue obtained in this manner was purified by chromatography on a Biotage system (10 g Snap column; mobile phase gradient ethyl acetate/hexane, starting with 20% ethyl acetate, then increasing rapidly to 100% ethyl acetate, then ethyl acetate/methanol, from 0% methanol increasing steadily to 30% methanol). This gave 44 mg (29% of theory) of the title compound.

$^1$H NMR (300 MHz, CDCl$_3$, δ/ppm): 9.12 (d, 1H), 8.55 (dd, 1H), 8.45 (d, 1H), 8.16-8.25 (m, 2H), 7.94 (s, 1H), 7.89 (s, 1H), 7.82 (s, 1H), 7.51 (d, 1H), 7.30-7.41 (m, 3H), 6.50 (s, 1H), 2.42 (s, 3H), 1.41 (s, 9H).

LC/MS (Method 5, ESIpos): R$_t$=1.18 min, m/z=475 [M+H]$^+$.

Example 80

3-Cyano-N-{2-methyl-3-[6-(pyridin-3-yl)-1H-imidazo[1,2-b]pyrazol-1-yl]phenyl}-5-(pentafluoro-λ$^6$-sulphanyl)benzamide

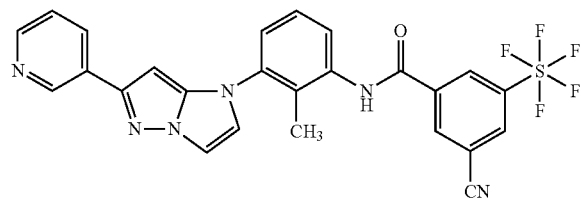 [SMILES: Cc1c(NC(=O)c2cc(C#N)cc(S(F)(F)(F)(F)F)c2)cccc1-n1ccn2nc(-c3cccnc3)cc12]

100 mg (0.346 mmol) of the compound of Example 69A and 111 mg (0.346 mmol, 85% pure) of the compound from Example 23A were dissolved in 1.9 ml of anhydrous DMF and 158 mg (0.415 mmol) of HATU and 72 μl (0.415 mmol) of N,N-diisopropylethylamine were added in succession. The reaction mixture was stirred at RT overnight (about 15 h) and then stirred into about 10 ml of water. The resulting precipitate was filtered off with suction, dissolved in dichloromethane and washed successively with semisaturated aqueous sodium bicarbonate solution and saturated sodium chloride solution. After drying over anhydrous magnesium sulphate, filtration and removal of the solvent on a rotary evaporator, the residue obtained in this manner was purified by preparative HPLC (Method 33). After evaporation of the product fractions, the solid was re-dissolved in ethyl acetate and washed with saturated aqueous sodium bicarbonate solution to convert the product into the form of the free base. After drying of the organic phase over anhydrous magnesium sulphate, filtration and evaporation, the product was finally triturated with 3 ml of pentane to which a few drops of diisopropyl ether had been added. Filtration with suction and drying of the solid under high vacuum gave 66 mg (35% of theory) of the title compound.

$^1$H NMR (400 MHz, CDCl$_3$, δ/ppm): 9.00 (s, 1H), 8.69 (s, broad, 1H), 8.63 (s, 1H), 8.52 (d, 1H), 8.45 (s, 1H), 8.23 (s, 1H), 8.15 (dt, 1H), 7.70 (d, 1H), 7.52 (d, 1H), 7.44 (t, 1H), 7.37 (d, 1H), 7.33 (dd, 1H), 6.95 (d, 1H), 5.96 (s, 1H), 2.24 (s, 3H).

LC/MS (Method 4, ESIpos): R$_t$=0.97 min, m/z=545 [M+H]$^+$.

Example 81

3-Cyano-N-{2-fluoro-3-[6-(pyridin-3-yl)-1H-imidazo[1,2-b]pyrazol-1-yl]phenyl}-5-(pentafluoro-λ$^6$-sulphanyl)benzamide

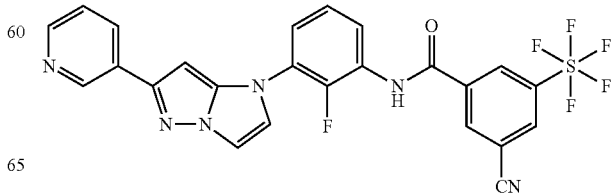

Analogously to the process described in Example 96, 100 mg (0.341 mmol) of the compound of Example 70A and 110 mg (0.341 mmol, 85% pure) of the compound from Example 23A gave 52 mg (28% of theory) of the title compound. Here, purification was by preparative HPLC according to Method 33, and final trituration of the product could be dispensed with.

$^1$H NMR (400 MHz, CDCl$_3$, δ/ppm): 9.05 (d, 1H), 8.59 (broad, 1H), 9.58 (s, 1H), 8.55 (dd, 1H), 8.39 (s, 1H), 8.27-8.23 (m, 2H), 8.17 (dt, 1H), 7.55 (d, 1H), 7.45 (td, 1H), 7.39 (t, 1H), 7.35 (dd, 1H), 7.18 (t, 1H), 6.25 (s, 1H).

LC/MS (Method 4, ESIpos): R$_t$=1.00 min, m/z=549 [M+H]$^+$.

Example 82

N-{2-Hydroxy-3-[6-(pyridin-3-yl)-1H-imidazo[1,2-b]pyrazol-1-yl]phenyl}-3-(pentafluoro-λ$^6$-sulphanyl)benzamide

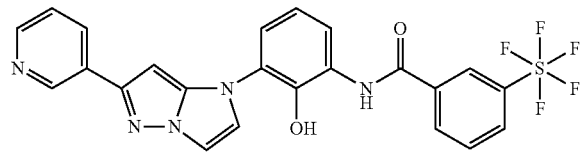 [SMILES: O=C(Nc1cccc(-n2ccn3nc(-c4cccnc4)cc23)c1O)c1cccc(S(F)(F)(F)(F)F)c1]

80 mg (0.192 mmol) of the compound of Example 71A and 48 mg (0.192 mmol) of 3-(pentafluoro-λ$^6$-sulphanyl)benzoic acid were dissolved in 1.5 ml anhydrous DMF, and 88 mg (0.231 mmol) of HATU and 40 μl (0.231 mmol) of N,N-diisopropylethylamine were added in succession. The reaction mixture was stirred at RT for 30 min and then stirred into about 10 ml of water. The resulting precipitate was filtered off with suction and dissolved in 3 ml of methanol, and 385 μl (0.385 mmol) of 1 M aqueous sodium hydroxide solution were added. The mixture was then stirred at RT for 30 min and then, by preparative HPLC, separated completely into its components (Method 33). The product fractions were combined and freed from the solvent. The residue was triturated with a mixture of 5 ml of pentane and 1 ml of dichloromethane at RT. Filtration with suction and drying of the solid under high vacuum gave 32 mg (32% of theory) of the title compound.

$^1$H NMR (400 MHz, DMSO-d$_6$, δ/ppm): 10.36 (s, broad, 1H), 9.78 (s, broad, 1H), 9.05 (d, 1H), 8.51 (s, 1H), 8.49 (dd, 1H), 8.33 (d, 1H), 8.20-8.15 (m, 2H), 7.87 (d, 1H), 7.82 (t, 1H), 7.57 (d, 1H), 7.47-7.41 (m, 3H), 7.07 (t, 1H), 6.40 (s, 1H).

LC/MS (Method 3, ESIpos): R$_t$=0.98 min, m/z=522 [M+H]$^+$.

Example 83

3-Cyano-N-{2-hydroxy-3-[6-(pyridin-3-yl)-1H-imidazo[1,2-b]pyrazol-1-yl]phenyl}-5-(pentafluoro-λ$^6$-sulphanyl)benzamide

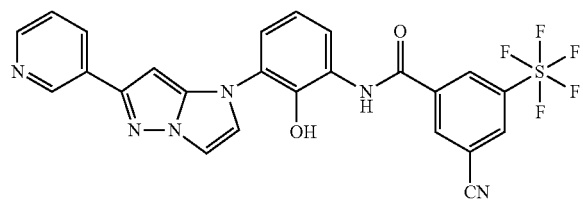 [SMILES: N#Cc1cc(C(=O)Nc2cccc(-n3ccn4nc(-c5cccnc5)cc34)c2O)cc(S(F)(F)(F)(F)F)c1]

74 mg (0.178 mmol, 70% pure) of the compound from Example 71A and 44 mg (0.160 mmol) of the compound of Example 23A were dissolved in 1 ml anhydrous DMF, and 81 mg (0.213 mmol) of HATU and 37 μl (0.213 mmol) of N,N-diisopropylethylamine were added in succession. The reaction mixture was stirred at RT for 30 min and then stirred into about 10 ml of water. The resulting precipitate was filtered off with suction, dissolved in about 3 ml of methanol and separated into its components by preparative HPLC (Method 33). The product fractions were combined and freed from the solvent. The residue obtained was triturated with a little dichloromethane at RT. Filtration with suction and drying of the solid under high vacuum gave 36 mg (37% of theory) of the title compound.

$^1$H NMR (400 MHz, DMSO-d$_6$, δ/ppm): 10.49 (s, broad, 1H), 9.81 (s, broad, 1H), 9.05 (s, 1H), 8.86 (s, 1H), 8.76 (s, 1H), 8.75 (s, 1H), 8.49 (d, 1H), 8.19 (d, 1H), 7.88 (d, 1H), 7.57 (d, 1H), 7.48-7.41 (m, 3H), 7.07 (t, 1H), 6.41 (s, 1H).

LC/MS (Method 3, ESIpos): R$_t$=0.97 min, m/z=547 [M+H]$^+$.

Example 84

N-{4-Methyl-3-[6-(pyrazin-2-yl)-1H-imidazo[1,2-b]pyrazol-1-yl]phenyl}-3-(pentafluoro-λ$^6$-sulphanyl)benzamide

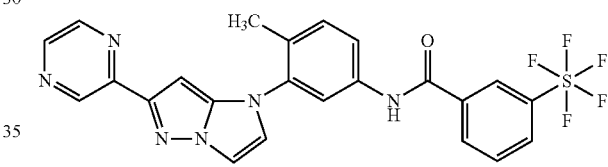

Analogously to Example 90, 80 mg (0.28 mmol) of the compound of Example 72A and 75 mg (0.30 mmol) of 3-(pentafluoro-λ$^6$-sulphanyl)benzoic acid gave 64 mg (45% of theory) of the title compound.

$^1$H NMR (400 MHz, DMSO-d$_6$, δ/ppm): 10.65 (s, 1H), 9.16 (d, 1H), 8.58 (dd, 1H), 8.50 (d, 1H), 8.37 (t, 1H), 8.24 (d, 1H), 8.12 (dd, 1H), 7.94 (t, 2H), 7.72-7.82 (m, 2H), 7.62 (d, 1H), 7.43 (d, 1H), 6.36 (d, 1H), 2.26 (s, 3H).

LC/MS (Method 7, ESIpos): R$_t$=1.29 min, m/z=521 [M+H]$^+$.

Example 85

3-Cyano-N-{4-methyl-3-[6-(1H-pyrazol-4-yl)-1H-imidazo[1,2-b]pyrazol-1-yl]phenyl}-5-(pentafluoro-λ$^6$-sulphanyl)benzamide

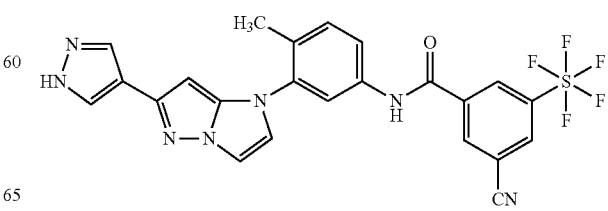

80 mg (0.10 mmol) of the compound of Example 75A were stirred in 0.8 ml of trifluoroacetic acid at 90° C. for 60 min. The reaction was then concentrated under reduced pressure and the residue was purified by preparative HPLC (Method 34). This gave 49 mg (90% of theory) of the title compound.

$^1$H NMR (400 MHz, DMSO-d$_6$, δ/ppm): 12.86 (broad, 1H), 10.78 (s, 1H), 8.86 (s, 1H), 8.74 (s, 1H), 8.66 (s, 1H), 8.02 (s, 1H), 7.92 (d, 1H), 7.82-7.74 (m, 3H), 7.48 (d, 1H), 7.42 (d, 1H), 5.92 (s, 1H), 2.28 (s, 3H).

LC/MS (Method 3, ESIpos): R$_t$=1.03 min, m/z=534 [M+H]$^+$.

Example 86

3-Cyano-N-{2,4-dimethyl-5-[6-(1H-pyrazol-4-yl)-1H-imidazo[1,2-b]pyrazol-1-yl]phenyl}-5-(pentafluoro-λ$^6$-sulphanyl)benzamide

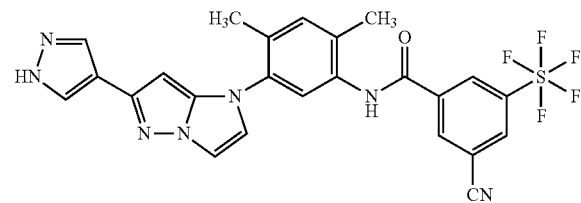 [SMILES: Cc1cc(C)c(-n2ccn3nc(-c4cn[nH]c4)cc23)cc1NC(=O)c1cc(C#N)cc(S(F)(F)(F)(F)F)c1]

120 mg (0.19 mmol) of the compound of Example 76A were reacted and worked up analogously to Example 12. This gave 61 mg (61% of theory) of the title compound.

$^1$H NMR (400 MHz, DMSO-d$_6$, δ/ppm): 12.84 (broad, 1H), 10.40 (s, 1H), 8.85 (s, 1H), 8.73 (s, 1H), 8.66 (s, 1H), 7.99 (s, 1H), 7.76 (d, 2H), 7.49 (s, 1H), 7.36 (d, 2H), 5.86 (s, 1H), 2.30 (s, 3H), 2.25 (s, 3H).

LC/MS (Method 3, ESIpos): R$_t$=1.03 min, m/z=548 [M+H]$^+$.

Example 87

3-Cyano-5-(pentafluoro-λ$^6$-sulphanyl)-N-{3-[6-(pyridin-3-yl)-1H-imidazo[1,2-b]pyrazol-1-yl]phenyl}benzamide

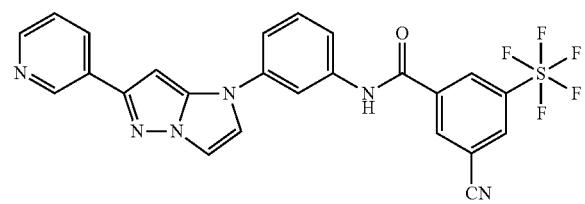 [SMILES: N#Cc1cc(C(=O)Nc2cccc(-n3ccn4nc(-c5cccnc5)cc34)c2)cc(S(F)(F)(F)(F)F)c1]

Analogously to the process described in Example 26, 100 mg (0.363 mmol) of the compound of Example 62A and 117 mg (0.363 mmol) of the compound of Example 23A gave 62 mg (32% of theory) of the title compound. In this case, the reaction time was about 15 h.

$^1$H NMR (400 MHz, CDCl$_3$, δ/ppm): 9.57 (s, broad, 1H), 9.09 (d, 1H), 8.68 (s, 1H), 8.55-8.53 (m, 2H), 8.22-8.16 (m, 3H), 7.53-7.51 (m, 3H), 7.36 (dd, 1H), 7.32-7.27 (m, 2H), 6.47 (s, 1H).

LC/MS (Method 4, ESIpos): R$_t$=1.04 min, m/z=531 [M+H]$^+$.

Example 88

3-Fluoro-N-{4-methyl-3-[6-(pyridin-3-yl)-1H-imidazo[1,2-b]pyrazol-1-yl]phenyl}-5-(pentafluoro-λ$^6$-sulphanyl)benzamide

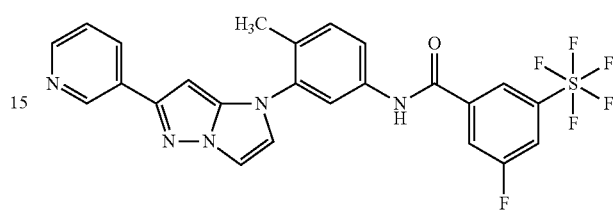

Analogously to the process described in Example 26, 100 mg (0.346 mmol) of the compound of Example 6A and 97 mg (0.363 mmol) of 3-fluoro-5-(pentafluoro-λ$^6$-sulphanyl)benzoic acid (JRD Fluorochemicals Ltd., United Kingdom) gave 165 mg (89% of theory) of the title compound. In this case, the reaction time was about 15 h.

$^1$H NMR (400 MHz, DMSO-d$_6$, δ/ppm): 10.72 (s, broad, 1H), 9.06 (d, 1H), 8.49 (dd, 1H), 8.30 (s, 1H), 8.25 (dt, 1H), 8.21-8.17 (m, 2H), 7.95 (d, 1H), 7.93 (d, 1H), 7.79 (dd, 1H), 7.56 (d, 1H), 7.49 (d, 1H), 6.42 (dd, 1H), 6.37 (s, 1H), 2.29 (s, 3H).

LC/MS (Method 4, ESIpos): R$_t$=1.08 min, m/z=538 [M+H]$^+$.

Example 89

3-Bromo-N-{4-methyl-3-[6-(pyridin-3-yl)-1H-imidazo[1,2-b]pyrazol-1-yl]phenyl}-5-(pentafluoro-λ$^6$-sulphanyl)benzamide

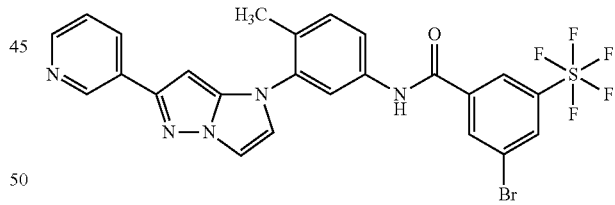

10.0 g (34.6 mmol) of the compound of Example 6A and 11.3 g (34.6 mmol) of the compound of Example 15A were dissolved in 120 ml anhydrous DMF, and 15.8 g (41.5 mmol) of HATU and 7.2 ml (41.5 mmol) of N,N-diisopropylethylamine were added in succession. The reaction mixture was stirred at RT overnight (about 15 h) and then stirred into 1.6 liters of water. After 40 minutes, the resulting precipitate was filtered off with suction, washed thoroughly with a further 0.5 liter of water and finally dissolved in 1.8 liters of ethyl acetate. The organic solution was washed successively with water and saturated sodium chloride solution. After drying over anhydrous magnesium sulphate, the mixture was filtered and the solvent was removed on a rotary evaporator. The crude product obtained in this manner was purified by filtration with suction (about 330 g of silica gel, mobile phase gradient cyclohexane/ethyl acetate 1:1→1:3). This gave 11.95 g (57% of theory) of the title compound.

$^1$H NMR (400 MHz, DMSO-d$_6$, δ/ppm): 10.73 (s, broad, 1H), 9.06 (d, 1H), 8.50 (s, 1H), 8.48 (dd, 1H), 8.43 (s, 1H), 8.40 (s, 1H), 8.19 (dt, 1H), 7.93 (m, 2H), 7.79 (dd, 1H), 7.55 (d, 1H), 7.49 (d, 1H), 7.42 (dd, 1H), 6.37 (s, 1H), 2.28 (s, 3H).

LC/MS (Method 3, ESIpos): R$_t$=1.12 min, m/z=598/600 [M+H]$^+$.

Example 90

2-Methoxy-N-{4-methyl-3-[6-(pyridin-3-yl)-1H-imidazo[1,2-b]pyrazol-1-yl]phenyl}-5-(pentafluoro-λ$^6$-sulphanyl)benzamide

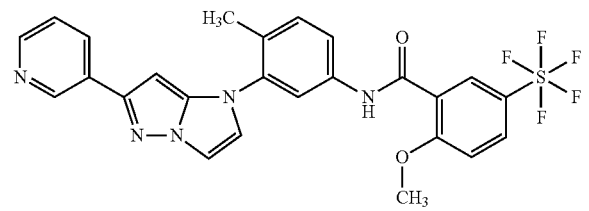 [SMILES: COc1ccc(S(F)(F)(F)(F)F)cc1C(=O)Nc1ccc(C)c(-n2ccn3nc(-c4cccnc4)cc23)c1]

394 mg (1.04 mmol) of HATU and 127 mg (1.04 mmol) of 4-N,N-dimethylaminopyridine (DMAP) were added to a solution of 200 mg (0.69 mmol) of the compound of Example 6A and 288 mg (1.04 mmol) of 2-methoxy-5-(pentafluoro-λ$^6$-sulphanyl)benzoic acid in 2.2 ml of DMF. The reaction was stirred at 50° C. for 16 h. The reaction mixture was then purified directly by preparative HPLC (Method 16). This gave 222 mg (53% of theory) of the title compound.

$^1$H NMR (400 MHz, DMSO-d$_6$, δ/ppm): 10.40 (s, 1H), 9.01 (d, 1H), 8.45 (dd, 1H), 8.15 (dt, 1H), 7.96-8.05 (m, 2H), 7.87 (d, 2H), 7.68 (dd, 1H), 7.49 (d, 1H), 7.29-7.44 (m, 3H), 6.30 (s, 1H), 3.93 (s, 3H), 2.22 (s, 3H).

LC/MS (Method 7, ESIpos): R$_t$=1.32 min, m/z=550 [M+H]$^+$.

Example 91

2-Methyl-N-{4-methyl-3-[6-(pyridin-3-yl)-1H-imidazo[1,2-b]pyrazol-1-yl]phenyl}-5-(pentafluoro-λ$^6$-sulphanyl)benzamide

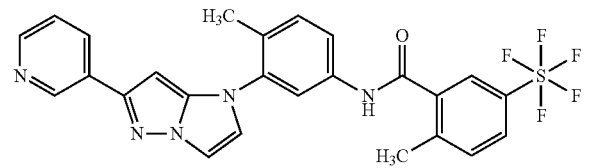 [SMILES: Cc1ccc(S(F)(F)(F)(F)F)cc1C(=O)Nc1ccc(C)c(-n2ccn3nc(-c4cccnc4)cc23)c1]

Analogously to Example 90, 200 mg (0.69 mmol) of the compound of Example 6A and 272 mg (1.04 mmol) of 2-methyl-5-(pentafluoro-λ$^6$-sulphanyl)benzoic acid gave 150 mg (39% of theory) of the title compound.

$^1$H NMR (400 MHz, DMSO-d$_6$, δ/ppm): 10.65 (s, 1H), 9.01 (d, 1H), 8.44 (dd, 1H), 8.14 (dt, 1H), 7.82-7.95 (m, 4H), 7.67 (dd, 1H), 7.53 (d, 1H), 7.49 (d, 1H), 7.42 (d, 1H), 7.38 (ddd, 1H), 6.30 (s, 1H), 2.41 (s, 3H), 2.23 (s, 3H).

LC/MS (Method 7, ESIpos): R$_t$=1.29 min, m/z=534 [M+H]$^+$.

Example 92

3-Cyano-5-(1-hydroxycyclobutyl)-N-{4-methyl-3-[6-(pyridin-3-yl)-1H-imidazo[1,2-b]pyrazol-1-yl]phenyl}benzamide

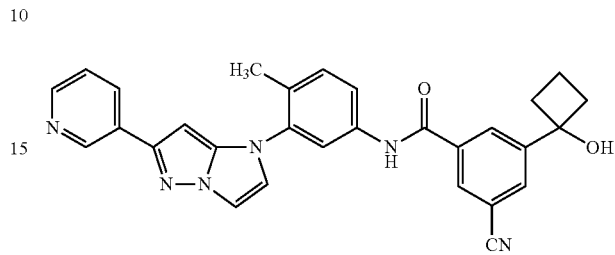

Analogously to the process described in Example 26, 80 mg (0.276 mmol) of the compound of Example 6A and 60 mg (0.276 mmol) of the compound of Example 73A gave 115 mg (82% of theory, 96% pure) of the title compound. In this case, the reaction time was 1 h. Final trituration of the product was carried out using a mixture of 10 ml of pentane and 2 ml of diisopropyl ether.

$^1$H NMR (400 MHz, DMSO-d$_6$, δ/ppm): 10.61 (s, broad, 1H), 9.06 (d, 1H), 8.48 (dd, 1H), 8.33 (dd, 1H), 8.30 (dd, 1H), 8.19 (dt, 1H), 8.12 (dd, 1H), 7.96 (d, 1H), 7.93 (d, 1H), 7.81 (dd, 1H), 7.56 (d, 1H), 7.48 (d, 1H), 7.42 (dd, 1H), 6.38 (s, 1H), 5.92 (s, 1H), 2.51-2.43 (m, 2H, partially obscured by the DMSO signal), 2.37-2.27 (m, 2H), 2.28 (s, 3H), 2.03-1.92 (m, 1H), 1.80-1.69 (m, 1H).

LC/MS (Method 3, ESIpos): R$_t$=0.88 min, m/z=489 [M+H]$^+$.

Example 93

2-tert-Butyl-6-cyano-N-{4-methyl-3-[6-(pyridin-3-yl)-1H-imidazo[1,2-b]pyrazol-1-yl]phenyl}-isonicotinamide

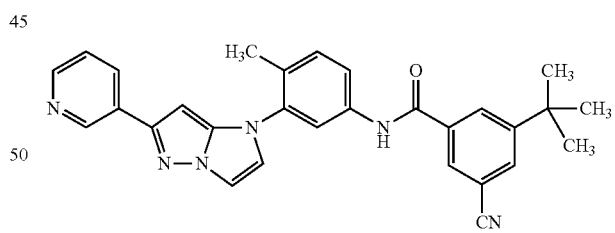

Under argon, a mixture of 137 mg (0.28 mmol) of the compound of Example 65, 4.04 mg (0.012 mmol) of palladium(II) trifluoroacetate, 9.91 mg (0.025 mmol) of racemic 2-di-tert-butylphosphino-1,1'-binaphthyl, 3.51 mg (0.054 mmol) of zinc flakes and 18.6 mg (0.16 mmol) of zinc cyanide in 1.5 ml N,N-dimethylacetamide was stirred at 95° C. for 20 hours. After cooling, the mixture was diluted with 80 ml of ethyl acetate and the mixture was washed in each case once with 10 ml of water and 10 ml saturated sodium chloride solution. The organic phase was dried over sodium sulphate and, after filtration, concentrated under reduced pressure. The residue obtained in this manner was purified by chromatography on a Biotage system (25 g Snap column; mobile phase gradient ethyl acetate/hexane, starting with 70% ethyl acetate, then increasing rapidly to 100% ethyl acetate). Further purification was by preparative thick-layer chromatography (2 mm layer thickness with concentration zone, mobile phase ethyl acetate, elution with methylene chloride/methanol 7:3). This gave 56 mg (38% of theory) of the title compound.

$^1$H NMR (400 MHz, DMSO-d$_6$, δ/ppm): 10.75 (s, 1H), 9.01 (d, 1H), 8.45 (dd, 1H), 8.29 (d, 1H), 8.11-8.19 (m, 2H), 7.90 (dd, 2H), 7.75 (dd, 1H), 7.51 (d, 1H), 7.46 (d, 1H), 7.38 (dd, 1H), 6.32 (s, 1H), 2.25 (s, 3H), 1.34 (s, 9H).

LC/MS (Method 7, ESIpos): R$_t$=1.21 min, m/z=476 [M+H]$^+$.

Example 94

3-Bromo-5-(pentafluoro-λ$^6$-sulphanyl)-N-{3-[6-(pyridin-3-yl)-1H-imidazo[1,2-b]pyrazol-1-yl]-4-(trifluoromethyl)phenyl}benzamide

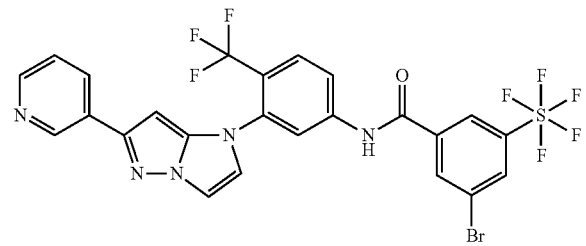 [SMILES: O=C(Nc1ccc(C(F)(F)F)c(-n2ccn3nc(-c4cccnc4)cc23)c1)c1cc(Br)cc(S(F)(F)(F)(F)F)c1]

Analogously to Example 90, 660 mg (1.92 mmol) of the compound of Example 63A and 692 mg (2.12 mmol) of the compound of Example 15A gave 253 mg (70% pure, 14% of theory) of the title compound. In this case, the reaction time was 80 h in total at a temperature of 60° C., with more HATU and DMAP being added at intervals. Purification of the crude product was by double chromatography on a Biotage system (25 g Snap column; mobile phase gradient initially ethyl acetate/hexane with rapidly increasing proportion of ethyl acetate to 100%, then ethyl acetate/methanol, from 0-20% methanol increasing slowly).

LC/MS (Method 7, ESIpos): R$_t$=1.36 min, m/z=652/654 [M+H]$^+$.

Example 95

3-Cyano-5-(pentafluoro-λ$^6$-sulphanyl)-N-{3-[6-(pyridin-3-yl)-1H-imidazo[1,2-b]pyrazol-1-yl]-4-(trifluoromethyl)phenyl}benzamide

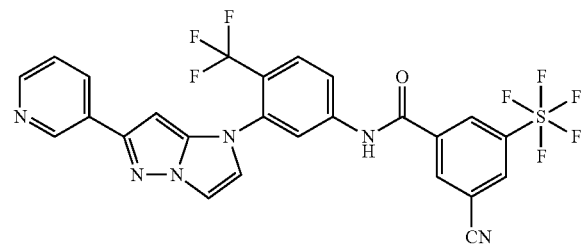 [SMILES: N#Cc1cc(C(=O)Nc2ccc(C(F)(F)F)c(-n3ccn4nc(-c5cccnc5)cc34)c2)cc(S(F)(F)(F)(F)F)c1]

Analogously to Example 79, 253 mg (0.39 mmol) of the compound of Example 94 gave 27 mg (11% of theory) of the title compound. Here, purification of the crude product was carried out by preparative HPLC (Method 16).

$^1$H NMR (400 MHz, DMSO-d$_6$, δ/ppm): 10.83 (s, 1H), 9.08 (d, 1H), 8.87 (t, 1H), 8.69 (s, 2H), 8.50 (dd, 1H), 8.20 (dt, 1H), 8.09 (d, 1H), 8.05 (d, 1H), 7.89-7.97 (m, 3H), 7.44 (ddd, 1H), 7.05 (s, 1H).

LC/MS (Method 6, ESIpos): R$_t$=1.23 min, m/z=599 [M+H]$^+$.

Example 96

N-{4-Chloro-3-[6-(pyridin-3-yl)-1H-imidazo[1,2-b]pyrazol-1-yl]phenyl}-3-(pentafluoro-λ$^6$-sulphanyl)benzamide

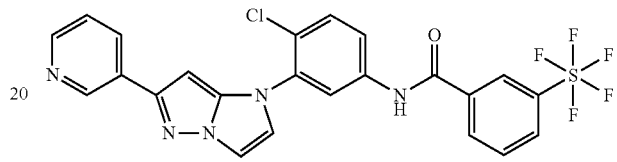

130 mg (0.420 mmol) of the compound of Example 64A and 104 mg (0.420 mmol) of 3-(pentafluoro-λ$^6$-sulphanyl)benzoic acid were dissolved in 2.5 ml of anhydrous DMF, and 191 mg (0.504 mmol) of HATU and 88 μl (0.504 mmol) of N,N-diisopropylethylamine were added in succession. The reaction mixture was stirred at RT for 15 h and then diluted with a few ml of methanol and subsequently separated completely into its components by preparative HPLC (Method 9). The product fractions were combined and concentrated to dryness on a rotary evaporator. In this manner, the title compound was obtained in the form of its formic acid salt. To convert the product into the salt-free form, saturated aqueous sodium bicarbonate solution was added and the mixture was extracted with ethyl acetate. The organic extract was dried over anhydrous magnesium sulphate, filtered and freed from the solvent on a rotary evaporator. The residue obtained in this manner was finally triturated with 3 ml of pentane to which a few drops of diisopropyl ether had been added. Filtration with suction and drying of the solid under high vacuum gave 53 mg (22% of theory, 95% pure) of the title compound.

$^1$H NMR (400 MHz, CDCl$_3$, δ/ppm): 9.10 (s, broad, 1H), 9.02 (s, 1H), 8.49 (d, 1H), 8.35 (s, 1H), 8.12-8.04 (m, 3H), 7.94 (d, 1H), 7.71 (d, 1H), 7.64-7.55 (m, 2H), 7.48 (s, 1H), 7.32 (dd, 1H), 7.17 (d, 1H), 6.09 (s, 1H).

LC/MS (Method 3, ESIpos): R$_t$=1.07 min, m/z=540/542 [M+H]$^+$.

Example 97

N-{4-Chloro-3-[6-(pyridin-3-yl)-1H-imidazo[1,2-b]pyrazol-1-yl]phenyl}-3-cyano-5-(pentafluoro-λ$^6$-sulphanyl)benzamide

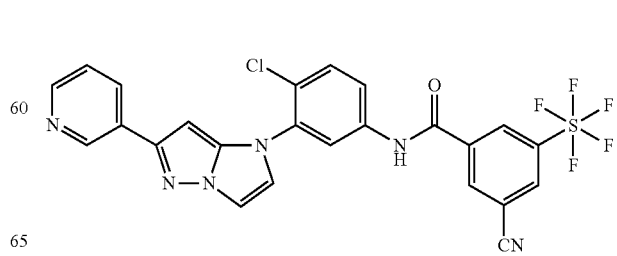

Analogously to the process described in Example 96, 130 mg (0.420 mmol) of the compound of Example 64A and 135 mg (0.420 mmol, 85% pure) of the compound from Example 23A gave 49 mg (19% of theory, 95% pure) of the title compound.

$^1$H NMR (400 MHz, CDCl$_3$, δ/ppm): 9.95 (s, broad, 1H), 9.02 (d, 1H), 8.67 (s, 1H), 8.53 (s, 1H), 8.51 (dd, 1H), 8.18 (s, 1H), 8.11 (d, 1H), 8.07 (d, 1H), 7.80 (dd, 1H), 7.58 (d, 1H), 7.50 (d, 1H), 7.34 (dd, 1H), 7.19 (d, 1H), 6.11 (s, 1H).

LC/MS (Method 3, ESIpos): R$_t$=1.07 min, m/z=565/567 [M+H]$^+$.

Example 98

3-Bromo-N-{4-methoxy-3-[6-(pyridin-3-yl)-1H-imidazo[1,2-b]pyrazol-1-yl]phenyl}-5-(pentafluoro-λ$^6$-sulphanyl)benzamide

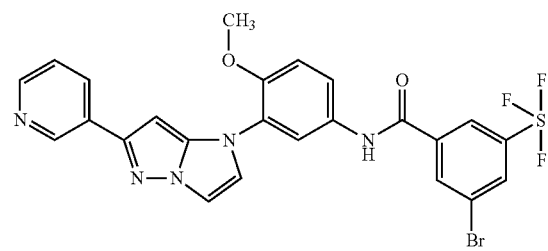

Analogously to Example 50, 400 mg (1.31 mmol) of the compound of Example 10A and 428 mg (1.31 mmol) of the compound of Example 15A gave, after single chromatographic purification on a Biotage system, 701 mg (78% of theory) of the title compound.

$^1$H NMR (400 MHz, DMSO-d$_6$, δ/ppm): 10.61 (s, 1H), 9.02 (d, 1H), 8.47 (s, 1H), 8.46 (dd, 1H), 8.36-8.40 (m, 2H), 8.15 (dt, 1H), 7.98 (d, 1H), 7.84 (d, 1H), 7.74 (dd, 1H), 7.52 (d, 1H), 7.39 (ddd, 1H), 7.31 (d, 1H), 6.38 (s, 1H), 3.87 (s, 3H).

LC/MS (Method 7, ESIpos): R$_t$=1.27 min, m/z=614/616 [M+H]$^+$.

Example 99

3-Cyano-N-{4-methoxy-3-[6-(pyridin-3-yl)-1H-imidazo[1,2-b]pyrazol-1-yl]phenyl}-5-(pentafluoro-λ$^6$-sulphanyl)benzamide

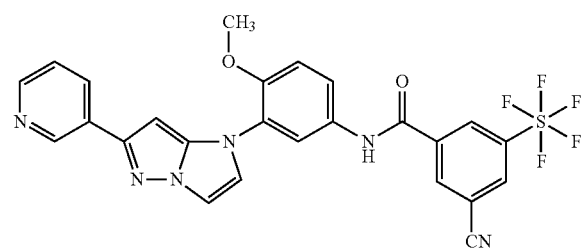 [SMILES: COc1ccc(NC(=O)c2cc(C#N)cc(S(F)(F)(F)(F)F)c2)cc1-n1ccn2nc(-c3cccnc3)cc12]

Analogously to Example 79, 700 mg (1.14 mmol) of the compound of Example 98 gave, after double chromatographic purification on a Biotage system and final preparative HPLC (Method 16), 75 mg (11% of theory) of the title compound.

$^1$H NMR (400 MHz, DMSO-d$_6$, δ/ppm): 10.68 (s, 1H), 9.02 (d, 1H), 8.80 (dd, 1H), 8.71 (s, 1H), 8.61-8.66 (m, 1H), 8.47 (dd, 1H), 8.17 (dt, 1H), 7.99 (d, 1H), 7.85 (d, 1H), 7.73 (dd, 1H), 7.53 (d, 1H), 7.41 (dd, 1H), 7.32 (d, 1H), 6.38 (s, 1H), 3.87 (s, 3H).

LC/MS (Method 7, ESIpos): R$_t$=1.24 min, m/z=561 [M+H]$^+$.

Example 100

N-{3,4-Dimethyl-5-[6-(pyridin-3-yl)-1H-imidazo[1,2-b]pyrazol-1-yl]phenyl}-3-(pentafluoro-λ$^6$-sulphanyl)benzamide

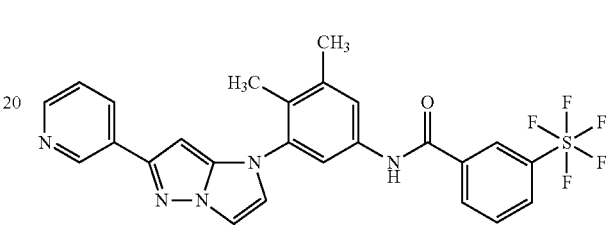

Analogously to Example 90, 150 mg (0.49 mmol) of the compound of Example 65A and 134 mg (0.54 mmol) of 3-(pentafluoro-λ$^6$-sulphanyl)benzoic acid gave 178 mg (66% of theory) of the title compound.

$^1$H NMR (400 MHz, DMSO-d$_6$, δ/ppm): 10.58 (s, 1H), 9.02 (s, 1H), 8.45 (d, 1H), 8.38 (t, 1H), 8.23 (d, 1H), 8.17 (dt, 1H), 8.12 (dd, 1H), 7.88 (d, 1H), 7.77 (dd, 2H), 7.68 (d, 1H), 7.46 (d, 1H), 7.39 (dd, 1H), 6.29 (s, 1H), 2.34 (s, 3H), 2.09 (s, 3H).

LC/MS (Method 7, ESIpos): R$_t$=1.21 min, m/z=534 [M+H]$^+$.

Example 101

3-Bromo-N-{3,4-dimethyl-5-[6-(pyridin-3-yl)-1H-imidazo[1,2-b]pyrazol-1-yl]phenyl}-5-(pentafluoro-λ$^6$-sulphanyl)benzamide

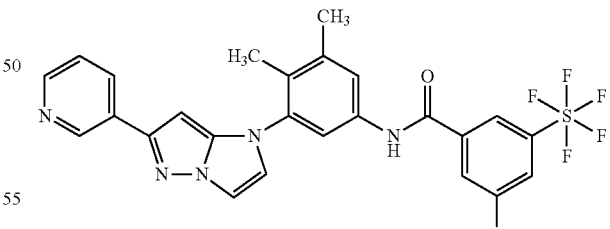

Analogously to Example 90, 370 mg (1.22 mmol) of the compound of Example 65A and 439 mg (1.34 mmol) of the compound of Example 15A gave a crude product which, in deviation from Example 90, was purified by chromatography on a Biotage system (25 g Snap column; mobile phase gradient hexane/ethyl acetate, from 70% ethyl acetate increasing steadily to 100% ethyl acetate). This gave 977 mg (>100% of theory) of the title compound which were not purified any further.

LC/MS (Method 7, ESIpos): $R_t$=1.36 min, m/z=612/614 [M+H]$^+$.

Example 102

3-Cyano-N-{3,4-dimethyl-5-[6-(pyridin-3-yl)-1H-imidazo[1,2-b]pyrazol-1-yl]phenyl}-5-(pentafluoro-$\lambda^6$-sulphanyl)benzamide

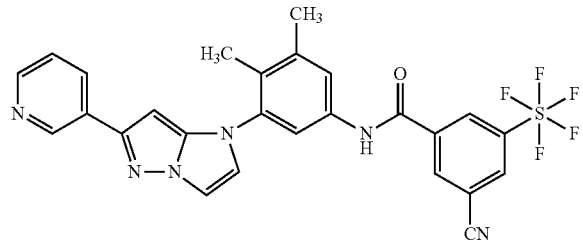 [SMILES: Cc1cc(NC(=O)c2cc(C#N)cc(S(F)(F)(F)(F)F)c2)cc(-n2ccn3nc(-c4cccnc4)cc23)c1C]

Analogously to Example 79, 970 mg (1.58 mmol) of the compound of Example 101 gave, after purification by HPLC (Method 16), 221 mg (24% of theory) of the title compound.

$^1$H NMR (400 MHz, DMSO-d$_6$, δ/ppm): 10.68 (s, 1H), 9.01 (d, 1H), 8.81 (d, 1H), 8.70 (s, 1H), 8.63 (d, 1H), 8.44 (dd, 1H), 8.14 (dt, 1H), 7.88 (d, 1H), 7.76 (d, 1H), 7.66 (d, 1H), 7.45 (d, 1H), 7.38 (ddd, 1H), 6.27 (s, 1H), 2.35 (s, 3H), 2.10 (s, 3H).

LC/MS (Method 7, ESIpos): $R_t$=1.20 min, m/z=559 [M+H]$^+$.

Example 103

N-{3-Fluoro-4-methyl-5-[6-(pyridin-3-yl)-1H-imidazo[1,2-b]pyrazol-1-yl]phenyl}-3-(pentafluoro-$\lambda^6$-sulphanyl)benzamide

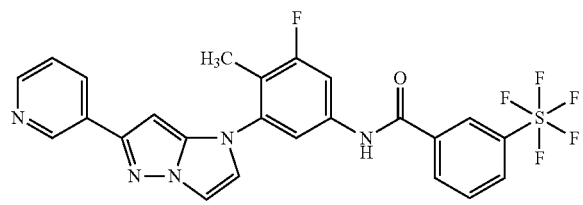 [SMILES: Cc1c(F)cc(NC(=O)c2cccc(S(F)(F)(F)(F)F)c2)cc1-n1ccn2nc(-c3cccnc3)cc12]

Analogously to Example 90, 150 mg (0.49 mmol) of the compound of Example 66A and 133 mg (0.54 mmol) of 3-(pentafluoro-$\lambda^6$-sulphanyl)benzoic acid gave 151 mg (58% of theory) of the title compound.

$^1$H NMR (400 MHz, DMSO-d$_6$, δ/ppm): 10.78 (s, 1H), 9.02 (d, 1H), 8.45 (dd, 1H), 8.37 (t, 1H), 8.24 (d, 1H), 8.11-8.18 (m, 2H), 7.92 (d, 1H), 7.71-7.85 (m, 3H), 7.55 (d, 1H), 7.39 (dd, 1H), 6.41 (s, 1H), 2.17 (d, 3H).

LC/MS (Method 7, ESIpos): $R_t$=1.24 min, m/z=538 [M+H]$^+$.

Example 104

3-Bromo-N-{3-fluoro-4-methyl-5-[6-(pyridin-3-yl)-1H-imidazo[1,2-b]pyrazol-1-yl]phenyl}-5-(pentafluoro-$\lambda^6$-sulphanyl)benzamide

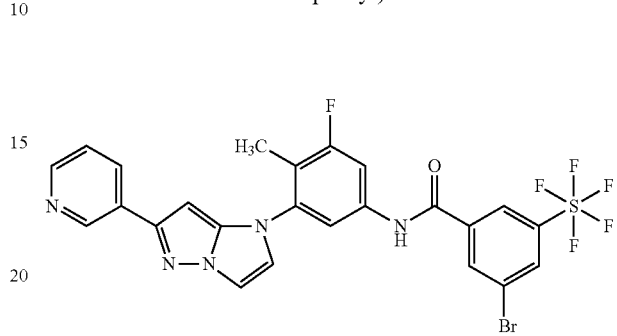

Analogously to Example 90, 400 mg (1.30 mmol) of the compound of Example 66A and 468 mg (1.43 mmol) of the compound of Example 15A gave a crude product which was purified by chromatography on a Biotage system (25 g Snap column; mobile phase gradient hexane/ethyl acetate, from 70% ethyl acetate increasing steadily to 100% ethyl acetate). This gave 772 mg (94% of theory) of the title compound.

$^1$H NMR (400 MHz, DMSO-d$_6$, δ/ppm): 10.80 (s, 1H), 9.02 (d, 1H), 8.43-8.48 (m, 2H), 8.40 (t, 1H), 8.36 (t, 1H), 8.15 (dt, 1H), 7.92 (d, 2H), 7.79 (dd, 1H), 7.71 (s, 1H), 7.54 (d, 1H), 7.39 (ddd, 1H), 6.40 (d, 1H), 2.17 (d, 3H).

LC/MS (Method 7, ESIpos): $R_t$=1.38 min, m/z=616/618 [M+H]$^+$.

Example 105

3-Cyano-N-{3-fluoro-4-methyl-5-[6-(pyridin-3-yl)-1H-imidazo[1,2-b]pyrazol-1-yl]phenyl}-5-(pentafluoro-$\lambda^6$-sulphanyl)benzamide

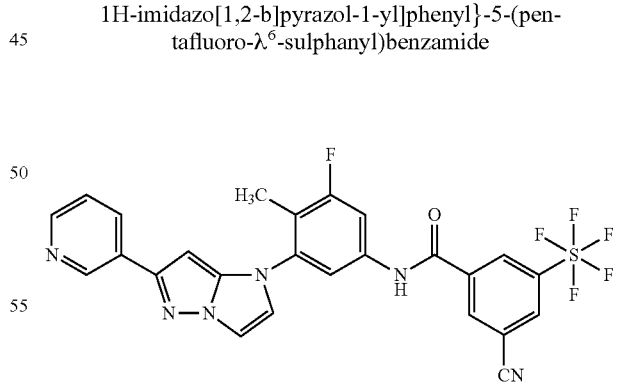

Analogously to Example 79, 755 mg (1.23 mmol) of the compound of Example 104 gave, after purification by HPLC (Method 16), 287 mg (41% of theory) of the title compound.

$^1$H NMR (400 MHz, DMSO-d$_6$, δ/ppm): 10.87 (s, 1H), 9.02 (dd, 1H), 8.83 (dd, 1H), 8.70 (s, 1H), 8.62 (dd, 1H), 8.46 (dd, 1H), 8.15 (dt, 1H), 7.92 (dd, 1H), 7.78 (dd, 1H), 7.71 (s, 1H), 7.55 (d, 1H), 7.39 (ddd, 1H), 6.39 (s, 1H), 2.17 (d, 3H).

Example 106

N-{3-Chloro-4-methyl-5-[6-(pyridin-3-yl)-1H-imidazo[1,2-b]pyrazol-1-yl]phenyl}-3-(pentafluoro-λ⁶-sulphanyl)benzamide

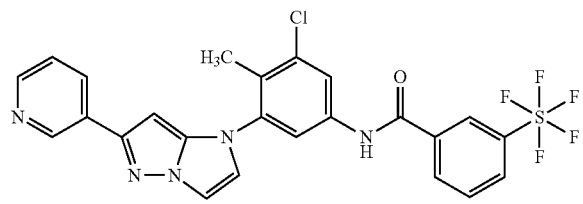

Analogously to Example 90, 240 mg (0.74 mmol) of the compound of Example 67A and 202 mg (0.82 mmol) of 3-(pentafluoro-λ⁶-sulphanyl)benzoic acid gave 242 mg (59% of theory) of the title compound.

¹H NMR (400 MHz, DMSO-d₆, δ/ppm): 10.75 (s, 1H), 9.02 (d, 1H), 8.45 (dd, 1H), 8.39 (t, 1H), 8.24 (d, 1H), 8.11-8.18 (m, 2H), 8.06 (d, 1H), 7.92 (d, 1H), 7.88 (d, 1H), 7.79 (t, 1H), 7.54 (d, 1H), 7.38 (ddd, 1H), 6.39 (s, 1H), 2.26 (s, 3H).

LC/MS (Method 7, ESIpos): $R_t$=1.30 min, m/z=554/556 [M+H]⁺.

Example 107

N-{2,4-Dimethyl-5-[6-(pyridin-3-yl)-1H-imidazo[1,2-b]pyrazol-1-yl]phenyl}-3-fluoro-5-(pentafluoro-λ⁶-sulphanyl)benzamide

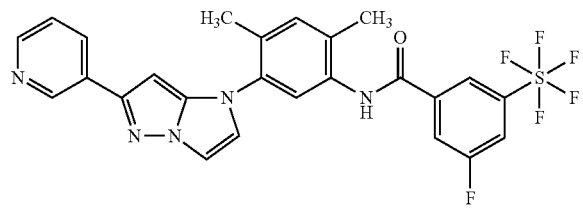 [SMILES: Cc1cc(C)c(-n2ccn3nc(-c4cccnc4)cc23)cc1NC(=O)c1cc(F)cc(S(F)(F)(F)(F)F)c1]

Analogously to the process described in Example 26, 100 mg (0.330 mmol) of the compound of Example 11A and 88 mg (0.330 mmol) of 3-fluoro-5-(pentafluoro-λ⁶-sulphanyl) benzoic acid (JRD Fluorochemicals Ltd., United Kingdom) gave 103 mg (56% of theory) of the title compound. In this case, the reaction time was 1 h. Here, final neutralization using a bicarbonate cartridge could be dispensed with since, after HPLC purification, the product had already been obtained as the free base.

¹H NMR (400 MHz, DMSO-d₆, δ/ppm): 10.36 (s, 1H), 9.05 (d, 1H), 8.49 (dd, 1H), 8.30 (s, 1H), 8.25 (dt, 1H), 8.22-8.15 (m, 2H), 7.90 (d, 1H), 7.50-7.49 (m, 2H), 7.44 (dd, 1H), 7.40 (s, 1H), 6.32 (s, 1H), 2.30 (s, 3H), 2.26 (s, 3H).

LC/MS (Method 5, ESIpos): $R_t$=1.22 min, m/z=563 [M+H]⁺.

Example 108

3-Chloro-N-{2,4-dimethyl-5-[6-(pyridin-3-yl)-1H-imidazo[1,2-b]pyrazol-1-yl]phenyl}-5-(pentafluoro-λ⁶-sulphanyl)benzamide

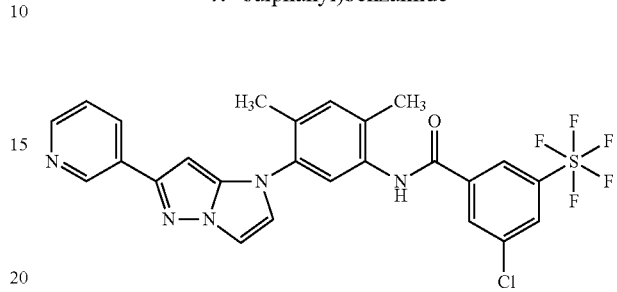

Analogously to the process described in Example 107, 90 mg (0.297 mmol) of the compound of Example 11A and 84 mg (0.297 mmol) of the compound of Example 33A gave 119 mg (70% of theory) of the title compound.

¹H NMR (400 MHz, DMSO-d₆, δ/ppm): 10.38 (s, 1H), 9.05 (d, 1H), 8.49 (dd, 1H), 8.38-8.35 (m, 3H), 8.19 (dt, 1H), 7.90 (d, 1H), 7.51-7.49 (m, 2H), 7.43 (dd, 1H), 7.40 (s, 1H), 6.31 (s, 1H), 2.30 (s, 3H), 2.26 (s, 3H).

LC/MS (Method 3, ESIpos): $R_t$=1.10 min, m/z=568/570 [M+H]⁺.

Example 109

3-Bromo-N-{2,4-dimethyl-5-[6-(pyridin-3-yl)-1H-imidazo[1,2-b]pyrazol-1-yl]phenyl}-5-(pentafluoro-λ⁶-sulphanyl)benzamide

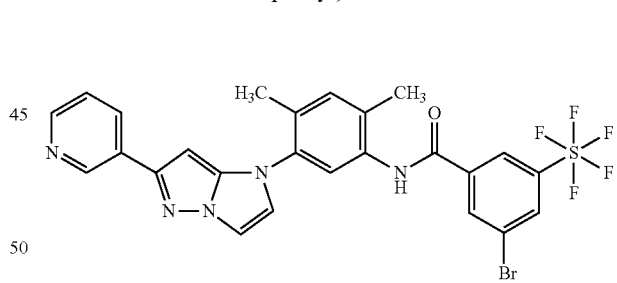

Analogously to the process described in Example 89, 1.75 g (5.77 mmol) of the compound of Example 11A and 1.89 g (5.77 mmol) of the compound of Example 15A gave 3.02 g (85% of theory) of the title compound. Here, the product obtained after chromatographic purification was finally triturated with pentane/dichloromethane 10:1.

¹H NMR (400 MHz, DMSO-d₆, δ/ppm): 10.38 (s, 1H), 9.04 (s, 1H), 8.50-8.47 (m, 2H), 8.44 (s, 1H), 8.41 (s, 1H), 8.17 (d, 1H), 7.90 (d, 1H), 7.51-7.48 (m, 2H), 7.41 (d, 1H), 7.39 (s, 1H), 6.31 (s, 1H), 2.30 (s, 3H), 2.26 (s, 3H).

Example 110

3-({2,4-Dimethyl-5-[6-(pyridin-3-yl)-1H-imidazo[1,2-b]pyrazol-1-yl]phenyl}carbamoyl)-5-(pentafluoro-λ⁶-sulphanyl)benzoic acid

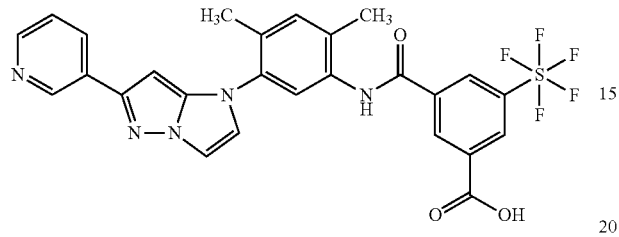

100 mg (0.142 mmol, 80% pure) of the compound from Example 77A were dissolved in 2 ml of DMSO, and a solution of 48 mg (0.350 mmol) of sodium dihydrogenphosphate hydrate in 0.7 ml of water was added at RT. A solution of 39 mg (0.342 mmol) of sodium chlorite in 0.3 ml of water was then added dropwise. The reaction mixture was stirred at RT for 24 h and then diluted with 100 ml of water and extracted three times with in each case about 100 ml of ethyl acetate. The combined organic extracts were washed with saturated sodium chloride solution, dried over anhydrous magnesium sulphate, filtered and freed from the solvent on a rotary evaporator. The crude product obtained in this manner was purified by preparative HPLC (Method 32). After evaporation of the product fractions, the residue was stirred in a mixture of 2 ml of pentane, 0.5 ml of dichloromethane and 0.5 ml of diisopropyl ether for 10 min. Filtration with suction and drying of the solid under high vacuum gave 43 mg (52% of theory) of the title compound.

$^1$H NMR (400 MHz, DMSO-d$_6$, δ/ppm): 14.04 (broad, 1H), 10.53 (s, 1H), 9.04 (s, 1H), 8.82 (s, 1H), 8.66 (s, 1H), 8.49-8.46 (m, 2H), 8.18 (dt, 1H), 7.90 (d, 1H), 7.50-7.49 (m, 2H), 7.41 (dd, 1H), 7.40 (s, 1H), 6.32 (s, 1H), 2.30 (s, 3H), 2.26 (s, 3H).

LC/MS (Method 3, ESIpos): R$_t$=1.01 min, m/z=578 [M+H]$^+$.

Example 111

N-{2,4-Dimethyl-5-[6-(pyridin-3-yl)-1H-imidazo[1,2-b]pyrazol-1-yl]phenyl}-3-methyl-5-(pentafluoro-λ⁶-sulphanyl)benzamide

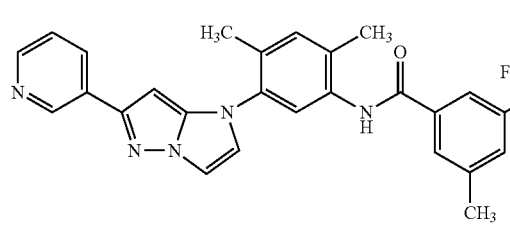

Analogously to the process described in Example 107, 100 mg (0.330 mmol) of the compound of Example 11A and 86 mg (0.330 mmol) of the compound of Example 34A gave 105 mg (58% of theory) of the title compound.

$^1$H NMR (400 MHz, DMSO-d$_6$, δ/ppm): 10.27 (s, 1H), 9.05 (d, 1H), 8.49 (dd, 1H), 8.22 (s, 1H), 8.20 (dt, 1H), 8.11 (s, 1H), 8.00 (s, 1H), 7.90 (d, 1H), 7.49 (d, 1H), 7.48 (s, 1H), 7.43 (dd, 1H), 7.39 (s, 1H), 6.32 (s, 1H), 2.29 (s, 3H), 2.26 (s, 3H).

LC/MS (Method 3, ESIpos): R$_t$=1.17 min, m/z=548 [M+H]$^+$.

Example 112

N-{2,4-Dimethyl-5-[6-(pyridin-3-yl)-1H-imidazo[1,2-b]pyrazol-1-yl]phenyl}-3-(methoxymethyl)-5-(pentafluoro-λ⁶-sulphanyl)benzamide

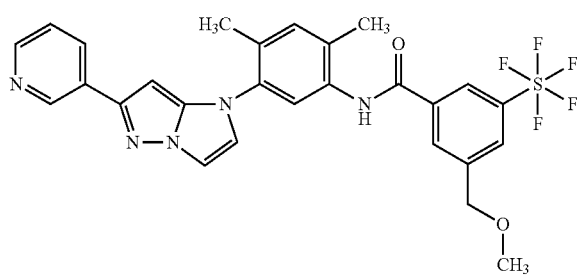 [SMILES: COCc1cc(C(=O)Nc2cc(-n3ccn4nc(-c5cccnc5)cc34)c(C)cc2C)cc(S(F)(F)(F)(F)F)c1]

75 mg (0.198 mmol) of HATU, 24 mg (0.198 mmol) of 4-N,N-dimethylaminopyridine (DMAP) and 50 mg (0.165 mmol) of the compound of Example 11A were added to a solution of 51 mg (0.173 mmol) of the compound of Example 74A in 1 ml of anhydrous DMF. The reaction mixture was stirred at RT for 1 h, then diluted with about 2 ml of methanol and subsequently directly separated into its components by preparative HPLC (Method 32). Evaporation of the product fractions and drying of the residue under high vacuum gave 60 mg (63% of theory) of the title compound.

$^1$H NMR (400 MHz, DMSO-d$_6$, δ/ppm): 10.36 (s, 1H), 9.06 (s, 1H), 8.50 (d, 1H), 8.36 (s, 1H), 8.24 (d, 1H), 8.22 (d, 1H), 8.06 (s, 1H), 7.90 (s, 1H), 7.50-7.48 (m, 2H), 7.45 (dd, 1H), 7.39 (s, 1H), 6.33 (s, 1H), 4.62 (s, 2H), 3.38 (s, 3H), 2.30 (s, 3H), 2.26 (s, 3H).

LC/MS (Method 3, ESIpos): R$_t$=1.06 min, m/z=578 [M+H]$^+$.

Example 113

3-Bromo-5-tert-butyl-N-{2,4-dimethyl-5-[6-(pyridin-3-yl)-1H-imidazo[1,2-b]pyrazol-1-yl]phenyl}benzamide

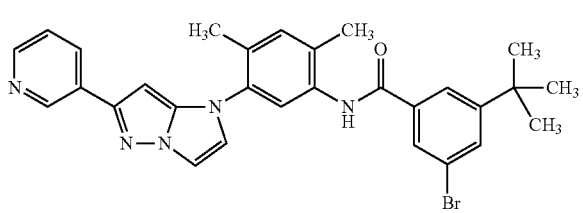

250 mg (0.82 mmol) of the compound of Example 11A and 212 mg (0.82 mmol) of 3-bromo-5-tert-butylbenzoic acid were reacted and worked up analogously to Example 77. The crude product obtained in this manner was purified by single chromatography on a Biotage system (25 g Snap column; mobile phase gradient ethyl acetate/hexane, starting with 70% ethyl acetate, then increasing rapidly to 100% ethyl acetate). This gave 352 mg (71% of theory) of the title compound.

$^1$H NMR (400 MHz, DMSO-$d_6$, δ/ppm): 10.05 (s, 1H), 9.00 (d, 1H), 8.44 (dd, 1H), 8.14 (dt, 1H), 7.91-7.97 (m, 2H), 7.85 (d, 1H), 7.74 (t, 1H), 7.28-7.46 (m, 4H), 6.26 (s, 1H), 2.25 (s, 3H), 2.21 (s, 3H), 1.29 (s, 9H).

LC/MS (Method 7, ESIpos): $R_t$=1.36 min, m/z=542/544 [M+H]$^+$.

Example 114

3-tert-Butyl-5-cyano-N-{2,4-dimethyl-5-[6-(pyridin-3-yl)-1H-imidazo[1,2-b]pyrazol-1-yl]phenyl}-benzamide

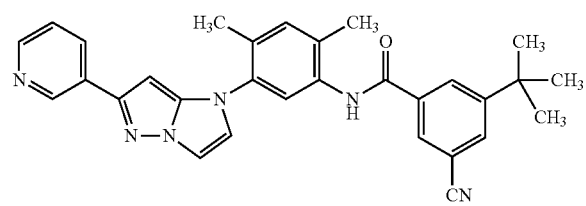 [SMILES: Cc1cc(C)c(-n2ccn3nc(-c4cccnc4)cc23)cc1NC(=O)c1cc(C#N)cc(C(C)(C)C)c1]

Analogously to Example 79, 347 mg (0.64 mmol) of the compound of Example 113 gave a crude product which was purified by preparative HPLC (Method 16). This gave 82 mg (26% of theory) of the title compound.

$^1$H NMR (400 MHz, DMSO-$d_6$, δ/ppm): 10.11 (s, 1H), 9.03 (d, 1H), 8.48 (dd, 1H), 8.18-8.24 (m, 3H), 8.06 (t, 1H), 7.86 (d, 1H), 7.42-7.49 (m, 3H), 7.35 (s, 1H), 6.29 (s, 1H), 2.28 (s, 3H), 2.22 (s, 3H), 1.31 (s, 9H).

LC/MS (Method 7, ESIpos): $R_t$=1.20 min, m/z=489 [M+H]$^+$.

Example 115

2-tert-Butyl-6-chloro-N-{2,4-dimethyl-5-[6-(pyridin-3-yl)-1H-imidazo[1,2-b]pyrazol-1-yl]-phenyl}isonicotinamide

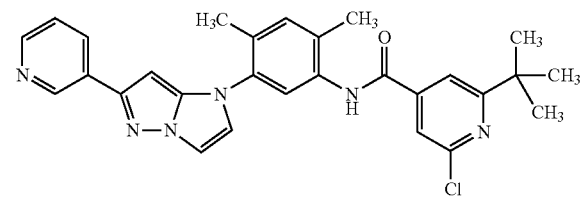 [SMILES: Cc1cc(C)c(-n2ccn3nc(-c4cccnc4)cc23)cc1NC(=O)c1cc(Cl)nc(C(C)(C)C)c1]

250 mg (0.82 mmol) of the compound of Example 11A and 176 mg (0.82 mmol) of 2-tert-butyl-6-chloro-4-pyridinecarboxylic acid were reacted and worked up analogously to Example 77. The crude product obtained in this manner was purified by single chromatography on a Biotage system (25 g Snap column; mobile phase gradient ethyl acetate/hexane, starting with 70% ethyl acetate, then increasing rapidly to 100% ethyl acetate). This gave 341 mg (71% of theory) of the title compound.

$^1$H NMR (400 MHz, DMSO-$d_6$, δ/ppm): 10.27 (s, 1H), 9.00 (d, 1H), 8.44 (dd, 1H), 8.13 (dt, 1H), 7.81-7.87 (m, 2H), 7.77 (s, 1H), 7.42-7.48 (m, 2H), 7.32-7.41 (m, 2H), 6.26 (s, 1H), 2.26 (s, 3H), 2.22 (s, 3H), 1.31 (s, 9H).

LC/MS (Method 7, ESIpos): $R_t$=1.28 min, m/z=499 [M+H]$^+$.

Example 116

2-tert-Butyl-6-cyano-N-{2,4-dimethyl-5-[6-(pyridin-3-yl)-1H-imidazo[1,2-b]pyrazol-1-yl]phenyl}-isonicotinamide

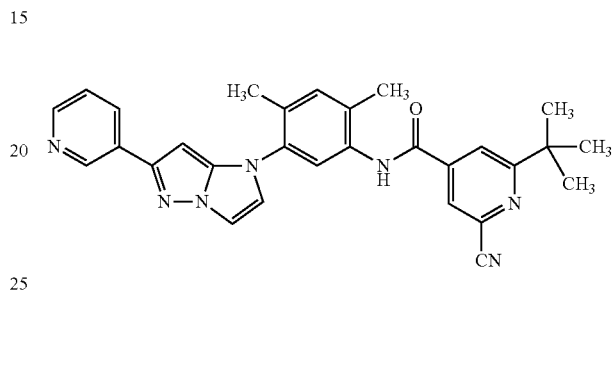

Analogously to Example 79, 337 mg (0.68 mmol) of the compound of Example 115 gave a crude product which was purified by preparative HPLC (Method 16). This gave 105 mg (32% of theory) of the title compound.

$^1$H NMR (400 MHz, DMSO-$d_6$, δ/ppm): 10.33 (s, 1H), 9.01 (d, 1H), 8.45 (dd, 1H), 8.28 (d, 1H), 8.13-8.19 (m, 2H), 7.86 (d, 1H), 7.49 (s, 1H), 7.45 (d, 1H), 7.40 (dd, 1H), 7.37 (s, 1H), 6.26 (s, 1H), 2.28 (s, 3H), 2.23 (s, 3H), 1.34 (s, 9H).

LC/MS (Method 7, ESIpos): $R_t$=1.20 min, m/z=490 [M+H]$^+$.

Example 117

3-Bromo-5-tert-butyl-N-{2-fluoro-4-methyl-5-[6-(pyridin-3-yl)-1H-imidazo[1,2-b]pyrazol-1-yl]-phenyl}benzamide

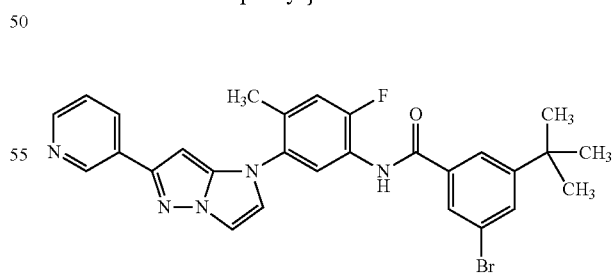

Analogously to Example 50, 235 mg (0.77 mmol) of the compound of Example 12A and 197 mg (0.77 mmol) of 3-bromo-5-tert-butylbenzoic acid gave, after single chromatography on a Biotage system (25 g Snap column; mobile phase gradient hexane/70-100% ethyl acetate), 180 mg (66% pure, 29% of theory) of the title compound.

LC/MS (Method 7, ESIpos): $R_t$=1.37 min, m/z=546/548 [M+H]$^+$.

Example 118

3-tert-Butyl-5-cyano-N-{2-fluoro-4-methyl-5-[6-(pyridin-3-yl)-1H-imidazo[1,2-b]pyrazol-1-yl]-phenyl}benzamide

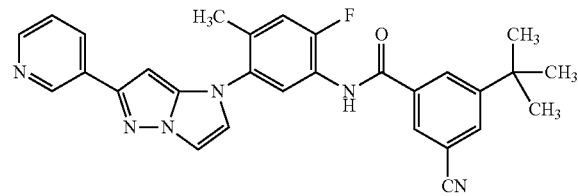 [SMILES: Cc1cc(F)c(NC(=O)c2cc(C#N)cc(C(C)(C)C)c2)cc1-n1ccn2nc(-c3cccnc3)cc12]

Analogously to Example 79, 180 mg (0.33 mmol) of the compound of Example 117 gave, after purification by preparative HPLC (Method 16), 35 mg (22% of theory) of the title compound.

$^1$H NMR (400 MHz, DMSO-d$_6$, δ/ppm): 10.42 (s, 1H), 9.01 (dd, 1H), 8.44 (dd, 1H), 8.20 (dt, 2H), 8.14 (dt, 1H), 8.07 (t, 1H), 7.87 (dd, 1H), 7.76 (d, 1H), 7.42-7.50 (m, 2H), 7.37 (ddd, 1H), 6.30 (d, 1H), 2.24 (s, 3H), 1.31 (s, 9H).

LC/MS (Method 7, ESIpos): $R_t$=1.17 min, m/z=493 [M+H]$^+$.

Example 119

N-{2,4-Dimethyl-3-[6-(pyridin-3-yl)-1H-imidazo[1,2-b]pyrazol-1-yl]phenyl}-3-(pentafluoro-λ$^6$-sulphanyl)benzamide

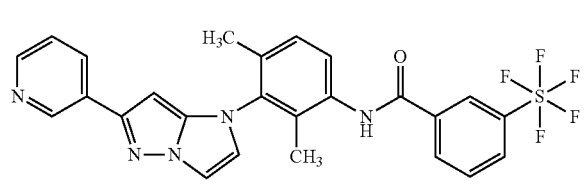 [SMILES: Cc1ccc(NC(=O)c2cccc(S(F)(F)(F)(F)F)c2)c(C)c1-n1ccn2nc(-c3cccnc3)cc12]

Analogously to Example 50, 125 mg (0.41 mmol) of the compound of Example 68A and 102 mg (0.41 mmol) of 3-(pentafluoro-λ$^6$-sulphanyl)benzoic acid gave a crude product which, after the first run on the Biotage system, was purified further by preparative HPLC (Method 16). This gave 90 mg (41% of theory) of the title compound.

$^1$H NMR (400 MHz, DMSO-d$_6$, δ/ppm): 10.37 (s, 1H), 9.01 (d, 1H), 8.44 (dd, 1H), 8.41 (s, 1H), 8.27 (d, 1H), 8.09-8.19 (m, 2H), 7.89 (d, 1H), 7.78 (t, 1H), 7.43 (d, 1H), 7.29-7.40 (m, 3H), 6.13 (s, 1H), 2.07 (s, 3H), 1.91 (s, 3H).

LC/MS (Method 7, ESIpos): $R_t$=1.13 min, m/z=534 [M+H]$^+$.

Example 120

3-Bromo-N-{2,4-dimethyl-3-[6-(pyridin-3-yl)-1H-imidazo[1,2-b]pyrazol-1-yl]phenyl}-5-(pentafluoro-λ$^6$-sulphanyl)benzamide

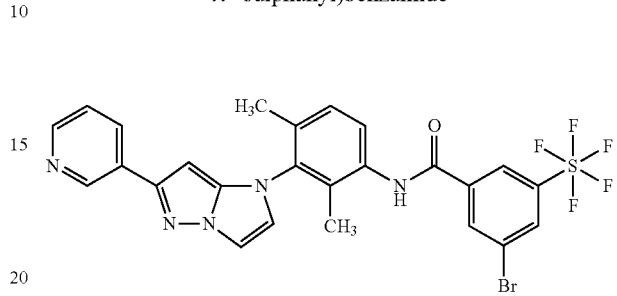

Analogously to Example 50, 370 mg (1.22 mmol) of the compound of Example 68A and 398 mg (1.22 mmol) of the compound of Example 15A gave a crude product which was purified by single chromatography on a Biotage system (25 g Snap column; mobile phase gradient hexane/70-100% ethyl acetate). This gave 573 mg (65% of theory) of the title compound.

$^1$H NMR (400 MHz, DMSO-d$_6$, δ/ppm): 10.41 (s, 1H), 9.00 (dd, 1H), 8.48 (s, 1H), 8.43 (dd, 1H), 8.37-8.41 (m, 2H), 8.14 (dt, 1H), 7.88 (dd, 1H), 7.43 (d, 1H), 7.34-7.40 (m, 2H), 7.32 (d, 1H), 6.12 (s, 1H), 2.65 (s, 6H).

LC/MS (Method 6, ESIpos): $R_t$=1.27 min, m/z=612/614 [M+H]$^+$.

Example 121

3-Cyano-N-{2,4-dimethyl-3-[6-(pyridin-3-yl)-1H-imidazo[1,2-b]pyrazol-1-yl]phenyl}-5-(pentafluoro-λ$^6$-sulphanyl)benzamide

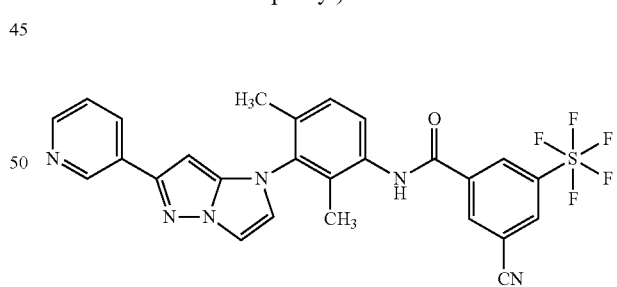

Analogously to Example 79, two separate reactions with 560 mg (0.91 mmol) and 535 mg (0.87 mmol), respectively, of the compound of Example 120 gave, after purification by preparative HPLC (Method 16), 47 mg (4.8% of theory) of the title compound.

$^1$H NMR (400 MHz, DMSO-d$_6$, δ/ppm): 10.48 (s, 1H), 9.00 (d, 1H), 8.82 (s, 1H), 8.71 (s, 1H), 8.65 (s, 1H), 8.43 (dd, 1H), 8.14 (dt, 1H), 7.89 (d, 1H), 7.45 (d, 1H), 7.35-7.41 (m, 2H), 7.33 (d, 1H), 6.13 (s, 1H), 2.07 (s, 3H), 1.93 (s, 3H).

LC/MS (Method 6, ESIpos): R$_t$=1.14 min, m/z=559 [M+H]$^+$.

Example 122

N-{4-Methyl-3-[6-(pyridin-3-yl)-1H-imidazo[1,2-b]pyrazol-1-yl]phenyl}-3-sulphamoyl-5-(trifluoromethyl)benzamide

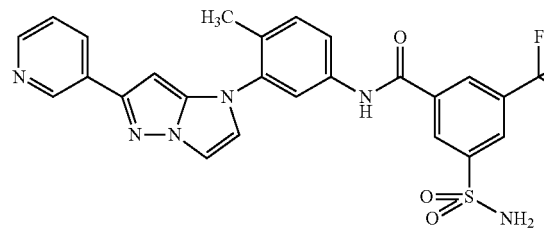

Analogously to Example 90, 150 mg (0.52 mmol) of the compound of Example 6A and 129 mg (0.47 mmol) of 3-sulphamoyl-5-(trifluoromethyl)benzoic acid gave, after 3 h of stirring at 50° C. and HPLC purification (Method 16), 68.5 mg (23% of theory) of the title compound.

$^1$H NMR (400 MHz, DMSO-d$_6$, δ/ppm): 10.83 (s, 1H), 9.08 (d, 1H), 8.63 (s, 1H), 8.51-8.55 (m, 2H), 8.35 (dt, 1H), 8.30 (s, 1H), 7.93 (d, 1H), 7.91 (d, 1H), 7.77 (dd, 1H), 6.42 (s, 1H), 7.69 (s, 2H), 7.53-7.59 (m, 2H), 7.47 (d, 1H), 2.25 (s, 3H).

LC/MS (Method 7, ESIpos): R$_t$=1.27 min, m/z=451 [M+H]$^+$.

Example 123

3-tert-Butyl-N-{4-methyl-3-[6-(pyridin-3-yl)-1H-imidazo[1,2-b]pyrazol-1-yl]phenyl}benzamide

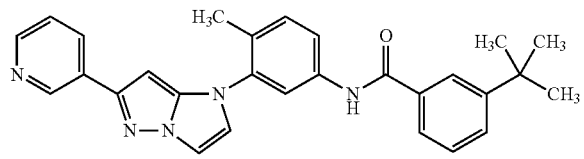

Analogously to Example 90, 200 mg (0.69 mmol) of the compound of Example 6A and 136 mg (0.76 mmol) of 3-tert-butylbenzoic acid gave, after 16 h of stirring at RT and HPLC purification (Method 16), 165 mg (52% of theory) of the title compound.

$^1$H NMR (400 MHz, DMSO-d$_6$, δ/ppm): 10.32 (s, 1H), 9.02 (d, 1H), 8.44 (dd, 1H), 8.15 (dt, 1H), 7.94 (d, 1H), 7.89 (t, 1H), 7.87 (dd, 1H), 7.72-7.79 (m, 2H), 7.58-7.62 (m, 1H), 7.50 (d, 1H), 7.35-7.46 (m, 3H), 6.32 (s, 1H), 2.23 (s, 3H), 1.30 (s, 9H).

LC/MS (Method 7, ESIpos): R$_t$=1.22 min, m/z=450 [M+H]$^+$.

Example 124

3-Methyl-N-{4-methyl-3-[6-(pyridin-3-yl)-1H-imidazo[1,2-b]pyrazol-1-yl]phenyl}-5-sulphamoyl-benzamide

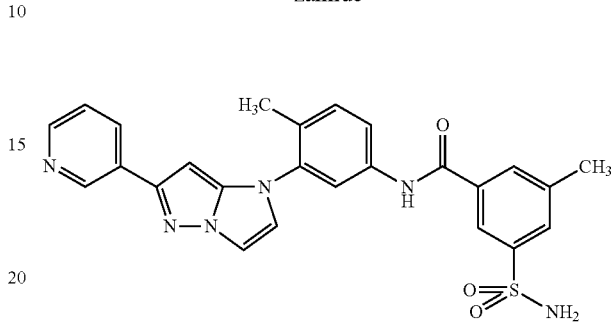

Analogously to Example 90, 150 mg (0.52 mmol) of the compound of Example 6A and 123 mg (0.57 mmol) of 3-methyl-5-sulphamoylbenzoic acid gave, after 3 h of stirring at RT and HPLC purification (Method 16), 92.7 mg (35% of theory) of the title compound.

$^1$H NMR (400 MHz, DMSO-d$_6$, δ/ppm): 10.59 (s, 1H), 9.08 (d, 1H), 8.53 (dd, 1H), 8.36 (dt, 1H), 8.15 (s, 1H), 7.97 (s, 1H), 7.95 (d, 1H), 7.91 (d, 1H), 7.82 (s, 1H), 7.77 (dd, 1H), 7.52-7.59 (m, 2H), 7.39-7.47 (m, 3H), 6.42 (s, 1H), 2.24 (s, 3H) [further signal hidden in the solvent peak].

LC/MS (Method 7, ESIpos): R$_t$=0.85 min, m/z=487 [M+H]$^+$.

Example 125

4-tert-Butyl-N-{4-methyl-3-[6-(pyridin-3-yl)-1H-imidazo[1,2-b]pyrazol-1-yl]phenyl}pyridine-2-carboxamide

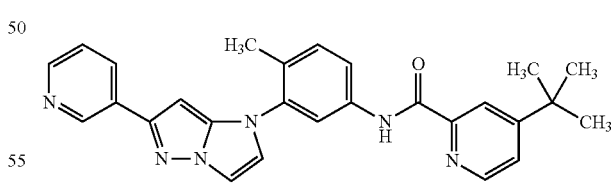

Analogously to Example 90, 200 mg (0.691 mmol) of the compound of Example 6A and 119 mg (0.63 mmol) of 4-tert-butylpyridine-2-carboxylic acid gave, after 3 h of stirring at 50° C. and HPLC purification (Method 16), 172 mg (54% of theory) of the title compound.

$^1$H NMR (400 MHz, DMSO-d$_6$, δ/ppm): 10.82 (s, 1H), 9.02 (d, 1H), 8.61 (d, 1H), 8.45 (dd, 1H), 8.16 (dt, 1H), 8.10 (t, 2H), 7.86-7.94 (m, 2H), 7.67 (dd, 1H), 7.51 (d, 1H), 7.35-7.44 (m, 2H), 6.35 (s, 1H), 2.24 (s, 3H), 1.30 (s, 9H).

LC/MS (Method 7, ESIpos): R$_t$=1.22 min, m/z=451 [M+H]$^+$.

Example 126

N-{2,4-Dimethyl-5-[6-(pyridin-3-yl)-1H-imidazo[1,2-b]pyrazol-1-yl]phenyl}-3-[(trifluoromethyl)-sulphanyl]benzamide

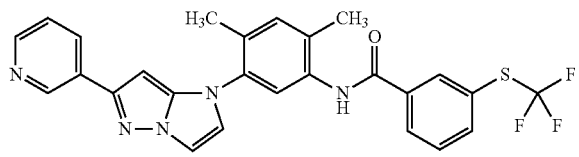 [SMILES: Cc1cc(C)c(-n2ccn3nc(-c4cccnc4)cc23)cc1NC(=O)c1cccc(SC(F)(F)F)c1]

80 mg (0.264 mmol) of the compound of Example 11A and 62 mg (0.277 mmol) of 3-[(trifluoromethyl)sulphanyl]benzoic acid were dissolved in 2 ml of DMF, and 120 mg (0.316 mmol) of HATU and 60 µl (0.343 mmol) of N,N-diisopropylethylamine were added in succession. After about 16 h of stirring at RT, the reaction mixture was diluted with 1 ml of acetonitrile and separated into its components by preparative HPLC (Method 36). Pooling of the product fractions, evaporation and drying under high vacuum gave 89 mg (95% pure, 63% of theory) of the title compound.

$^1$H NMR (400 MHz, DMSO-d$_6$, δ/ppm): 10.18 (s, 1H), 9.06 (s, 1H), 8.50 (d, 1H), 8.29 (s, 1H), 8.23-8.19 (m, 2H), 7.96 (d, 1H), 7.90 (d, 1H), 7.73 (t, 1H), 7.51 (s, 1H), 7.49 (d, 1H), 7.45 (dd, 1H), 7.38 (s, 1H), 6.32 (s, 1H), 2.31 (s, 3H), 2.26 (s, 3H).

LC/MS (Method 3, ESIpos): R$_t$=1.05 min, m/z=508 [M+H]$^+$.

Example 127

N-{2,4-Dimethyl-5-[6-(pyridin-3-yl)-1H-imidazo[1,2-b]pyrazol-1-yl]phenyl}-3-(trifluoromethoxy)benzamide

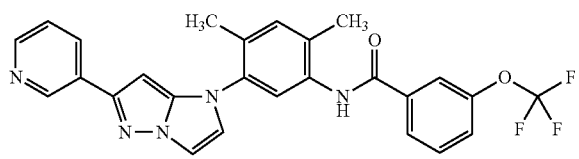 [SMILES: Cc1cc(C)c(-n2ccn3nc(-c4cccnc4)cc23)cc1NC(=O)c1cccc(OC(F)(F)F)c1]

Analogously to the process described in Example 126, 80 mg (0.264 mmol) of the compound of Example 11A and 57 mg (0.277 mmol) of 3-(trifluoromethoxy)benzoic acid gave 85 mg (65% of theory) of the title compound.

$^1$H NMR (400 MHz, DMSO-d$_6$, δ/ppm): 10.14 (s, 1H), 9.05 (d, 1H), 8.49 (dd, 1H), 8.20 (dt, 1H), 8.04 (d, 1H), 7.91 (s, 1H), 7.89 (d, 1H), 7.70 (t, 1H), 7.62 (d, 1H), 7.50 (s, 1H), 7.48 (d, 1H), 7.43 (dd, 1H), 6.38 (s, 1H), 6.32 (s, 1H), 2.31 (s, 3H), 2.25 (s, 3H).

LC/MS (Method 3, ESIpos): R$_t$=1.02 min, m/z=492 [M+H]$^+$.

Example 128

N-{2,4-Dimethyl-5-[6-(pyridin-3-yl)-1H-imidazo[1,2-b]pyrazol-1-yl]phenyl}-3-(difluoromethoxy)-benzamide

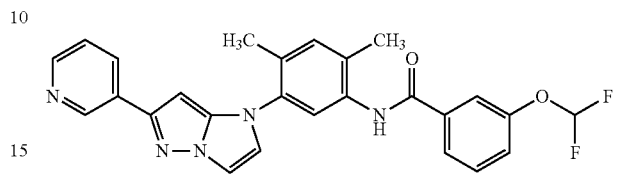

Analogously to the process described in Example 126, 80 mg (0.264 mmol) of the compound of Example 11A and 52 mg (0.277 mmol) of 3-(difluoromethoxy)benzoic acid gave 106 mg (84% of theory) of the title compound.

$^1$H NMR (400 MHz, DMSO-d$_6$, δ/ppm): 10.07 (s, 1H), 9.05 (d, 1H), 8.49 (dd, 1H), 8.21 (dt, 1H), 7.89 (d, 1H), 7.87 (d, 1H), 7.75 (s, 1H), 7.61 (t, 1H), 7.51-7.33 (m, 6H), 6.31 (s, 1H), 2.30 (s, 3H), 2.25 (s, 3H).

LC/MS (Method 3, ESIpos): R$_t$=0.93 min, m/z=474 [M+H]$^+$.

Example 129

N-{2,4-Dimethyl-5-[6-(pyridin-3-yl)-1H-imidazo[1,2-b]pyrazol-1-yl]phenyl}-3-(1,1,2,2-tetra-fluoroethoxy)benzamide

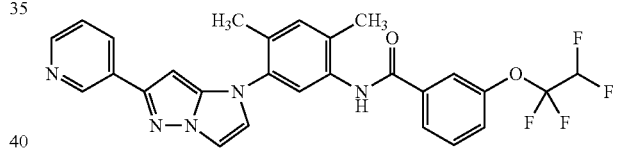

Analogously to the process described in Example 126, 80 mg (0.264 mmol) of the compound of Example 11A and 66 mg (0.277 mmol) of 3-(1,1,2,2-tetrafluoroethoxy)benzoic acid gave 87 mg (63% of theory) of the title compound.

$^1$H NMR (400 MHz, DMSO-d$_6$, δ/ppm): 10.14 (s, 1H), 9.06 (s, 1H), 8.50 (d, 1H), 8.23 (d, 1H), 8.00 (d, 1H), 7.89 (d, 1H), 7.86 (s, 1H), 7.66 (t, 1H), 7.53 (d, 1H), 7.50-7.45 (m, 3H), 7.38 (s, 1H), 6.86 (t, 1H), 6.33 (s, 1H), 2.30 (s, 3H), 2.25 (s, 3H).

LC/MS (Method 3, ESIpos): R$_t$=1.01 min, m/z=524 [M+H]$^+$.

Example 130

N-{2,4-Dimethyl-5-[6-(pyridin-3-yl)-1H-imidazo[1,2-b]pyrazol-1-yl]phenyl}-3-(2,2,2-trifluoroethoxy)benzamide

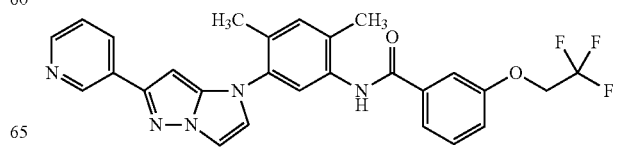

Analogously to the process described in Example 126, 80 mg (0.264 mmol) of the compound of Example 11A and 61 mg (0.277 mmol) of 3-(2,2,2-trifluoroethoxy)benzoic acid gave 95 mg (71% of theory) of the title compound.

$^1$H NMR (400 MHz, DMSO-$d_6$, δ/ppm): 9.96 (s, 1H), 9.07 (d, 1H), 8.50 (dd, 1H), 8.23 (dt, 1H), 7.89 (d, 1H), 7.67-7.64 (m, 2H), 7.53-7.45 (m, 4H), 7.37 (s, 1H), 7.30 (dd, 1H), 6.31 (s, 1H), 4.85 (quart, 2H), 2.30 (s, 3H), 2.25 (s, 3H).

LC/MS (Method 3, ESIpos): $R_t$=0.99 min, m/z=506 [M+H]$^+$.

Example 131

N-{2,4-Dimethyl-5-[6-(pyridin-3-yl)-1H-imidazo[1,2-b]pyrazol-1-yl]phenyl}-3-methoxybenzamide

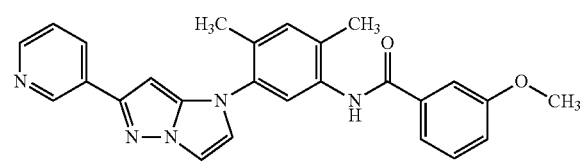 [SMILES: COc1cccc(C(=O)Nc2cc(-n3ccn4nc(-c5cccnc5)cc34)c(C)cc2C)c1]

Analogously to the process described in Example 126, 80 mg (0.264 mmol) of the compound of Example 11A and 42 mg (0.277 mmol) of 3-methoxybenzoic acid gave 83 mg (71% of theory) of the title compound.

$^1$H NMR (400 MHz, DMSO-$d_6$, δ/ppm): 9.93 (s, 1H), 9.10 (d, 1H), 8.56 (d, 1H), 8.37 (d, 1H), 7.90 (d, 1H), 7.60-7.55 (m, 2H), 7.52-7.50 (m, 3H), 7.45 (t, 1H), 7.37 (s, 1H), 7.16 (dd, 1H), 6.37 (s, 1H), 3.83 (s, 3H), 2.30 (s, 3H), 2.25 (s, 3H).

LC/MS (Method 3, ESIpos): $R_t$=0.88 min, m/z=438 [M+H]$^+$.

Example 132

N-{2,4-Dimethyl-5-[6-(pyridin-3-yl)-1H-imidazo[1,2-b]pyrazol-1-yl]phenyl}-3-isopropoxy-benzamide

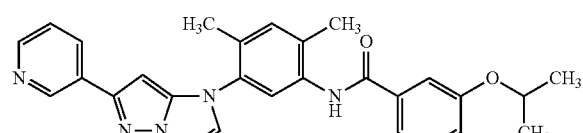

Analogously to the process described in Example 126, 80 mg (0.264 mmol) of the compound of Example 11A and 50 mg (0.277 mmol) of 3-isopropoxybenzoic acid gave 88 mg (71% of theory) of the title compound.

$^1$H NMR (400 MHz, DMSO-$d_6$, δ/ppm): 9.90 (s, 1H), 9.05 (d, 1H), 8.50 (d, 1H), 8.22 (d, 1H), 7.89 (d, 1H), 7.53-7.43 (m, 5H), 7.42 (t, 1H), 7.36 (s, 1H), 7.14 (dd, 1H), 6.31 (s, 1H), 4.70 (sept, 1H), 2.30 (s, 3H), 2.24 (s, 3H), 1.29 (d, 6H).

LC/MS (Method 3, ESIpos): $R_t$=0.99 min, m/z=466 [M+H]$^+$.

Example 133

N-{2,4-Dimethyl-5-[6-(pyridin-3-yl)-1H-imidazo[1,2-b]pyrazol-1-yl]phenyl}-3-isobutoxy-benzamide

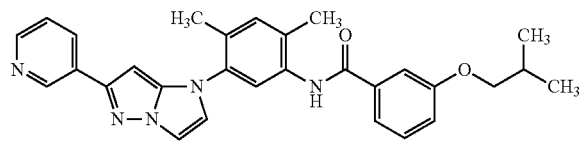 [SMILES: Cc1cc(C)c(-n2ccn3nc(-c4cccnc4)cc23)cc1NC(=O)c1cccc(OCC(C)C)c1]

Analogously to the process described in Example 126, 80 mg (0.264 mmol) of the compound of Example 11A and 54 mg (0.277 mmol) of 3-isobutoxybenzoic acid gave 84 mg (66% of theory) of the title compound.

$^1$H NMR (400 MHz, DMSO-$d_6$, δ/ppm): 9.93 (s, 1H), 9.05 (d, 1H), 8.49 (d, 1H), 8.20 (d, 1H), 7.89 (d, 1H), 7.55-7.41 (m, 6H), 7.36 (s, 1H), 7.16 (dd, 1H), 6.30 (s, 1H), 3.82 (d, 1H), 2.29 (s, 3H), 2.25 (s, 3H), 2.04 (m, 1H), 1.00 (d, 6H).

LC/MS (Method 3, ESIpos): $R_t$=1.10 min, m/z=480 [M+H]$^+$.

Example 134

3-tert-Butoxy-N-{2,4-dimethyl-5-[6-(pyridin-3-yl)-1H-imidazo[1,2-b]pyrazol-1-yl]phenyl}-benzamide

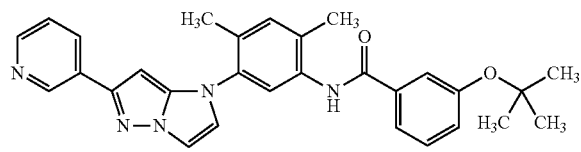 [SMILES: Cc1cc(C)c(-n2ccn3nc(-c4cccnc4)cc23)cc1NC(=O)c1cccc(OC(C)(C)C)c1]

Analogously to the process described in Example 126, 100 mg (0.330 mmol) of the compound of Example 11A and 74 mg (0.363 mmol, content 95%) of 3-tert-butoxybenzoic acid gave 131 mg (83% of theory) of the title compound.

$^1$H NMR (400 MHz, DMSO-$d_6$, δ/ppm): 9.93 (s, 1H), 9.04 (d, 1H), 8.48 (d, 1H), 8.19 (d, 1H), 7.88 (d, 1H), 7.69 (d, 1H), 7.54-7.36 (m, 6H), 7.21 (d, 1H), 6.29 (s, 1H), 2.30 (s, 3H), 2.24 (s, 3H), 1.34 (s, 9H).

LC/MS (Method 3, ESIpos): $R_t$=1.02 min, m/z=480 [M+H]$^+$.

Example 135

N-{2,4-Dimethyl-5-[6-(pyridin-3-yl)-1H-imidazo[1,2-b]pyrazol-1-yl]phenyl}-3-(2-ethoxyethoxy)-benzamide

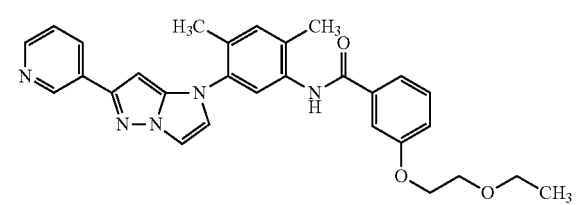 [SMILES: CCOCCOc1cccc(C(=O)Nc2cc(-n3ccn4nc(-c5cccnc5)cc34)c(C)cc2C)c1]

Analogously to the process described in Example 126, 80 mg (0.264 mmol) of the compound of Example 11A and 58 mg (0.277 mmol) of 3-(2-ethoxyethoxy)benzoic acid gave 103 mg (78% of theory) of the title compound.

$^1$H NMR (400 MHz, DMSO-d$_6$, δ/ppm): 9.93 (s, 1H), 9.06 (d, 1H), 8.50 (d, 1H), 8.23 (dt, 1H), 7.89 (d, 1H), 7.59-7.53 (m, 2H), 7.50-7.42 (m, 4H), 7.37 (s, 1H), 7.18 (dd, 1H), 6.32 (s, 1H), 4.16 (dd, 2H), 3.72 (dd, 2H), 3.51 (quart, 2H), 2.30 (s, 3H), 2.25 (s, 3H), 1.13 (t, 3H).

LC/MS (Method 3, ESIpos): R$_t$=0.94 min, m/z=496 [M+H]$^+$.

Example 136

N-{2,4-Dimethyl-5-[6-(pyridin-3-yl)-1H-imidazo[1,2-b]pyrazol-1-yl]phenyl}-3-(2-hydroxy-ethoxy)benzamide

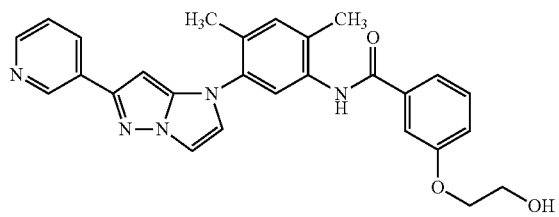 [SMILES: Cc1cc(C)c(-n2ccn3nc(-c4cccnc4)cc23)cc1NC(=O)c1cccc(OCCO)c1]

Analogously to the process described in Example 126, 100 mg (0.330 mmol) of the compound of Example 11A and 63 mg (0.346 mmol) of 3-(2-hydroxyethoxy)benzoic acid gave 82 mg (51% of theory, 97% pure) of the title compound. In this case, for preparative HPLC purification, Method 38 was used.

$^1$H NMR (400 MHz, DMSO-d$_6$, δ/ppm): 9.92 (s, 1H), 9.14 (d, 1H), 8.61 (d, 1H), 8.49 (d, 1H), 7.92 (d, 1H), 7.69 (dd, 1H), 7.56-7.50 (m, 4H), 7.44 (t, 1H), 7.38 (s, 1H), 7.17 (dd, 1H), 6.42 (s, 1H), 4.06 (t, 2H), 3.74 (t, 2H), 2.31 (s, 3H), 2.24 (s, 3H).

LC/MS (Method 3, ESIpos): R$_t$=0.78 min, m/z=486 [M+H]$^+$.

Example 137

3-[2-(Dimethylamino)ethoxy]-N-{2,4-dimethyl-5-[6-(pyridin-3-yl)-1H-imidazo[1,2-b]pyrazol-1-yl]phenyl}benzamide

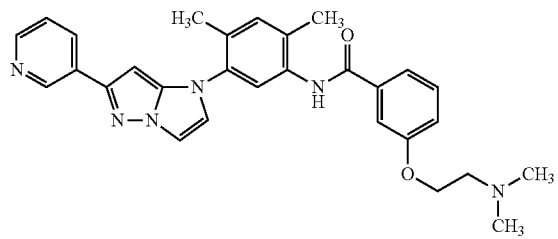 [SMILES: Cc1cc(C)c(-n2ccn3nc(-c4cccnc4)cc23)cc1NC(=O)c1cccc(OCCN(C)C)c1]

Analogously to the process described in Example 126, 80 mg (0.264 mmol) of the compound of Example 11A and 68 mg (0.277 mmol) of the hydrochloride of 3-[2-(dimethylamino)-ethoxy]benzoic acid [lit.: U.S. Pat. No. 6,069,149, Production Example 8] gave 72 mg (55% of theory) of the title compound. In deviation from Example 126, here 2.5 equivalents (115 μl, 0.659 mmol) of N,N-diisopropylethylamine were employed. After preparative HPLC purification, the title compound was initially isolated as formic acid salt. The base was liberated by dissolving the formate in a small amount of methanol and followed by percolation through a bicarbonate cartridge (from Polymerlabs, Stratospheres SPE, PL-HCO$_3$ MP SPE, capacity 0.9 mmol). Evaporation of the percolate and drying of the residue under high vacuum gave the title compound in the amount mentioned above.

$^1$H NMR (400 MHz, DMSO-d$_6$, δ/ppm): 9.92 (s, 1H), 9.04 (d, 1H), 8.48 (d, 1H), 8.17 (d, 1H), 7.88 (d, 1H), 7.56-7.39 (m, 6H), 7.36 (s, 1H), 7.17 (dd, 1H), 6.29 (s, 1H), 4.12 (t, 2H), 2.64 (t, 2H), 2.30 (s, 3H), 2.25 (s, 3H), 2.22 (s, 6H).

LC/MS (Method 3, ESIpos): R$_t$=0.69 min, m/z=495 [M+H]$^+$.

Example 138

3-(4,4-Difluoropiperidin-1-yl)-N-{2,4-dimethyl-5-[6-(pyridin-3-yl)-1H-imidazo[1,2-b]pyrazol-1-yl]phenyl}benzamide

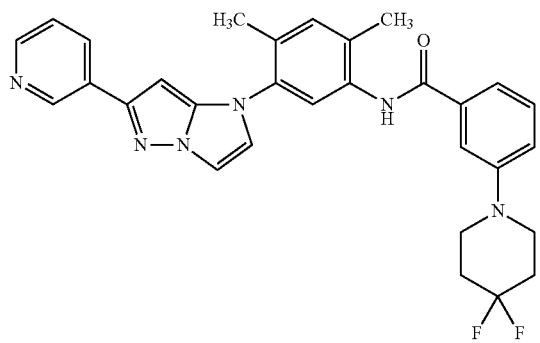 [SMILES: Cc1cc(C)c(-n2ccn3nc(-c4cccnc4)cc23)cc1NC(=O)c1cccc(N2CCC(F)(F)CC2)c1]

Analogously to the process described in Example 126, 100 mg (0.330 mmol) of the compound of Example 11A and 87 mg (0.363 mmol) of the compound of Example 90A gave 110 mg (63% of theory) of the title compound.

$^1$H NMR (400 MHz, DMSO-d$_6$, δ/ppm): 9.88 (s, 1H), 9.05 (d, 1H), 8.49 (dd, 1H), 8.21 (dt, 1H), 7.89 (d, 1H), 7.54 (s, 1H), 7.48-7.35 (m, 6H), 7.23 (d, 1H), 6.30 (s, 1H), 3.41 (m, 4H), 2.30 (s, 3H), 2.25 (s, 3H), 2.07 (m, 4H).

LC/MS (Method 3, ESIpos): R$_t$=1.00 min, m/z=527 [M+H]$^+$.

Example 139

N-{2,4-Dimethyl-5-[6-(pyridin-3-yl)-1H-imidazo[1,2-b]pyrazol-1-yl]phenyl}-3-(1,1,1-trifluoro-2-methylpropan-2-yl)benzamide

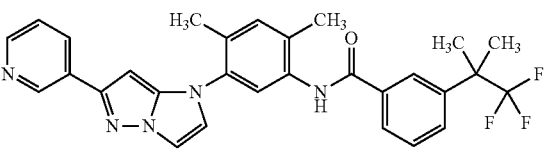 [SMILES: Cc1cc(C)c(-n2ccn3nc(-c4cccnc4)cc23)cc1NC(=O)c1cccc(C(C)(C)C(F)(F)F)c1]

Analogously to the process described in Example 126, 100 mg (0.330 mmol) of the compound of Example 11A and 80 mg (0.346 mmol) of the compound of Example 91A gave 115 mg (64% of theory) of the title compound.

$^1$H NMR (400 MHz, DMSO-d$_6$, δ/ppm): 10.05 (s, 1H), 9.06 (d, 1H), 8.50 (dd, 1H), 8.23 (d, 1H), 8.10 (s, 1H), 7.99 (d, 1H), 7.89 (dd, 1H), 7.78 (d, 1H), 7.57 (t, 1H), 7.50 (s, 1H), 7.49 (d, 1H), 7.45 (dd, 1H), 7.38 (s, 1H), 6.31 (s, 1H), 2.31 (s, 3H), 2.25 (s, 3H), 1.61 (s, 6H).

LC/MS (Method 3, ESIpos): R$_t$=1.05 min, m/z=518 [M+H]$^+$.

Example 140

N-{2,4-Dimethyl-5-[6-(pyridin-3-yl)-1H-imidazo[1,2-b]pyrazol-1-yl]phenyl}-3-(3-methyloxetan-3-yl)benzamide

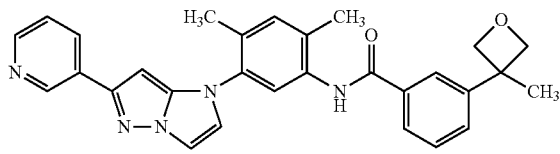 [SMILES: Cc1cc(C)c(-n2ccn3nc(-c4cccnc4)cc23)cc1NC(=O)c1cccc(C2(C)COC2)c1]

In a microwave reaction vessel, 302 mg (1.98 mmol) of 1,8-diazabicyclo[5.4.0]undec-7-ene (DBU) were added to a mixture of 200 mg (0.660 mmol) of the compound of Example 11A, 150 mg (0.660 mmol) of the compound of Example 99A, 209 mg (0.793 mmol) of molybdenum hexacarbonyl, 19 mg (0.066 mmol) of tri-tert-butylphosphonium tetrafluoroborate and 62 mg (0.066 mmol) of trans-bis-(acetato)-bis-[o-(di-o-tolylphosphino)benzyl]dipalladium(II) in 4.5 ml of THF. After addition of the DBU, the reaction vessel was quickly closed with a crimp closure. The mixture was then heated in a microwave oven (Biotage Initiator, with Dynamic Field Tuning) at 140° C. for 30 min. After cooling to RT, about 15 ml of water were added and the reaction mixture was extracted three times with in each case about 15 ml of ethyl acetate. The combined organic extracts were washed with saturated aqueous sodium chloride solution and then dried over magnesium sulphate. After filtration and evaporation of the solvent, the residue that remained was separated into its components by preparative HPLC (Method 33). Since the product fractions were still impure, the preparative HPLC purification was repeated with this fraction using the same method. This gave an impure fraction of 15 mg and a clean fraction consisting of 6 mg (2% of theory) of the title compound.

$^1$H NMR (400 MHz, DMSO-d$_6$, δ/ppm): 9.99 (s, 1H), 9.05 (s, 1H), 8.48 (s, 1H), 8.18 (d, 1H), 7.90-7.82 (m, 3H), 7.54-7.46 (m, 4H), 7.41 (dd, 1H), 7.37 (s, 1H), 6.30 (s, 1H), 4.87 (d, 2H), 4.58 (d, 2H), 2.30 (s, 3H), 2.26 (s, 3H), 1.67 (s, 3H).

LC/MS (Method 3, ESIpos): R$_t$=0.87 min, m/z=478 [M+H]$^+$.

Example 141

N-{2,4-Dimethyl-5-[6-(pyridin-3-yl)-1H-imidazo[1,2-b]pyrazol-1-yl]phenyl}-3-(2-hydroxypropan-2-yl)benzamide

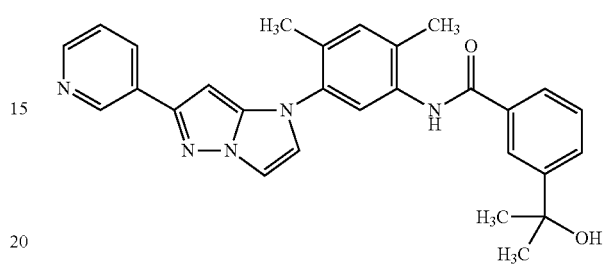

250 mg (0.824 mmol) of the compound of Example 11A and 156 mg (0.865 mmol) of the compound of Example 92A were dissolved in 6.3 ml of DMF, and 376 mg (0.989 mmol) of HATU and 215 µl (1.24 mmol) of N,N-diisopropylethylamine were added in succession. After about 16 h of stirring at RT, the reaction mixture was diluted with about 3 ml of acetonitrile and then, in three portions, separated into its components by preparative HPLC (Method 36). After pooling and evaporation of the product fractions, the residue obtained was dissolved in a small amount of methanol and passed through a bicarbonate cartridge (from Polymerlabs, Stratospheres SPE, PL-HCO$_3$ MP SPE, capacity 0.9 mmol) to prepare the free base from the formate salt from HPLC purification. Since the product obtained in this manner was still impure, it was purified further by MPLC (about 15 g of silica gel, mobile phase: cyclohexane/ethyl acetate/methanol 50:50:0→0:100:0→0:91:9). Evaporation of the product fractions and drying of the residue under high vacuum gave 238 mg (58% of theory, 95% pure) of the title compound.

$^1$H NMR (400 MHz, DMSO-d$_6$, δ/ppm): 9.94 (s, 1H), 9.04 (d, 1H), 8.48 (dd, 1H), 8.18 (dt, 1H), 8.07 (s, 1H), 7.88 (d, 1H), 7.82 (d, 1H), 7.68 (d, 1H), 7.50-7.39 (m, 4H), 7.37 (s, 1H), 6.30 (s, 1H), 5.13 (s, 1H), 2.30 (s, 3H), 2.25 (s, 3H), 1.47 (s, 6H).

LC/MS (Method 3, ESIpos): R$_t$=0.83 min, m/z=466 [M+H]$^+$.

Example 142

N-{2,4-Dimethyl-5-[6-(pyridin-3-yl)-1H-imidazo[1,2-b]pyrazol-1-yl]phenyl}-3-(2-fluoropropan-2-yl)benzamide

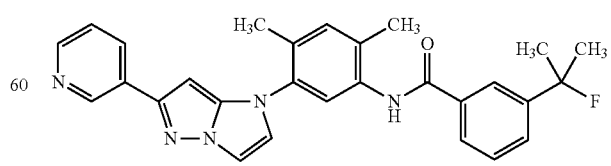

At −78° C., a solution of 34 µl (0.258 mmol) of diethylaminosulphur trifluoride (DAST) in 0.5 ml of anhydrous dichloromethane was added dropwise to a solution of 100 mg (0.215 mmol) of the compound of Example 141 in 4.5 ml of anhydrous dichloromethane. The reaction mixture was stirred at −78° C. for 1 h, about 5 ml of saturated aqueous sodium bicarbonate solution were then added and the mixture was warmed to RT. The mixture was diluted with about 10 ml of water and extracted three times with in each case about 10 ml of dichloromethane. The combined organic extracts were washed once with saturated aqueous sodium chloride solution and dried over magnesium sulphate. After filtration and evaporation, the residue obtained was separated into its components by preparative HPLC (Method 9). Evaporation of the product fractions and drying of the residue under high vacuum gave 40 mg (39% of theory) of the title compound.

$^1$H NMR (400 MHz, DMSO-d$_6$, δ/ppm): 10.02 (s, 1H), 9.04 (d, 1H), 8.48 (dd, 1H), 8.17 (dt, 1H), 8.00 (s, 1H), 7.92 (d, 1H), 7.88 (d, 1H), 7.64 (d, 1H), 7.54 (t, 1H), 7.49 (s, 1H), 7.48 (d, 1H), 7.41 (dd, 1H), 7.37 (s, 1H), 6.29 (s, 1H), 2.30 (s, 3H), 2.25 (s, 3H), 1.70 (d, 6H).

LC/MS (Method 3, ESIpos): R$_t$=0.96 min, m/z=468 [M+H]$^+$.

Example 143

N-{2,4-Dimethyl-5-[6-(pyridin-3-yl)-1H-imidazo[1,2-b]pyrazol-1-yl]phenyl}-3-(pentafluoro-λ$^6$-sulphanyl)-5-(piperidin-1-yl)benzamide

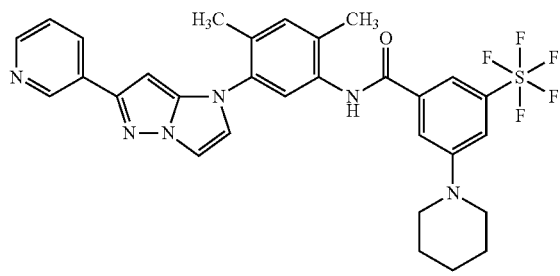 [SMILES: Cc1cc(C)c(-n2ccn3nc(-c4cccnc4)cc23)cc1NC(=O)c1cc(N2CCCCC2)cc(S(F)(F)(F)(F)F)c1]

Analogously to the process described in Example 126, 35 mg (0.115 mmol) of the compound of Example 11A and 40 mg (0.121 mmol) of the compound of Example 93A gave 53 mg (74% of theory) of the title compound.

41 NMR (400 MHz, DMSO-d$_6$, δ/ppm): 10.20 (s, 1H), 9.05 (s, 1H), 8.48 (m, 1H), 8.19 (d, 1H), 7.89 (s, 1H), 7.75 (s, 1H), 7.70 (s, 1H), 7.49-7.39 (m, 5H), 6.30 (s, 1H), 3.32 (m, 4H, partially obscured by the water signal), 2.28 (s, 3H), 2.25 (s, 3H), 1.66-1.55 (m, 6H).

LC/MS (Method 3, ESIpos): R$_t$=1.27 min, m/z=617 [M+H]$^+$.

Example 144

3-(4-Cyanopiperidin-1-yl)-N-{2,4-dimethyl-5-[6-(pyridin-3-yl)-1H-imidazo[1,2-b]pyrazol-1-yl]-phenyl}-5-(pentafluoro-λ$^6$-sulphanyl)benzamide

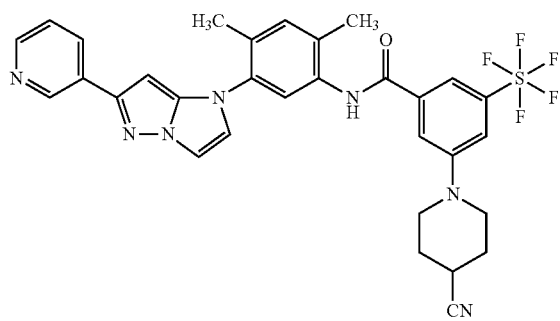 [SMILES: Cc1cc(C)c(-n2ccn3nc(-c4cccnc4)cc23)cc1NC(=O)c1cc(N2CCC(C#N)CC2)cc(S(F)(F)(F)(F)F)c1]

Analogously to the process described in Example 126, 122 mg (0.401 mmol) of the compound of Example 11A and 150 mg (0.421 mmol) of the compound of Example 94A gave 120 mg (44% of theory) of the title compound.

$^1$H NMR (400 MHz, DMSO-d$_6$, δ/ppm): 10.21 (s, 1H), 9.04 (d, 1H), 8.48 (dd, 1H), 8.18 (dt, 1H), 7.90 (d, 1H), 7.77 (s, 1H), 7.75 (s, 1H), 7.55 (t, 1H), 7.48 (d, 1H), 7.46 (s, 1H), 7.41 (dd, 1H), 7.39 (s, 1H), 6.30 (s, 1H), 3.59-3.52 (m, 2H), 3.27-3.20 (m, 2H), 3.13-3.07 (m, 1H), 2.29 (s, 3H), 2.26 (s, 3H), 2.05-1.98 (m, 2H), 1.89-1.80 (m, 2H).

LC/MS (Method 3, ESIpos): R$_t$=1.08 min, m/z=642 [M+H]$^+$.

Example 145

N-{2,4-Dimethyl-5-[6-(pyridin-3-yl)-1H-imidazo[1,2-b]pyrazol-1-yl]phenyl}-3-(4-methoxypiperidin-1-yl)-5-(pentafluoro-λ$^6$-sulphanyl)benzamide

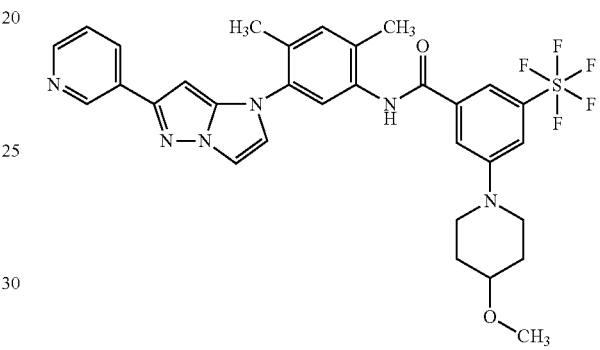

Analogously to the process described in Example 126, 39 mg (0.127 mmol) of the compound of Example 11A and 48 mg (0.133 mmol) of the compound of Example 95A gave 54 mg (66% of theory) of the title compound.

$^1$H NMR (400 MHz, DMSO-d$_6$, δ/ppm): 10.21 (s, 1H), 9.04 (d, 1H), 8.48 (dd, 1H), 8.18 (dt, 1H), 7.89 (d, 1H), 7.76 (s, 1H), 7.71 (s, 1H), 7.50-7.48 (m, 2H), 7.46 (s, 1H), 7.41 (dd, 1H), 7.39 (s, 1H), 6.30 (s, 1H), 3.67-3.61 (m, 2H), 3.44-3.37 (m, 2H), 3.28 (s, 3H), 3.13-3.07 (m, 1H), 2.28 (s, 3H), 2.25 (s, 3H), 1.99-1.92 (m, 2H), 1.59-1.50 (m, 2H).

LC/MS (Method 3, ESIpos): R$_t$=1.14 min, m/z=647 [M+H]$^+$.

Example 146

N-{2,4-Dimethyl-5-[6-(pyridin-3-yl)-1H-imidazo[1,2-b]pyrazol-1-yl]phenyl}-3-(3-methoxyazetidin-1-yl)-5-(pentafluoro-λ$^6$-sulphanyl)benzamide

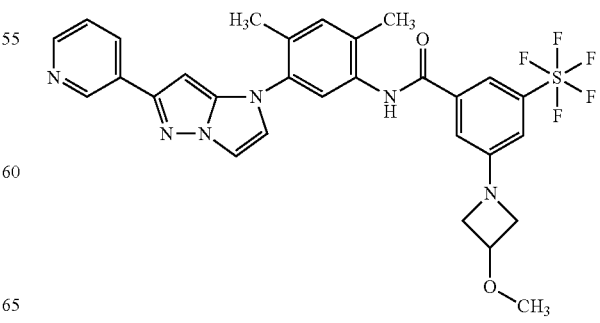

Analogously to the process described in Example 126, 61 mg (0.200 mmol) of the compound of Example 11A and 70 mg (0.210 mmol) of the compound of Example 96A gave 75 mg (61% of theory) of the title compound.

$^1$H NMR (400 MHz, DMSO-d$_6$, δ/ppm): 10.16 (s, 1H), 9.04 (d, 1H), 8.48 (dd, 1H), 8.17 (dt, 1H), 7.88 (d, 1H), 7.66 (s, 1H), 7.47 (d, 1H), 7.45 (s, 1H), 7.41 (dd, 1H), 7.38 (s, 1H), 7.26 (s, 1H), 6.98 (t, 1H), 6.29 (s, 1H), 4.38-4.33 (m, 1H), 4.19 (dd, 2H), 3.78 (dd, 2H), 3.26 (s, 3H), 2.28 (s, 3H), 2.25 (s, 3H).

LC/MS (Method 3, ESIpos): R$_t$=1.09 min, m/z=619 [M+H]$^+$.

Example 147

3-Cyano-N-{2,4-dimethyl-5-[6-(pyridin-3-yl)-1H-imidazo[1,2-b]pyrazol-1-yl]phenyl}-5-(pentafluoro-λ$^6$-sulphanyl)benzamide dihydrochloride

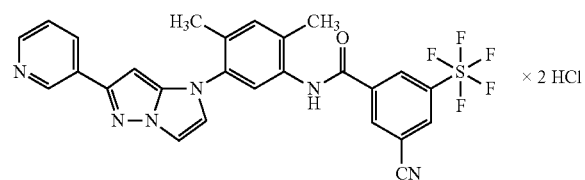

1.0 g (1.79 mmol) of the compound of Example 74 were dissolved in 9 ml of dioxane, and 4.5 ml (17.9 mmol) of a 4 M solution of hydrogen chloride in dioxane were added. After the mixture had been stirred at RT for about 16 h, it was concentrated to dryness on a rotary evaporator. The residue was dried under high vacuum. This gave 1.14 g (100% of theory) of the title compound. By recrystallization from 23 ml of ethanol, 496 mg of this material were converted into a crystalline state.

$^1$H NMR (400 MHz, DMSO-d$_6$, δ/ppm): 10.58 (s, 1H), 9.26 (d, 1H), 8.88 (d, 1H), 8.85 (s, 1H), 8.80 (s, 1H), 8.78 (d, 1H), 8.68 (s, 1H), 8.03 (dd, 1H), 7.98 (d, 1H), 7.60 (d, 1H), 7.54 (s, 1H), 7.42 (s, 1H), 6.62 (s, 1H), 2.33 (s, 3H), 2.26 (s, 3H).

LC/MS (Method 3, ESIpos): R$_t$=1.04 min, m/z=559 [M+H]$^+$.

Example 148

N-{2,4-Dimethyl-5-[6-(pyridin-3-yl)-1H-imidazo[1,2-b]pyrazol-1-yl]phenyl}-3-(2-hydroxypropan-2-yl)-5-(pentafluoro-λ$^6$-sulphanyl)benzamide

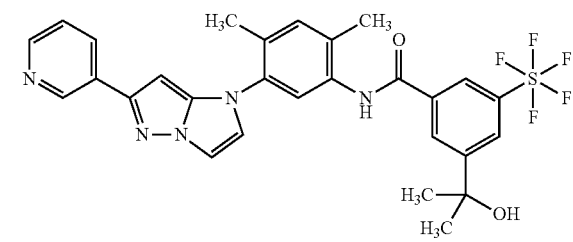 [SMILES: Cc1cc(C)c(-n2ccn3nc(-c4cccnc4)cc23)cc1NC(=O)c1cc(C(C)(C)F)cc(S(F)(F)(F)(F)F)c1]

Analogously to the process described in Example 126, 250 mg (0.824 mmol) of the compound of Example 11A and 252 mg (0.824 mmol) of the compound of Example 19A gave 281 mg (57% of theory) of the title compound. Here, purification of the crude product by preparative HPLC was carried out in two portions. The product fractions were combined, concentrated, taken up in a little methanol and then passed through a bicarbonate cartridge (from Polymerlabs, Stratospheres SPE, PL-HCO$_3$ MP SPE, capacity 0.9 mmol) to prepare the free base from the formate salt obtained in the HPLC purification.

$^1$H NMR (400 MHz, DMSO-d$_6$, δ/ppm): 10.31 (s, 1H), 9.04 (d, 1H), 8.48 (dd, 1H), 8.32 (s, 1H), 8.28 (s, 1H), 8.19-8.16 (m, 2H), 7.89 (d, 1H), 7.49-7.47 (m, 2H), 7.41 (dd, 1H), 7.40 (s, 1H), 7.29 (s, 1H), 5.52 (s, 1H), 2.30 (s, 3H), 2.26 (s, 3H), 1.51 (s, 6H).

LC/MS (Method 3, ESIpos): R$_t$=1.03 min, m/z=592 [M+H]$^+$.

Example 149

N-{2,4-Dimethyl-5-[6-(pyridin-3-yl)-1H-imidazo[1,2-b]pyrazol-1-yl]phenyl}-3-(2-fluoropropan-2-yl)-5-(pentafluoro-λ$^6$-sulphanyl)benzamide

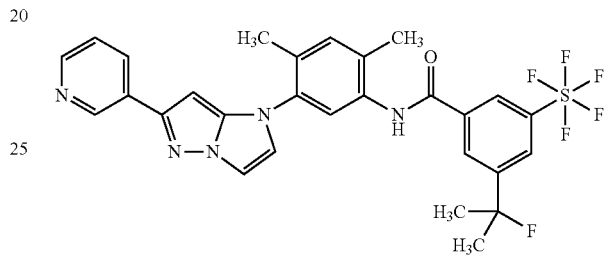

At −78° C., a solution of 27 µl (0.203 mmol) of diethylaminosulphur trifluoride (DAST) in 0.5 ml of anhydrous dichloromethane was added to a solution of 100 mg (0.169 mmol) of the compound of Example 148 in 3.5 ml of anhydrous dichloromethane. After the reaction mixture had been stirred at −78° C. for 1 h, 1 ml of saturated aqueous sodium bicarbonate solution was added and the mixture was warmed to RT. Using an Extrelut cartridge NT3 (from Merck, Darmstadt, Germany), the mixture was freed from salts and aqueous components. After concentration, the residue obtained was separated into its components by preparative HPLC (Method 36). Evaporation of the product fractions and drying of the residue under high vacuum gave 50 mg (50% of theory) of the title compound.

$^1$H NMR (400 MHz, DMSO-d$_6$, δ/ppm): 10.37 (s, 1H), 9.04 (d, 1H), 8.48 (dd, 1H), 8.38 (s, 1H), 8.31 (s, 1H), 8.17 (dt, 1H), 8.07 (s, 1H), 7.89 (d, 1H), 7.49 (s, 1H), 7.47 (d, 1H), 7.41 (dd, 1H), 7.40 (s, 1H), 6.29 (s, 1H), 2.30 (s, 3H), 2.26 (s, 3H), 1.75 (d, 6H).

LC/MS (Method 3, ESIpos): R$_t$=1.15 min, m/z=594 [M+H]$^+$.

Example 150 tert-Butyl [3-({2,4-dimethyl-5-[6-(pyridin-3-yl)-1H-imidazo[1,2-b]pyrazol-1-yl]phenyl}-carbamoyl)-5-(pentafluoro-λ$^6$-sulphanyl)phenyl]acetate

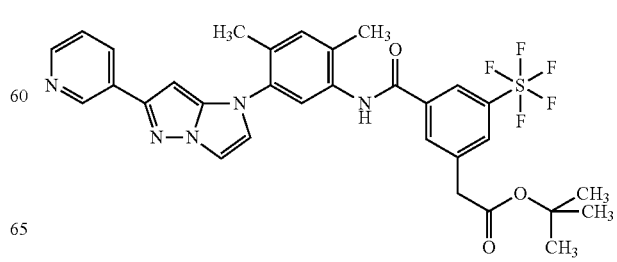

836 mg (2.31 mmol) of the compound of Example 97A and 1.05 g (2.77 mmol) of HATU were dissolved in 14 ml of DMF, and 338 mg (2.77 mmol) of 4-N,N-dimethylaminopyridine (DMAP) were added slowly. 700 mg (2.31 mmol) of the compound of Example 11A were then added. The reaction mixture was stirred at RT for 3 h. About 200 ml of water were then added, and the mixture was extracted three times with in each case about 200 ml of ethyl acetate. The combined organic extracts were washed with saturated aqueous sodium chloride solution, dried over magnesium sulphate, filtered and concentrated to dryness. The crude product obtained in this manner was purified by MPLC on about 100 g of silica gel with cyclohexane/ethyl acetate 50:50→0:100 as mobile phase. Evaporation of the product fractions and drying of the residue under high vacuum gave 966 mg (64% of theory) of the title compound.

$^1$H NMR (400 MHz, CDCl$_3$, δ/ppm): 9.04 (d, 1H), 8.52 (dd, 1H), 8.19-8.15 (m, 2H), 7.95-7.93 (m, 2H), 7.88 (s, 1H), 7.83 (s, 1H), 7.49 (d, 1H), 7.33 (dd, 1H), 6.94 (d, 1H), 6.01 (s, 1H), 3.69 (s, 2H), 2.39 (s, 3H), 2.28 (s, 3H), 1.46 (s, 9H) [a further signal is obscured by the CHCl$_3$ peak].

LC/MS (Method 3, ESIpos): R$_t$=1.21 min, m/z=648 [M+H]$^+$.

Example 151

[3-({2,4-Dimethyl-5-[6-(pyridin-3-yl)-1H-imidazo[1,2-b]pyrazol-1-yl]phenyl}carbamoyl)-5-(pentafluoro-λ$^6$-sulphanyl)phenyl]acetic acid

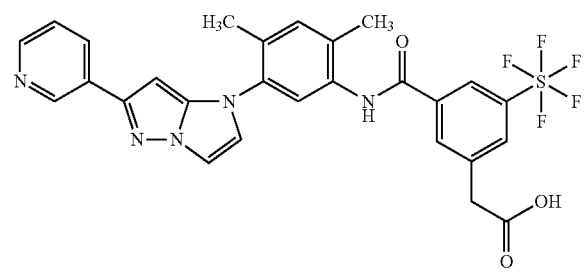

920 mg (1.42 mmol) of the compound of Example 150 were dissolved in 18 ml (71 mmol) of a 4 M solution of hydrogen chloride in dioxane. After the reaction mixture had been stirred at RT for 2 h, about 5 ml of methanol were added and all volatile components were then removed on a rotary evaporator. 85 mg of the crude product obtained in this manner were purified by preparative HPLC (Method 36). Pooling of the product fractions, evaporation and drying under high vacuum gave 31 mg of the title compound and 34 mg of the corresponding methyl ester (see Example 152). The remaining crude product was purified by MPLC on about 30 g of silica gel with ethyl acetate as mobile phase. Here, after pooling of the product fractions, evaporation and drying under high vacuum, 301 mg of the title compound and 387 mg of the corresponding methyl ester were obtained. This gave a total of 332 mg (39% of theory) of the title compound.

$^1$H NMR (400 MHz, DMSO-d$_6$, δ/ppm): 12.62 (broad, 1H), 10.30 (s, 1H), 9.04 (s, 1H), 8.48 (d, 1H), 8.33 (s, 1H), 8.18-8.16 (m, 2H), 8.08 (s, 1H), 7.89 (d, 1H), 7.49-7.47 (m, 2H), 7.41 (dd, 1H), 7.39 (s, 1H), 6.30 (s, 1H), 3.87 (s, 2H), 2.30 (s, 3H), 2.26 (s, 3H).

LC/MS (Method 3, ESIpos): R$_t$=0.95 min, m/z=592 [M+H]$^+$.

Example 152

Methyl [3-({2,4-dimethyl-5-[6-(pyridin-3-yl)-1H-imidazo[1,2-b]pyrazol-1-yl]phenyl}carbamoyl)-5-(pentafluoro-λ$^6$-sulphanyl)phenyl]acetate

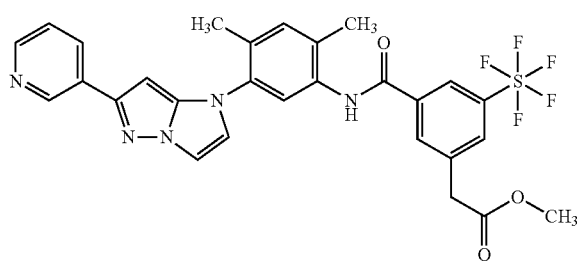 [SMILES: COC(=O)Cc1cc(C(=O)Nc2cc(-n3ccn4nc(-c5cccnc5)cc34)c(C)cc2C)cc(S(F)(F)(F)(F)F)c1]

920 mg (1.42 mmol) of the compound of Example 150 were dissolved in 18 ml (71 mmol) of a 4 M solution of hydrogen chloride in dioxane. The reaction mixture was stirred at RT for 2 h, and about 5 ml of methanol were then added, and all volatile components were then removed on a rotary evaporator. 85 mg of the crude product obtained in this manner were purified by preparative HPLC (Method 36). Pooling of the product fractions, evaporation and drying under high vacuum gave 34 mg of the title compound and 31 mg of the corresponding carboxylic acid (see Example 151). The remaining crude product was purified by MPLC on about 30 g of silica gel with ethyl acetate as mobile phase. Here, after pooling of the product fractions, evaporation and drying under high vacuum, 387 mg of the title compound and 301 mg of the corresponding carboxylic acid were obtained. This gave a total of 421 mg (48% of theory) of the title compound.

$^1$H NMR (400 MHz, CDCl$_3$, δ/ppm): 9.03 (s, 1H), 9.52 (d, 1H), 8.20 (s, 1H), 8.17 (s, 1H), 8.15 (s, 1H), 7.97 (s, 1H), 7.93-7.86 (m, 3H), 7.49 (d, 1H), 7.32 (dd, 1H), 6.94 (d, 1H), 6.00 (s, 1H), 3.79 (s, 2H), 3.75 (s, 3H), 2.39 (s, 3H), 2.28 (s, 3H).

LC/MS (Method 3, ESIpos): R$_t$=1.05 min, m/z=606 [M+H]$^+$.

Example 153

3-(2-Amino-2-oxoethyl)-N-{2,4-dimethyl-5-[6-(pyridin-3-yl)-1H-imidazo[1,2-b]pyrazol-1-yl]-phenyl}-5-(pentafluoro-λ$^6$-sulphanyl)benzamide

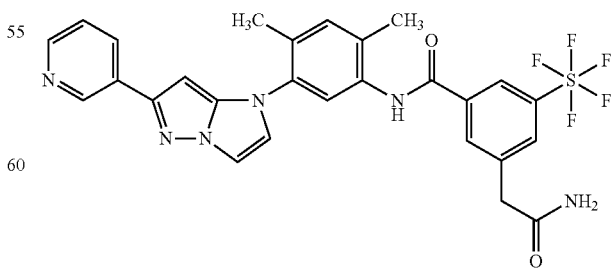

85 mg (0.128 mmol) of the compound of Example 151 and 58 mg (0.154 mmol) of HATU were initially charged in 2 ml of DMF, and 67 µl (0.384 mmol) of N,N-diisopropylethylamine and 1.3 ml (0.640 mmol) of a 0.5 M solution of ammonia in THF were then added. After the reaction mixture had been stirred at RT for about 16 h, the entire mixture was separated into its components by preparative HPLC (Method 36). The product fractions were combined and concentrated to dryness on a rotary evaporator. For further purification, the product was triturated for 10 min at RT with a few ml of pentane/diisopropyl ether 4:1. The solid was separated off and dried under high vacuum. This gave 9 mg (11% of theory, 95% pure) of the title compound.

$^1$H NMR (400 MHz, DMSO-$d_6$, δ/ppm): 10.33 (s, 1H), 9.04 (s, 1H), 8.48 (d, 1H), 8.33 (s, 1H), 8.18 (d, 1H), 8.14 (s, 1H), 8.04 (s, 1H), 7.89 (d, 1H), 7.63 (s, 1H), 7.49-7.48 (m, 2H), 7.41 (dd, 1H), 7.39 (s, 1H), 7.06 (s, 1H), 6.31 (s, 1H), 3.64 (s, 2H), 2.29 (s, 3H), 2.26 (s, 3H).

LC/MS (Method 3, ESIpos): $R_t$=0.88 min, m/z=591 [M+H]$^+$.

Example 154

N-{2,4-Dimethyl-5-[6-(pyridin-3-yl)-1H-imidazo[1,2-b]pyrazol-1-yl]phenyl}-3-(2-hydroxy-2-methylpropyl)-5-(pentafluoro-λ$^6$-sulphanyl)benzamide

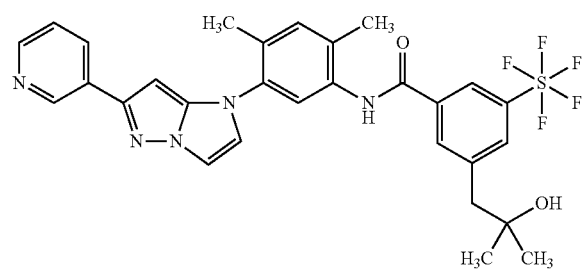 [SMILES: Cc1cc(C)c(-n2ccn3nc(-c4cccnc4)cc23)cc1NC(=O)c1cc(CC(C)(C)O)cc(S(F)(F)(F)(F)F)c1]

Under argon and at 0° C., 661 µl (0.661 mmol) of a 1 M solution of methylmagnesium bromide in THF were added to a solution of 100 mg (0.165 mmol) of the compound of Example 152 in 3 ml of anhydrous THF. The ice/water bath was removed and stirring was continued at RT. After about 16 h, 0.5 ml of saturated aqueous ammonium chloride solution were added to the reaction mixture. The mixture was stirred for another couple of minutes and then diluted with about 20 ml of ethyl acetate. Solid magnesium sulphate was added with stirring. The mixture was then filtered and the filtrate was concentrated to dryness. The residue obtained was taken up in 5 ml of pentane, and a few drops of diisopropyl ether were added. The solid was stirred in this mixture at RT for 10 min. The solid was then filtered off with suction, washed with pentane and dried under high vacuum. This gave 60 mg (57% of theory, 95% pure) of the title compound.

$^1$H NMR (400 MHz, CDCl$_3$, δ/ppm): 9.00 (s, 1H), 8.50 (d, 1H), 8.16 (s, 1H), 8.14 (dt, 1H), 8.02 (s, 1H), 7.94 (s, 1H), 7.91 (s, 1H), 7.82 (s, 1H), 7.47 (d, 1H), 7.31 (dd, 1H), 7.25 (s, 1H), 6.93 (d, 1H), 5.97 (s, 1H), 2.90 (s, 2H), 2.37 (s, 3H), 2.27 (s, 3H), 1.27 (s, 6H).

LC/MS (Method 3, ESIpos): $R_t$=1.04 min, m/z=606 [M+H]$^+$.

Example 155

N-{2,4-Dimethyl-5-[6-(pyridin-3-yl)-1H-imidazo[1,2-b]pyrazol-1-yl]phenyl}-3-[(2-methoxy-ethoxy)methyl]-5-(pentafluoro-λ$^6$-sulphanyl)benzamide

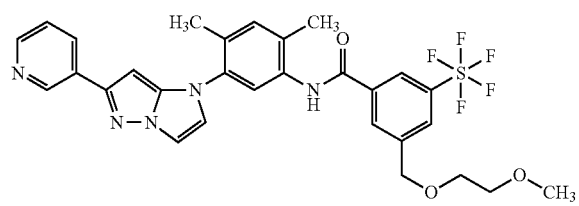 [SMILES: COCCOCc1cc(C(=O)Nc2cc(-n3ccn4nc(-c5cccnc5)cc34)c(C)cc2C)cc(S(F)(F)(F)(F)F)c1]

58 mg (0.173 mmol) of the compound of Example 98A and 75 mg (0.198 mmol) of HATU were dissolved in 1 ml of DMF, and 24 mg (0.198 mmol) of 4-N,N-dimethylaminopyridine (DMAP) were added slowly. 50 mg (0.165 mmol) of the compound of Example 11A were then added. The reaction mixture was stirred at RT for about 16 h and then separated into its components by preparative HPLC (Method 36). Pooling of the product fractions, evaporation and drying of the residue under high vacuum gave 76 mg (75% of theory) of the title compound.

$^1$H NMR (400 MHz, DMSO-$d_6$, δ/ppm): 10.33 (s, 1H), 9.06 (d, 1H), 8.50 (dd, 1H), 8.35 (s, 1H), 8.24-8.21 (m, 2H), 8.07 (s, 1H), 7.89 (d, 1H), 7.50-7.48 (m, 2H), 7.46 (dd, 1H), 7.39 (s, 1H), 6.32 (s, 1H), 4.70 (s, 2H), 3.65 (dd, 2H), 3.52 (dd, 2H), 3.26 (s, 3H), 2.30 (s, 3H), 2.26 (s, 3H).

LC/MS (Method 3, ESIpos): $R_t$=1.07 min, m/z=622 [M+H]$^+$.

Example 156

3-Cyano-N-{2-hydroxy-4-methyl-3-[6-(pyridin-3-yl)-1H-imidazo[1,2-b]pyrazol-1-yl]phenyl}-5-(pentafluoro-λ$^6$-sulphanyl)benzamide

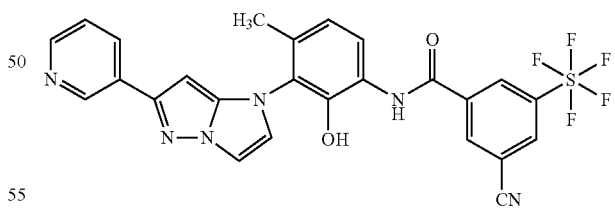

Analogously to the process described in Example 155, 37 mg (0.109 mmol) of the compound of Example 82A and 28 mg (0.104 mmol) of the compound of Example 23A were reacted to give 9 mg (15% of theory) of the title compound. Here, preparative HPLC purification was carried out according to Method 37.

$^1$H NMR (400 MHz, DMSO-$d_6$, δ/ppm): 10.39 (s, 1H), 9.62 (s, 1H), 9.10 (s, 1H), 8.83 (s, 1H), 8.73-8.72 (m, 2H), 8.56 (d, 1H), 8.41 (d, 1H), 7.86 (d, 1H), 7.62 (dd, 1H), 7.45 (d, 1H), 7.36 (d, 1H), 6.96 (d, 1H), 6.27 (s, 1H), 2.10 (s, 3H).

LC/MS (Method 3, ESIpos): $R_t$=1.00 min, m/z=561 [M+H]$^+$.

Example 157

N-{4-Chloro-2-methyl-5-[6-(pyridin-3-yl)-1H-imidazo[1,2-b]pyrazol-1-yl]phenyl}-3-(pentafluoro-$\lambda^6$-sulphanyl)benzamide

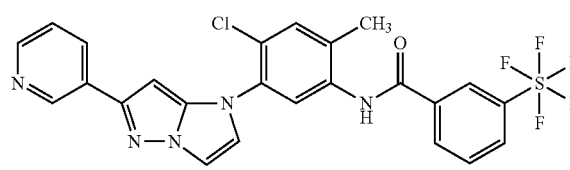

Analogously to Example 90, 330 mg (1.02 mmol) of the compound of Example 84A and 278 mg (0.63 mmol) of 3-(pentafluoro-$\lambda^6$-sulphanyl)benzoic acid gave, after 16 h of stirring at 50° C. and HPLC purification (Method 16), 57.2 mg (10% of theory) of the title compound.

$^1$H NMR (400 MHz, DMSO-d$_6$, δ/ppm): 10.37 (s, 1H), 9.01 (d, 1H), 8.46 (dd, 1H), 8.38 (t, 1H), 8.25 (d, 1H), 8.11-8.18 (m, 3H), 7.90 (d, 1H), 7.79 (t, 1H), 7.74 (s, 1H), 7.68 (s, 1H), 7.51 (d, 1H), 7.39 (dd, 1H), 6.32 (s, 1H), 2.31 (s, 3H).

LC/MS (Method 7, ESIpos): $R_t$=1.30 min, m/z=554/556 [M+H]$^+$.

Example 158

N-{3-[7-Fluoro-6-(pyridin-3-yl)-1H-imidazo[1,2-b]pyrazol-1-yl]-4-methylphenyl}-3-(pentafluoro-$\lambda^6$-sulphanyl)benzamide

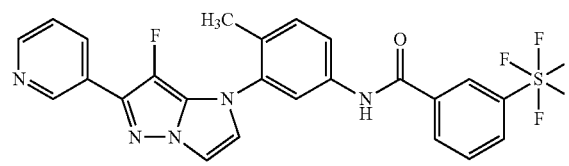

Analogously to the process described in Example 126, 60 mg (0.195 mmol) of the compound of Example 83A and 48 mg (0.195 mmol) of 3-(pentafluoro-$\lambda^6$-sulphanyl)benzoic acid gave 35 mg (33% of theory) of the title compound. The product obtained from the preparative HPLC purification was dissolved in a little methanol and passed through a bicarbonate cartridge (from Polymerlabs, Stratospheres SPE, PL-HCO$_3$ MP SPE, capacity 0.9 mmol). After concentration of the eluate, the residue was dried under high vacuum.

$^1$H NMR (400 MHz, DMSO-d$_6$, δ/ppm): 8.98 (m, 1H), 8.55 (dd, 1H), 8.41 (m, 1H), 8.28 (d, 1H), 8.17-8.12 (m, 2H), 7.98 (m, 1H), 7.94 (d, 1H), 7.84-7.78 (m, 2H), 7.61 (d, 1H), 7.51-7.47 (m, 2H), 2.30 (s, 3H).

LC/MS (Method 3, ESIpos): $R_t$=1.12 min, m/z=538 [M+H]$^+$.

Example 159

3-Cyano-N-{3-[7-fluoro-6-(pyridin-3-yl)-1H-imidazo[1,2-b]pyrazol-1-yl]-4-methylphenyl}-5-(pentafluoro-$\lambda^6$-sulphanyl)benzamide

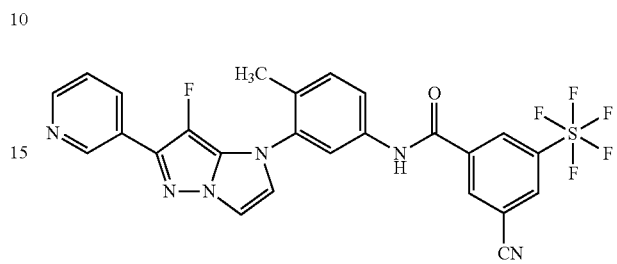

Analogously to the process described in Example 126, 60 mg (0.195 mmol) of the compound of Example 83A and 53 mg (0.195 mmol) of the compound of Example 23A gave 61 mg (55% of theory) of the title compound. The product obtained from the preparative HPLC purification was dissolved in a little methanol and passed through a bicarbonate cartridge (from Polymerlabs, Stratospheres SPE, PL-HCO$_3$ MP SPE, capacity 0.9 mmol). After concentration of the eluate, the residue was dried under high vacuum.

$^1$H NMR (400 MHz, DMSO-d$_6$, δ/ppm): 10.79 (s, 1H), 8.99 (d, 1H), 8.84 (dd, 1H), 8.74 (s, 1H), 8.66 (t, 1H), 8.55 (dd, 1H), 8.13 (dt, 1H), 7.96 (d, 1H), 7.94 (d, 1H), 7.78 (dd, 1H), 7.61 (d, 1H), 7.51-7.48 (m, 2H), 2.31 (s, 3H).

LC/MS (Method 3, ESIpos): $R_t$=1.12 min, m/z=563 [M+H]$^+$.

Example 160

N-{3-[7-Fluoro-6-(pyridin-3-yl)-1H-imidazo[1,2-b]pyrazol-1-yl]-4-methylphenyl}-3-(2-hydroxypropan-2-yl)-5-(pentafluoro-$\lambda^6$-sulphanyl)benzamide

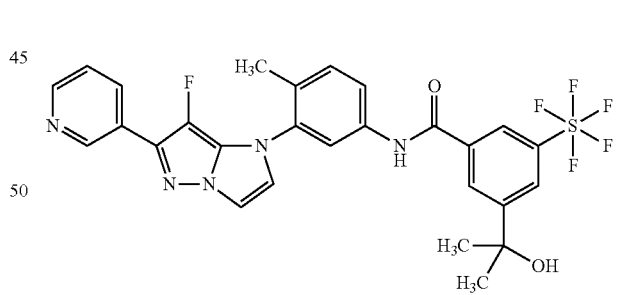

60 mg (0.195 mmol) of the compound of Example 83A and 60 mg (0.195 mmol) of the compound of Example 19A were dissolved in 2 ml of DMF, and 89 mg (0.234 mmol) of HATU and 41 μl (0.234 mmol) of N,N-diisopropylethylamine were added in succession. After about 16 h of stirring at RT, the reaction mixture was diluted with 1 ml of acetonitrile and separated into its components by preparative HPLC (Method 36). The product fractions were combined and freed from the solvent on a rotary evaporator. The residue was dissolved in a little methanol and the solution was passed through a bicarbonate cartridge (from Polymerlabs, Stratospheres SPE, PL-HCO$_3$ MP SPE, capacity 0.9 mmol) to convert the formate salt obtained after preparative HPLC into the free base. Evaporation and drying under high vacuum gave 42 mg (35% of theory) of the title compound.

$^1$H NMR (400 MHz, DMSO-d$_6$, δ/ppm): 10.66 (s, 1H), 8.99 (m, 1H), 8.55 (dd, 1H), 8.29 (s, 1H), 8.27 (t, 1H), 8.17 (t, 1H), 8.13 (dt, 1H), 7.97 (d, 1H), 7.94 (dd, 1H), 7.79 (dd, 1H), 7.61 (d, 1H), 7.51-7.47 (m, 2H), 5.52 (s, 1H), 2.30 (s, 3H).

LC/MS (Method 3, ESIpos): R$_t$=1.09 min, m/z=596 [M+H]$^+$.

Example 161

3-Bromo-N-{4-methyl-3-[6-(pyrazin-2-yl)-1H-imidazo[1,2-b]pyrazol-1-yl]phenyl}-5-(pentafluoro-λ$^6$-sulphanyl)benzamide

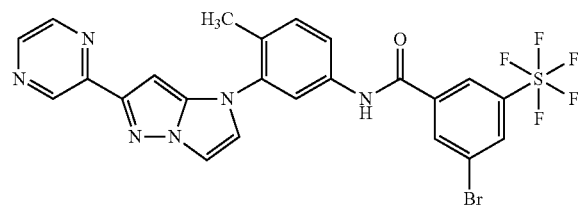 [SMILES: Cc1ccc(NC(=O)c2cc(Br)cc(S(F)(F)(F)(F)F)c2)cc1-n1ccn2nc(-c3cnccn3)cc12]

Analogously to Example 90, 170 mg (0.59 mmol) of the compound of Example 72A and 211 mg (0.64 mmol) of the compound of Example 15A gave, after 20 h at RT, a crude product which, after chromatography on a Biotage system (25 g Snap column; mobile phase gradient ethyl acetate/methanol increasing to 8% methanol), afforded 261 mg (65% of theory) of the title compound.

$^1$H NMR (400 MHz, DMSO-d$_6$, δ/ppm): 10.71 (s, 1H), 9.19 (d, 1H), 8.61 (dd, 1H), 8.53 (d, 1H), 8.49 (s, 1H), 8.37-8.44 (m, 2H), 7.96 (dd, 2H), 7.76 (dd, 1H), 7.64 (d, 1H), 7.47 (d, 1H), 6.39 (s, 1H), 2.29 (s, 3H).

LC/MS (Method 7, ESIpos): R$_t$=1.42 min, m/z=599/601 [M+H]$^+$.

Example 162

3-Cyano-N-{4-methyl-3-[6-(pyrazin-2-yl)-1H-imidazo[1,2-b]pyrazol-1-yl]phenyl}-5-(pentafluoro-λ$^6$-sulphanyl)benzamide

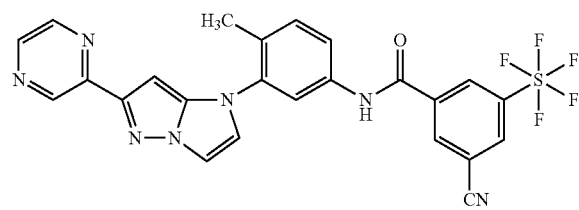 [SMILES: Cc1ccc(NC(=O)c2cc(C#N)cc(S(F)(F)(F)(F)F)c2)cc1-n1ccn2nc(-c3cnccn3)cc12]

Analogously to Example 79, 241 mg (0.40 mmol) of the compound of Example 161 gave, after purification by HPLC (Method 16), 58.4 mg (25% of theory) of the title compound.

$^1$H NMR (400 MHz, DMSO-d$_6$, δ/ppm): 10.75 (s, 1H), 9.16 (d, 1H), 8.80 (dd, 1H), 8.71 (s, 1H), 8.61-8.63 (m, 1H), 8.59 (dd, 1H), 8.51 (d, 1H), 7.92-7.96 (m, 2H), 7.73 (dd, 1H), 7.62 (d, 1H), 7.46 (d, 1H), 6.36 (s, 1H), 2.28 (s, 3H).

LC/MS (Method 7, ESIpos): R$_t$=1.27 min, m/z=546 [M+H]$^+$.

Example 163

N-{4-Methyl-3-[6-(pyrimidin-5-yl)-1H-imidazo[1,2-b]pyrazol-1-yl]phenyl}-3-(pentafluoro-λ$^6$-sulphanyl)benzamide

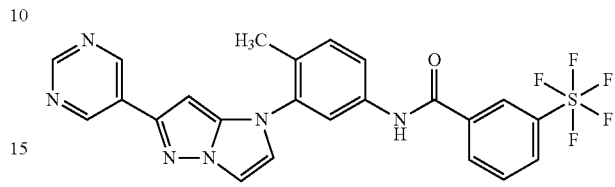

Analogously to Example 90, 107 mg (0.37 mmol) of the compound of Example 85A and 101 mg (0.41 mmol) of 3-(pentafluoro-λ$^6$-sulphanyl)benzoic acid gave, after 20 h at RT, a crude product which, after HPLC purification (Method 16), afforded 108 mg (54% of theory) of the title compound.

$^1$H NMR (400 MHz, DMSO-d$_6$, δ/ppm): 10.65 (s, 1H), 9.18 (s, 2H), 9.06 (s, 1H), 8.38 (t, 1H), 8.24 (d, 1H), 8.12 (dd, 1H), 7.90-7.94 (m, 2H), 7.74-7.81 (m, 2H), 7.55 (d, 1H), 7.45 (d, 1H), 6.45 (s, 1H), 2.23 (s, 3H).

LC/MS (Method 7, ESIpos): R$_t$=1.26 min, m/z=521 [M+H]$^+$.

Example 164

N-{2,4-Dimethyl-5-[6-(pyrimidin-5-yl)-1H-imidazo[1,2-b]pyrazol-1-yl]phenyl}-3-(pentafluoro-λ$^6$-sulphanyl)benzamide

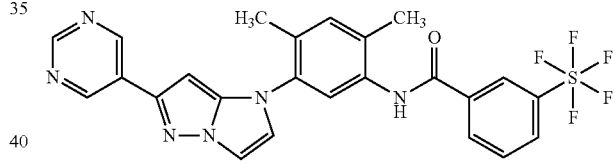

Analogously to Example 90, 80 mg (0.26 mmol) of the compound of Example 86A and 72 mg (0.29 mmol) of 3-(pentafluoro-λ$^6$-sulphanyl)benzoic acid gave, after 20 h of stirring at RT and purification by HPLC (Method 16), 75.8 mg (54% of theory) of the title compound.

$^1$H NMR (400 MHz, DMSO-d$_6$, δ/ppm): 10.29 (s, 1H), 9.20 (s, 2H), 9.09 (s, 1H), 8.41 (s, 1H), 8.28 (d, 1H), 8.14 (dd, 1H), 7.92 (d, 1H), 7.80 (t, 1H), 7.47-7.52 (m, 2H), 7.39 (s, 1H), 6.41 (s, 1H), 2.29 (s, 3H), 2.24 (s, 3H).

LC/MS (Method 7, ESIpos): R$_t$=1.26 min, m/z=535 [M+H]$^+$.

Example 165

3-Bromo-N-{2,4-dimethyl-5-[6-(pyrimidin-5-yl)-1H-imidazo[1,2-b]pyrazol-1-yl]phenyl}-5-(pentafluoro-λ$^6$-sulphanyl)benzamide

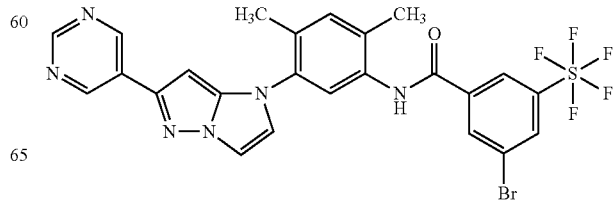

Analogously to Example 90, 210 mg (0.69 mmol) of the compound of Example 86A and 248 mg (0.76 mmol) of the compound of Example 15A gave, after 20 h at RT, a crude product was, after chromatography on a Biotage system (25 g Snap column; mobile phase gradient ethyl acetate/methanol increasing to 8% methanol), afforded 356 mg (72% of theory) of the title compound.

$^1$H NMR (400 MHz, DMSO-$d_6$, δ/ppm): 10.33 (s, 1H), 9.17 (s, 2H), 9.06 (s, 1H), 8.46 (s, 1H), 8.35-8.40 (m, 2H), 7.90 (d, 1H), 7.48 (d, 1H), 7.46 (s, 1H), 7.36 (s, 1H), 6.38 (s, 1H), 2.26 (s, 3H), 2.21 (s, 3H).

LC/MS (Method 7, ESIpos): $R_t$=1.38 min, m/z=613/615 [M+H]$^+$ ($^{79}$Br/$^{81}$Br).

Example 166

3-Cyano-N-{2,4-dimethyl-5-[6-(pyrimidin-5-yl)-1H-imidazo[1,2-b]pyrazol-1-yl]phenyl}-5-(pentafluoro-λ$^6$-sulphanyl)benzamide

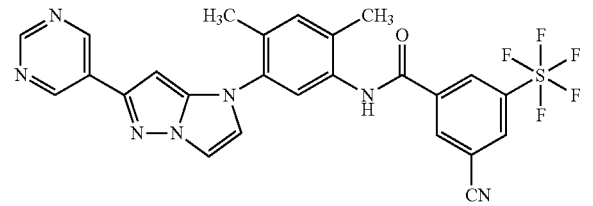 [SMILES: Cc1cc(C)c(-n2ccn3nc(-c4cncnc4)cc23)cc1NC(=O)c1cc(C#N)cc(S(F)(F)(F)(F)F)c1]

Analogously to Example 79, 340 mg (0.55 mmol) of the compound of Example 165 gave, after purification by HPLC (Method 16), 117 mg (36% of theory) of the title compound.

$^1$H NMR (400 MHz, DMSO-$d_6$, δ/ppm): 10.40 (s, 1H), 9.19 (s, 2H), 9.09 (s, 1H), 8.83 (t, 1H), 8.72 (s, 1H), 8.65 (s, 1H), 7.92 (d, 1H), 7.49-7.53 (m, 2H), 7.40 (s, 1H), 6.41 (s, 1H), 2.31 (s, 3H), 2.24 (s, 3H).

LC/MS (Method 6, ESIpos): $R_t$=1.25 min, m/z=560 [M+H]$^+$.

Example 167

3-Bromo-N-{4-methyl-3-[6-(pyridazin-4-yl)-1H-imidazo[1,2-b]pyrazol-1-yl]phenyl}-5-(pentafluoro-λ$^6$-sulphanyl)benzamide

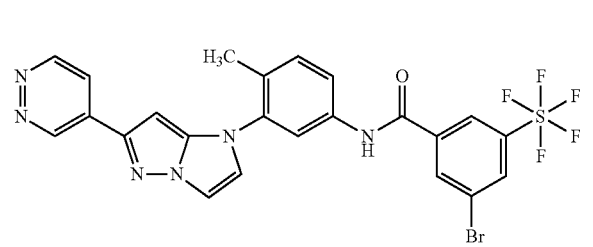 [SMILES: Cc1ccc(NC(=O)c2cc(Br)cc(S(F)(F)(F)(F)F)c2)cc1-n1ccn2nc(-c3ccnnc3)cc12]

Analogously to Example 90, 250 mg (0.86 mmol) of the compound of Example 87A and 310 mg (0.95 mmol) of the compound of Example 15A gave, after 20 h at RT, a crude product which, after chromatography on a Biotage system (25 g Snap column; mobile phase gradient ethyl acetate/methanol increasing to 8% methanol), afforded 429 mg (79% of theory) of the title compound.

$^1$H NMR (400 MHz, DMSO-$d_6$, δ/ppm): 10.69 (s, 1H), 9.63 (dd, 1H), 9.16 (dd, 1H), 8.47 (s, 1H), 8.38 (dt, 2H), 7.94-7.99 (m, 2H), 7.90 (d, 1H), 7.77 (dd, 1H), 7.61 (d, 1H), 7.47 (d, 1H), 6.58-6.62 (m, 1H), 2.23 (s, 3H).

LC/MS (Method 7, ESIpos): $R_t$=1.34 min, m/z=599/601 [M+H]$^+$ ($^{79}$Br/$^{81}$Br).

Example 168

3-Cyano-N-{4-methyl-3-[6-(pyridazin-4-yl)-1H-imidazo[1,2-b]pyrazol-1-yl]phenyl}-5-(pentafluoro-λ$^6$-sulphanyl)benzamide

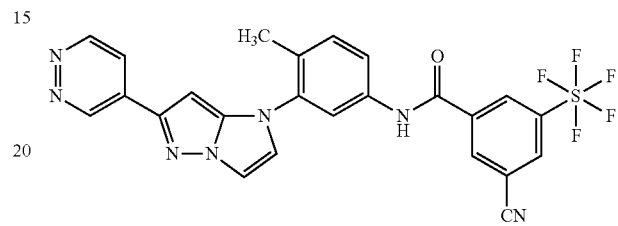

Analogously to Example 79, 413 mg (0.69 mmol) of the compound of Example 167 gave, after purification by HPLC (Method 16), 39 mg (10% of theory) of the title compound.

$^1$H NMR (400 MHz, DMSO-$d_6$, δ/ppm): 10.77 (s, 1H), 9.63 (dd, 1H), 9.16 (dd, 1H), 8.82 (t, 1H), 8.70 (s, 1H), 8.63 (t, 1H), 7.94-7.99 (m, 2H), 7.90 (d, 1H), 7.77 (dd, 1H), 7.62 (d, 1H), 7.48 (d, 1H), 6.61 (s, 1H), 2.24 (s, 3H).

LC/MS (Method 7, ESIpos): $R_t$=1.26 min, m/z=546 [M+H]$^+$.

Example 169

N-{2,4-Dimethyl-5-[6-(pyridazin-3-yl)-1H-imidazo[1,2-b]pyrazol-1-yl]phenyl}-3-(pentafluoro-λ$^6$-sulphanyl)benzamide

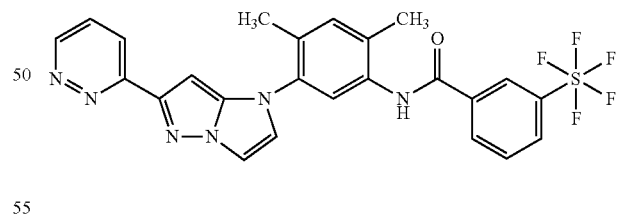

Analogously to Example 90, 50 mg (0.16 mmol) of the compound of Example 88A and 45 mg (0.18 mmol) of 3-(pentafluoro-λ$^6$-sulphanyl)benzoic acid gave, after 20 h of stirring at RT and purification by HPLC (Method 16), 61.3 mg (70% of theory) of the title compound.

$^1$H NMR (400 MHz, DMSO-$d_6$, δ/ppm): 10.29 (s, 1H), 9.12 (dd, 1H), 8.41 (s, 1H), 8.28 (d, 1H), 8.10-8.18 (m, 2H), 7.94 (d, 1H), 7.80 (t, 1H), 7.71 (dd, 1H), 7.59 (d, 1H), 7.54 (s, 1H), 7.38 (s, 1H), 6.47 (s, 1H), 2.30 (s, 3H), 2.29 (s, 3H).

LC/MS (Method 7, ESIpos): R$_t$=1.24 min, m/z=535 [M+H]$^+$.

Example 170

3-Bromo-N-{2,4-dimethyl-5-[6-(pyridazin-3-yl)-1H-imidazo[1,2-b]pyrazol-1-yl]phenyl}-5-(pentafluoro-λ$^6$-sulphanyl)benzamide

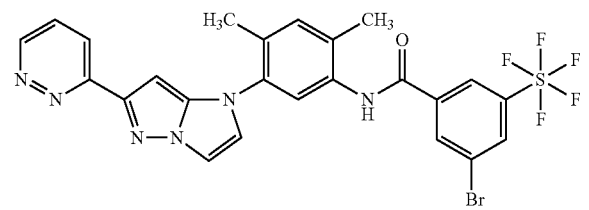 [SMILES: Cc1cc(C)c(-n2ccn3nc(-c4cccnn4)cc23)cc1NC(=O)c1cc(Br)cc(S(F)(F)(F)(F)F)c1]

Analogously to Example 90, 115 mg (0.38 mmol) of the compound of Example 88A and 136 mg (0.42 mmol) of the compound of Example 15A gave, after 20 h at RT, a crude product which, after chromatography on a Biotage system (10 g Snap column; mobile phase gradient ethyl acetate/methanol increasing to 8% methanol), afforded 226 mg (78% of theory) of the title compound.

$^1$H NMR (400 MHz, DMSO-d$_6$, δ/ppm): 10.33 (s, 1H), 9.10 (dd, 1H), 8.46 (s, 1H), 8.37 (d, 2H), 8.12 (dd, 1H), 7.92 (d, 1H), 7.65-7.72 (m, 1H), 7.56 (d, 1H), 7.51 (s, 1H), 7.36 (s, 1H), 6.44 (s, 1H), 2.27 (s, 3H), 2.26 (s, 3H).

LC/MS (Method 7, ESIpos): R=1.36 min, m/z=613/615 [M+H]$^+$ ($^{79}$Br/$^{81}$Br).

Example 171

3-Cyano-N-{2,4-dimethyl-5-[6-(pyridazin-3-yl)-1H-imidazo[1,2-b]pyrazol-1-yl]phenyl}-5-(pentafluoro-λ$^6$-sulphanyl)benzamide

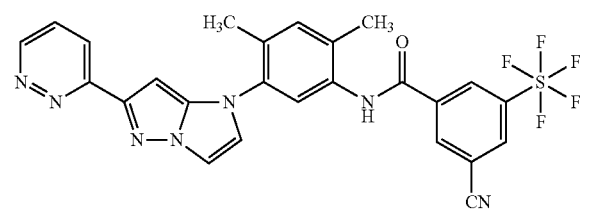

Analogously to Example 79, 215 mg (0.35 mmol) of the compound of Example 170 gave, after purification by HPLC (Method 16), 76 mg (39% of theory) of the title compound.

$^1$H NMR (400 MHz, DMSO-d$_6$, δ/ppm): 10.40 (s, 1H), 9.12 (dd, 1H), 8.82 (s, 1H), 8.73 (s, 1H), 8.66 (s, 1H), 8.15 (dd, 1H), 7.94 (d, 1H), 7.71 (dd, 1H), 7.59 (d, 1H), 7.57 (s, 1H), 7.39 (s, 1H), 6.47 (s, 1H), 2.31 (s, 3H), 2.29 (s, 3H).

LC/MS (Method 7, ESIpos): R$_t$=1.23 min, m/z=560 [M+H]$^+$.

Example 172

N-{4-Methyl-3-[6-(1,3-thiazol-5-yl)-1H-imidazo[1,2-b]pyrazol-1-yl]phenyl}-3-(pentafluoro-λ$^6$-sulphanyl)benzamide

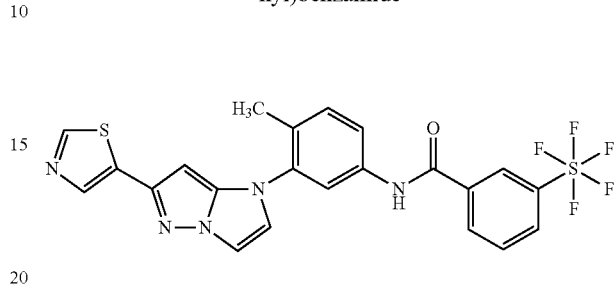

193 mg (0.51 mmol) of HATU and 62 mg (0.51 mmol) of 4-N,N-dimethylaminopyridine (DMAP) were added to a solution of 100 mg (0.34 mmol) of the compound of Example 89A and 92 mg (0.37 mmol) of 3-(pentafluoro-λ$^6$-sulphanyl)benzoic acid in 2 ml of DMF. The reaction was stirred at RT for 20 h. The reaction mixture was then purified directly by preparative HPLC (Method 16). This gave 50.2 mg (27% of theory) of the title compound.

$^1$H NMR (400 MHz, DMSO-d$_6$, δ/ppm): 10.66 (s, 1H), 8.98 (s, 1H), 8.40 (s, 1H), 8.27 (d, 1H), 8.23 (s, 1H), 8.15 (dd, 1H), 7.93 (d, 1H), 7.87 (d, 1H), 7.78-7.84 (m, 2H), 7.53 (d, 1H), 7.46 (d, 1H), 6.25 (s, 1H), 2.26 (s, 3H).

LC/MS (Method 7, ESIpos): R$_t$=1.30 min, m/z=526 [M+H]$^+$.

Example 173

3-Fluoro-N-{4-methyl-3-[6-(1,3-thiazol-5-yl)-1H-imidazo[1,2-b]pyrazol-1-yl]phenyl}-5-(pentafluoro-λ$^6$-sulphanyl)benzamide

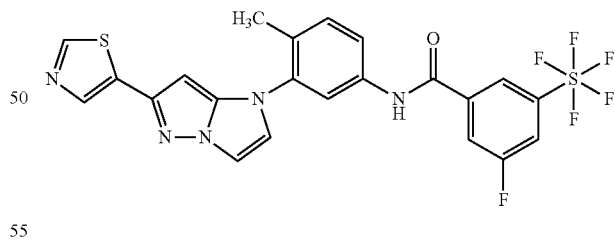

Analogously to Example 90, 100 mg (0.34 mmol) of the compound of Example 89A and 99 mg (0.37 mmol) of 3-fluoro-5-(pentafluoro-λ$^6$-sulphanyl)benzoic acid gave, after 20 h of stirring at RT and HPLC purification (Method 16), 27.8 mg (15% of theory) of the title compound.

$^1$H NMR (400 MHz, DMSO-d$_6$, δ/ppm): 10.68 (s, 1H), 8.98 (s, 1H), 8.28 (s, 1H), 8.19-8.24 (m, 2H), 8.17 (d, 1H), 7.92 (d, 1H), 7.87 (d, 1H), 7.78 (dd, 1H), 7.52 (d, 1H), 7.47 (d, 1H), 6.25 (s, 1H), 2.26 (s, 3H).

LC/MS (Method 7, ESIpos): $R_t$=1.34 min, m/z=544 [M+H]$^+$.

Example 174

3-Chloro-N-{4-methyl-3-[6-(1,3-thiazol-5-yl)-1H-imidazo[1,2-b]pyrazol-1-yl]phenyl}-5-(pentafluoro-$\lambda^6$-sulphanyl)benzamide

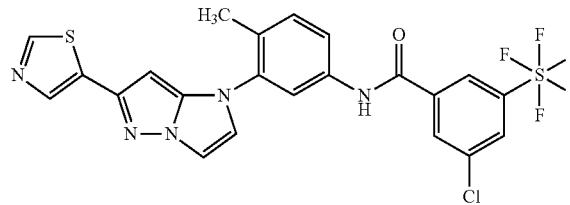

Analogously to Example 90, 100 mg (0.34 mmol) of the compound of Example 89A and 105 mg (0.37 mmol) of the compound of Example 33A gave, after 20 h of stirring at RT and HPLC purification (Method 16), 47.2 mg (25% of theory) of the title compound.

$^1$H NMR (400 MHz, DMSO-d$_6$, δ/ppm): 10.71 (s, 1H), 8.98 (s, 1H), 8.35-8.38 (m, 2H), 8.32-8.34 (m, 1H), 8.22 (s, 1H), 7.91 (d, 1H), 7.87 (d, 1H), 7.78 (dd, 1H), 7.53 (s, 1H), 7.47 (d, 1H), 6.25 (s, 1H), 2.26 (s, 3H).

LC/MS (Method 7, ESIpos): $R_t$=1.41 min, m/z=560/562 [M+H]$^+$ ($^{35}$Cl/$^{37}$Cl).

Example 175

3-Bromo-N-{4-methyl-3-[6-(1,3-thiazol-5-yl)-1H-imidazo[1,2-b]pyrazol-1-yl]phenyl}-5-(pentafluoro-$\lambda^6$-sulphanyl)benzamide

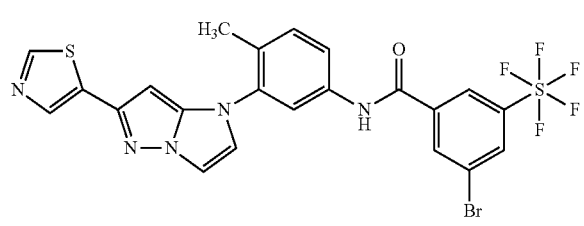 [SMILES: Cc1ccc(NC(=O)c2cc(Br)cc(S(F)(F)(F)(F)F)c2)cc1-n1ccn2nc(-c3cncs3)cc12]

Analogously to Example 90, 250 mg (0.85 mmol) of the compound of Example 89A and 305 mg (0.93 mmol) of the compound of Example 15A gave, after 20 h at RT, a crude product which, after chromatography on a Biotage system (25 g Snap column; mobile phase gradient ethyl acetate/methanol increasing to 8% methanol), afforded 264 mg (49% of theory) of the title compound.

$^1$H NMR (400 MHz, DMSO-d$_6$, δ/ppm): 10.69 (s, 1H), 8.96 (s, 1H), 8.46 (s, 1H), 8.38-8.41 (m, 1H), 8.35-8.38 (m, 1H), 8.20 (s, 1H), 7.88 (d, 1H), 7.85 (d, 1H), 7.76 (dd, 1H), 7.51 (d, 1H), 7.45 (d, 1H), 6.23 (s, 1H), 2.23 (s, 3H).

LC/MS (Method 7, ESIpos): $R_t$=1.42 min, m/z=604/606 [M+H]$^+$ ($^{79}$Br/$^{81}$Br).

Example 176

3-(Methylsulphonyl)-N-{4-methyl-3-[6-(1,3-thiazol-5-yl)-1H-imidazo[1,2-b]pyrazol-1-yl]phenyl}-5-(pentafluoro-$\lambda^6$-sulphanyl)benzamide

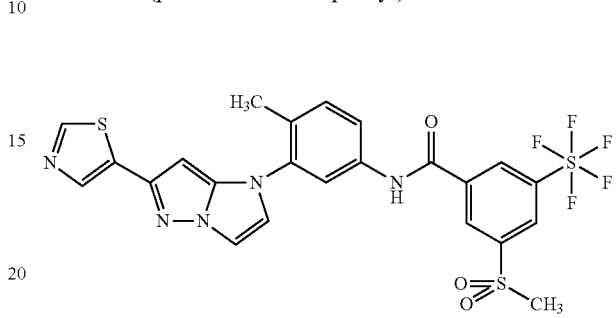

193 mg (0.51 mmol) of HATU and 62 mg (0.51 mmol) of 4-N,N-dimethylaminopyridine (DMAP) were added to a solution of 100 mg (0.34 mmol) of the compound of Example 89A and 122 mg (0.37 mmol) of the compound of Example 32A in 2 ml of DMF. The reaction was stirred at RT for 20 h. The reaction mixture was then purified directly by preparative HPLC (Method 16). This gave 86.4 mg (42% of theory) of the title compound.

$^1$H NMR (400 MHz, DMSO-d$_6$, δ/ppm): 10.91 (s, 1H), 8.98 (d, 1H), 8.79 (s, 1H), 8.74 (t, 1H), 8.55 (t, 1H), 8.22 (d, 1H), 7.92 (d, 1H), 7.87 (dd, 1H), 7.80 (dd, 1H), 7.53 (d, 1H), 7.49 (d, 1H), 6.25 (s, 1H), 3.45 (s, 3H), 2.27 (s, 3H).

LC/MS (Method 7, ESIpos): $R_t$=1.23 min, m/z=604 [M+H]$^+$.

Example 177

3-Cyano-N-{4-methyl-3-[6-(1,3-thiazol-5-yl)-1H-imidazo[1,2-b]pyrazol-1-yl]phenyl}-5-(pentafluoro-$\lambda^6$-sulphanyl)benzamide

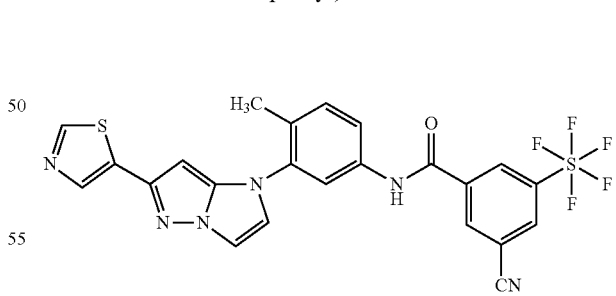

Analogously to Example 79, 260 mg (0.43 mmol) of the compound of Example 175 gave, after purification by HPLC (Method 16), 57.2 mg (23% of theory) of the title compound.

$^1$H NMR (400 MHz, DMSO-d$_6$, δ/ppm): 10.77 (s, 1H), 7.91 (d, 1H), 8.98 (s, 1H), 8.81-8.85 (m, 1H), 8.73 (s, 1H), 8.63-8.68 (m, 1H), 8.22 (s, 1H), 7.87 (d, 1H), 7.78 (dd, 1H), 7.53 (d, 1H), 7.49 (d, 1H), 6.24 (s, 1H), 2.26 (s, 3H).

LC/MS (Method 7, ESIpos): R$_t$=1.29 min, m/z=551 [M+H]$^+$.

Example 178

3-(2-Hydroxypropan-2-yl)-N-{4-methyl-3-[6-(1,3-thiazol-5-yl)-1H-imidazo[1,2-b]pyrazol-1-yl]-phenyl}-5-(pentafluoro-λ6-sulphanyl)benzamide

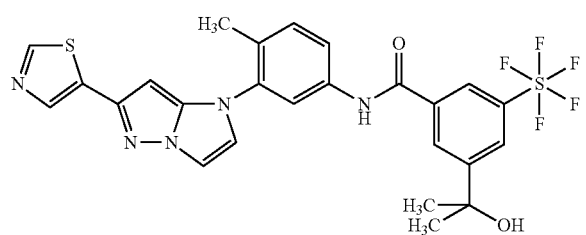 [SMILES: Cc1ccc(NC(=O)c2cc(C(C)(C)O)cc(S(F)(F)(F)(F)F)c2)cc1-n1ccn2nc(-c3cncs3)cc12]

Analogously to Example 90, 100 mg (0.34 mmol) of the compound of Example 89A and 114 mg (0.37 mmol) of the compound of Example 19A gave, after 20 h of stirring at RT and HPLC purification (Method 16), 76.2 mg (35% of theory) of the title compound.

$^1$H NMR (400 MHz, DMSO-d$_6$, δ/ppm): 10.63 (s, 1H), 8.98 (s, 1H), 8.25-8.30 (m, 2H), 8.23 (s, 1H), 8.16 (t, 1H), 7.92 (d, 1H), 7.87 (d, 1H), 7.79 (dd, 1H), 7.52 (d, 1H), 7.47 (d, 1H), 6.25 (s, 1H), 5.49-5.52 (m, 1H), 2.25 (s, 3H), 1.50 (s, 6H).

LC/MS (Method 7, ESIpos): R$_t$=1.27 min, m/z=584 [M+H]$^+$.

B. ASSESSMENT OF PHARMACOLOGICAL ACTIVITY

The pharmacological activity of the compounds according to the invention can be demonstrated by in vitro and in vivo studies, as known to the person skilled in the art. The use examples below describe the biological activity of the compounds according to the invention without limiting the invention to these examples.

Abbreviations and Acronyms

Ahx 6-aminohexanoic acid
ATP adenosine triphosphate
BSA bovine serum albumin
DMSO dimethyl sulphoxide
EDTA ethylenediamine-N,N,N',N'-tetraacetic acid
EGTA ethylene glycol-bis(aminoethylether)-N,N,N'N'-tetraacetic acid
ELISA enzyme-linked immunosorbent assay
FCS foetal calf serum
GST glutathione S-transferase
HEPES 4-(2-hydroxyethyl)piperazine-1-ethanesulphonic acid
HRP horseradish peroxidase
HUVEC human umbilical vein endothelial cells
PAGE polyacrylamide gel electrophoresis
PBS phosphate-buffered saline
PEG polyethylene glycol
PMSF phenylmethylsulphonyl fluoride
pTyr phosphotyrosine
SDS sodium dodecylsulphate
Tris tris(hydroxymethyl)aminomethane
VEGF vascular endothelial growth factor
v/v ratio by volume (of a solution)
w/v ratio by weight (of a solution)

B-1. Tie2 Kinase Assay:

The Tie2-inhibitory activity of the substances according to the invention was determined with the aid of one of the Tie2-TR-FRET assays described in the sections below at an ATP concentration of 1 mM (TR-FRET=Time-Resolved Fluorescence Resonance Energy Transfer):

The enzyme used was a recombinant fusion protein of glutathione S-transferase (GST) and the intracellular domain of human Tie2 (amino acids 776-1124) which was expressed in Baculovirus-infected insect cells (Hi5) and was purified by affinity chromatography on glutathione-Sepharose. Alternatively, it is also possible to use commercially available GST-His6-Tie2 fusion protein (ProQinase GmbH, Freiburg im Breisgau, Germany). The substrate used for the kinase reaction was the biotinylated peptide biotin-Ahx-EPKDDAY-PLYSDFG (C-terminus in amide form) which is commercially available (for example from Biosyntan, Berlin, Germany).

For the assay, 50 nl of a 100-fold concentrated solution of the respective test substance in DMSO were pipetted into a black low-volume 384-well microtitre plate (Greiner Bio-One, Frickenhausen, Germany) 2 μl of a solution of the Tie2 fusion protein in assay buffer [50 mM HEPES/HCl pH 7, mM MgCl$_2$, 2.5 mM MnCl$_2$, 1 mM dithiothreitol, 0.01% (v/v) Nonidet P-40, 0.1% (w/v) bovine serum albumin (BSA), 1× Complete EDTA-free protease inhibitor mixture (Roche)] were added, and the mixture was incubated for 15 min to allow pre-binding of the substance to the enzyme prior to the kinase reaction. The kinase reaction was then started by adding 3 μl of a solution of adenosine triphosphate (ATP, 1.67 mM→final concentration in 5 μl assay volume=1 mM) and substrate (1.67 μM→final concentration in 5 μl assay volume=1 μM) in assay buffer, and the resulting mixture was incubated for a reaction time of 60 min at 22° C. The concentration of the Tie2 fusion protein was adapted to the respective activity of the enzyme and adjusted such that the assay was carried out in the linear range. Typical concentrations were in the range of 30 ng/ml.

The reaction was stopped by addition of 5 μl of a solution of TR-FRET detection reagents [200 nM streptavidin-XL665 and 2 nM PT66-Eu chelate, a europium chelate-labelled anti-phosphotyrosine antibody (Perkin-Elmer); alternatively, it is also possible to use PT66-Tb cryptate (Cisbio Bioassays, Codolet, France)] in aqueous EDTA solution [90 mM EDTA, 0.28% (w/v) bovine serum albumin (BSA) in 50 mM HEPES pH 7.5]. The resulting mixture was incubated at 22° C. for 1 h to allow formation of the complex of the biotinylated phosphorylated substrate and the detection reagents. The amount of phosphorylated substrate was then determined by measuring the resonance energy transfer from PT66-Eu chelate to streptavidin-XL665. To this end, the fluorescence emissions at 620 nm and 665 nm after excitation at 350 nm were measured in a TR-FRET measuring instrument (for example Viewlux, Perkin-Elmer). The ratio of the emissions at 665 nm and at 620 nm was taken as a measure of the amount of phosphorylated substrate. The data obtained in this manner were normalized (enzyme reaction without inhibitor=0% inhibition; all other assay components, but no enzyme=100% inhibition).

Usually, the test substance in question was tested on the same microtitre plate at ten different concentrations in the range from 20 μM to 0.073 nM (for example at 20 μM, 5.7 μM, 1.6 μM, 0.47 μM, 0.13 μM, 38 nM, 11 nM, 3.1 nM, 0.89 nM, 0.25 nM and 0.073 nM) in duplicate for each concentration. The dilution series were prepared prior to the assay at the stage of the 100-fold concentrated solution by serial dilution (the exact concentrations may vary depending on the pipettors used in each case). $IC_{50}$ values were calculated using a 4-parameter fit, with the aid of inhouse software.

Table 1 below lists the $IC_{50}$ values from this assay for individual working examples (in some cases as means of several independent individual determinations):

TABLE 1

| Example No. | $IC_{50}$ [nmol/l] |
|---|---|
| 1 | 0.3 |
| 2 | 6.0 |
| 3 | 1.2 |
| 4 | 0.6 |
| 5 | 380 |
| 6 | 5.0 |
| 7 | 105 |
| 8 | 1.9 |
| 9 | 6.7 |
| 10 | 0.3 |
| 11 | 0.3 |
| 12 | 0.7 |
| 13 | 1.3 |
| 14 | 0.4 |
| 15 | 24 |
| 16 | 0.7 |
| 17 | 0.3 |
| 18 | 0.7 |
| 19 | 0.9 |
| 20 | 3.1 |
| 21 | 2.1 |
| 22 | 0.6 |
| 23 | 0.3 |
| 24 | 0.8 |
| 25 | 1.9 |
| 26 | 0.8 |
| 27 | 3.1 |
| 28 | 2.1 |
| 29 | 2.0 |
| 30 | 2.0 |
| 31 | 1.1 |
| 32 | 0.4 |
| 33 | 2.5 |
| 34 | 2.1 |
| 35 | 0.5 |
| 36 | 0.3 |
| 37 | 0.4 |
| 38 | 15 |
| 39 | 320 |
| 40 | 0.5 |
| 41 | 35 |
| 42 | 1.5 |
| 43 | 56 |
| 44 | 130 |
| 45 | 740 |
| 46 | 980 |
| 47 | 0.3 |
| 48 | 0.3 |
| 49 | 0.3 |
| 50 | 1.2 |
| 51 | 0.7 |
| 52 | 230 |
| 53 | 340 |
| 54 | 670 |
| 55 | 275 |
| 56 | 52 |
| 57 | 995 |
| 58 | 330 |
| 59 | 600 |
| 60 | 125 |
| 61 | 260 |
| 62 | 500 |
| 63 | 770 |
| 64 | 41 |
| 65 | 57 |
| 66 | 7.9 |
| 67 | 57 |

TABLE 1-continued

| Example No. | $IC_{50}$ [nmol/l] |
|---|---|
| 68 | 71 |
| 69 | 580 |
| 70 | 105 |
| 71 | 34 |
| 72 | 350 |
| 73 | 0.3 |
| 74 | 0.5 |
| 75 | 0.5 |
| 76 | 82 |
| 77 | 13 |
| 78 | 115 |
| 79 | 26 |
| 80 | 725 |
| 81 | 435 |
| 82 | 250 |
| 83 | 110 |
| 84 | 220 |
| 85 | 20 |
| 86 | 1.1 |
| 87 | 980 |
| 88 | 23 |
| 89 | 2.3 |
| 90 | 91 |
| 91 | 215 |
| 92 | 29 |
| 93 | 19 |
| 95 | 350 |
| 96 | 47 |
| 97 | 9.2 |
| 98 | 595 |
| 99 | 240 |
| 100 | 175 |
| 102 | 19 |
| 103 | 130 |
| 105 | 39 |
| 106 | 110 |
| 107 | 0.6 |
| 108 | 0.7 |
| 109 | 0.5 |
| 110 | 5.0 |
| 111 | 0.7 |
| 112 | 0.7 |
| 113 | 0.6 |
| 114 | 0.3 |
| 115 | 0.8 |
| 116 | 0.5 |
| 118 | 0.4 |
| 119 | 110 |
| 120 | 37 |
| 121 | 18 |
| 122 | 3.9 |
| 123 | 56 |
| 124 | 297 |
| 125 | 280 |
| 126 | 1.2 |
| 127 | 1.4 |
| 128 | 43 |
| 129 | 3.2 |
| 130 | 24 |
| 131 | 252 |
| 132 | 4.6 |
| 133 | 53 |
| 134 | 55 |
| 135 | 607 |
| 136 | 687 |
| 137 | 409 |
| 138 | 65 |
| 139 | 0.5 |
| 140 | 0.5 |
| 141 | 62 |
| 142 | 0.9 |
| 143 | 1.3 |
| 144 | 0.6 |
| 145 | 0.9 |
| 146 | 0.7 |
| 147 | 0.2 |
| 148 | 0.4 |
| 149 | 2.3 |

TABLE 1-continued

| Example No. | IC$_{50}$ [nmol/l] |
|---|---|
| 150 | 2.4 |
| 151 | 6.1 |
| 152 | 0.4 |
| 153 | 0.3 |
| 154 | 0.4 |
| 155 | 0.7 |
| 156 | 5.9 |
| 157 | 0.5 |
| 158 | 58 |
| 159 | 10 |
| 160 | 1.0 |
| 162 | 28 |
| 163 | 8.9 |
| 164 | 0.4 |
| 165 | 1.7 |
| 166 | 0.3 |
| 168 | 726 |
| 169 | 1.0 |
| 170 | 1.2 |
| 171 | 0.3 |
| 172 | 7.8 |
| 173 | 9.3 |
| 174 | 2.8 |
| 175 | 3.2 |
| 176 | 0.8 |
| 177 | 1.8 |
| 178 | 0.8 |

B-2. Tie2-pTyr-ELISA:

The cellular activity of the compounds according to the invention as Tie2 kinase inhibitors was determined in human endothelial cells (HUVEC) by measuring the inhibition of the autophosphorylation, elevated by treatment with sodium orthovanadate, of the endogenous Tie2 receptor by means of a Tie2/phosphotyrosine sandwich ELISA.

Cell Culture:

Human endothelial cells (human umbilical vein endothelial cells, HUVEC) were obtained from Cellsystems (FC-0003), cultured in Vasculife VEGF complete medium (Cellsystems, LL-1020) with 2% foetal calf serum (FCS) at 37° C./5% CO$_2$ and used for Tie2-ELISA measurements up to passage 8.

Cell Treatment:

HUVEC were plated in a culture volume of 100 µl of Vasculife VEGF complete medium at a cell density of 30 000 cells per well in transparent collagen-coated 96-well cell culture plates (Falcon, #353075) and incubated in an incubation cabinet at 37° C./5% CO$_2$ overnight. The test substances dissolved in DMSO were used to prepare in each case one dilution series in Vasculife VEGF low-serum medium [basal medium with LifeFactors (Cellsystems, LM-0002), without FCS, with 0.1% BSA] without sodium orthovanadate and one dilution series in Vasculife VEGF low-serum-medium with 8 mM sodium orthovanadate in the desired concentrations in the range from 10 µM to 10 µM, the final DMSO concentration being 1%. After removal of the complete medium, 100 µl per well of the dilute substances in low-serum medium without sodium orthovanadate were pipetted onto the cells, and the plates were incubated in an incubation cabinet at 37° C./5% CO$_2$ for 10 min. A further 100 µl of the same substance dilution in low-serum medium with 8 mM sodium orthovanadate were then pipetted into the respective well and the cells were incubated in a volume of now 200 µl in the presence of 4 mM sodium orthovanadate at the desired substance concentration in an incubation cabinet at 37° C./5% CO$_2$ for a further 20 min. The cell supernatant of the plates was then removed and the cells were washed once with 250 µl per well of cold PBS which contained 4 mM sodium orthovanadate. 120 µl of Duschl lysis buffer [50 mM HEPES pH 7.2, 150 mM NaCl, 1 mM MgCl$_2$, 10% glycerol, 1.5% Triton X-100, 4 mM sodium orthovanadate, 250 µl S-PIC phosphatase inhibitor cocktail 2 (Sigma, P5726) and 1 tablet of Complete proteinase inhibitor mixture (Roche, #1836145) per 10 ml] were then added to the cells in each well. The plates were shaken briefly and then incubated on ice for 20 min, and the lysates in the cell culture plates were then frozen at −80° C. for at least 30 min.

Sandwich ELISA:

For measuring the autophosphorylation of the endogenous Tie2 receptor in the cell lysates prepared, a self-prepared anti-Tie2 antibody directed against the N-terminus of the Tie-2 receptor (1.09 mg/ml) and an HRP-coupled anti-phosphotyrosine antibody (Sigma, A4595, clone pY-20) were used. White 96-well ELISA plates (Lumitrac600, Greiner, #655074) were incubated with 100 µl per well of a 1:1000 dilution of the anti-Tie2 antibody in coating buffer [15 mM Na$_2$CO$_3$, 35 mM NaHCO$_3$, pH 9.6] with shaking at 4° C. overnight. The coated ELISA plates were washed three times with 250 µl PBST buffer [0.1% Tween-20 in PBS], the wells were blocked with 250 µl 3% BSA in PBST buffer with shaking at RT for 1-6 h and washed three more times with 250 µl PBST buffer. From the cell lysate plates thawed in the fridge, in each case 100 µl of lysate were transferred into the coated wells of the ELISA plates, and the plates were incubated with shaking at 4° C. overnight. The plates were washed three times with in each case 250 µl of PBST buffer, and 100 µl of a 1:5000 dilution of the anti-phosphotyrosine HRP antibody in 3% Prionex (Calbiochem, #529600) in PBST were then pipetted into each well and the plates were incubated with shaking and protected from light at 4° C. overnight. The plates were washed three times with in each case 250 µl of PBST, and 100 µl of chemiluminescent substrate [BM Chemiluminescence ELISA Substrate (POD) Reagent A and B 1:100, Roche, #1582950] were then pipetted into each well, and after 3 min the plates were measured using a luminescence reader. Means and standard deviations of individual measurements were calculated from triple determinations using Microsoft Excel. For data analysis and determination of the IC$_{50}$ values, the GraphPad Prism 5 software package was used.

Table 2 below lists the IC$_{50}$ values, determined from 2-7 independent measurements, from this assay for representative working examples:

TABLE 2

| Example No. | IC$_{50}$ [nmol/l] |
|---|---|
| 2 | 7.6 |
| 3 | 3.4 |
| 4 | 4.7 |
| 6 | 17 |
| 12 | 4.7 |
| 16 | 3.2 |
| 18 | 11 |
| 26 | 3.0 |
| 28 | 3.6 |
| 32 | 2.1 |
| 40 | 2.3 |
| 48 | 6.4 |
| 51 | 8.8 |
| 66 | 46 |
| 73 | 0.8 |
| 74 | 0.6 |
| 75 | 1.7 |
| 77 | 8.8 |
| 85 | 44 |
| 88 | 41 |
| 102 | 18 |
| 107 | 0.9 |

TABLE 2-continued

| Example No. | IC$_{50}$ [nmol/l] |
|---|---|
| 112 | 1.4 |
| 116 | 2.9 |
| 157 | 1.0 |
| 162 | 8.9 |

B-3. Inhibition of the Ang1-Mediated Tie2 Phosphorylation in Vivo:

To assess the activity of selected compounds according to the invention on the target protein in vivo, the inhibition of the phosphorylation of Tie2 in the lungs of immunodeficient mice was examined in ex vivo analyses.

To this end, at time point 0, 50 or 100 mg/kg of the respective test substance was administered p.o. to three animals per group, and the Tie2 phosphorylation was induced after 2 h 45 min by i.v. administration of 12.5 µg of angiopoietin-1 (R&D Systems, order No. 923-AN/CF) per animal. After 15 min, the animals were sacrificed and the lungs were removed and immediately shock-frozen in liquid nitrogen. The lungs were comminuted with dry-ice cooling and dispersed in orthovanadate- and protease inhibitor-containing lysis buffer [50 mM Tris-Cl pH~8, 150 mM NaCl, 10% glycerol, 1.5% Triton X-100, 1 mM EGTA, 50 mM NaF, 10 mM $Na_4P_2O_7$, 4 mM $Na_3VO_4$, 1% phosphatase inhibitor cocktail 2 (Sigma, P5726), 1 mM PMSF, Complete mini EDTA-free Protease Inhibitor Cocktail Tablet (Roche, order No. 1836170)] using an Ultra-Turrax (T10 basic, IKA-Werke, Germany). After 20 minutes of incubation on ice, the lung homogenizates were centrifuged at 4° C. and 13 000 rpm for 10 min and the protein concentration of the supernatants (lung lysates) were determined by BCA assay (Pierce Thermo Scientific, order No. 23225).

For immunoprecipitation, 5-8 mg of lysate protein were mixed with 5 µg of a monoclonal antibody directed against the human Tie2 receptor (anti-human Tie2 mouse monoclonal Ab, USBiological, #T5498-72) and incubated for 1 h at 4° C. on a rotator rotating overhead. 30 µl of packed protein G-Sepharose beads (Protein G Sepharose 4 Fast Flow, GE Healthcare, order No. 17-0618-01) washed in lysis buffer were then added to the lysate antibody solution and the mixture was incubated further under identical conditions overnight. The protein G-Sepharose beads were sedimented by centrifugation (30 sec), the supernatant was discarded and the beads were washed three times with cold lysis buffer. The beads were heated in in each case 40-70 µl reducing SDS-PAGE sample buffer [NuPAGE LDS Sample Buffer (4×), Invitrogen, #NP0007, NuPAGE Sample Reducing Agent, Invitrogen, #NP0004] at 95° C. for 7 min, and 15-25 µl of each sample per gel lane were separated on a 4-12% Criterion gel (Criterion XT Precast Gel, BIO-RAD). The proteins were transferred from the polyacrylamide gel by means of a Trans-Blot Semi-Dry apparatus (BIO-RAD Trans-Blot SD Semi-Dry Electrophoretic Transfer Cell, Cat. No. 170-3940) to a nitrocellulose membrane (BIO-RAD Trans-Blot Transfer Medium Pure Nitrocellulose Membrane, Cat. No. 162-0114). To block unspecific binding sites, the membrane was incubated with shaking at RT in TBST buffer [50 mM Tris-Cl pH 7.5, 150 mM NaCl, 0.05% Tween-20] with 3% BSA for 1 h.

For the detection of phosphorylated Tie2, the membrane was incubated overnight at 4° C. with a solution of 0.5 µg/ml of an anti-phospho(Y992)-Tie2 antibody (R&D Systems, order No. AF2720) in the same BSA-containing buffer, washed three times with TBST and incubated for 1 h at RT with an appropriate HRP-coupled second antibody (Dianova, order No. 711-035-152). After three further wash steps, the bands corresponding to the Tie2 protein phosphorylated at tyrosine-992 were detected via chemiluminescence (Super-Signal® West Dura Extended Duration Substrate, Pierce Thermo Scientific, #34075) with the BIO-RAD Molecular Imager ChemiDoc XRS. For the detection of Tie2 total protein on the blot membrane, initially the antibodies bound on the membrane were removed by heating for 30 minutes in a water bath at 50° C. in a Tris-HCl buffer (62.5 mM Tris-Cl pH 6.5) with 2% SDS and 100 mM β-mercaptoethanol and then washing three times. The membranes were then incubated overnight at 4° C. with an antibody able to recognize the total Tie2 protein (Anti-mouse Tie2 goat polyclonal Ab, R&D Systems, #AF762, 0.2 µg/ml). After washing and incubation with the appropriate second antibody (Dianova, #705-035-147), the Tie2 protein bands were detected as described above. The protein bands were evaluated densitometrically using the software of the BIO-RAD imager and the ratio of phosphorylated to total Tie2 protein was determined.

B-4. Inhibition of Tumour Growth in Human Tumour Xenograft Models:

Human tumour xenograft models in immunodeficient mice were used to assess the effect of the substances. For this purpose, tumour cells were cultured in vitro and implanted subcutaneously into nu/nu mice. The animals were treated by peroral administration of the test substance after the tumour had been established. The state of health of the animals was checked daily, and the treatments were performed in accordance with animal welfare regulations. The tumour area was measured with slide gauges (length L, breadth B=shorter dimension). The tumour volume was calculated by the formula (L×B$^2$)/2. The inhibition in tumour growth was determined at the end of the study as the T/C ratio of the tumour areas and tumour weights and as the TGI value (tumour growth inhibition, calculated from the formula [1-(T/C)]× 100) (T=tumour size in the treated group; C=tumour size in the untreated control group).

B-5. Determination of Pharmacokinetic Parameters after Intravenous and Peroral Administration:

The substance to be examined was administered to animals (for example mice or rats) intravenously as a solution (for example in corresponding plasma with a small addition of DMSO or in a PEG/ethanol/water mixture), and peroral administration was effected as a solution (for example in Solutol/ethanol/water or PEG/ethanol/water mixtures) or as a suspension (e.g. in tylose), in each case via a gavage. After administration of the substance, blood was taken from the animals at fixed times. The blood was heparinized, then plasma was obtained therefrom by centrifugation. The substance was quantified analytically in the plasma via LC-MS/MS. From the plasma concentration/time plots determined in this way, using an internal standard and with the aid of a validated computer program, the pharmacokinetic parameters, such as AUC (area under the concentration/time curve), $C_{max}$ (maximum plasma concentration), $t_{1/2}$ (half life), $V_{SS}$ (distribution volume) and CL (clearance), and the absolute and relative bioavailability F and $F_{rel}$ (i.v./p.o. comparison or comparison of suspension to solution after p.o. administration), were calculated.

C. WORKING EXAMPLES OF PHARMACEUTICAL COMPOSITIONS

The compounds according to the invention can be converted to pharmaceutical formulations as follows:

Tablet:
Composition:
100 mg of the compound according to the invention, 50 mg of lactose (monohydrate), 50 mg of maize starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Preparation:
The mixture of the compound according to the invention, lactose and starch is granulated with a 5% solution (w/w) of the PVP in water. After drying, the granules are mixed with the magnesium stearate for 5 minutes. This mixture is pressed with a conventional tableting press (for tablet dimensions see above). The guide value used for the pressing is a pressing force of 15 kN.

Suspension for Oral Administration:
Composition:
1000 mg of the compound according to the invention, 1000 mg of ethanol (96%), 400 mg of Rhodigel® (xanthan gum from FMC, Pennsylvania, USA) and 99 g of water.

A single dose of 100 mg of the compound according to the invention corresponds to 10 ml of oral suspension.

Preparation:
The Rhodigel is suspended in ethanol and the compound according to the invention is added to the suspension. The water is added while stirring. The mixture is stirred for approx. 6 h until swelling of the Rhodigel has ended.

Solution for Oral Administration:
Composition:
500 mg of the compound according to the invention, 2.5 g of polysorbate and 97 g of polyethylene glycol 400. A single dose of 100 mg of the compound according to the invention corresponds to 20 g of oral solution.

Preparation:
The compound according to the invention is suspended in the mixture of polyethylene glycol and polysorbate while stirring. The stirring operation is continued until dissolution of the compound according to the invention is complete.

i.v. Solution:
The compound according to the invention is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

The invention claimed is:

1. Compound of the formula (I)

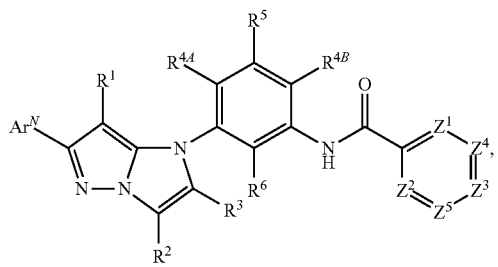

in which
$Ar^N$ represents 5- or 6-membered azaheteroaryl selected from the group consisting of

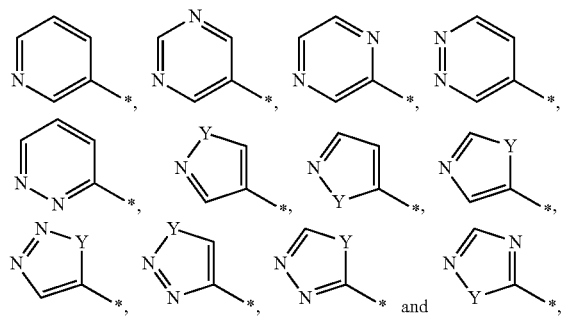

in which * marks the attachment to the imidazopyrazole grouping
and
Y represents O, S or NH,
$R^1$ represents hydrogen or fluorine,
$R^2$ represents hydrogen or $(C_1-C_4)$-alkyl,
$R^3$ represents hydrogen,
$R^{4A}$ and $R^{4B}$ independently of one another represent hydrogen, fluorine, chlorine, methyl, fluoromethyl, difluoromethyl, trifluoromethyl, hydroxymethyl, methoxymethyl, ethyl, hydroxy, methoxy or trifluoromethoxy,
$R^5$ represents hydrogen, fluorine, chlorine or methyl,
$R^6$ represents hydrogen, fluorine, methyl or hydroxy,
$Z^1$ represents C—$R^{7A}$ or N,
$Z^2$ represents C—$R^{7B}$ or N,
$Z^3$ represents C—$R^8$ or N,
$Z^4$ represents C—$R^9$ or N
and
$Z^5$ represents C—$R^{10}$ or N,
where in total at most one of the ring members $Z^1$, $Z^2$, $Z^3$, $Z^4$ and $Z^5$ represents N
and in which
$R^{7A}$ and $R^{7B}$ independently of one another represent hydrogen, fluorine, chlorine, methyl, hydroxy or methoxy,
$R^8$ represents hydrogen, fluorine, chlorine or methyl,
$R^9$ represents hydrogen, pentafluorosulphanyl, (trifluoromethyl)sulphanyl, trimethylsilyl, $(C_1-C_6)$-alkyl, $(C_1-C_6)$-alkoxy, $(C_3-C_6)$-cycloalkyl, oxetanyl or tetrahydropyranyl,
where $(C_1-C_6)$-alkyl and $(C_1-C_6)$-alkoxy may be substituted up to six times by fluorine
and
$(C_3-C_6)$-cycloalkyl, oxetanyl and tetrahydropyranyl may be substituted up to two times by identical or different radicals selected from the group consisting of fluorine, methyl, trifluoromethyl and hydroxy,
and
$R^{10}$ represents hydrogen, fluorine, chlorine, bromine, cyano, $(C_1-C_6)$-alkyl, hydroxy, $(C_1-C_6)$-alkoxy, $(C_1-C_4)$-alkylsulphonyl, $(C_3-C_6)$-cycloalkyl, phenyl, 5- or 6-membered heteroaryl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$,
where $(C_1-C_6)$-alkyl and $(C_1-C_6)$-alkoxy may be substituted by a radical selected from the group consisting of hydroxy, methoxy, ethoxy, 2-hydroxyethoxy, 2-methoxyethoxy, 2-ethoxyethoxy, amino, methylamino and dimethylamino or up to six times by fluorine and $(C_3-C_6)$-cycloalkyl may be substituted up to two times by identical or different radicals selected from the group consisting of methyl, hydroxy, methoxy, ethoxy, amino, methylamino and dimethylamino and phenyl and 5- or 6-membered heteroaryl may be substituted up to two times by identical or different radicals selected from the group consisting of fluorine, chlorine, cyano, methyl and trifluoromethyl, and in which $L^1$ represents a bond or —$CH_2$—, $L^2$ represents a bond or —$CH_2$—, $L^3$ represents a bond or —O—, $R^{11}$ represents hydrogen or $(C_1-C_4)$-alkyl, $R^{12A}$, $R^{12B}$, $R^{13A}$ and $R^{13B}$ independently of one another represent hydrogen or $(C_1-C_4)$-alkyl, where $(C_1-C_4)$-alkyl may in each case be substituted by a radical selected from the group consisting of hydroxy, methoxy, ethoxy, amino, methylamino and dimethylamino, or $R^{12A}$ and $R^{12B}$ and $R^{13A}$ and $R^{13B}$, respectively, are attached to one another and together with the nitrogen atom to which they are respectively attached form a 4- to 6-membered heterocycle which may contain a further ring heteroatom from the group consisting of N, O and S and which may be substituted up to two times by identical or different radicals selected from the group consisting of fluorine, cyano, $(C_1-C_4)$-alkyl, hydroxy, $(C_1-C_4)$-alkoxy and oxo, and $R^{14}$ represents a 4- to 6-membered heterocycle which is attached via a ring carbon atom and contains a ring heteroatom from the group consisting of N, O and S and which may be substituted up to two times by identical or different radicals selected from the group consisting of fluorine, cyano, $(C_1-C_4)$-alkyl, hydroxy, $(C_1-C_4)$-alkoxy and oxo, where $R^{10}$ does not represent hydrogen, fluorine, chlorine or bromine if $Z^4$ represents CH or N, and $Z^5$ does not represent N if $Z^4$ represents CH, and its salts, solvates and solvates of the salts.

2. Compound of the formula (I) according to claim 1 in which $Ar^N$ represents 5- or 6-membered azaheteroaryl selected from the group consisting of

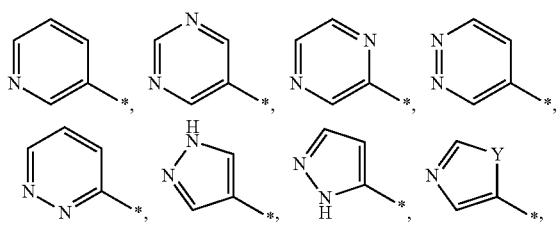

-continued

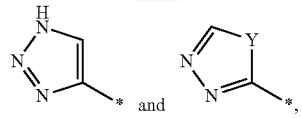

in which * marks the attachment to the imidazopyrazole grouping and

Y represents S or NH, $R^1$ represents hydrogen or fluorine, $R^2$ represents hydrogen or $(C_1-C_4)$-alkyl, $R^3$ represents hydrogen, $R^{4A}$ and $R^{4B}$ independently of one another represent hydrogen, fluorine, chlorine, methyl, fluoromethyl, difluoromethyl, trifluoromethyl, ethyl or methoxy, $R^5$ represents hydrogen, fluorine, chlorine or methyl, $R^6$ represents hydrogen, fluorine, methyl or hydroxy, $Z^1$ represents C—$R^{7A}$ or N, $Z^2$ represents C—$R^{7B}$ or N, $Z^3$ represents C—$R^8$ or N, $Z^4$ represents C—$R^9$ and $Z^5$ represents C—$R^{10}$ or N, where in total at most one of the ring members $Z^1$, $Z^2$, $Z^3$, $Z^4$ and $Z^5$ represents N and in which $R^{7A}$ and $R^{7B}$ independently of one another represent hydrogen or fluorine, $R^8$ represents hydrogen or fluorine, $R^9$ represents hydrogen, pentafluorosulphanyl, (trifluoromethyl)sulphanyl, $(C_1-C_4)$-alkyl, $(C_1-C_4)$-alkoxy, cyclopropyl, cyclobutyl or oxetanyl, where $(C_1-C_4)$-alkyl and $(C_1-C_4)$-alkoxy may be substituted up to six times by fluorine and cyclopropyl, cyclobutyl and oxetanyl may be substituted up to two times by identical or different radicals selected from the group consisting of fluorine, methyl, trifluoromethyl and hydroxy, and $R^{10}$ represents hydrogen, fluorine, chlorine, bromine, cyano, $(C_1-C_4)$-alkyl, hydroxy, $(C_1-C_4)$-alkoxy, $(C_1-C_4)$-alkylsulphonyl, 5-membered azaheteroaryl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$, where $(C_1-C_4)$-alkyl and $(C_1-C_4)$-alkoxy may be substituted by a radical selected from the group consisting of hydroxy, methoxy, ethoxy and amino or up to three times by fluorine and 5-membered azaheteroaryl may be substituted up to two times by methyl, and in which $L^1$ represents a bond or —$CH_2$—, $L^2$ represents a bond, $L^3$ represents a bond or —O—, $R^{11}$ represents hydrogen or $(C_1-C_4)$-alkyl, $R^{12A}$, $R^{12B}$, $R^{13A}$ and $R^{13B}$ independently of one another represent hydrogen or $(C_1-C_4)$-alkyl or $R^{12A}$ and $R^{12B}$ and $R^{13A}$ and $R^{13B}$, respectively, are attached to one another and together with the nitrogen atom to which they are respectively attached form a 4- to 6-membered heterocycle which may contain a further ring heteroatom from the group consisting of N and O and which may be substituted up to two times by identical or different radicals selected from the group consisting of fluorine, cyano, methyl, ethyl, hydroxy, methoxy and ethoxy, and $R^{14}$ represents a 4- to 6-membered heterocycle which is attached via a ring carbon atom and contains a ring heteroatom from the group consisting of N and O and which may be substituted up to two times by identical or different radicals selected from the group consisting of fluorine, cyano, methyl, ethyl, hydroxy, methoxy and ethoxy, where $R^{10}$ does not represent hydrogen, fluorine, chlorine or bromine if $Z^4$ represents CH, and $Z^5$ does not represent N if $Z^4$ represents CH, and its salts, solvates and solvates of the salts.

3. Compound of the formula (I) according to claim 1 in which $Ar^N$ represents 5- or 6-membered azaheteroaryl of the formula

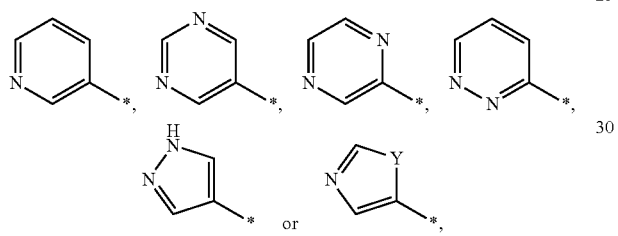

in which * marks the attachment to the imidazopyrazole grouping and

Y represents S or NH, $R^1$ represents hydrogen or fluorine, $R^2$ represents hydrogen or methyl, $R^3$ represents hydrogen, $R^{4A}$ represents chlorine, methyl or trifluoromethyl, $R^{4B}$ represents hydrogen, fluorine, chlorine or methyl, $R^5$ represents hydrogen, fluorine, chlorine or methyl, $R^6$ represents hydrogen, fluorine, methyl or hydroxy, $Z^1$ represents CH, $Z^2$ represents CH, $Z^3$ represents CH or N, $Z^4$ represents C—$R^9$, in which $R^9$ represents pentafluorosulphanyl, (trifluoromethyl)sulphanyl, trifluoromethyl, trifluoromethoxy, ($C_2$-$C_4$)-alkyl, ($C_2$-$C_4$)-alkoxy, cyclopropyl, cyclobutyl or oxetan-3-yl, where ($C_2$-$C_4$)-alkyl and ($C_2$-$C_4$)-alkoxy may be substituted up to five times by fluorine and cyclopropyl, cyclobutyl and oxetan-3-yl may be substituted by a radical selected from the group consisting of fluorine, methyl, trifluoromethyl and hydroxy, and $Z^5$ represents C—$R^{10}$, in which $R^{10}$ represents hydrogen, fluorine, chlorine, bromine, cyano, ($C_1$-$C_4$)-alkyl, hydroxy, ($C_1$-$C_4$)-alkoxy, methylsulphonyl, 1H-imidazol-1-yl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$, where ($C_1$-$C_4$)-alkyl and ($C_1$-$C_4$)-alkoxy may be substituted by a radical selected from the group consisting of hydroxy, methoxy, ethoxy and amino or up to three times by fluorine and 1H-imidazol-1-yl may be substituted up to two times by methyl, and in which $L^1$ represents a bond or —$CH_2$—, $L^2$ represents a bond, $L^3$ represents a bond or —O—, $R^{11}$ represents hydrogen or ($C_1$-$C_4$)-alkyl, $R^{12A}$ and $R^{12B}$ independently of one another represent hydrogen or ($C_1$-$C_4$)-alkyl or $R^{12A}$ and $R^{12B}$ are attached to one another and together with the nitrogen atom to which they are attached form a 4- to 6-membered heterocycle which may contain a further ring heteroatom from the group consisting of N and O and which may be substituted by a radical selected from the group consisting of cyano, methyl, hydroxy and methoxy or up to two times with fluorine, $R^{13A}$ and $R^{13B}$ independently of one another represent hydrogen or ($C_1$-$C_4$)-alkyl, and $R^{14}$ represents a 4- to 6-membered heterocycle which is attached via a ring carbon atom and, as ring heteroatom, contains a nitrogen atom and which may be substituted by a radical selected from the group consisting of cyano, methyl, hydroxy and methoxy or up to two times with fluorine, and its salts, solvates and solvates of the salts.

4. Compound of the formula (I) according to claim 1, in which $Ar^N$ represents 5- or 6-membered azaheteroaryl of the formula

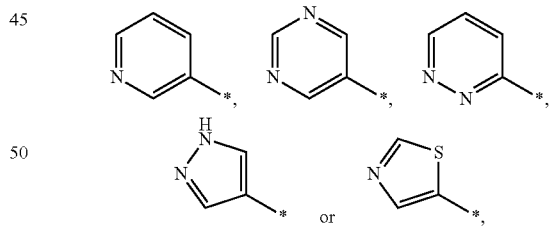

in which * marks the attachment to the imidazopyrazole grouping $R^1$ represents hydrogen, $R^2$ represents hydrogen or methyl, $R^3$ represents hydrogen, $R^{4A}$ represents chlorine or methyl, $R^{4B}$ represents hydrogen, fluorine, chlorine or methyl, $R^5$ represents hydrogen, $R^6$ represents hydrogen, $Z^1$ represents CH, $Z^2$ represents CH, $Z^3$ represents CH or N, $Z^4$ represents C—$R^9$, in which $R^9$ represents pentafluorosulphanyl, (trifluoromethyl)sulphanyl, trifluoromethyl, 2-fluoropropan-2-yl, tert-butyl, 1,1,1-trifluoro-2-methylpropan-2-yl, trifluoromethoxy, 1,1,2,2-tetrafluoroethoxy or 3-methyloxetan-3-yl, and $Z^5$ represents C—$R^{10}$, in which $R^{10}$ represents hydrogen, fluorine, chlorine, cyano, ($C_1$-$C_4$)-alkyl, hydroxy, ($C_1$-$C_4$)-alkoxy, methylsulphonyl, 2-methyl-1H-imidazol-1-yl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$, where ($C_1$-$C_4$)-alkyl and ($C_1$-$C_4$)-alkoxy may be substituted by a radical selected from the group consisting of hydroxy, methoxy, ethoxy and amino or up to three times by fluorine, and in which $L^1$ represents a bond or —$CH_2$—,
$L^2$ represents a bond,
$L^3$ represents a bond or —O—,
$R^{11}$ represents hydrogen,
$R^{12A}$ and $R^{12B}$ independently of one another represent hydrogen or methyl or $R^{12A}$ and $R^{12B}$ are attached to one another and together with the nitrogen atom to which they are attached form an azetidin-1-yl, pyrrolidin-1-yl or piperidin-1-yl ring, each of which may be substituted by a radical selected from the group consisting of cyano, hydroxy and methoxy, or a piperazin-1-yl, 4-methylpiperazin-1-yl or morpholin-4-yl ring, $R^{13A}$ and $R^{13B}$ represent independently of one another hydrogen or methyl, and $R^{14}$ represents an azetidin-3-yl, pyrrolidin-3-yl, piperidin-3-yl or piperidin-4-yl ring, each of which may be substituted by hydroxy, and its salts, solvates and solvates of the salts.

5. Process for preparing a compound of the formula (I) according to claim 1, wherein

[A] an aniline derivative of the formula (II)

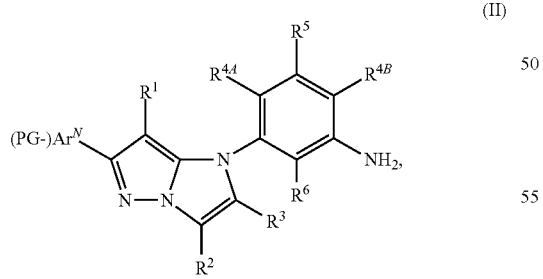

(II)

in which $Ar^N$, $R^1$, $R^2$, $R^3$, $R^{4A}$, $R^{4B}$, $R^5$ and $R^6$ have the meanings given in claim 1 and (PG-) represents an optional nitrogen protective group in the case that Y in $Ar^N$ represents NH, is coupled in an inert solvent in the presence of a condensing agent with a carboxylic acid of the formula (III)

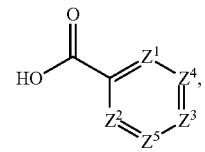

(III)

in which $Z^1$, $Z^2$, $Z^3$, $Z^4$ and $Z^5$ have the meanings given in claim 1, to give the carboxamide of the formula (IV)

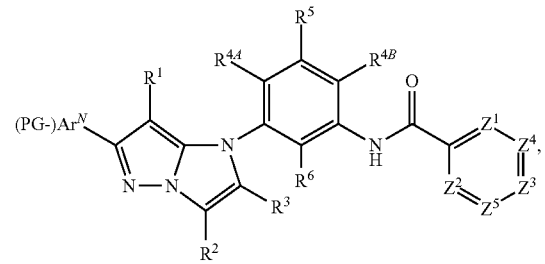

(IV)

in which $Ar^N$, (PG-), $R^1$, $R^2$, $R^3$, $R^{4A}$, $R^{4B}$, $R^5$, $R^6$, $Z^1$, $Z^2$, $Z^3$, $Z^4$ and $Z^5$ have the meanings given above, and the protective group PG, if present, is then removed, or

[B] a 1H-imidazo[1,2-b]pyrazole derivative of the formula (V)

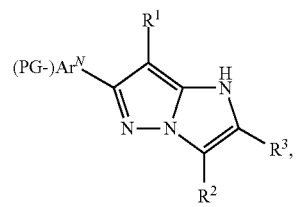

(V)

in which $Ar^N$, $R^1$, $R^2$ and $R^3$ have the meanings given in claim 1 and (PG-) represents an optional nitrogen protective group in the case that Y in $Ar^N$ represents NH, is coupled in an inert solvent with copper(I) catalysis with a phenyl bromide of the formula (VI)

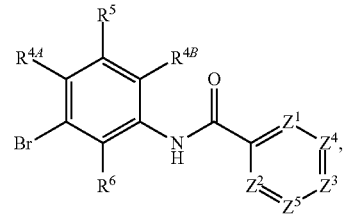

(VI)

in which $R^{4A}$, $R^{4B}$, $R^5$, $R^6$, $Z^1$, $Z^2$, $Z^3$, $Z^4$ and $Z^5$ have the meanings given in claim 1, to give the 1-phenyl-1H-imidazo[1,2-b]pyrazole derivative of the formula (IV)

(IV)

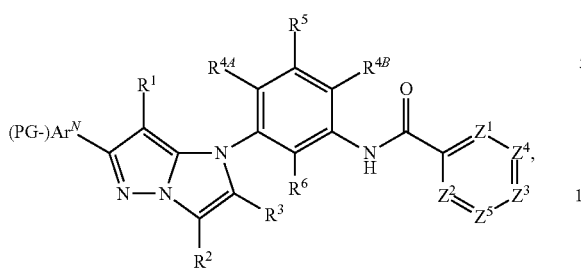

in which $Ar^N$, (PG-), $R^1$, $R^2$, $R^3$, $R^{4A}$, $R^{4B}$, $R^5$, $R^6$, $Z^1$, $Z^2$, $Z^3$, $Z^4$ and $Z^5$ have the meanings given above,
and the protective group PG, if present, is then removed,
or
[C] an aminopyrazole derivative of the formula (VII)

(VII)

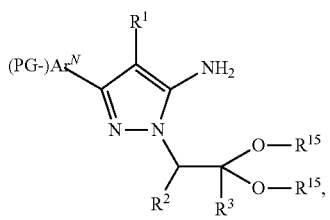

in which $Ar^N$, $R^1$, $R^2$ and $R^3$ have the meanings given in claim 1,
$R^{15}$ represents methyl or ethyl,
and
(PG-) represents an optional nitrogen protective group in the case that Y in $Ar^N$ represents NH,
is coupled in an inert solvent under palladium catalysis with a phenyl bromide of the formula (VI)

(VI)

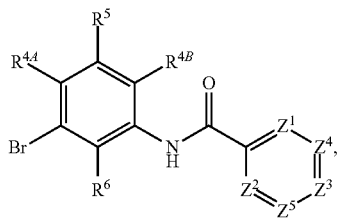

in which $R^{4A}$, $R^{4B}$, $R^5$, $R^6$, $Z^1$, $Z^2$, $Z^3$, $Z^4$ and $Z^5$ have the meanings given in claim 1,
to give a compound of the formula (VIII)

(VIII)

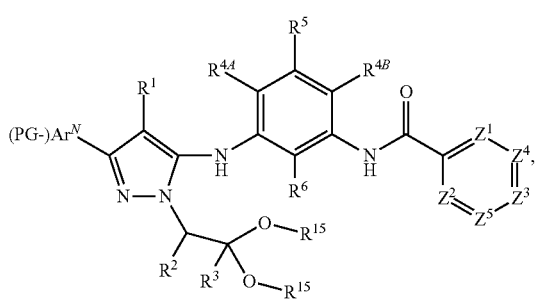

in which $Ar^N$, (PG-), $R^1$, $R^2$, $R^3$, $R^{4A}$, $R^{4B}$, $R^5$, $R^6$, $R^{15}$, $Z^1$, $Z^2$, $Z^3$, $Z^4$ and $Z^5$ have the meanings given above,
the compound of the formula (VIII) is then cyclised by treatment with acid to give the 1-phenyl-1H-imidazo[1,2-b]pyrazole derivative of the formula (IV)

(IV)

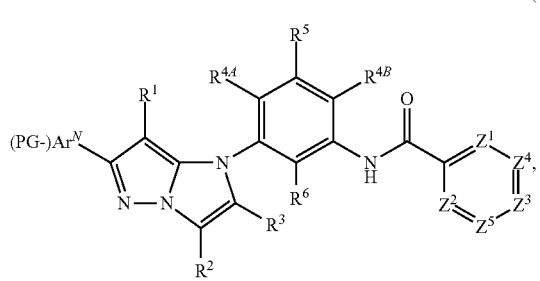

in which $Ar^N$, (PG-), $R^1$, $R^2$, $R^3$, $R^{4A}$, $R^{4B}$, $R^5$, $R^6$, $Z^1$, $Z^2$, $Z^3$, $Z^4$ and $Z^5$ have the meanings given above,
and the protective group PG, if present, is then removed,
and the compound of the formula (I) obtained in this manner is optionally converted with the appropriate (i) solvents and/or (ii) acids or bases into a solvate, salt and/or solvate of a salt.

6. Pharmaceutical composition comprising a compound of the formula (I) according to claim 1 in combination with one or more inert, nontoxic, pharmaceutically suitable auxiliaries.

7. Pharmaceutical composition comprising a compound of the formula (I) according to claim 1 in combination with one or more further active compounds.

8. Method for the inhibition of Tie2 receptor kinase activity in the treatment of a neoplastic disorder or tumour disorder comprising administering to a human or animal in need thereof an effective amount of at least one compound of the formula (I) according to claim 1.

9. Compound of the formula (I) according to claim 2 in which
$Ar^N$ represents 5- or 6-membered azaheteroaryl of the formula

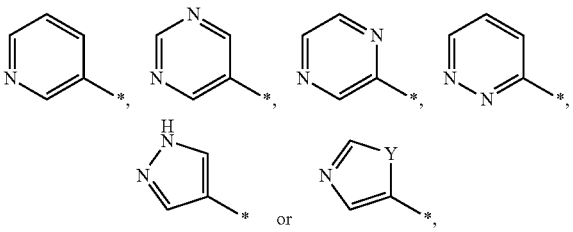

in which * marks the attachment to the imidazopyrazole grouping
and
Y represents S or NH,
$R^1$ represents hydrogen or fluorine,
$R^2$ represents hydrogen or methyl,
$R^3$ represents hydrogen,
$R^{4A}$ represents chlorine, methyl or trifluoromethyl,
$R^{4B}$ represents hydrogen, fluorine, chlorine or methyl,
$R^5$ represents hydrogen, fluorine, chlorine or methyl,
$R^6$ represents hydrogen, fluorine, methyl or hydroxy,
$Z^1$ represents CH, $Z^2$ represents CH, $Z^3$ represents CH or N, $Z^4$ represents C—$R^9$, in which $R^9$ represents pentafluorosulphanyl, (trifluoromethyl)sulphanyl, trifluoromethyl, trifluoromethoxy, ($C_2$-$C_4$)-alkyl, ($C_2$-$C_4$)-alkoxy, cyclopropyl, cyclobutyl or oxetan-3-yl, where ($C_2$-$C_4$)-alkyl and ($C_2$-$C_4$)-alkoxy may be substituted up to five times by fluorine and cyclopropyl, cyclobutyl and oxetan-3-yl may be substituted by a radical selected from the group consisting of fluorine, methyl, trifluoromethyl and hydroxy, and $Z^5$ represents C—$R^{10}$, in which $R^{10}$ represents hydrogen, fluorine, chlorine, bromine, cyano, ($C_1$-$C_4$)-alkyl, hydroxy, ($C_1$-$C_4$)-alkoxy, methylsulphonyl, 1H-imidazol-1-yl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$, where ($C_1$-$C_4$)-alkyl and ($C_1$-$C_4$)-alkoxy may be substituted by a radical selected from the group consisting of hydroxy, methoxy, ethoxy and amino or up to three times by fluorine and 1H-imidazol-1-yl may be substituted up to two times by methyl, and in which $L^1$ represents a bond or —$CH_2$—, $L^2$ represents a bond, $L^3$ represents a bond or —O—, $R^{11}$ represents hydrogen or ($C_1$-$C_4$)-alkyl, $R^{12A}$ and $R^{12B}$ independently of one another represent hydrogen or ($C_1$-$C_4$)-alkyl or $R^{12A}$ and $R^{12B}$ are attached to one another and together with the nitrogen atom to which they are attached form a 4- to 6-membered heterocycle which may contain a further ring heteroatom from the group consisting of N and O and which may be substituted by a radical selected from the group consisting of cyano, methyl, hydroxy and methoxy or up to two times with fluorine, $R^{13A}$ and $R^{13B}$ independently of one another represent hydrogen or ($C_1$-$C_4$)-alkyl, and $R^{14}$ represents a 4- to 6-membered heterocycle which is attached via a ring carbon atom and, as ring heteroatom, contains a nitrogen atom and which may be substituted by a radical selected from the group consisting of cyano, methyl, hydroxy and methoxy or up to two times with fluorine, and its salts, solvates and solvates of the salts.

10. Compound of the formula (I) according to claim 2 in which $Ar^N$ represents 5- or 6-membered azaheteroaryl of the formula

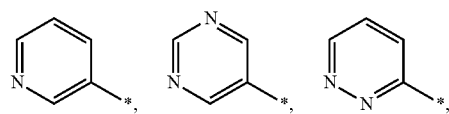

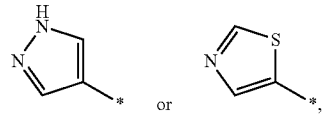

in which * marks the attachment to the imidazopyrazole grouping $R^1$ represents hydrogen, $R^2$ represents hydrogen or methyl, $R^3$ represents hydrogen, $R^{4A}$ represents chlorine or methyl, $R^{4B}$ represents hydrogen, fluorine, chlorine or methyl, $R^5$ represents hydrogen, $R^6$ represents hydrogen, $Z^1$ represents CH, $Z^2$ represents CH, $Z^3$ represents CH or N, $Z^4$ represents C—$R^9$, in which $R^9$ represents pentafluorosulphanyl, (trifluoromethyl)sulphanyl, trifluoromethyl, 2-fluoropropan-2-yl, tert-butyl, 1,1,1-trifluoro-2-methylpropan-2-yl, trifluoromethoxy, 1,1,2,2-tetrafluoroethoxy or 3-methyloxetan-3-yl, and $Z^5$ represents C—$R^{10}$, in which $R^{10}$ represents hydrogen, fluorine, chlorine, cyano, ($C_1$-$C_4$)-alkyl, hydroxy, ($C_1$-$C_4$)-alkoxy, methylsulphonyl, 2-methyl-1H-imidazol-1-yl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$, where ($C_1$-$C_4$)-alkyl and ($C_1$-$C_4$)-alkoxy may be substituted by a radical selected from the group consisting of hydroxy, methoxy, ethoxy and amino or up to three times by fluorine, and in which $L^1$ represents a bond or —$CH_2$—, $L^2$ represents a bond, $L^3$ represents a bond or —O—, $R^{11}$ represents hydrogen, $R^{12A}$ and $R^{12B}$ independently of one another represent hydrogen or methyl or $R^{12A}$ and $R^{12B}$ are attached to one another and together with the nitrogen atom to which they are attached form an azetidin-1-yl, pyrrolidin-1-yl or piperidin-1-yl ring, each of which may be substituted by a radical selected from the group consisting of cyano, hydroxy and methoxy, or a piperazin-1-yl, 4-methylpiperazin-1-yl or morpholin-4-yl ring, $R^{13A}$ and $R^{13B}$ represent independently of one another hydrogen or methyl, and $R^{14}$ represents an azetidin-3-yl, pyrrolidin-3-yl, piperidin-3-yl or piperidin-4-yl ring, each of which may be substituted by hydroxy, and its salts, solvates and solvates of the salts.

11. Compound of the formula (I) according to claim 3 in which $Ar^N$ represents 5- or 6-membered azaheteroaryl of the formula

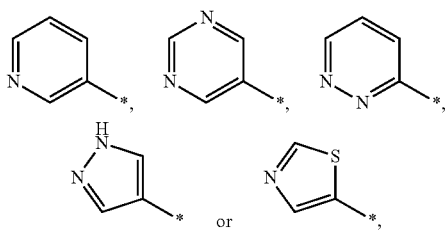

in which * marks the attachment to the imidazopyrazole grouping $R^1$ represents hydrogen,
$R^2$ represents hydrogen or methyl,
$R^3$ represents hydrogen,
$R^{4A}$ represents chlorine or methyl,
$R^{4B}$ represents hydrogen, fluorine, chlorine or methyl,
$R^5$ represents hydrogen,
$R^6$ represents hydrogen,
$Z^1$ represents CH,
$Z^2$ represents CH,
$Z^3$ represents CH or N,
$Z^4$ represents C—$R^9$, in which
  $R^9$ represents pentafluorosulphanyl, (trifluoromethyl)sulphanyl, trifluoromethyl, 2-fluoropropan-2-yl, tert-butyl, 1,1,1-trifluoro-2-methylpropan-2-yl, trifluoromethoxy, 1,1,2,2-tetrafluoroethoxy or 3-methyloxetan-3-yl,
and
$Z^5$ represents C—$R^{10}$, in which
  $R^{10}$ represents hydrogen, fluorine, chlorine, cyano, ($C_1$-$C_4$)-alkyl, hydroxy, ($C_1$-$C_4$)-alkoxy, methylsulphonyl, 2-methyl-1H-imidazol-1-yl or a group of the formula -$L^1$-C(=O)—$OR^{11}$, -$L^1$-$NR^{12A}R^{12B}$, -$L^1$-C(=O)—$NR^{13A}R^{13B}$, -$L^2$-S(=O)$_2$—$NR^{13A}R^{13B}$ or -$L^3$-$R^{14}$, where ($C_1$-$C_4$)-alkyl and ($C_1$-$C_4$)-alkoxy may be substituted by a radical selected from the group consisting of hydroxy, methoxy, ethoxy and amino or up to three times by fluorine, and in which
$L^1$ represents a bond or —$CH_2$—,
$L^2$ represents a bond,
$L^3$ represents a bond or —O—,
$R^{11}$ represents hydrogen,
$R^{12A}$ and $R^{12B}$ independently of one another represent hydrogen or methyl or
$R^{12A}$ and $R^{12B}$ are attached to one another and together with the nitrogen atom to which they are attached form an azetidin-1-yl, pyrrolidin-1-yl or piperidin-1-yl ring, each of which may be substituted by a radical selected from the group consisting of cyano, hydroxy and methoxy, or a piperazin-1-yl, 4-methylpiperazin-1-yl or morpholin-4-yl ring,
$R^{13A}$ and $R^{13B}$ represent independently of one another hydrogen or methyl,
and
$R^{14}$ represents an azetidin-3-yl, pyrrolidin-3-yl, piperidin-3-yl or piperidin-4-yl ring, each of which may be substituted by hydroxy, and its salts, solvates and solvates of the salts.